US009879230B2

(12) United States Patent
Chebloune et al.

(10) Patent No.: US 9,879,230 B2
(45) Date of Patent: Jan. 30, 2018

(54) CHIMERIC NON-INTEGRATING LENTIVIRAL GENOMES AS VACCINES AGAINST HIV-1

(75) Inventors: Yahia Chebloune, Bourgoin-Jallieu (FR); Delphine Aldebert, Grenoble (FR); Géraldine Arrode-Bruses, Meylan (FR)

(73) Assignee: CENTRE NATIONAL DE LA RECHERCHE SCIENTIFIQUE (C.N.R.S), Paris (FR)

( * ) Notice: Subject to any disclaimer, the term of this patent is extended or adjusted under 35 U.S.C. 154(b) by 53 days.

(21) Appl. No.: 14/344,360

(22) PCT Filed: Sep. 12, 2012

(86) PCT No.: PCT/EP2012/067863

§ 371 (c)(1), (2), (4) Date: Sep. 4, 2014

(87) PCT Pub. No.: WO2013/037841

PCT Pub. Date: Mar. 21, 2013

(65) Prior Publication Data

US 2014/0370051 A1 Dec. 18, 2014

(30) Foreign Application Priority Data

Sep. 12, 2011 (FR) ..................................... 11 58096

(51) Int. Cl.

*A61K 39/21* (2006.01)
*C12N 7/00* (2006.01)
*C12N 15/86* (2006.01)

(52) U.S. Cl.

CPC ............... *C12N 7/00* (2013.01); *C12N 15/86* (2013.01); *C12N 2740/15022* (2013.01);

(Continued)

(58) Field of Classification Search

None

See application file for complete search history.

(56) References Cited

U.S. PATENT DOCUMENTS

2001/0039669 A1* 11/2001 Douvas ................. C12N 15/86 800/278

FOREIGN PATENT DOCUMENTS

| | | | |
|---|---|---|---|
| WO | 9525806 | A2 | 9/1995 |
| WO | 2005027844 | A2 | 3/2005 |
| WO | 2006074963 | A2 | 7/2006 |

OTHER PUBLICATIONS

Jin et al.Changes of biological properties and pathogenesis of CAEV chimeras expressing Nef and Vpx/Vpr accessory proteins ininfected goats. Retrovirol. 2009; 6(Suppl 2):p. 22.*

(Continued)

*Primary Examiner* — Janet L Andres
*Assistant Examiner* — Stuart W Snyder
(74) *Attorney, Agent, or Firm* — Young & Thompson

(57) ABSTRACT

Novel nucleic acids include non-integrative chimeric retroviral genomes including the 5' and 3' long terminal repeat sequences (LTRs) of the caprine lentivirus: the Caprine Arthritis Encephalitis Virus (CAEV) or of another retrovirus not integrating human cells and at least one viral gene of another retrovirus. A vector including such a nucleic acid, an immunogenic or vaccinal composition including the vector or the nucleic acid, as well as their use for treating and/or preventing an infection by a retrovirus or a disease induced by a pathogenic agent are also described.

17 Claims, 17 Drawing Sheets

(52) U.S. Cl.
CPC .............. *C12N 2740/15034* (2013.01); *C12N 2740/15043* (2013.01); *C12N 2740/16134* (2013.01); *C12N 2740/16234* (2013.01); *C12N 2740/16334* (2013.01); *C12N 2770/00021* (2013.01); *C12N 2770/00034* (2013.01)

(56) References Cited

OTHER PUBLICATIONS

Shibata and Adachi, SIV/HIV Recombinants and Their Use in Studying Biological Properties. AIDS Res. Human Retrovir. 1992; 8(3): 403-409.*
Woerner and Marcus-Sekura (Characterization of a DNA binding domain in the C-terminus of HIV-1 integrase by deletion mutagenesis. Nucl. Acids Res. 1993; 21(15): 3507-3511.*
Arrode-Bruses et al., "Novel Non-Integrative One-Cycle Lentiral Genomes Derived from a Naturally Attenuated Animal Lentivirus as HIV Vaccines", Conference on AIDS Vaccine, Thailand, 2011, A-106, Poster Abstracts, p. 19.11, XP002674303.
Bouzar et al., "Simian immunodeficiency virus Vpr/Vpx proteins kill bystander noninfected CD4+ T-lymphocytes by induction of apoptosis", Virology, 2004, vol. 326, pp. 47-56.
Bouzar et al., "Activation/proliferation and apoptosis of bystander goat lymphocytes induced by a macrophage-tropic chimeric caprine arthritis encephalitis virus expressing SIV Nef", Virology, 2007, vol. 364, pp. 269-280.
Chebloune et al., "Immune Response and Resistance to Rous Sarcoma Virus Challenge of Chikens Immunized with Cell-Associated Glycoproteins Provided with a Recombinant Avian Leukosis Virus", Journal of Virology, 1991, vol. 65, No. 10, pp. 5374-5380.
Chebloune et al., "A novel non-integrative one-cycle lentiviral genome derived from a naturally attenuated animal lentivirus as HIV-1 vaccine", J. Vaccines Vaccin, 2012, vol. 3, Issue 4, pp. 78.
Cosset et al., "Newcastle Virus (NDV) Vaccine Based on Immunization with Avian Cells Expressing the NDV Hemagglutinin-Neuraminidase Glycoprotein", Virology, 1991, vol. 185, pp. 862-866.
Desrosiers, Ronald C., "Safety Issues Facing Development of a Live-Attenuated, Multiply Deleted HIV-1 Vaccine", Letter to the Editor, AIDS Research and Human Retroviruses, 1994, vol. 10, No. 4, pp. 331-332.
Genesca et al. "Antiviral CD8 T cells in the genital tract control viral replication and delay progression to AIDS after vaginal SIV challenge in rhesus macaques immunized with virulence attenuated SHIV 89.6", J. Intern Med, 2009, vol. 265, pp. 67-77.
Hofmann-Lehmann et al., "Live attenuated, nef-deleted SIV is pathogenic in most adult macaques after prolonged observation", AIDS, 2003, vol. 17, pp. 157-166.
Jin et al., "Dramatic Rise in Plasma Viremia after CD8+ T Cell Depletion in Simian Immunodeficiency Virus-infected Macaques", J. Exp. Med., 1999, vol. 189, No. 6, pp. 991-998.
Jin et al., "Changes of biological properties and pathogenesis of CAEV chimeras expressing Nef and Vpx/Vpr accessory proteins in infected goats", Retrovirology, 2009, vol. 6, Suppl. 2, p. 22.
Johnson et al., "Importance of B-Cell Responses of Immunological Control of Variant Strains of Simian Immunodeficiency Virus", Journal of Virology, 2003, vol. 77, No. 1, pp. 375-381.
Kalams et al., "Association between Virus-Specific Cytotoxic T-Lymphocyte and Helper Responses in Human Immunodeficiency Virus Type 1 Infection", Journal of Virology, 1999, vol. 73, No. 8, pp. 6715-6720.
Liu et al., "Immunoprophylaxis against AIDS in macaques with a lentiviral DNA vaccine", Virology, 2006, vol. 351, pp. 444-454.
Makedonas et al., "HIV-specific CD8 T-cell activity in uninfected injection drug users is associated with maintenance of seronegativity", Concise Communication, AIDS, 2002, vol. 16, pp. 1595-1602.
Reynolds et al., "Macaques vaccinated with live-attenuated SIV control replication of heterologous virus", J. Exp. Med., 2008, vol. 205, No. 11, pp. 2537-2550.
Rinaldo et al., "High Levels of Anti-Human Immunodeficiency Virus Type 1 (HIV-1) Memory Cytotoxic T-Lymphocyte Activity and Low Viral Load Are Associated with Lack of Disease in HIV-1 Infected Long-Term Nonprogressors", Journal of Virology, 1995, vol. 69, No. 9, pp. 5838-5842.
Robinson et al., "Protection against a lethal influenza virus challenge by immunization with a haemagglutinin-expressing plasmid DNA", Vaccine, 1993, vol. 11, Issue 9, pp. 957-960.
Whitney et al., "Live attenuated HIV vaccines: pitfalls and prospects", Curr. Opin. Infect. Dis., 2004, vol. 17, pp. 17-26.
Yankee et al., "Longitudinal study to assess the safety and efficacy of a live-attenuated SHIV vaccine in long term immunized rhesus macaques", Virology, 2009, vol. 383, pp. 103-111.
Zeilfelder et al., "Properties of Wild-Type, C-Terminally Truncated, and Chimeric Maedi-Visna Virus Glycoprotein and Putative Pseudotyping of Retroviral Vector Particles", Journal of Virology, 2001, vol. 75, No. 1, pp. 548-555.
International Search Report, dated Apr. 4, 2013, from corresponding PCT application.
Amara et al., "A Combination DNA and Attenuated Simian Immunodeficiency Virus Vaccine Strategy Provides Enhanced Protection from Simian/Human Immunodeficiency Virus-Induced Disease", Journal of Virology, 2005, vol. 79, No. 24, pp. 15356-15367.
Arrode-Bruses et al., "Characterization of T-Cell Responses in Macaques Immunized with a Single Dose of Hiv DNA Vaccine", Journal of Virology, 2010, vol. 84, No. 3, pp. 1243-1253.
Arrode-Bruses et al., "Immunogenicity of a lentiviral-based DNA vaccine driven by the 5'Ltr of the naturally attenuated caprine arthritis encephalitis virus (CAEV) in mice and macaques", 2012, vol. 30, pp. 2956-2962.
Arrode-Bruses et al., "Novel Non-Integrative One-Cycle Lentiral Genomes Derived from a Naturally Attenuated Animal Lentivirus as HIV Vaccines", Conference on AIDS Vaccine, Thailand, 2011, A-106, Poster Abstracts, P19.11, XP002674303.
Baba et al., "Live attenuated, multiply deleted simian immunodeficiency virus causes AIDS in infant and adult macaques", Nature Medicine, 1999, vol. 5, No. 2, pp. 194-203.
Baba et al., "Pathogenicity of Live, Attenuated SIV After Mucosal Infection of Neonatal Macaques", Science, 1995, vol. 267, pp. 1820-1825.
Berkowitz et al., "Gene Transfer Systems Derived from Visna Virus: Analysis of Virus Production and Infectivity", 2001, Virology, vol. 279, 116-129.
Bouzar et al., "Specific G2 arrest of caprine cells infected with a caprine arthritis encephalitis virus expressing vpr and vpx genes from simian immunodeficiency virus", Virology, 2003, vol. 309, pp. 41-52.
Bouzar et al., "Simian immunodeficiency virus Vpr/Npx proteins kill bystander noninfected CD4+ T-lymphocytes by induction of apoptosis", Virology, 2004, vol. 326, pp. 47-56.

* cited by examiner

HIV-1 proviral genome 5'&3' CAEV LTR
9696 bp

HIV-1 proviral genome 5'&3' CAEV LTR IN-
8926 bp

HIV2ST complete genome CAEV 5'3'LTR IN-
9224 bp

FIV full proviral genome CAEV5&3LTR IN-
8975 bp

CHIMERIC NON-INTEGRATING LENTIVIRAL GENOMES AS VACCINES AGAINST HIV-1

The object of the present invention is nucleic acids comprising non-integrative chimeric retroviral genomes comprising the repeated terminal sequences (STR, or LTR for Long Terminal Repeat) 5' and 3' of the caprine lentivirus: the Caprine Arthritis Encephalitis Virus (CAEV) or of another retrovirus which does not integrate into human cells and at least one viral gene of another retrovirus. The invention also relates to a vector comprising such a nucleic acid, an immunogenic or vaccinal composition comprising said vector or said nucleic acid, as well as to their use for treating and/or preventing an infection by a retrovirus or a disease induced by a pathogenic agent.

At present, the development of effective vaccines against retroviral infections is a major public health challenge worldwide. Recently, vaccines have been developed based on the use of vectors having the capability of expressing immunogenic proteins in the vaccinated host. These vaccinal vectors, after amplification in bacteria, are purified and directly injected into the host requiring vaccination. The vector is thus managed by the cells of the host, the immunogenic proteins are expressed and presented to the molecules of the major histocompatibility complex of class I and II, thereby allowing generation of immune responses against these immunogenic proteins. The first vaccination tests by means of retroviral vaccinal vectors gave the possibility of showing that immunization against the Rous sarcoma virus (Chebloune et al., 1991, J Virol, 65, 5374-5380), the New Castle disease virus (Cosset, Bouquet et al., 1991, Virology 185, 862-866) and then the influenza virus (Robinson, Hunt et Webster, 1993, *Vaccine,* 11(9): 957-960) was possible in chickens.

This vaccinal approach is particularly of interest for controlling the human immunodeficiency virus (HIV). The acquired immunodeficiency syndrome (AIDS) today continues to be a worldwide public health problem with more than 33 million infected individuals, and with more than 2 million deaths and about 3 million new infections per year. Africa is the most affected continent, but the infection is rapidly growing in Asia and in certain Eastern European countries, this phenomenon being certainly due to the lack of means for early detection and to the lack of treatment of the infection. Further, because of limitations of an economical nature, many patients infected by HIV in developing countries do not benefit from any treatment, and therefore contribute to massive dissemination of the infection. The economical impact of AIDS will therefore certainly be very important during the next few years. In Europe, AIDS remains one of the most significant transmissible pathologies with about one million persons living with AIDS and more than 20,000 new infections per year in Western Europe and in Central Europe; and with about 1.5 million persons living with AIDS and more than 200,000 new infections per year in Eastern Europe. The development of a prophylactic vaccine stopping this infection therefore remains a priority.

In spite of many efforts, to this day, there is no secure and satisfactory vaccine providing protection for humans against infection by the HIV or against the pathogenesis induced by this virus. Nevertheless, much research carried out has given the possibility of accumulating precious knowledge in order to understand the failures of the vaccinal strategies used up to now, and of defining the required properties of a vaccine inducing immune responses giving protection against the lentiviruses responsible for AIDS.

The vaccine should notably induce a CD8+ T lymphocyte response, which is associated with controlling the virus during primary infection, and the presence of which has been shown as being indispensable for controlling the viral load in infected non-human primates (Jin et al., 1999, *J Exp Med,* 189: 991-998). Further, cytotoxic T lymphocytes (CTL) are present in long term non-progressive patients (LTNP) (Rinaldo et al., 1995, *J Virol,* 69: 5838-5842), or further in subjects exposed to but not infected by the HIV (Makedonas et al., 2002, *AIDS,* 16: 1595-1602). These elements and other ones, show the importance of such responses in controlling viral replication and/or preventing the disease.

Further, vaccination should induce a response of CD4+ T cells, which are indispensable for stimulating and maintaining response based on anti-HIV CD8+ T lymphocytes (Kalams et al., 1999, *J Virol,* 73: 6715-6720). CD4+ T cells are also indispensable for setting up and maintaining the response based on antibodies produced by B lymphocytes (BL). It was thus shown that macaques infected by the SIV and depleted in BL did not control their viral load as well as control monkeys (Johnson et al., 2003, *J Virol,* 77: 375-381). Considering these results and the foregoing results, it seems therefore to be necessary that a vaccine against HIV should stimulate the B and T responses of the immune system.

Among the many tested vaccinal strategies, are found those involving so called attenuated lentiviruses. It was thus shown that the latter gives the possibility of reproducibly inducing the best protection against homologous and heterologous test viruses (Yankee et al., 2009, *Virology,* 383: 103-111; Genesca, McChesney and Miller, 2009, *J Intern Med,* 265: 67-77; Reynolds et al., 2008, *J Exp Med,* 205: 2537-2550; Amara et al., 2005, *J Virol,* 79: 15356-15367; Whitney and Ruprecht, 2004, *Curr Opin Infect Dis,* 17: 17-26). However, because of their irreversible integration into the genome of the host and of the recurrent infection probability related to proviral latencies, these viruses are pathogenic in certain adults and in newborns (Desrosiers, 1994, *AIDS Res Hum Retroviruses,* 10: 331-332; Hofmann-Lehmann et al., 2003, *AIDS,* 17: 157-166; Baba et al., 1999, *Nat Med,* 5: 194-203; Baba et al., 1995, *Science,* 267: 1820-1825; Yankee et al., 2009, *Virol,* 383: 103-111). For ethical and safety reasons, these attenuated lentiviruses cannot therefore be used as such in humans.

DNA vaccination based on viral vectors, as for it, has never been associated with development of pathologies, either in humans, or in animals, and consequently is more safe. However, tested in monkeys, these vectors prove to be incapable of protecting the animals against an experimental infection (Liu et al., 2006, *Virology,* 351: 444-454; Singh et al., 2005, *J Virol,* 79: 3419-3428).

Therefore, there exists the need for novel vaccinating vectors allowing expression of the lentiviral antigens at higher levels both in quantity and in quality, with the purpose of inducing protective responses against pathogenic viruses.

Previously, the inventors have described infectious viral genomes comprising a complete viral genome including the RTLs of the CAEV as well as one or two genes of another retroviral genome (Bouzar et al., 2007, *Virology,* 364(2): 269-280; Bouzar et al., 2004, *Virology,* 326(1): 47-56; Bouzar et al., 2003, *Virology,* 309(1): 41-52; Yuhai et al., 2009, *Retrovirology,* 6(2): 22). These genomes were used for studying the mechanisms of pathogenesis induced by highly pathogenic retroviruses of humans and monkeys.

The inventors have discovered that the use of Repeated Terminal Sequences (RTS, or LTR for Long Terminal Repeat) of the Caprine Arthritis Encephalitis Virus (CAEV) gave the possibility of improving the expression of vaccinating retroviral genomes and the induction of protective responses against pathogenic retroviruses, while avoiding their integration into the host cells. The inventors in particular demonstrated that the Long Terminal Repeat Sequences (LTRs) of the Caprine Arthritis Encephalitis Virus (CAEV) allowed constitutive expression of the genes associated with them and were not dependent on the viral tat gene of the CAEV, more particularly on the protein of the viral tat gene of the CAEV, for expressing the genes of a viral genome to which they are merged, thus allowing strong expression of viral antigens. The inventors thus developed chimeric genomes, between the lentiviruses of primates of the SIV and HIV type (HIV for Human Immunodeficiency Virus) and the CAEV, which have the properties of not being integrative and non-replicative, while being capable of carrying out a replication cycle for expressing all the antigens of the HIV and of the SIV present in the genomes. The inventors demonstrated that transfection of these genomes in primate cells (HEK293) allows expression of all the proteins of the genes present and that these proteins are assembled into viral particles capable of carrying out a single infection cycle (i.e. a pseudo-cycle) in target cells, without integrating the viral genome into these target cells. The immunization of NOD/SCID mice, humanized with human mononuclear cells demonstrated the presence of strong specific humoral and cellular immune responses against viral antigens.

Definitions

By «nucleic acid», is meant the phosphate ester polymeric form of ribonucleosides (adenosine, guanosine, uridine or cytidine; "RNA molecules") or of deoxyribonucleosides (deoxyadenosine, deoxyguanosine, deoxythymidine or deoxycytidine; "DNA molecules") in a monoquaternary form or in the form of a bi-quaternary helix. Bi-quaternary helices DNA-DNA, DNA-RNA and RNA-RNA are possible. The term of nucleic acid, and in particular of DNA or RNA molecule, only refers to the primary or secondary structure of the molecule, and is by no means limited to particular tertiary forms. Thus, this term comprises bi-quaternary DNA which is found, inter alia, in linear or circular DNA molecules (for example, restriction fragments), viruses, plasmids and chromosomes. When the structure of particular bi-quaternary DNA molecules is mentioned, the sequences may be described here according to the normal convention which only gives the sequence in the 5' to 3' direction along the non-transcribed strand of the DNA (i.e. the strand having a homologous sequence to the mRNA).

Within the context of the invention, «a nucleic acid comprising a non-integrative chimeric retroviral genome» refers to a nucleic acid which comprises the nucleic acid sequences acting in the cis position of at least two retroviruses, said nucleic acid not being capable of integrating the genome of a host cell. The nucleic acid includes the Long Terminal Repeat Sequences (LTR) in 5' and 3' of a first retrovirus, and at least one viral gene of a second retrovirus.

By "retrovirus", is meant a virus for which the genome consists of an RNA molecule and which comprises a reverse transcriptase, i.e., a member of the family of Retroviridae. The retroviruses are divided into three kinds: oncoviruses, lentiviruses and spumaviruses. Oncoviruses notably consist of the following species: the murine leukemia virus (MLV), the avian leukosis virus (ALV), the Rous sarcoma virus (RSV for Rous Sarcoma Virus), or the simian Mason-Pfizer virus. Lentiviruses consist of the following species: the human immunodeficiency virus of type 1 (HIV-1), the human immunodeficiency virus of type 2 (HIV-2), the simian immunodeficiency virus (SIV), the feline immunodeficiency virus (FIV), the bovine immunodeficiency virus (BIV), the sheep Visna Maedi virus (VMV), the Caprine Arthritis Encephalitis Virus (CAEV) or the Equine Infectious Anaemia Virus (EIAV). The spumavirus may be HFV. When the retrovirus is HIV-1, it may be of any serogroup, for example of serogroup M (serotype A-D, F-H, J, K), serogroup O, N or P. When the retrovirus is HIV-2, it may be of any serogroup, for example of serogroup A or B.

By «viral gene», is meant a gene present in the retroviral genome. Within the context of the invention, the viral gene may be gag, pol, vif, vpx, vpr, nef, tat, rev, vpu or env gene.

The gene «gag» meaning «group specific antigen» codes for the precursor polyprotein gag which is cleaved for giving the fundamental structural proteins of the retroviruses, which are the capsid proteins, proteins of the nucleocapsid, and the proteins of the matrix. For example, the protein gag of the HIV is the precursor of the capsid protein p24, of the proteins of the p6 and p7 nucleocapsid, and of the protein of matrix p17. As a non-limiting example, the gene gag is the gene gag of the HIV-1 (NCBI gene ID No. 155030, updated on Aug. 20, 2011), of the HIV-2 (NCBI gene ID No. 14900001, updated on Aug. 27, 2011), of the SIV (NCBI gene ID No. 956108, updated on Aug. 27, 2011) or of the FIV (NCBI gene ID No. 1489988, updated on Aug. 20, 2011).

The gene «pol» codes for a reverse transcriptase, an integrase and a protease. As a non-limiting example, the gene pol is the gene pol of the HIV-1 (NCBI gene ID No. 155348, updated on Aug. 27, 2011), of the HIV-2 (NCBI gene ID No. 1490001, updated on Aug. 27, 2011), of the FIV (NCBI gene ID No. 1489989, updated on Aug. 27, 2011) or of the SIV (NCBI gene ID No. 956107, updated on Aug. 20, 2011).

The gene «vif» or «viral infectivity factor» codes for a protein required for producing infectious virions. As a non-limiting example, the gene vif is the gene vif of HIV-1 (NCBI gene ID No. 155459, updated on Aug. 7, 2011), of the HIV-2 (NCBI gene ID No. 1724712, updated on Jan. 21, 2010), of FIV (NCBI gene ID No. 1724709, updated on Feb. 7, 2010) or of the SIV (NCBI gene ID No. 1490005, updated on Jan. 21, 2010).

The gene «vpr» codes for the viral protein R which plays an important role in the stopping of the cell cycle in phase G2, and in the regulation of the transport of the pre-integration complex from the cytoplasm to the nucleus, the viral replication. As a non-limiting example, the gene vpr is the gene vpr of HIV-1 (NCBI gene ID No. 155807, updated on Aug. 7, 2011), of HIV-2 (NCBI gene ID No. 1724718, updated on Jan. 21, 2010) or of SIV (NCBI gene ID No. 956112, updated on Jan. 15, 2011).

The gene «vpx» code for the viral protein X is related to the gene vpr. As a non-limiting example, the gene vpx is the gene vpx of HIV-2 (NCBI gene ID No. 1724714, updated on Mar. 19, 2011) or of SIV (NCBI gene ID No. 1490006, updated on Jul. 16, 2011).

The gene «nef» codes for the myristoylated protein of 27 to 25 kDa, called a Negative Regulation Factor, which plays a key role in the depletion of CD4 lymphocytes in vivo. As a non-limiting example, the gene nef is the gene nef of HIV-1 (NCBI gene ID No. 156110, updated on Aug. 7, 2011), of HIV-2 (NCBI gene ID No. 1724715, updated on Mar. 19, 2011) or of SIV (NCBI gene ID No. 1490008, updated on Jul. 2, 2011).

The gene «tat» codes for a protein of 86 to 101 amino acids, called a «Trans-Activator of Transcription», which increases the transcription rate of the retroviral genome. As a non-limiting example, the gene tat is the gene tat of HIV-1 (NCBI gene ID No. 155871, updated on Aug. 20, 2011), of HIV-2 (NCBI gene ID No. 1724713, updated on Feb. 7, 2010) or of SIV (NCBI gene ID No. 956113, updated on Feb. 7, 2010).

The gene «rev» codes for a protein called «Regulator of Virion Expression» which allows export of the viral RNA from the nucleus to the cytoplasm. As a non-limiting example, the gene rev is the gene rev of HIV-1 (NCBI gene ID No. 155908, updated on Aug. 7, 2011), of HIV-2 (NCBI gene ID No. 1724716, updated on May 21, 2011) or of SIV (NCBI gene ID No. 1490003, updated on Jan. 15, 2011).

The gene «vpu» codes for a protein called a «Viral Protein U» which is involved in viral budding and improvement in the release of virions. As a non-limiting example, the gene vpu is the gene vpu of HIV-1 (NCBI gene ID No. 155945, updated on Aug. 7, 2011) or of SIV (NCBI gene ID No. 2828723, updated on Jan. 21, 2010).

The gene «env» codes for the precursor protein gp160 which is ripened and cleaved in order to give the proteins of the envelope gp120 and gp41. As a non-limiting example, the gene env is the gene env of HIV-1 (NCBI gene ID No. 155971, updated on Aug. 7, 2011), of HIV-2 (NCBI gene ID No. 1724717, updated on Jun. 18, 2011), of FIV (NCBI gene ID No. 1489987, updated on Jun. 18, 2011) or of SIV (NCBI gene ID No. 1490007, updated on Jun. 18, 2011).

In the sense of the present application, the term of «comprises» or «comprising» refers according to a particular mode to «consist in» or «consisting in».

Nucleic Acid

The inventors have demonstrated that Long Terminal Repeat Sequences (LTR) of the Caprine Arthritis Encephalitis Virus (CAEV) allowed constitutive expression of the genes associated with them and were not dependent on the viral gene tat for expressing the genes of a viral genome to which they are merged, thus allowing strong expression of viral antigens. Further, the inventors showed that the sole presence of these LTRs prevented integration of a heterologous retroviral genome to which they are merged.

The invention therefore relates to a nucleic acid comprising a non-integrative chimeric retroviral genome, in which said chimeric retroviral genome comprises:

- Long Terminal Repeat Sequences (LTR) in 5' and in 3' of a first retrovirus, said first retrovirus being a lentivirus, such as the Caprine Arthritis Encephalitis Virus (CAEV), the ovine Visna Maedi virus (VMV), the Equine Infectious Anaemia Virus (EIAV), or an oncovirus or a spumavirus, and
- at least one viral gene of a second retrovirus, said second retrovirus not being the first retrovirus.

The LTR sequences used preferably stem from a retrovirus which does not integrate the genome of a «host« or »patient», said host or patient being a host or patient in the genome of which the second and/or third retroviruses may be integrated. For example, when the first retrovirus is CAEV, said host or patient is not a caprine but may be a human, a monkey, a cat, or a horse, or when the first retrovirus is EIAV, said host or patient is not a horse but may be a human, a monkey, a cat, or an ovine, or when the first retrovirus is VMV, said host or patient is not an ovine but may be a human, a monkey, a cat, or a horse.

In a particularly preferred embodiment, the «first retrovirus» is the Caprine Arthritis Encephalitis Virus or CAEV. The CAEV is a retrovirus of the lentivirus type of goats which is related to the human immunodeficiency virus (HIV), but does not cause any pathology of the AIDS type in its host.

By «Long Terminal Repeated Sequences» (LTR), is meant a sequence allowing control of the transcription, i.e. comprising an enhancer, a promoter, one or several signals for initiating the transcription, one or several signals for ending the transcription, one or several signals for poly-adenylation. Within the context of the invention, the LTRs of CAEV comprise an enhancer, a promoter and a signal for initiating transcription as well as a signal for ending the transcription and a poly-adenylation signal. Preferably, the LTRs in 5' and in 3' of the CAEV are identical and comprise or consist in the sequence SEQ ID NO.: 3.

In other embodiments, the LTRs of the Visna Maedi Virus (VMV) or those of the lentivirus of equidae EIAV are used. The LTR in 5' of VMV comprises or consists in the sequence found in position 1 to 161 of the Reference Sequence NCBI NC_001452.1 (updated on Dec. 8, 2008). The LTR in 3' of VMV comprises or consists in the sequence found in position 9106 to 9202 of the Reference Sequence NCBI NC_001452.1 (updated on Dec. 8, 2008). The LTR in 5' of EIAV comprises of consists in the sequence found in position 61 to 381 of the Reference Sequence NCBI NC_001450 (updated on Mar. 11, 2010). The LTR in 3' of EIAV comprises or consists in the sequence found in position 7269 to 8289 of the Reference Sequence NCBI NC_001450 (updated on Mar. 11, 2010).

In still other embodiments, the LTRs of an oncovirus, such as the murine leukemia virus (MLV), the avian leukemia virus (ALV), the Rous sarcoma virus (RSV), or the simian Mason-Pfizer virus, or the LTRs of a spumavirus, such as HFV are used. The LTR in 5' of the MLV comprises or consists in the sequence found in position 1 to 210 of the Reference Sequence NCBI NC_001702.1 (updated on Feb. 5, 2011). The LTR in 3' of the MLV comprises or consists in the sequence found in position 5735 to 8135 of the Reference Sequence NCBI NC_001702.1 (updated on Feb. 5, 2011). The LTR in 5' of the ALV comprises or consists in the sequence found in position 1 to 594 of the Reference Sequence NCBI NC_015116.1 (updated on Apr. 18, 2011). The LTR in 3' of the ALV comprises or consists of the sequence found in position 5338 to 7489 of the Reference Sequence NCBI NC_015116.1 (updated on Apr. 18, 2011). The LTR in 5' of RSV comprises or consists of the sequence found in position 22 to 102 of the Reference Sequence NCBI NC_001407.1 (updated on Dec. 8, 2008). The LTR in 3' of the RSV comprises or consists of the sequence found in position 9058 to 9292 of the Reference Sequence NCBI NC_001407.1 (updated on Dec. 8, 2008). The LTR in 5' of the simian Mason-Pfizer virus comprises or consists of the sequence found in position 26 to 123 of the Reference Sequence NCBI NC_001550.1 (updated on Dec. 8, 2008). The LTR in 3' of the simian Mason-Pfizer virus comprises or consists of the sequence found in position 7573 to 7811 of the Reference Sequence NCBI NC_001550.1 (updated on Dec. 8, 2008). The LTR in 5' of the HFV comprises or consists of the sequence found in position 1 to 1760 of the Reference Sequence NCBI NC_001364.1 (updated on Apr. 22, 2009). The LTR in 3' of the HFV comprises or consists of the sequence found in position 11487 to 13246 of the Reference Sequence NCBI NC_001364.1 (updated on Apr. 22, 2009).

The inventors have shown that the Long Terminal Repeat Sequences (LTR) of the Caprine Arthritis Encephalitis Virus (CAEV) were not dependent on the viral gene tat for expressing the genes of a viral genome to which they are merged, advantageously, the nucleic acid according to the invention does not contain the tat gene of said first retrovirus.

Within the context of the invention, the « second retrovirus» is different from the first retrovirus. It may be an oncovirus, a lentivirus or a spumavirus. Thus, for example, when the LTRs of the CAEV are used, the second retrovirus is not the CAEV. Preferably, the second retrovirus is an oncovirus, such as the murine leukemia virus (MLV), the avian leukosis virus (ALV), the Rous sarcoma virus (RSV), or the simian Mason-Pfizer virus, a lentivirus, such as the human immunodeficiency virus of type 1 (HIV-1), the human immunodeficiency virus of type 2 (HIV-2), the simian immunodeficiency virus (SIV), the feline immunodeficiency virus (FIV) or the equine infectious anaemia virus (EIAV), or a spumavirus, such as HFV. More preferably, the second retrovirus is HIV-1, HIV-2, SIV or FIV.

Preferably, at least one viral gene of said second retrovirus is selected from the gag, pol, vif, vpx, vpr, nef, tat, rev, vpu and env genes. In a particular aspect, said chimeric retroviral genome comprises at least two, three (for example the genes gag, pol, vif, or the genes gag, pol, env), four, five, six, seven, eight, nine, ten viral genes of said second retrovirus. Advantageously, said chimeric retroviral genome comprises the gene tat of said second retrovirus. Still more preferably, said chimeric retroviral genome comprises the set of genes gag, pol, vif, vpx, vpr, nef, tat, rev, vpu and env of said second retrovirus.

In a particularly preferred aspect, said chimeric retroviral genome comprises the gag, pol, vif, vpx, vpr, nef, tat, rev, vpu and env genes of the SIV, HIV-1, HIV-2 or FIV. In a still preferred aspect, said chimeric retroviral genome comprises or consists of the sequence of the retroviral genome of SIV (SEQ ID NO.: 4), of the retroviral genome of HIV-1 (SEQ ID NO: 2), of the retroviral genome of HIV-2 (SEQ ID NO: 5), or the retroviral genome of FIV (SEQ ID NO: 6).

The chimeric retroviral genomes of the SIV, HIV-1, HIV-2 and FIV are schematically illustrated in FIGS. 1 to 4, respectively.

In a particular embodiment, said chimeric retroviral genome further comprises at least one viral gene of a third retrovirus, said third retrovirus not being the first retrovirus, i.e. being different from said first retrovirus. Thus, for example, when the LTRs of the CAEV are used, said third retrovirus is not the CAEV. Said « third retrovirus» may be selected from one of the retroviruses as defined above.

When said chimeric retroviral genome comprises at least one viral gene of a second retrovirus and at least one viral gene of a third retrovirus, said second retrovirus and third retrovirus are different. Said second retrovirus and third retrovirus may be or not be of different kinds, for example said second and third retroviruses may each be an oncovirus, a lentivirus, or a spumavirus, or said second and third retroviruses may respectively be (i) a lentivirus and a spumavirus, or conversely a spumavirus and a lentivirus, (ii) an oncovirus and a lentivirus, or conversely a lentivirus and an oncovirus, or (iii) a spumavirus and an oncovirus, or conversely an oncovirus and a spumavirus.

Preferentially, when said chimeric retroviral genome comprises at least one viral gene of a second retrovirus and at least one viral gene of a third retrovirus, said second retrovirus and third retrovirus each are a lentivirus, and preferably, said lentivirus is selected from HIV-1, HIV-2, SIV, FIV or EIAV. Still more preferably, the second retrovirus and the third retrovirus are lentiviruses of different species, serogroup, or serotype. Thus for example when said second retrovirus is HIV-1, said third retrovirus is HIV-2, or further when said second retrovirus is HIV-1 of serogroup M, said third retrovirus is HIV-1 of serogroup 0, or further when said second retrovirus is HIV-1 of serogroup M and of serotype 1, said third retrovirus is HIV-1 of serogroup M and of serotype B.

Preferably, said at least one viral gene of said third retrovirus is selected from the gag, pol, vif, vpx, vpr, nef, tat, rev, vpu and env genes. In a particular aspect, said chimeric retroviral genome further comprises at least two, three, four, five, six, seven, eight, nine or ten viral genes of said third retrovirus, advantageously including the gene tat.

Still more preferably, said chimeric retroviral genome further comprises the set of genes gag, pol, vif, vpx, vpr, nef, tat, rev, vpu and env of said third retrovirus, i.e. said chimeric retroviral genome comprises the set of gag, pol, vif, vpx, vpr, nef, tat, rev, vpu and env genes of said second retrovirus and the set of gag, pol, vif, vpx, vpr, nef, tat, rev, vpu and env genes of said third retrovirus.

Said chimeric retroviral genome may therefore comprise a viral gene of said second retrovirus and nine viral genes of said third retrovirus, or two viral genes of said second retrovirus and eight viral genes of said third retrovirus, or three viral genes of said second retrovirus and seven viral genes of said third retrovirus, or four viral genes of said second retrovirus and six viral genes of said third retrovirus, or five viral genes of said second retrovirus and five viral genes of said third retrovirus, or six viral genes of said second retrovirus and four viral genes of said third retrovirus, or seven viral genes of said second retrovirus and three viral genes of said third retrovirus, or eight viral genes of said second retrovirus and two viral genes of said third retrovirus, or nine viral genes of said second retrovirus and one viral gene of said third retrovirus. As non-limiting examples, said chimeric retroviral genome may therefore comprise the gag gene of said second retrovirus and the pol, vif, vpx, vpr, nef, tat, rev, vpu and env genes of said third retrovirus; or the gag and pol genes of said second retrovirus and the vif, vpx, vpr, nef, tat, rev, vpu and env genes of said third retrovirus; or the gag, pol, vif genes of said second retrovirus and the vpx, vpr, nef, tat, rev, vpu and env genes of said third retrovirus; or the gag, pol, vif, vpx genes of said second retrovirus and the vpr, nef, tat, rev, vpu and env genes of said third retrovirus; or gag, pol, vif, vpx, vpr of said second retrovirus and the nef, tat, rev, vpu and env genes of said third retrovirus; or the gag, pol, vif, vpx, vpr, nef genes of said second retrovirus and the tat, rev, vpu and env genes of said third retrovirus; or the gag, pol, vif, vpx, vpr, nef, tat genes of said second retrovirus and the rev, vpu and env genes of said third retrovirus; or the gag, pol, vif, vpx, vpr, nef, tat, rev genes of said second retrovirus and the vpu and env genes of said third retrovirus; or the gag, pol, vif, vpx, vpr, nef, tat, rev, vpu genes of said second retrovirus and the env gene of said third retrovirus.

In a particularly preferred aspect, said chimeric retroviral genome comprises the gag, pol, vif, vpx and vpr genes of said second retrovirus and the nef, tat, rev, vpu and env genes of said third retrovirus.

In a still more preferred aspect, said chimeric retroviral genome comprises the gag, pol, vif, vpx and vpr genes of the SIV and the nef, tat, rev, vpu and env genes of the HIV-1, or conversely the gag, pol, vif, vpx and vpr genes of the HIV-1 and the nef, tat, rev, vpu and env genes of the SIV. In another particularly preferred aspect, said chimeric retroviral genome comprises the gag, pol, vif, vpx and vpr genes of the HIV-1 and the nef, tat, rev, vpu and env genes of the HIV-2, or conversely the gag, pol, vif, vpx and vpr genes of the HIV-2 and the nef, tat, rev, vpu and env genes of the HIV-1. In a still more preferred aspect, said chimeric retroviral genome comprises or consists in sequence SEQ ID NO: 7 (a schematic representation of this chimeric retroviral genome is found in FIG. 5).

In a particular embodiment, when the pol gene is present in the chimeric retroviral genome, said pol gene is a deleted pol gene from the sequence coding for the integrase (in). Preferably, said pol gene is deleted from the sequence SEQ ID NO: 8 (sequence of the integrase of SIV), SEQ ID NO: 9 (sequence of the integrase of HIV-1), SEQ ID NO: 10 (sequence of the integrase of HIV-2), or SEQ ID NO: 11 (sequence of integrase of FIV).

Thus, in a particularly preferred embodiment, said retroviral genome comprises or consists in the sequences SEQ ID NO: 1, SEQ ID NO: 12, SEQ ID NO: 13, SEQ ID NO: 14 or SEQ ID NO: 15.

The chimeric retroviral genomes comprising or consisting in the sequences SEQ ID NO: 1, SEQ ID NO: 12, SEQ ID NO: 13, SEQ ID NO: 14 or SEQ ID NO: 15 are schematically illustrated in FIGS. 6 to 10, respectively.

The invention also relates to a vector comprising a nucleic acid according to invention.

The term of «vector» designates an extrachromosomal element through which a DNA or RNA sequence (i.e. a «foreign» gene) may be introduced into a host cell, so as to transform the host and to allow expression (i.e. transcription and translation) of the introduced sequence. The extrachromosomal element may be a self-replicating sequence, a phage sequence or a nucleotide sequence, a single or dual strand DNA or RNA, a plasmid, a cosmid. A vector typically contains the DNA of a transmissible agent, into which a foreign DNA is inserted and a selection marker. A common means for inserting a DNA fragment into another DNA segment involves the use of enzymes, called restriction enzymes, which cleave the DNA at specific sites (specific groups of nucleotides), called restriction sites. Generally, the foreign DNA is inserted at one or several restriction sties of the DNA vector, and is then transported by the vector into a host cell with a DNA of the transmissible agent. A DNA segment or sequence comprising an added or inserted DNA, such as the vector, may also be called «a DNA construct». A common type of vector is a «plasmid», which generally is an autonomous dual strand DNA molecule, generally of bacterial origin, which may easily accept an additional (foreign) DNA and which may easily be introduced into a suitable host cell. A large number of vectors, including plasmids, have been described for the replication and/or expression in different eukaryotic and prokaryotic hosts. Within the context of the invention, the vector includes a selection marker, such as a gene for resistance to an antibiotic, or a nucleic acid according to the invention. Preferably, the resistance gene is a gene for resistance to ampicillin or kanamycin.

The nucleic acids and/or the vector according to the invention may be used for transforming or transfecting a cell or a host organism, i.e. for expressing the chimeric retroviral genome according to the invention.

The term of «host cell» refers to any cell of any organism which is selected, modified, transformed, transfected, transduced, cultivated, or used or manipulated in any way, for producing a substance by the cell, for example for the expression of a gene, of a DNA sequence, of a protein, of a virion by the cell. Within the context of the invention, the host cell is a mammal cell. Suitable host cells include, without being limited thereto, HEK293 cells, human CD4+ T lymphocyte lines CEMx174 and M8166, human CD4+ T lymphocytes, human CD8+ T lymphocytes, mononuclear cells of human blood.

The transformation of the cell or of the host organism by the nucleic acid and/or the vector according to the invention may be achieved according to standard techniques known to one skilled in the art, such as for example by transfection, electroporation, microinjection, transduction, merging of cells, DEAE-Dextran, precipitation with calcium phosphate, or use of a gene pistol, or a DNA vector transporter (see for example, Wu et al., 1992, *J Biol Chem* 267: 963-967; Wu et al., 1988, *J Biol Chem* 263: 14621-14624; Hartmut et al., Canadian patent application No. 2,012,311, published on Mar. 15, 1990).

Immunogenic or Vaccinal Composition and its Uses

The nucleic acid or the vector according to the invention may be used with an immunogenic or vaccinal purpose.

Thus, the invention also relates to an immunogenic or vaccinal composition comprising a nucleic acid or a vector according to the invention.

Within the context of the present application, the term of «vaccinal» relates to prophylactic or therapeutic vaccination.

By immunogenic or vaccinal composition, is meant a composition giving the possibility of inducing an immune response against a retrovirus as defined earlier. By immune response is meant a response involving T lymphocytes, for example CD4+ and CD8+ T lymphocytes, and B lymphocytes.

According to the embodiment, the immunogenic or vaccinal composition according to the invention is monovalent, i.e. it allows an immune response against a single retrovirus, for example against HIV-1 or HIV-2.

According to another embodiment, the immunogenic or vaccinal composition according to the invention is multivalent, i.e. it allows an immune response against several retroviruses, for example against HIV-1 and HIV-2 or several pathogenic agents, for example against HIV-1 and HCV (Hepatitis C Virus). In this case, the vaccinating vector expresses the antigens of either pathogenic agent.

According to another embodiment, the immunogenic or vaccinal composition according to the invention is polyvalent. Such an immunogenic or vaccinal composition may be obtained by combining several monovalent immunogenic or vaccinal compositions according to the invention. The immunogenic or vaccinal composition may further comprise at least one other vaccine, i.e. an attenuated live virus, an inactivated virus or a viral sub-unit, against another virus, such as a sexually transmissible virus, such as for example the hepatitis B virus, the hepatitis C virus or the papillomavirus.

In a preferred embodiment, the immunogenic or vaccinal composition according to the invention comprises a pharmaceutically acceptable carrier.

A «pharmaceutically acceptable carrier» refers to any carrier in which the immunogenic or vaccinal composition according to the invention may be formulated. This includes a saline solution such as a saline phosphate buffer. Generally, a diluent or a carrier is selected according to the administration method and route, and according to standard pharmaceutical practices. A pharmaceutically acceptable carrier includes, without any limitation, iron exchangers, aluminium, aluminium stearate, lecithin, systems for delivering self-emulsifying drugs such as D-α-tocopherol polyethyleneglycol 1000 succinate, surfactants used as a pharmaceutical dosage form such as Tweens or other polymeric delivery matrices, proteins of serum such as human albumin, buffer substances such as phosphates, glycine, sorbic acid, potassium sorbate, mixtures of saturated fatty acid glycerides of plants, water, salts or electrolytes, such as protamine sulfate, disodium hydrogen phosphate, potassium hydrogen phosphate, sodium chloride, zinc salts, colloidal silica, magnesium trisilicate, polyvinylpyrrolidone, substances based on cellulose, polyethylene glycol, sodium carboxymethylcellulose, polyacrylates, waxes, polyethylene-polyoxypropylene block polymers and wool fat. Cyclodextrins such as A-, B-, and g-cyclodextrins, or chemically modified derivatives such as hydroxyalkylcyclodextrins, including 2- and 3-hydroxypropyl-b-cyclodextrins, or other solubilized derivatives may also be advantageously used for improving delivery of the compositions according to the invention.

The compositions according to the invention may further contain an adjuvant. Any pharmaceutically acceptable adjuvant or mixture of adjuvants conventionally used in the field of vaccines may be used for this purpose. As examples of suitable adjuvants, mention may be made of aluminium salts such as aluminium hydroxide or aluminium phosphate and DC-Chol. Any pharmaceutically acceptable adjuvant or mixture of adjuvants conventionally used in the field of vaccines may be used for this purpose. As an example of a suitable adjuvant, mention may be made of aluminium salts such as aluminium hydroxide or aluminium phosphate and DC-Chol.

The compositions according to the invention may contain adjuvant genes, i.e. genes which express proteins which will play the role of adjuvants by increasing the immunogenicity of the expressed viral proteins. For example, the genes which code for cytokines such as interleukins (II) [IL-2, IL12, IL-15, . . . or GM-CSF (granulocyte-macrophage colony-stimulating factor)]. These adjuvant genes are either incorporated into the vaccinel plasmid or co-injected as separate expression plasmids.

Any method of administration known to one skilled in the art may be used. In particular, the nucleic acid, the vector, the immunogenic or vaccinel composition according to the invention may be administered orally, by inhalation, or via a parenteral route (in particular by intradermal, subcutaneous, intravenous, intramedullar or intramuscular injection). When the parenteral route is used, the nucleic acid, the vector, the immunogenic or vaccinel composition according to the invention may be in the form of injectable solutions and suspensions, packaged in ampoules or in flasks. The forms for parenteral delivery are generally obtained by mixing the nucleic acid, the vector, the immunogenic or vaccinal composition according to the invention with buffers, emulsifiers, stabilisers, preservatives, solubilizing agents. According to known techniques, these mixtures may then be sterilized and packaged in the forms of intradermal, subcutaneous, intravenous, intramedullar or intramuscular injections. One skilled in the art may use buffers based on organic phosphate salts as a buffer. Examples of emulsifiers include methylcellulose, acacia, sodium carboxymethylcellulose. Examples of stabilisers include sodium sulfite, sodium metasulfite, and examples of preservatives include sodium p-hydroxybenzoate, sorbic acid, cresol and chlorocresol. The nucleic acid, vector, the immunogenic or vaccinal composition may also be in freeze-dried form.

The vaccinal DNA solution may be directly injected or else administered by electroporation in vivo by using a commercial electroporator or else encapsulated in liposomes or nanoparticles or by using any in vivo transfection method which allows better introduction of the vaccinal DNA into the cells of the vaccinated host.

In one other aspect, the invention relates to a nucleic acid according to the invention, a vector according to the invention and/or an immunogenic or vaccinal composition according to the invention for use in preventing and/or treating an infection by a retrovirus.

By «prevent» or «prevention», is meant the inhibition of a retroviral infection, i.e. preventing the retrovirus from causing an infection, or preventing the propagation of the retrovirus inside an infected subject or from one subject to another.

By «treat» or «treatment, is meant the limitation of the severity of the disease, the prevention of recurrent infections, i.e. limiting the re-activation of latent or persistent infections, and finding a remedy to the symptoms of the infections by a retrovirus. The retrovirus is as defined earlier and preferably the retrovirus is HIV-1, HIV-2 or FIV.

The term of «patient» or «subject» or «host» refers to a human or non-human mammal or a bird. Preferentially, the patient is a primate, a murine (mouse), a feline (cat), a canine (dog), a member of the equidae (a horse), a bird, a human, including women, men, adults and children.

The present invention also relates to a method for vaccinating or treating a subject in need thereof comprising the administration of a prophylactically or therapeutically effective amount of a nucleic acid according to the invention, or of a vector according to the invention, or of an immunogenic or vaccinal composition according to the invention.

A «prophylactically or therapeutically effective amount» refers to an amount of nucleic acid, of a vector, an immunogenic or vaccinal composition capable of imparting a therapeutic or prophylactic effect on the treated subject. The therapeutic effect may be objective (i.e. measurable by tests or markers) or subjective (i.e. the subject gives an indication of an effect or feels an effect). An effective amount may vary from about 0.01 to 5,000 μg/kg, alternatively from about 0.1 to a 1,000 μg/kg, alternatively from about 1 to 500 μg/kg. The effective amounts will also vary according to the administration route, either the use or not of an in vivo transfection method, the size and weight of the subject, as well as according to the possibility of co-use with other agents.

Within the context of the invention, the administration mode of the nucleic acid according to the invention, or of the vector according to the invention, or of the immunogenic or vaccinal composition according to the invention may be achieved via an intravenous, subcutaneous, intradermal, intramedullar, or intramuscular route.

The invention will now be explained in more detail with the following examples, without limiting the scope thereof.

DESCRIPTION OF THE SEQUENCES

SEQ ID NO: 1 Represents the sequence of a chimeric retroviral genome comprising the LTRs of the SAEV and the genome of SHIV deleted from the sequences coding for the integrase.

SEQ ID NO: 2 Represents the sequence of a chimeric retroviral genome comprising the LTRs of the CAEV and the genome of the HIV-1.

SEQ ID NO: 3 Represents the sequence of the LTR of the CAEV.

SEQ ID NO: 4 Represents the sequence of a chimeric retroviral genome comprising the LTRs of the CAEV and the genome of SIV.

SEQ ID NO: 5 Represents the sequence of a chimeric retroviral genome comprising the LTRs of the CAEV and the genome of HIV-2.

SEQ ID NO: 6 Represents the sequence of a chimeric retroviral genome comprising the LTRs of the CAEV and the genome of the FIV.

SEQ ID NO: 7 Represents the sequence of a chimeric retroviral genome comprising the LTRs of the CAEV and the genome of SHIV.

SEQ ID NO: 8 Represents the sequence of the integrase of SIV.

SEQ ID NO: 9 Represents the sequence of the integrase of HIV-1.

SEQ ID NO: 10 Represents the sequence of the integrase of HIV-2.

SEQ ID NO: 11 Represents the sequence of the integrase of FIV.

SEQ ID NO: 12 Represents the sequence of a chimeric retroviral genome comprising the LTRs of the CAEV and the genome of HIV-1 deleted from the sequences coding for the integrase.

SEQ ID NO: 13 Represents the sequence of a chimeric retroviral genome comprising the LTRs of the CAEV and the genome of HIV-2 deleted from the sequences coding for the integrase.

SEQ ID NO: 14 Represents the sequence of a chimeric retroviral genome comprising the LTRs of the CAEV and genome of FIV deleted from the sequences coding for the integrase.

SEQ ID NO: 15 Represents the sequence of a chimeric retroviral genome comprising the LTRs of the CAEV and the genome of SIV deleted from the sequences coding for the integrase.

SEQ ID NO: 16 Represents the sequence of the vector pCA-LTR-SHIV$_{KU2}$.

SEQ ID NO: 17 Represents the sequence of the vector pCA-LTR-SHIV$_{KU2}$-IN-.

SEQ ID NO: 18 Represents the sequence of the vector CAL-HIV-IN-.

EXAMPLES

Figure 1:
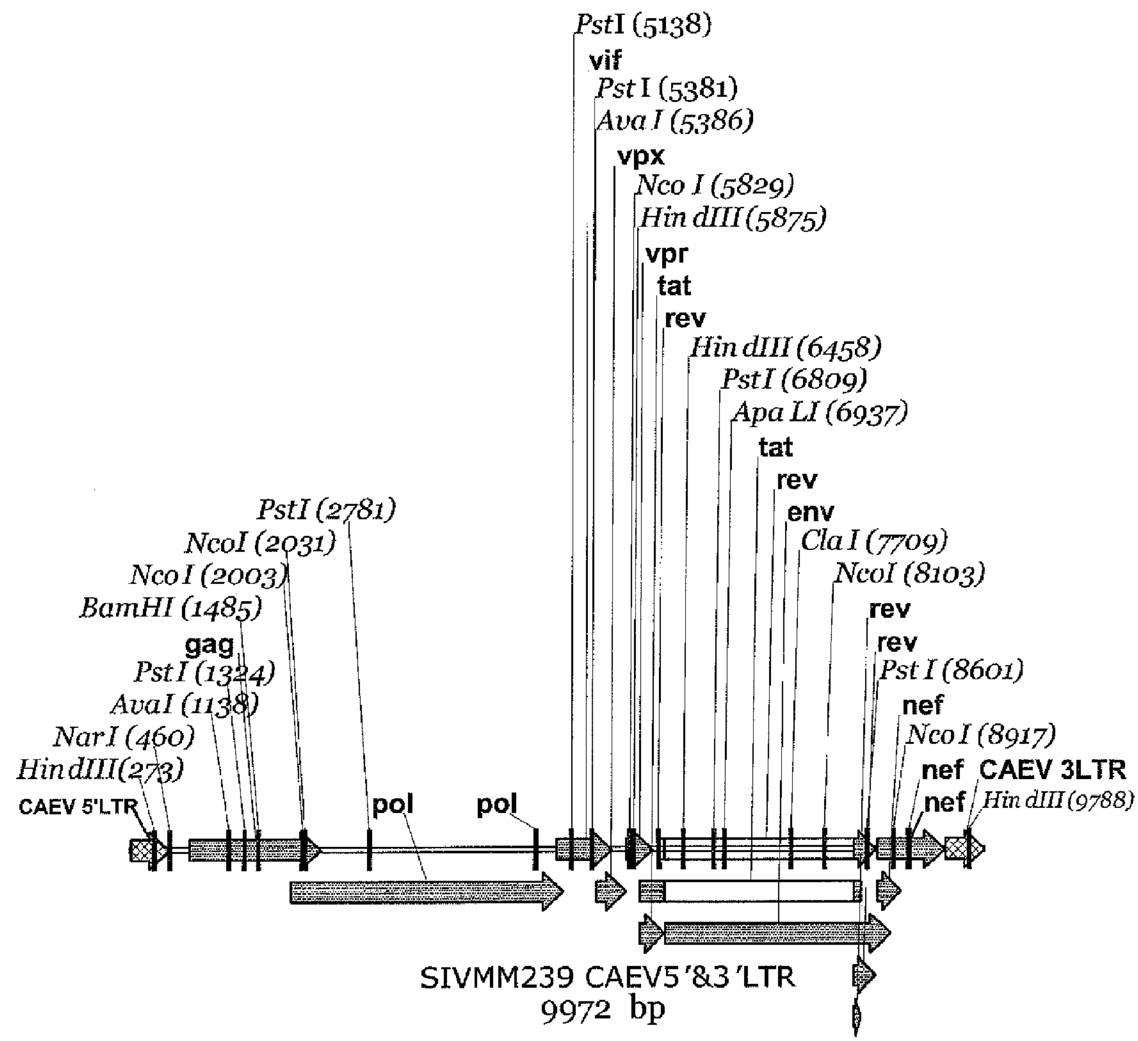
FIG. 1: Schematic illustration of the nucleic acid coded by the sequence SEQ ID NO.: 2.
Figure 2:
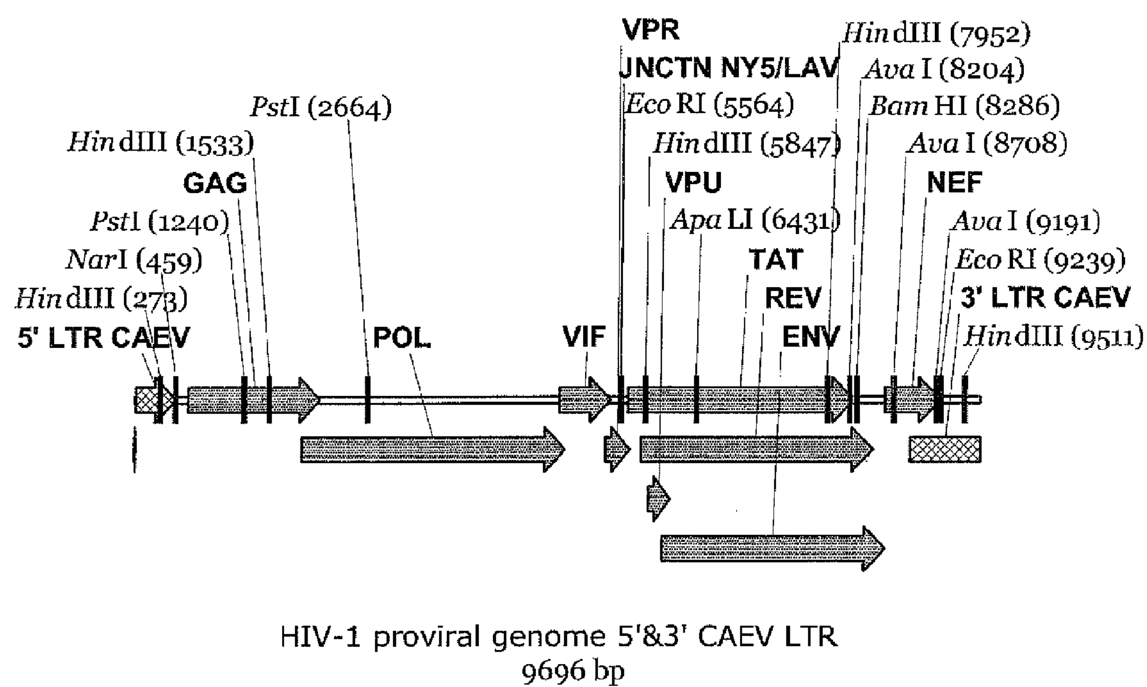
FIG. 2: Schematic illustration of the nucleic acid coded by the sequence SEQ ID NO.: 4.
Figure 3:
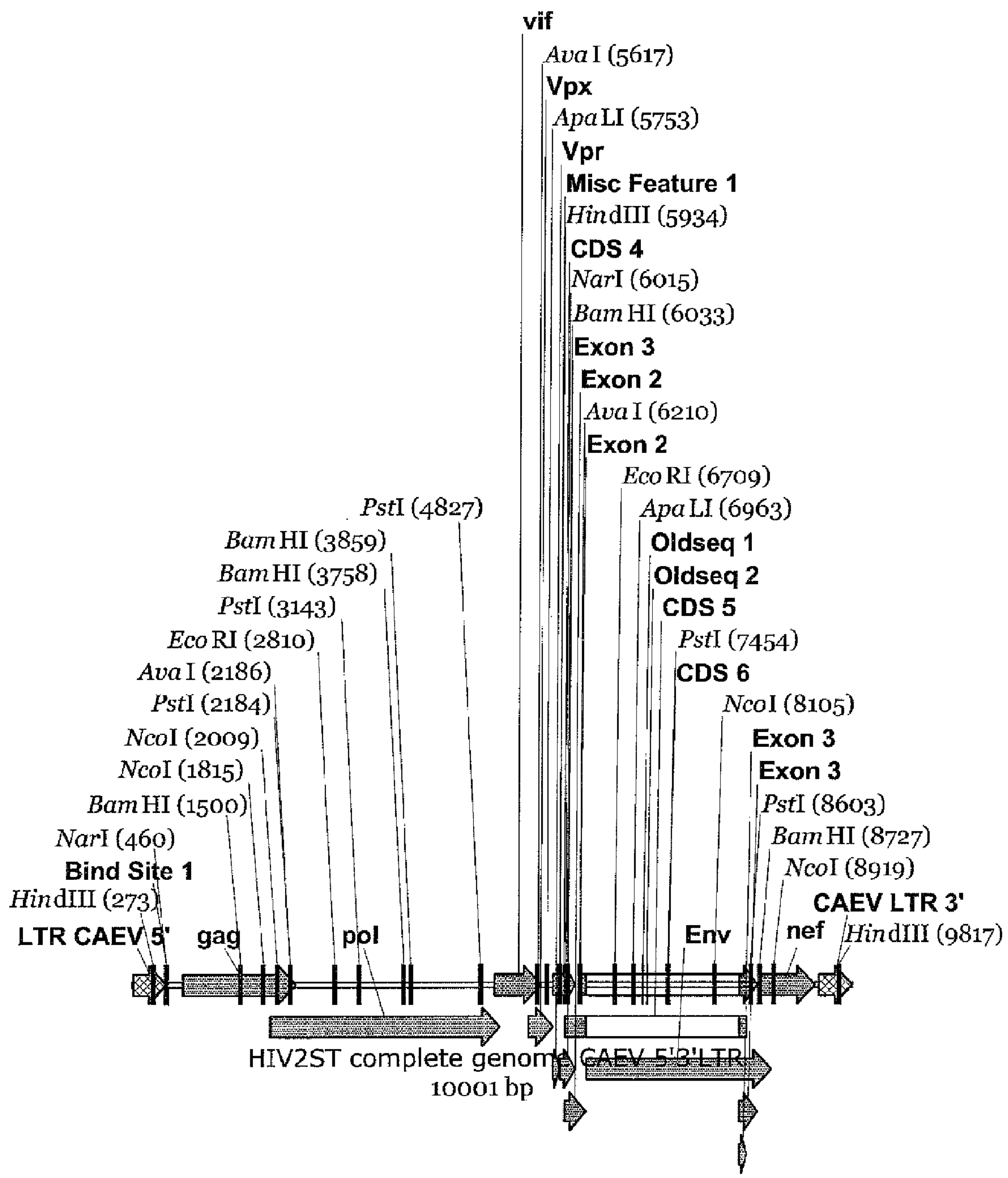
FIG. 3: Schematic illustration of the nucleic acid coded by the sequence SEQ ID NO.: 5.
Figure 4:
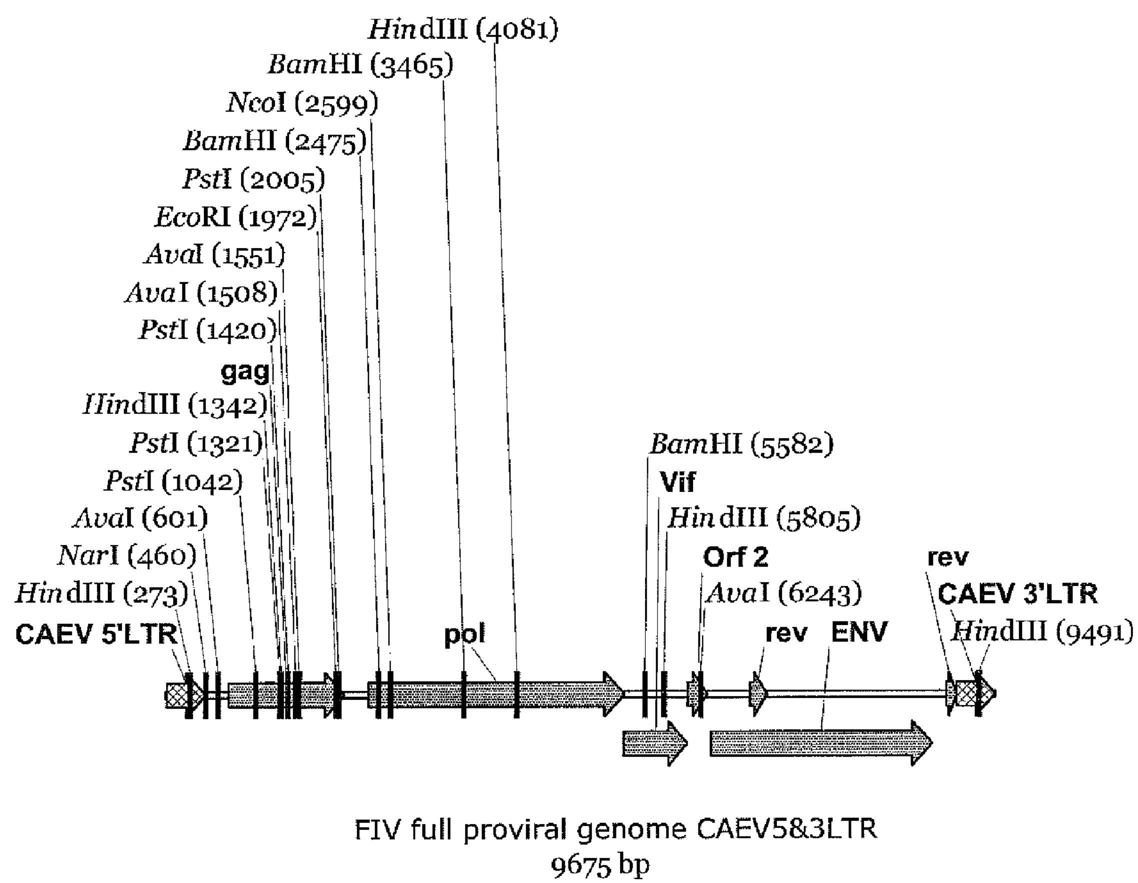
FIG. 4: Schematic illustration of the nucleic acid coded by the sequence SEQ ID NO.: 6.
Figure 5:
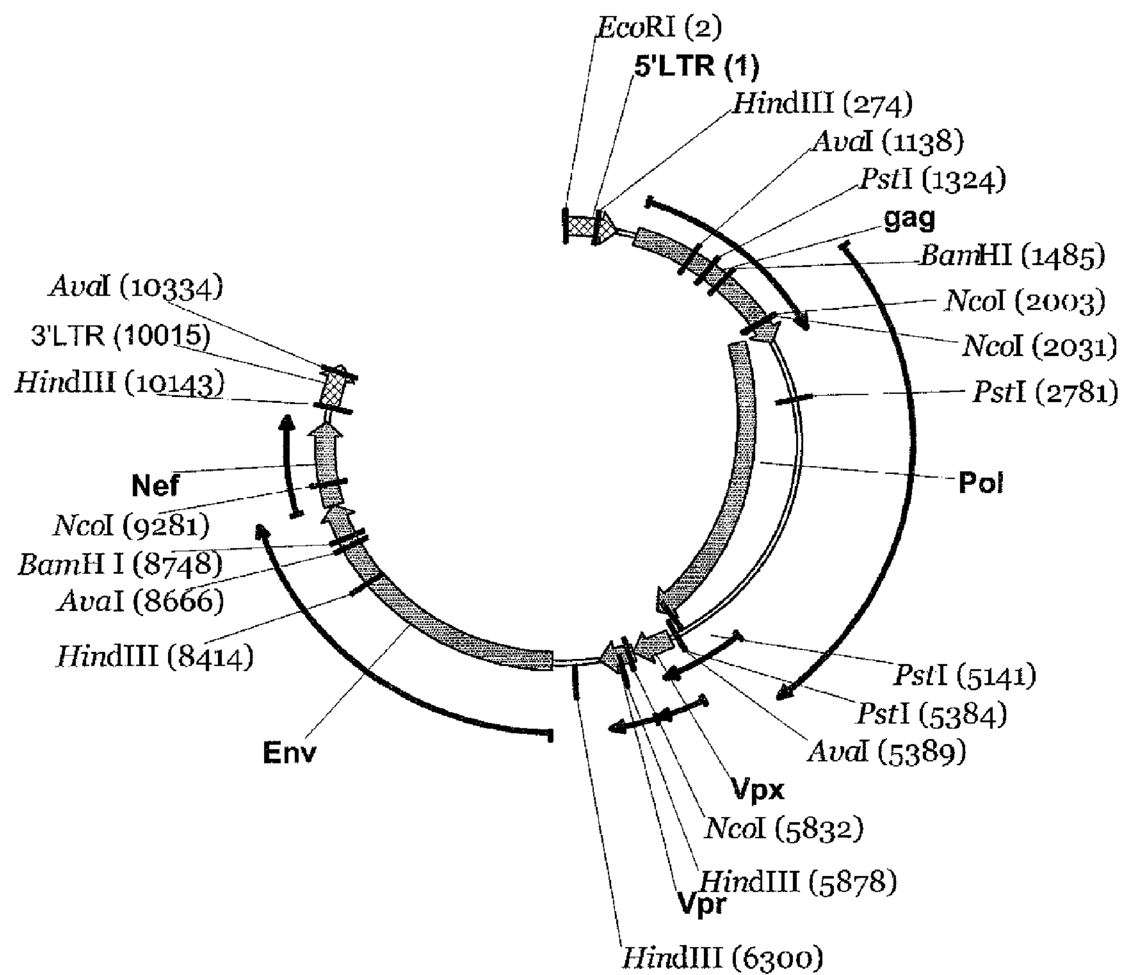
FIG. 5: Schematic illustration of the nucleic acid coded by the sequence SEQ ID NO.: 7.
Figure 6:
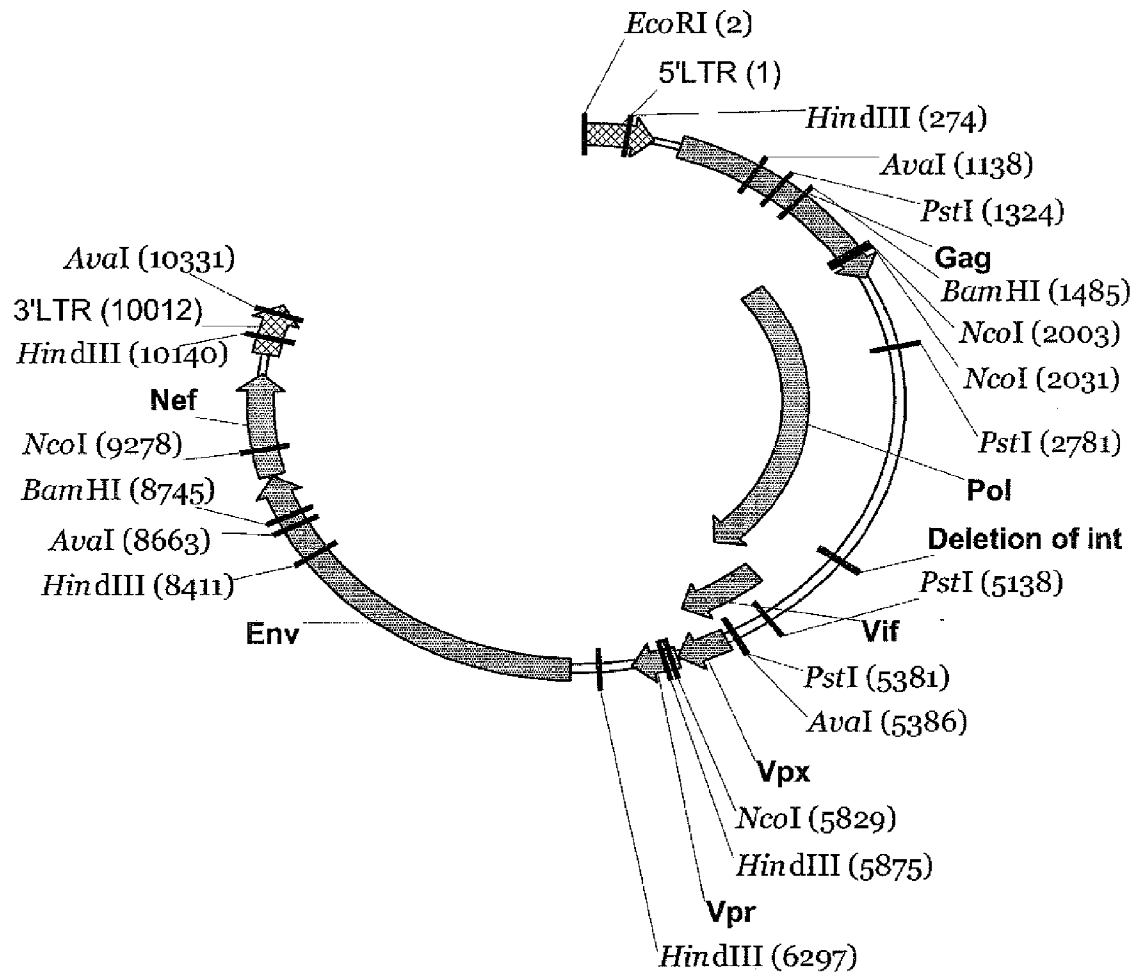
FIG. 6: Schematic illustration of the nucleic acid coded by the sequence SEQ ID NO.: 1.
Figure 7:
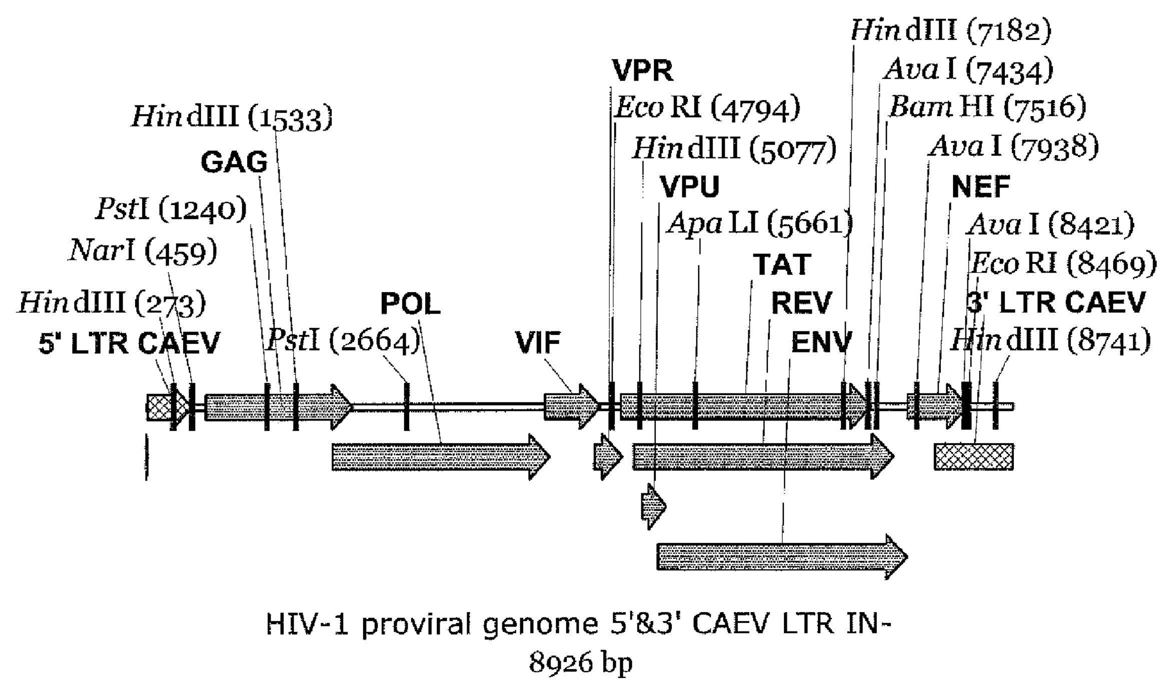
FIG. 7: Schematic illustration of the nucleic acid coded by the sequence SEQ ID NO.: 12.
Figure 8:
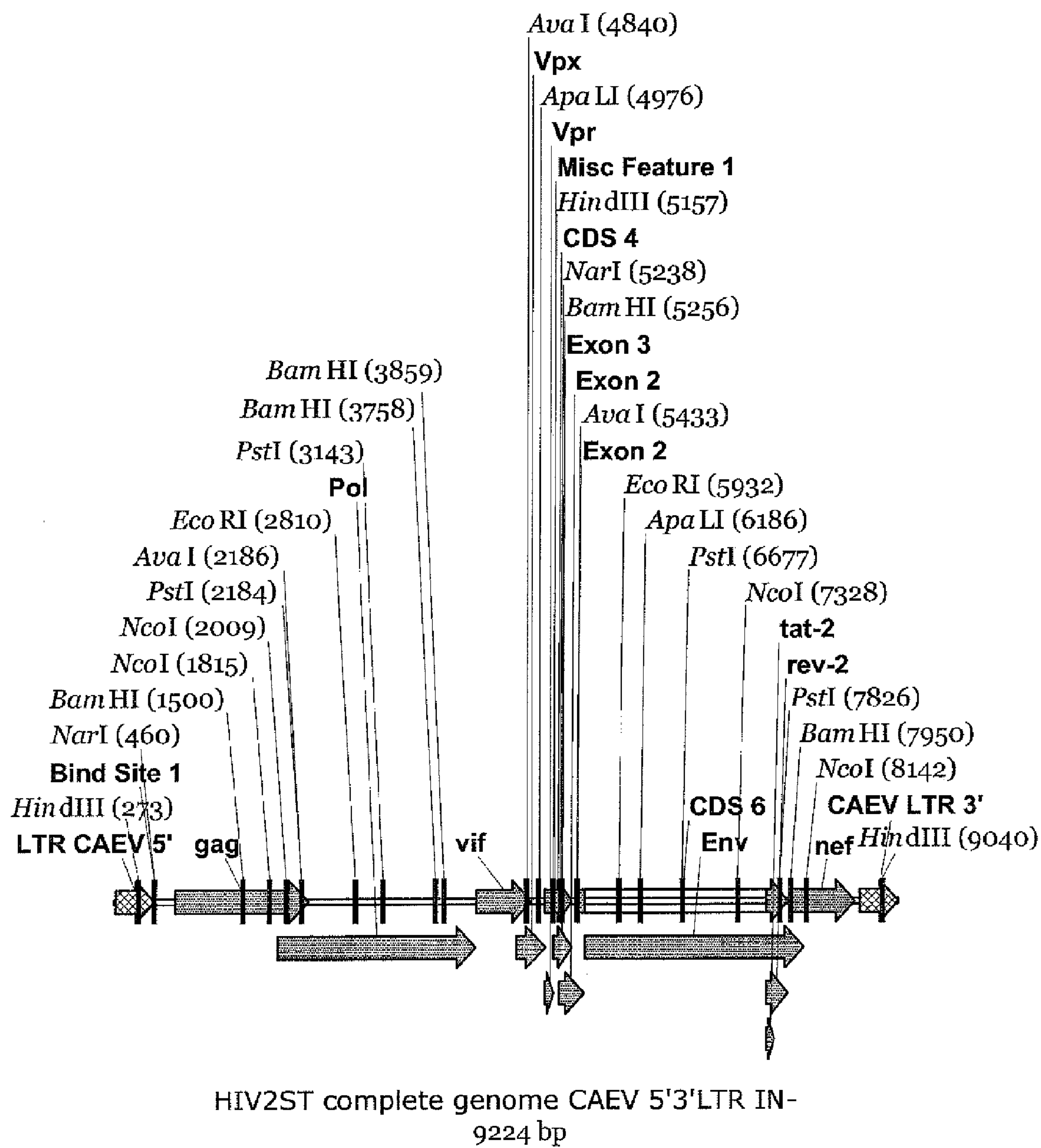
FIG. 8: Schematic illustration of the nucleic acid coded by the sequence SEQ ID NO.: 13.
Figure 9:
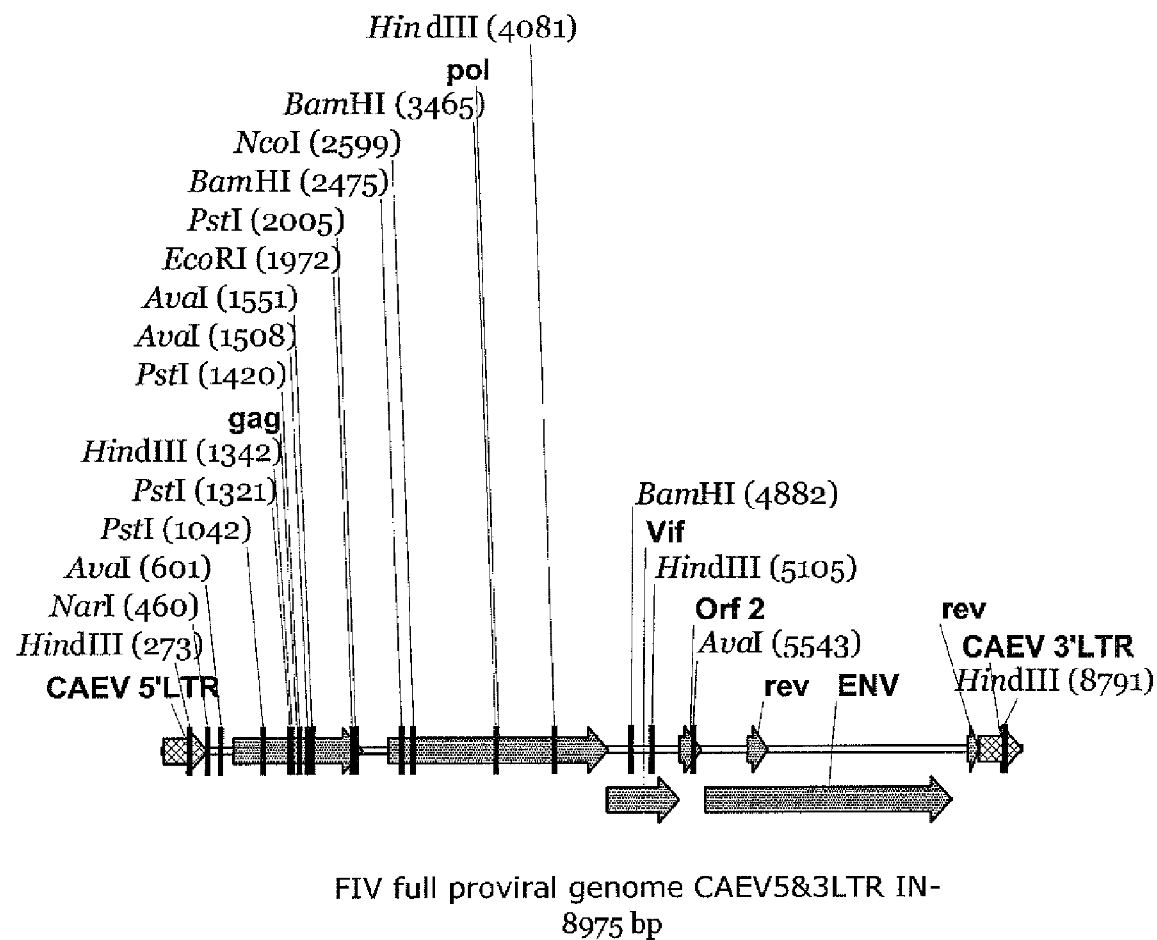
FIG. 9: Schematic illustration of the nucleic acid coded by the sequence SEQ ID NO.: 14.
Figure 10:
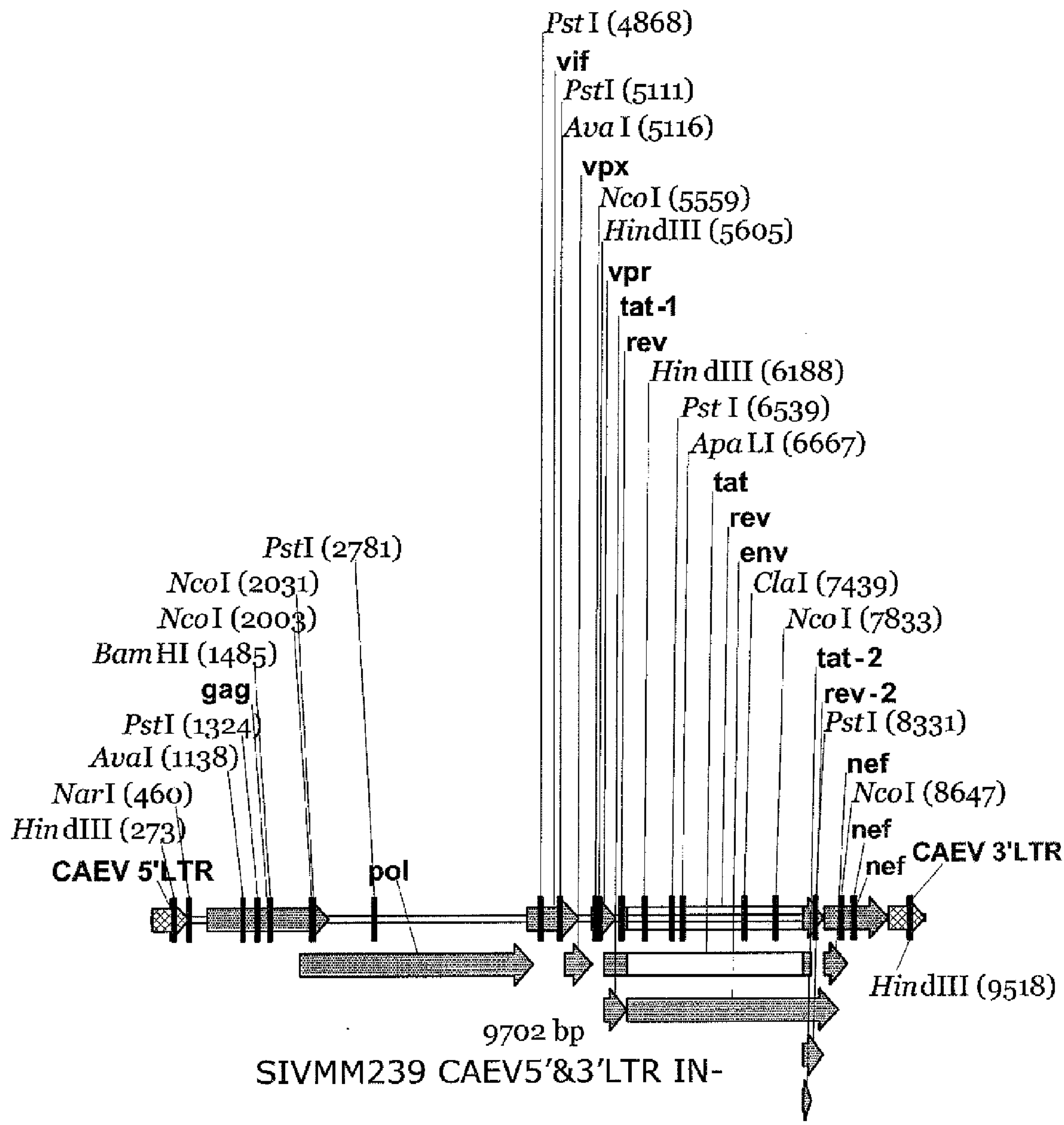
FIG. 10: Schematic illustration of the nucleic acid coded by the sequence SEQ ID NO.: 15.
Figure 11:
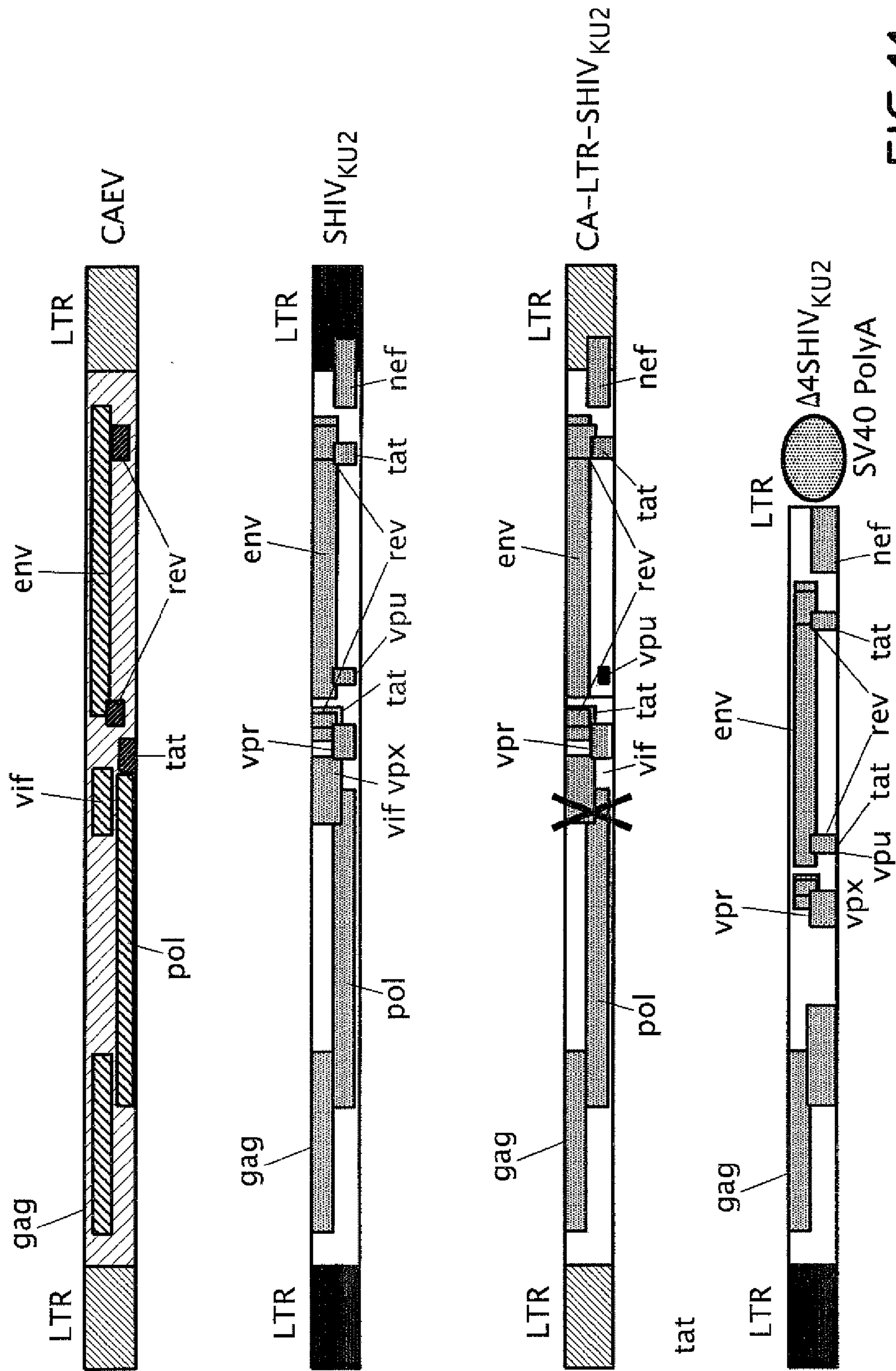
FIG. 11: Schematic illustration of the construction of the genome of CAEV, of the plasmid pSHIV$_{KU2}$, pCA-LTR-SHIV$_{KU2}$IN- and of pΔ4SHIV$_{KU2}$.

1. Material and Methods 1.1. The Vaccinating Vectors (FIG. 1)

1.1.1. The Vectors pCA-LTR-SHIV$_{KU2}$ and pCA-LTR-SHIV$_{KU2}$-IN-

Figure 15:
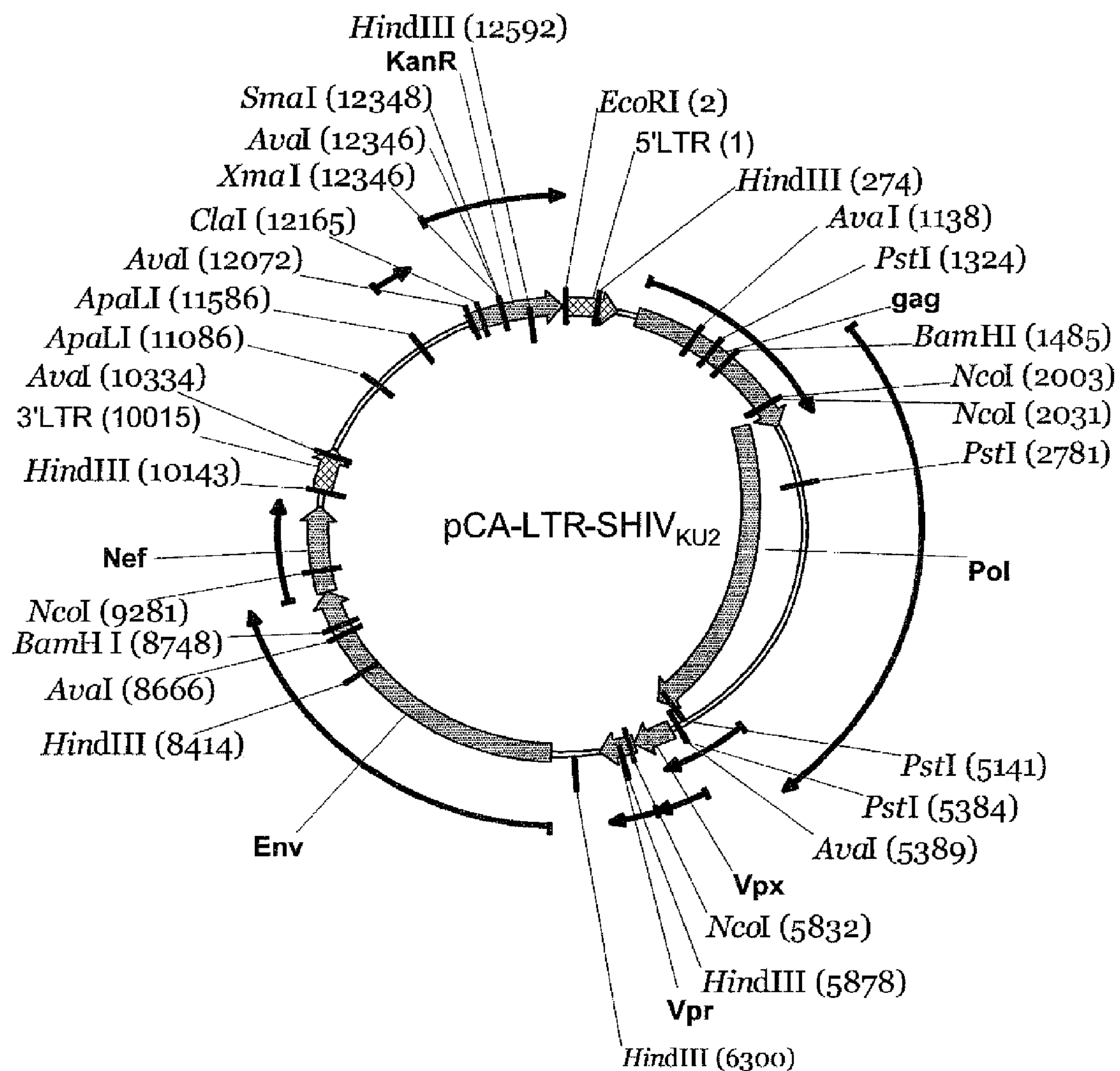
FIG. 15: Schematic illustration of the vector CA-LTR-SHIV$_{KU2}$.
Figure 16:
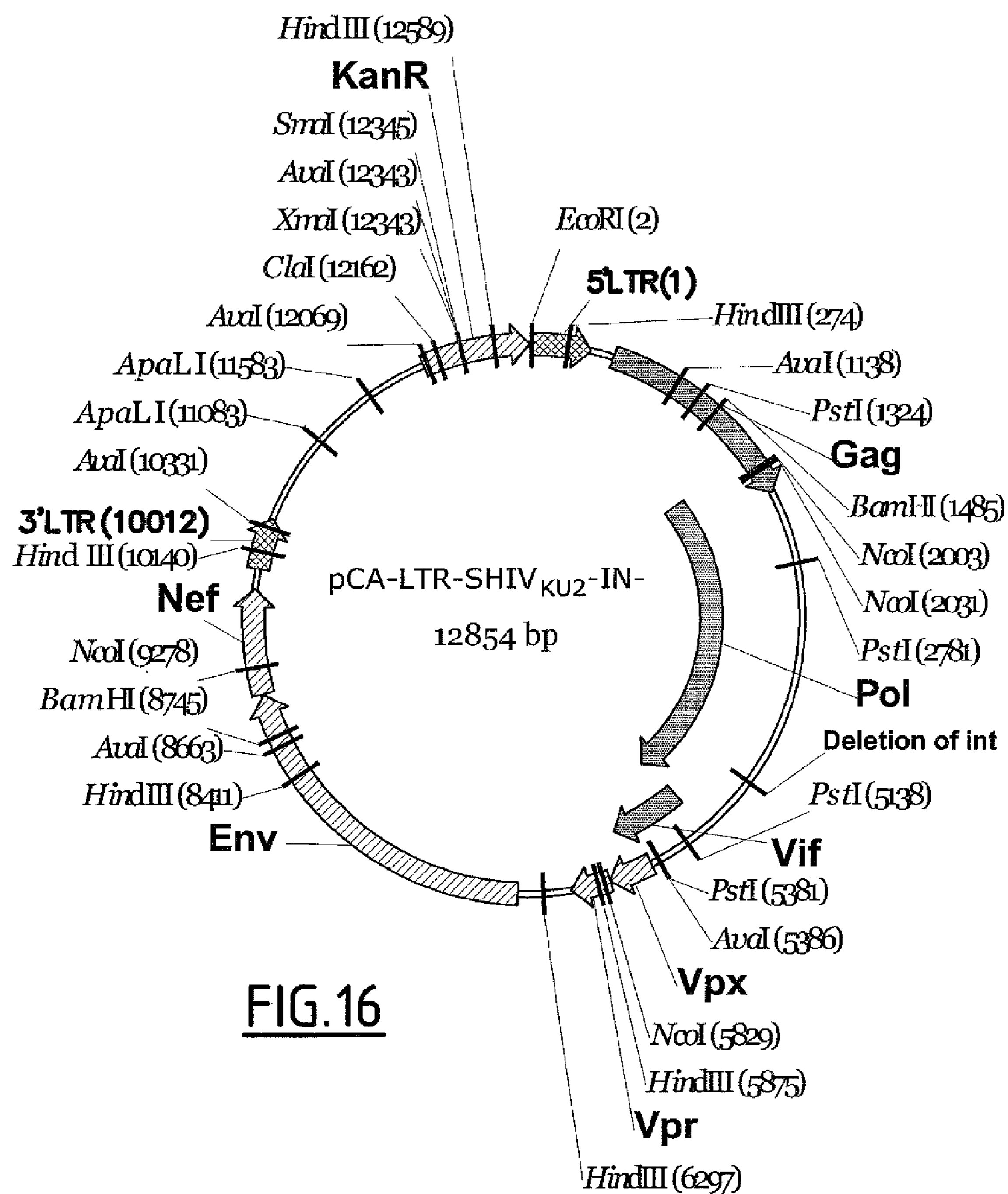
FIG. 16: Schematic illustration of the vector CA-LTR-SHIV$_{KU2}$-IN-.

The vector CA-LTR-SHIV$_{KU2}$ contains the genome of the Simian and Human Immunodeficiency Virus (SHIV) deleted from the LTRs of SIV and replaced with the LTRs of CAEV. The SHIV contains a chimeric genome consisting of the one of SIV-mac239 in which the tat, env and rev genes of the SIV were deleted and replaced with the vpu, tat, env and rev genes of the HIV-1. The vector therefore bears the vpr, vpx, gag, pol, vif and nef genes of SIV and the tat, rev, vpu and env genes of HIV-1 under the transcriptional control of the LTRs in 5' and 3' of the CAEV. The pol gene was deleted from the sequences coding for the integrase (in). The vaccinating vector pCA-LTR-SHIV$_{KU2}$ non-deleted from the sequences coding for the integrase consists in the sequence SEQ ID NO: 16 (FIG. 15). The vector pCA-LTR-SHIV$_{KU2}$-IN-, deleted from the sequences coding for the integrase consists in the SEQ ID NO: 17 (FIG. 16).

Figure 14:
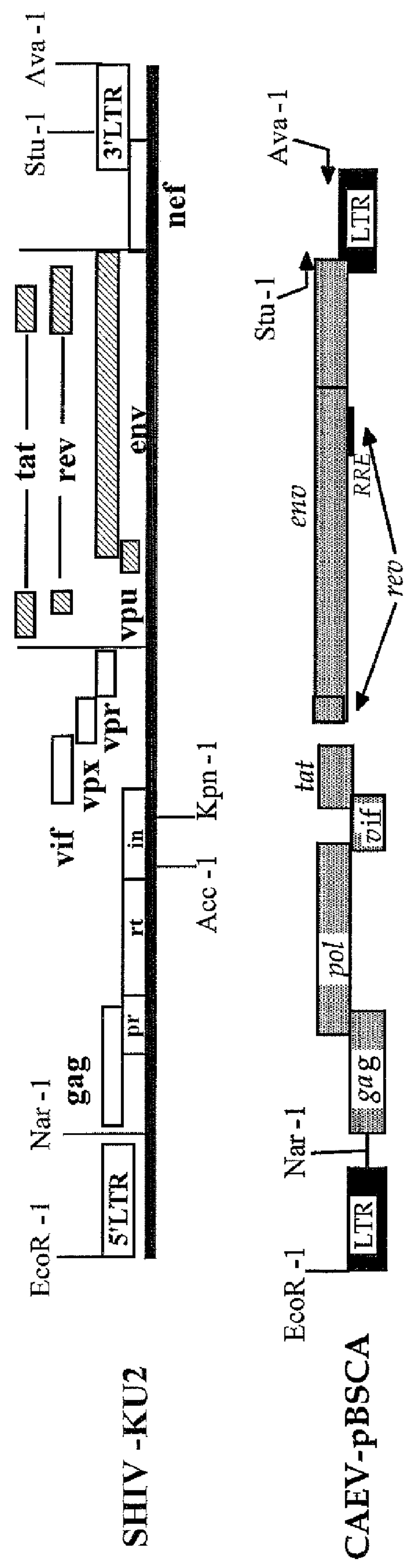
FIG. 14: Illustration of the preparation of the vector CA-LTR-SHIV$_{KU2}$-IN-.

The construction of a vector CA-LTR-SHIV$_{KU2}$-IN- was achieved in the following way (FIG. 14). The vector SHIV-$_{KU2}$ was digested with EcoR1 and Nar1, and then the LTR fragment of 0.8 kb was removed. The CAEV-pBSCA vector was then digested with EcoR1 and Nar1 and the fragment LTR of 0.5 kb was purified. Both fragments were then subject to ligation. The vector SHIV-1 LTRCA was then digested with Stu1 and Ava1 and the LTR fragment of 0.8 kb was removed. The LTR in 3' of the CAEV was amplified with timers Stu1 and Ava1, the PCR products were digested by Stu1 and Ava1 and the LTR fragment of 0.5 kb was purified. Both fragments were subject to ligation for generating the CAL-SHIV$_{KU2}$. Finally a digestion with Kpn1 and Acc1 in the pol gene was achieved in order to remove 314 bp of the gene of the integrase of SHIV for generating the CAL-SHIV$_{KU2}$-IN-.

1.1.2. Vectors $pSHIV_{KU2}$ and $\Delta 4SHIV_{KU2}$

The plasmids $pSHIV_{KU2}$ and $p\Delta 4SHIV_{KU2}$ are plasmids used as controls. Their constructions have been described in many publications (Liu Z Q et al., 2006, Ramakrisna Hegde et al., 2005).

1.2 Production of Vaccinal DNA 1.2.1. Bacterial Culture

*E. coli* K12 (JM109) bacteria containing the plasmid are put in a pre-culture in 5 ml of BL medium containing 0.05 mg/ml of kanamycin and then incubated for one night at 30° C. with stirring at 150 rpm. From the pre-culture, the bacterial suspension was diluted to 1:100,000 in the BL medium, and then 50 μl of the dilution are spread over the surface of the agar/BL/Kanamycin contained in a Petri dish which is then incubated at 32° C. for one night. The isolated colonies developed on the agar of the Petri dish are sown into 5 ml of liquid medium BL containing 0.05 mg/ml of kanamycin and cultivated with stirring at 150 rpm at 30° C. for one night. A fraction (1 ml) of the culture is used for rapid extraction of the DNA by means of the Mini-prep kit of Macherey-Nagel or Qiagen, according to the recommended procedure, and the extracted DNA is then separated on a 1% agarose gel for checking its quality. The bacteria corresponding to the DNA estimated to be satisfactory are used for sowing the 1 L cultures which are cultivated under the same conditions as earlier, for the isolation of DNA in a maxi-preparation.

1.2.2. Maxi-Preparation: Plasmid Extraction

The bacteria cultivated with stirring (150 rpm) at 30° C. for one night are harvested as a sediment by centrifugation (4000 g, 4° C., 15 min) and the sediment is re-suspended in 8 ml of re-suspension buffer (Tris-HCl 50 mM pH8, EDTA 10 mM). The cells are then lyzed by adding 8 ml of alkaline lysis buffer (NaOH 200 mM, 1% SDS) in order to release the plasmid DNA. The lyzate is neutralized by adding 8 ml of neutralization buffer (potassium acetate 3M pH 5.5). The mixture is then incubated for 5 min in ice and then centrifuged for 15 minutes at 15,000 g at 4° C. The solution containing the DNA is transferred into a column equilibrated beforehand, allowing retention of the plasmid DNA. The column is washed three times with the washing buffer and then the DNA is eluted and precipitated with isopropanol. The precipitated DNA sediment is obtained by centrifugation (30 min, 15,000 g at 4° C.). The DNA is then washed with 2 ml of 70% ethanol and centrifuged for 10 min at 4° C. at 15,000 g in order to remove the excess impurities and salts and then the sediment is dried and re-suspended in a suitable volume of ultra-pure water.

The concentration of the DNA solution was then determined by spectrophotometry at a wavelength λ equal to 260 nm and the quality of the plasmid is then checked by electrophoretic migration on a 1% agarose gel. The size of the plasmid and the integrity of the plasmid are checked on an agarose gel after digestion by restriction enzymes Bam H1 and Eco R1 for example.

1.2.3. Checking the Plasmid pCA-LTR-$SHIV_{KU2}$-IN- by Enzymatic Digestion

An aliquot fraction of 0.5 μg of the plasmid is subjected to digestion with 2 units of enzymes EcoR1, BamH1 or Sph1 for 60 minutes at 37° C. in a suitable 1× buffer for each enzyme, and in a final volume of 20 μl. The profile of the digestion is checked by electrophoretic migration in a 1% agarose gel with a TAE 1× buffer and revealed with ethidium bromide (ETB) and observation of the gel under UVs.

1.3 Cell Cultures and Treatments 1.3.1. Cell Models and Cultivation Conditions

The cell lines were obtained from the National Institute of Health AIDS Research and Reference Reagent Program in the United States. The cells are cryo-preserved in 10% of dimethylsulfoxide (DMSO), at −170° C. in liquid nitrogen. They are defrosted and then cultivated in cultivation flasks.

HEK293T (immortalized Human Embryonic Kidney 293) cells are a permanent line of human embryonic kidney cells. They are used because they are very easy to transfect, with very high transfection efficiencies which may attain 100%. The lentiviral genome is strongly expressed in these cells and the proteins assemble into infectious particles and their co-cultivation with the indicating cells (CEM or M8166) allows the formation of typical syncytia. The HEK293T cells are adherent, cultivated in a monolayer at the surface of the flasks in a MEM medium supplemented with 10% of fetal calf serum (FCS), 1% of penicillin 5,000 Units/ml streptomycin 5,000 μg/ml and 1% of gentamycin 10 mg/ml. The cells are maintained at 37° C. under a humid atmosphere with 5% $CO_2$. The culture medium is changed every three days. In order to carry out sub-cultivations, the nutritional medium is removed, the cells are washed with d PBS/EDTA and incubated for 1 minute at 37° C. in the presence of 0.5% trypsin-0.01% EDTA. After detachment of the cells, a volume of MEM medium is immediately added to the cells and the cells are then homogenized and transferred into new flasks.

The cells CEMx174 and M8166 are human CD4+ T lymphocytes which are permissive to infection by human and simian lentiviruses and form typical cytopathogenic effects (CPE). They are non-adherent and are cultivated in RPMI medium supplemented with 10% of SCS, 1% of penicillin-streptomycin and 1% of gentamycin. These cells are maintained at 37° C. under a humid atmosphere with 5% $CO_2$. The medium is changed every three days by carrying out a centrifugation step at 1,500 G for 5 minutes. The sediment is then re-suspended by successive suctions and discharges into a suitable volume of culture medium.

1.3.2. Functional Evaluation with an In Vitro Biological Test Transfection of the HEK293T with the Plasmids pCA-LTR-$SHIV_{KU2}$-IN- or $pSHIV_{KU2}$ The transfection method used is the method with ExGen500. ExGen500 (Euromedex, France) consists of a cationic polymer based on linear polyethylenimine. This polymer has a very large cationic charge density allowing it to form complexes with DNA through ionic bonds. These ExGen500/DNA complexes are then capable of interacting with the plasma membranes of the generally anionic cells (interaction via the sulfated proteoglycans). Endocytosis of the complex by the cells ensues as well as their transport towards endosomes/lysosomes. By its protonation capacity at acid pH, ExGen500 gives the possibility of buffering the medium of acid vesicles thereby preventing degradation of the transfected DNA. This property also causes an osmotic shock which allows the DNA to be released in the cytoplasm of the cell. ExGen500 then promotes the transport of the DNA towards the nucleus and avoid its degradation by cytoplasm nucleases.

Five μg of the DNA of the plasmid are added to 350 μl of 150 mM NaCl solution and to 15 μl of ExGen 500. The mixture is incubated for 40 minutes at room temperature. Next, the mixture is added into the flasks containing the HEK-293T covered with freshly renewed medium.

Infection of the CEMx174 and Amplification of the Viral Stock

The HEK-293T transfected with the DNA of pCA-LTR-$SHIV_{KU2}$-IN- or of $pSHIV_{KU2}$ are co-cultivated with the CEMx174, and from 48 hours onwards, the CEMx174 develop signs of infection expressed by the formation of ECP which results from the merging of the CEMx174 for forming syncytia. The infected CEMx174 are transferred into a new flask in the presence of fresh CEMx174 for amplifying the virus which is harvested in the supernatant.

Viral Production

The harvesting of the viral stock is carried out from 48 hours onwards by means of a syringe, and the cell debris are then removed by having them pass through a filter with a diameter of 0.22 μm before being put into tubes which are stored at −80° C.

Inoculation of the Cells with the Virus

An aliquot fraction (10-100 μl) of the virus supernatant is used for inoculating the target cells in order to evaluate its infectiousity by cytopathic development or by detection of expression of marker genes.

Titration of the Virus on Non-Adherent Cells

The supernatant containing the virus is diluted in tenfold steps (successive dilutions) in a medium for obtaining dilutions from $10^{-1}$ to $10^{-6}$ which are used for inoculating in quadruplicate wells containing $1 \cdot 10^5$ cells per well in 0.5 to 1 ml of RPMI medium in a 24-well plate. The thereby inoculated cells are incubated at 37° C. and with 5% $CO_2$ and sustained by changing medium every 3 days. They are regularly observed for development of ECP.

1.4. Electron Microscopy of HEK293T Cells Transfected with pCA-LTR-$SHIV_{KU2}$-IN- With the goal of examining whether the proteins produced by the vaccinal genome pCA-LTR-$SHIV_{KU2}$-IN- assembled into viral particles, the inventors conducted morphological studies by electron microscopy (EM).

The samples of HEK293T cells transfected with the pCA-LTR-$SHIV_{KU2}$-IN-, $pSHIV_{KU2}$ or $\Delta 4SHIV_{KU2}$ are fixed in a 2.5% glutaraldehyde solution diluted in a cacodylate buffer (0.1M sodium cacodylate). They are then post-fixed, at 4° C., in cacodylate buffer containing 1% osmium tetraoxide (OsO4), for 60 minutes. The samples are then incubated overnight at 4° C. in darkness in uranyl acetate at pH 4. The samples are then immersed in successive baths for 10 minutes of ethanol respectively diluted to 30%, 60%, 90% and 100%. Next, the samples are immersed for two hours in a 50/50 mixture of pure ethanol and of epoxy resin (8 ml of DDSA, 7 ml of MNA, or 13 ml of epoxy). The samples are then placed for two hours in pure epoxy resin before being included in Beem capsules and set to polymerize for 48 hours at 60° C.

Ultrathin cuts of these regions are carried out by means of a diamond cutter with an ultra-microtome. These cuts with a thickness of 70 nm are deposited on copper grids so as to be observed under a voltage of 80 kV by means of a Jeol 1200 EX transmission electron microscope.

1.5. Immunization of Mice with pCA-LTR-$SHIV_{KU2}$-IN-Vaccinal DNA 1.5.1. Humanization and Vaccination of NOD/SCID Mice The 6 week old mice are irradiated with a dose of 120 Centigrays of gamma radiation for 50 seconds.

Humanization of the Mice with PBMC of Human Blood

The total sample blood on sodium citrate is centrifuged (2000 g, 10 min, 20° C.) in order to recover the layer of white cells between the plasma and the red cells. The cells are diluted 3 times in PBS/EDTA, delicately deposited above a Ficoll cushion (a medium for separating lymphocytes) and then centrifuged for 45 minutes at 2,000 g at 20° C. The PBMCs are recovered, washed several times in PBS/EDTA and re-suspended in PBSx1 and then $50 \cdot 10^6$ PBMCs in 0.1 ml are injected for each mouse via an intra-peritoneal route.

Immunization of the Mice

After 48-72 h of post-humanization, the SCID-hu cells are injected via an intra-muscular route (IM) with 50 μg of DNA of the pCA-LTR-$SHIV_{KU2}$-IN-, $pSHIV_{KU2}$ or $p\Delta 4SHIV_{KU2}$. The BALB/c mice, 6-8 weeks old, are directly immunized by IM injection with 100 μg of each of the DNAs.

1.5.2. Method for Evaluating the Humoral Response

Abnova Sandwich ELISA Test:

This test is based on the detection of the antibodies directed against the viral antigens and which are bound to the bottom of the wells of the 96-well plate. The sera to be tested (recovered at different times post-immunization), the positive and negative controls are deposited in the wells. The anti-HIV Ac (antibodies) optionally present, bind onto the viral antigens. After several washings of the wells for removing the excess and the non-specific bindings, a secondary detection Ac is added which bears a biotin molecule which interacts with a streptavidin coupled to the HPRO enzyme. The formed antigens/Ac complexes will then be detected by adding the substrate of the enzyme, TMB, which will give rise to a colored reaction. The coloration is expressed in optical densities by readout with an ELISA reader photometer.

The reagents and products are brought to room temperature. The negative and positive controls (100 μl) provided in the kit, the blanks (100 μl) and the 10 μl and 50 μl serum samples are deposited in the wells in a final volume of 100 μl. The plate is incubated for 30 minutes at 37° C., and the rinsed with the washing solution. The secondary Ac solution diluted to 1:100 is added (100 μl) in all the wells except in the blanks. The plate is then covered with parafilm paper and incubated for 20 minutes at 37° C. A TMB solution A and B is added after a washing step and the plate is incubated 15 mins at the temperature of the laboratory. For stopping the coloration reaction, 100 μl of 2N $H_2SO_4$ are added per well. Readout of the plate is performed at 450 nm.

The samples having an absorbance value equal to or greater than the threshold value are considered to be positive, the threshold value being determined according to the formula: Cutoff Value=NCx+0.100 with NCx=the average of the absorbance values of the two negative controls.

Sero-Neutralization Test

This technique is based on the capability of sero-neutralizing Acs (sero-N) of inhibiting infection of cells sensitive to the virus. For the detection and evaluation of the seric sero-N Acs, a constant amount of infectious viruses is put into contact with serial dilutions of the serum to be tested, and the mixture is then inoculated to a permissive cell culture on microplates and incubated for 3 to 5 days. The virus is most often a cytopathogenic strain, and therefore the absence or the reduction in number of ECPs expresses the presence of Acs in the tested serum.

The viral stock $SHIV_{KU2}$ is diluted to 1:1000 in RPMI (the supernatant volume of the virus is determined for 100 $TCID_{50}$, which corresponds to the dilution of a virus for which 50% of the wells have syncytia) and the serums recovered from the NOD/SCID control mice, humanized and vaccinated with pCA-LTR-$SHIV_{KU2}$-IN- or $pSHIV_{KU2}$ are diluted in the same medium (at 10, 20, 40, 80, 160 and 320× dilutions). The diluted virus and the serum dilutions are mixed in a 96-well plate (100 μl/well) and the mixture is incubated for 1 h at 4° C. The mixture is then deposited on M8166 cells ($1\cdot10^5$ cells/well) cultivated beforehand in a 24-well plate. In this experiment, the positive control is represented by the virus stemming from pSHIV$_{KU2}$ without any serum and the negative control corresponds to the cells alone.

Method for Evaluating the Cell Response: Elispot Test

This test has the purpose of detecting and evaluating the proportion of T lymphocytes (TL) which secretes IFN-γ as a response specific to antigenic stimulation.

The mice are first deeply anesthetized and then the total blood and the spleen are taken. The spleens of the mice are put in RPMI medium in ice. The blood in dry tubes is used for isolating the serum. The splenocytes are isolated as a result of milling the spleen in a Petri dish between a pair of blades in the presence of PBS and 1% EDTA. The cells are washed twice in PBS/EDTA (centrifugation 2,000G, 5 min at 20° C.) in order to purify and to enrich them with splenocytes. After sowing the wells with the cells, the plate is washed with PBS and then incubated for 30 min with PBS+10% SCS at the temperature of the laboratory. The cells ($5\cdot10^5$ splenocytes) are sown in each well, and are inoculated with pools of peptides of the Gag, Env, Tat, Rev and Nef proteins at a final concentration of 2 μg/ml. Positive controls (CD3-2 included in the kit) and negative controls, are added to the test. The plate is covered with an aluminium foil pouch and incubated at 37° C. for 19 hours. The cells and peptides are washed, and then the biotinylated (7-b6-biotin) anti-IFN-γ monoclonal antibody is added, and the plate is covered and incubated for 2 h at room temperature. The streptavidin diluted in PBS containing 0.5% of FCS is added (100 μl/well) and the plate is incubated for 1 h at room temperature. The TMB, a developer substrate, is added subsequently after another washing step, and the plate is then washed and dried after the emergence of blue spots. Readout of the plate is accomplished with the binocular magnifying glass at a magnification of ×40.

The positivity criteria of a well are determined for each condition by calculating the average of the number of spots of the duplicates, as well as the standard deviations. The number of spots is calculated for 1 million PBMCs and is normalized to 20% for the data obtained in NOD/SCID mice. The test is considered as being positive if the value of the average of the spots is greater than 10 spots per million of PBMCs which corresponds to the average of spots obtained with the control cultures.

1.6. Phenotype and Functional Examinations of the Specific T Cells of the Antigen by Flow Cytometry 1.6.1. Isolation of the Peripheral Mononuclear Cells The mononuclear cells of human peripheral blood are prepared as indicated above. The splenocytes of mouse spleens isolated according to the procedure described above are also re-suspended in the AIM V medium without any serum for cultivation and cytometry tests.

1.6.2. Antigenic Stimulation and Cultivation of the Cells

In order to examine whether the specific cells of the antigen are capable of proliferating and of producing cytokines and lytic molecules, the splenocytes and the PBMCs are marked with CFSE (1 μg/ml) for 10 min at 37° C., and the cells are then washed with PBS 1× for removing the excess. The marked cells are sown in deep wells of 96-well plates in an amount of $2\cdot10^6$/well in 1 ml of AIM V medium, and then stimulated with different pools of peptides (Gag, Env and Tat+Rev+Nef) in an amount of 2 μg/ml in the presence of anti-CD49 and CD28 co-stimulation Acs. Cells without any peptides are used as a negative control and cells added with phytohemagglutinin (PHA) at 2 μg/ml are added as a positive control. The cells are cultivated for 5 days (37° C. with humidity) and then re-stimulated with the same pools of peptides for 6 hours before marking them. The cells are harvested by centrifugation (2,000G, 5 min, 4° C.), re-suspended in 100 μl of PBS and first marked with surface Acs (CD3, CD4 and CD8) [Pacific Blue anti-human CD3 (5 μl), PE anti-human CD4 (10 μl) and APC/Cy7 anti-human CD8 (10 μl)] for 30 mins at room temperature. The cells are then centrifuged and washed with PBS 1× and then fixed and made permeable in 100 μl of Cytofix Cytoperm of BD. The cells are then incubated for 20 minutes at 4° C. with « anti-human IFN-γ PE-Cy7 » and « Alexa Fluor 647 anti-human Granzyme A» Acs (5 μl) for cytoplasm markings. The cells are finally washed with PBS and fixed with 4% PFA before acquisition and analysis with the flow cytometer.

1.6.3. Instrumentation

An LSRII flow cytometer from BD connected to the BD FACSDiva6 software package was used. This instrument allows measurement of up to 13 fluorescence parameters and two physical parameters which are the FSC size (Forward Scatter) and the complexity or granulosity SSC (Side Scatter). The instrument is equipped with three lasers. The blue laser emitting at 488 nm may independently excite several fluorochromes (FITC, PE, PE-Cy7). The red laser which emits at 633 nm may excite the APC and APC-Cy7 fluorochromes and finally the violet laser which emits at 405 nm may excite the Pacific Blue fluorochrome.

1.7. Immunization of the Macaques

A total of 12 cynomolgus macaques is used in the study. Six macaques form the control group and six other ones form the vaccinated group. The animals were immunized with a single double injection of DNA via the intramuscular route (4 mg/animal) and 1 mg/animal by electroporation (EP).

The reasons for this immunization strategy with a single dose of the vaccine are multiple. One of the main reasons is not to perturb the generation, maturation and amplification of the memory T cells by the primary effector T cells associated with each re-immunization step.

The immunized animals were subject to longitudinal follow up (once a week for 4 weeks and then 1 week out of 2 up to week 32, and then 1 week out of 4 for 10 months) for examining the immune responses induced by the vaccine. The blood samples taken on weeks −2 and −1 before immunization were used for examining possible basal responses. The mononuclear cells of peripheral blood (PBMCs) are isolated and used for evaluating the responses of the T cells with the ELISPOT IFN-λ test, by surface and intracytoplasm markings, and analysis by flow cytometry.

2. Results 2.1. Qualitative and Quantitative Checking of the Construction of the pCA-LTR-SHIV$_{KU2}$-IN- Plasmid 2.1.1. Presence of the pCA-LTR-SHIV$_{KU2}$-IN- Plasmid When the plasmid DNA was isolated from a polyclonal bacterial culture obtained from a preculture in a BL medium used for sowing a large volume of BL liquid medium, a significant proportion of episome is observed around 2000 bp. The electrophoretic profile also shows the presence of a single DNA band around 14,000 bp (which theoretically is 13,739 bp) corresponding to the plasmid.

When the DNA is isolated from a bacterial culture first produced on a Petri dish in order to obtain isolated colonies, these colonies having been used for preculture and bulk culture used for isolating and purifying the plasmid DNA, the electrophoretic profile obtained after separation of 0.5 μg of DNA shows the absence of any episome and shows three bands of high molecular weight DNA corresponding to the circular, wound and superwound forms of the pCA-LTR- SHIV$_{KU2}$-IN- plasmid. The purity and the quantitative evaluation of the plasmid DNAs of our two preparations were checked by spectrophotometry. The values of the measurements of absorbents at wavelengths 230, 260 and 280 nm were used for determining the 260/280 ratios which were 1.75 and 1.82 and at 260/230 of 2.04 and 1.92 respectively, show satisfactory quality of our DNA. The DNA concentrations are 545 μg/ml and 765 μg/ml, respectively.

2.1.2. Enzymatic Digestion of pCA-LTR-SHIV$_{KU2}$-IN-

The profile of the digestion of the plasmid with EcoR1 reveals the presence of two bands of about 5,000 and 7,500 bp from cuts at both EcoRI sites, three bands with Bam H1 of 2400 bp, 4,900 bp and 7,400 bp resulting from cuts at both Bam H1 sites, and a band with Sph1 located at 10,000 bp resulting from the cut at the single Sph1 site. An additional band of 2,400 bp is also observed with the BamH1 digestion and it would result from the episome.

2.2. Evaluation of the Functionality: Effect of the Plasmid DNA on the Cells

The HEK293T cells were transfected with a control plasmid pCG-GFP expressing GFP, the plasmid pSHIV$_{KU2}$, and then with the plasmid pCA-LTR-SHIV$_{KU2}$-IN-. The cells transfected with the plasmid pCG-GFP gave the possibility of estimating the efficiency of transfection by evaluating the number of GFP+ cells.

In order to check that the HEK293T cells transfected with pCA-LTR-SHIV$_{KU2}$-IN- or pSHIV$_{KU2}$ produce virions which induce typical syncytia, these cells were co-cultivated with CEMx174, and the occurrence of the ECPs was then followed by observation under the microscope. Both cocultures produced characteristic ECPs.

In order to check whether the SHIV$_{KU2}$ virus produced by the transfected cells replicates several times, the supernatant of the transfected cells was used for infecting the M8166 human CD4+ T lymphocyte line. The results obtained with the SHIV$_{KU2}$, clearly show that it infects and induces ECPs especially with the highly permissive M8166 cell line. These ECPs appear as soon as after 48 hours but also at belated stages.

Next, in order to check that the DNA of the vaccinal vector pCA-LTR-SHIV$_{KU2}$-IN- only allows a single replication cycle (as it is deleted from the in gene), the recovered supernatant containing the CA-LTR-SHIV$_{KU2}$-IN- virus was inoculated a first time, and then a second time to M8166 cells being cultivated. The first inoculation produced ECPs from 48 hours onwards and at the end of 76 hours they were more numerous. The supernatant of these infected cells was recovered and inoculated once again to M8166. Unlike the previous inoculation, no ECP is visible either 48 or at 76 hours after inoculation. These results allow the conclusion to be drawn that pCA-LTR-SHIV$_{KU2}$-IN- gives the possibility of transducting only once the target cells being cultivated.

The presence of typical ECPs, suggest that the plasmid DNA is replicated in the HEK293T cells and has produced CA-LTR-SHIV$_{KU2}$-IN- virions. The ECPs of the first infection show the infectivity of the M8166 human CD4+ TL line by the produced particles, and their absence during the second infection shows the productive replication deficit in the cells.

2.3. Electron Microscopy Analysis of the Morphogenesis of Viral Particles in HEK293T Cells Transfected with pCA-LTR-SHIV$_{KU2}$-IN- It was next determined whether the proteins produced by the vaccinal pCA-LTR-SHIV$_{KU2}$-IN- genome properly assembled into viral particles in the HEK293T cells. The morphology of the HEK293T cells transfected with the plasmid pCA-LTR-SHIV$_{KU2}$-IN- was examined by EM.

The results showed that the viral particles are present at the surface of the cells in the form of buds and mature viral particles which have detached from the cells. Thus, the viral proteins of the pCA-LTR-SHIV$_{KU2}$-IN- vaccine assemble in order to give viral particles which bud on the outside of the cells.

2.4. In Vivo Test of the Vaccine on Humanized SCID Mice and on BALB/c Mice 2.4.1. Evaluation of the Humoral Response in SCID-Hu Mice Vaccinated with pCA-LTR-SHIV$_{KU2}$-IN- The serum samples of the immunized mice, taken at about 1 month after immunization are examined for the presence of Acs which specifically bind to the antigens of the virus by means of a commercial ELISA test. The results of this analysis are summarized in Table 1 (below). These results show that about half of the samples from the mice immunized with vaccinal pCA-LTR-SHIV$_{KU2}$-IN- DNA, like those immunized with DNA of SHIV$_{KU2}$, have lesser proportions of positives (44% and 37%, respectively) unlike those from the mice immunized with pΔ4SHIV$_{KU2}$ (50%). These results demonstrate the capability of the vaccinal pCA-LTR-SHIV$_{KU2}$-IN- DNA of inducing humoral responses in NOD/SCID-hu mice. One sample out of three of serum of the immunized mice with pΔ4SHIV$_{KU2}$, has its OD value greater than those obtained with the samples of serums of immunized mice with pCA-LTR-SHIV$_{KU2}$-IN- and pSHIV$_{KU2}$. This plasmid is non replicative, the proteins of the virus remain associated with the membrane of the transfected cells and therefore should induce less Acs.

TABLE 1

Detection of antibodies in samples of sera of control SCID, SCID-hu and SCID-hu mice, immunized with pΔ4SHIV$_{KU2}$, pCA-LTR-SHIV$_{KU2}$-IN- and pSHIV$_{KU2}$ and of the controls.

| | Samples | | | | | | |
|---|---|---|---|---|---|---|---|
| | Δ4SHIV | CA-LTR SHIV$_{KU2}$-IN- | SHIV | controls | Positive controls | Negative controls | Blanks |
| Number of samples | 6 | 16 | 19 | 2 | 2 | 2 | 2 |
| Positivity number | 3 | 7 | 7 | 2 | 2 | 2 | 2 |
| Absorbance positivity Interval | 0.3-1.823 | 0.26-0.9 | 0.34-1.64 | 0.01-0.19 | 1.9-2.2 | 0.15-0.16 | 0.01-0.03 |

2.4.2. Analysis of the Neutralizing Activity by Sero-Neutralization

The serums of SCID-hu mice vaccinated with the selected plasmids pCA-LTR-SHIV$_{KU2}$-IN- or SHIV$_{KU2}$ are those for which the OD was found positive by ELISA. Because of the small amount of serum, certain samples with a strong OD value for the ELISA test, were not able to be examined by sero-neutralization. A serum sample of SCID-hu mice and vaccinated with pCA-LTR-SHIV$_{KU2}$-IN- found to be negative was also used for the ELISA test for ensuring the reliability of the test.

TABLE 2

Analysis of the neutralizing activity of the sera of immunized mice. Dilutions (1/10, 1/20, . . . 1/320) were mixed with the virus SHIV$_{KU2}$ (100 TCID$_{50}$), incubated and then used for inoculating the M8166 cells. After 5 days after inoculation, the induced EPCs are listed and used for evaluating the sero-neutralizing activity. Caption: +++ correspond to strong neutralization, ++ quite high neutralization, + less neutralization, − no neutralization action. For the CA-LTR-SHIV$_{KU2}$ etc, two types of samples are represented, a type of sample having a less neutralizing profile as compared with the two other samples.

Samples

| | CA-LTR-SHIV$_{KU2}$-IN- (3 samples) | | SHIV (1 sample) | |
|---|---|---|---|---|
| Dilutions | Neutralization | ECP interval | Neutralization | ECP interval |
| 10 | +++/+++ | 5-9 | +++ | 4 |
| 20 | ++/++ | 14-19 | ++ | 12 |
| 40 | +/− | 25-44 | ++ | 20 |
| 80 | +/− | 27-49 | ++ | 15 |
| 160 | +/− | 31-57 | + | 26 |
| 320 | +/− | 28-69 | − | 44 |

The number of ECPs obtained is higher in the M8166 cells infected by the SHIV$_{KU2}$ virus incubated without any serum (76 ECPs) or with the serum of the non-immunized mice (42 ECPs) (negative control), which allowed us to set the negativity threshold of viral neutralization to 42 ECPs (data not shown in the table). On the other hand, the number of ECPs becomes quasi zero when the virus is incubated with 1/10 diluted serum of mice immunized with the DNA of CA-LTR-SHIV$_{KU2}$-IN- or SHIV$_{KU2}$. This number increases gradually as increases the dilution of the serums indicating a dose effect. For example, with the serum of a mouse immunized with pCA-LTR-SHIV$_{KU2}$-IN- at 1/10 dilution, 5 ECPs are obtained, whereas at 1/320 dilution, a value of 69 ECPs is obtained, a value similar to the one of the control without any serum.

Figure 12:
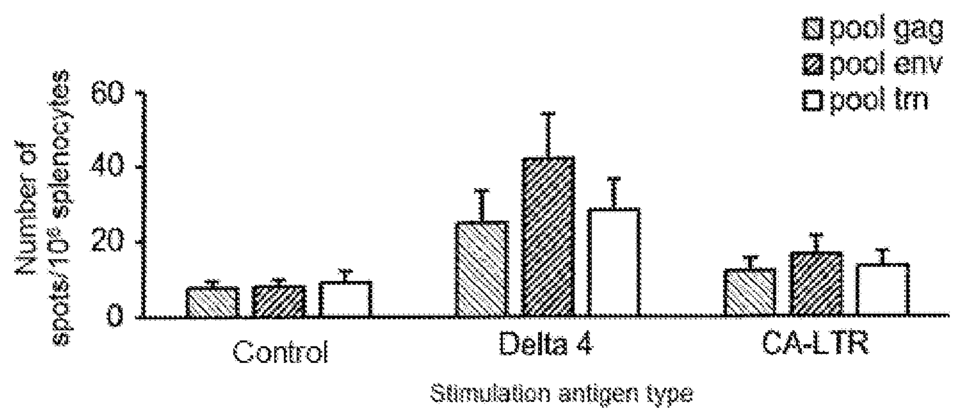
FIG. 12: Evaluation of the number of T lymphocytes secreting IFN-γ of Balb/c mice. Spleen cells of control BALB/c immunocompetent mice and immunized with pΔ4SHIV$_{KU2}$ and pCA-LTR-SHIV$_{KU2}$IN- and stimulated by the Gag, Env peptides and the peptide Tat+Rev+Nef pool. The number of spots was calculated for 1 million PBMCs.

2.4.3. Evaluation of the Immunogenicity of pCA-LTR-SHIV$_{KU2}$-IN- in Vaccinated BALB/c Mice In order to study the immunogenicity of the pCA-LTR-SHIV$_{KU2}$-IN- vaccine in BALB/c mice, the animals were injected with a single dose of 100 μg of DNA via an intramuscular route. The proportion of specific spleen cells (splenocytes) of the antigens was examined by ELISPOT. The results of this study actually show the capability of the DNAs used of inducing specific immune responses directed against all the studied antigens (FIG. 12). The T cell responses with the plasmid pΔ4SHIV$_{KU2}$ are twice higher than with the plasmid pCA-LTR-SHIV$_{KU2}$-IN-. This small difference in efficiency between both DNAs may be related to better quality of the DNA of pΔ4SHIV$_{KU2}$ than that of the pCA-LTRSHIV$_{KU2}$-IN-. These results nevertheless give the possibility of determining the base level of the immune responses induced by these vaccines in normal mice and give the possibility of performing a comparison with the immune responses obtained in the SCID-hu mouse.

Figure 13:
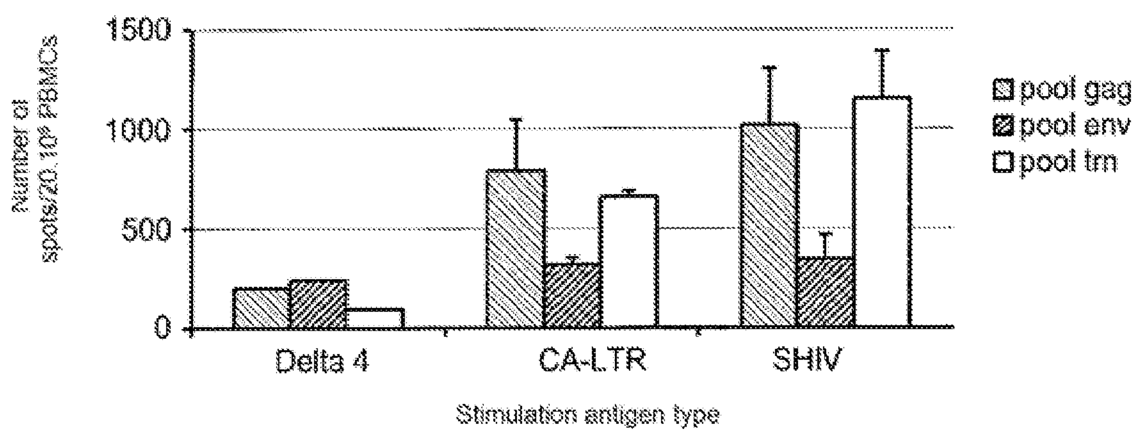
FIG. 13: Evaluation of the number of human T Lymphocytes secreting IFN-γ in immunized NOD/SCID-hu mice. Spleen cells of immunodeficient mice reconstructed by mononuclear cells of human blood and immunized with pΔ4SHIV$_{KU2}$ or pCA-LTR-SHIV$_{KU2}$IN- or pSHIV$_{KU2}$ are stimulated with Gag, Env peptides and with the peptide pool Tat+Rev+Nef. The number of spots was calculated for 1 million PBMCs and normalized to 20%.

2.4.4. Evaluation of the Cell Response in NOD/SCID-Hu Mice Immunized with the Different DNAs The NOD/SCID-hu mice were immunized by intramuscular injection with a single dose of 50 μg of DNA of CA-LTR-SHIV$_{KU2}$-IN-, Δ4SHIV$_{KU2}$ or SHIV$_{KU2}$, and the splenocytes were then used for examining the immune response by ELISPOT for evaluating the proportion of specific cells of the antigen and producing IFN-γ. As shown in FIG. 13, there is a significant number of T cells producing human INF-γ in response to stimulation by the Gag, Env or Tat+Rev+Nef antigens in the form of SIV or HIV peptides. It is interesting to note that the responses obtained after immunization with pCA-LTR-SHIV$_{KU2}$-IN- are quasi-similar to those obtained with pSHIV$_{KU2}$ and which are both clearly greater than those obtained after immunization with pΔ4SHIV$_{KU2}$. The predominancy of the responses induced by pCA-LTR-SHIV$_{KU2}$ is against the Gag and Tat+Rev+Nef antigens.

The whole of these results demonstrates that the DNA of pCA-LTR-SHIV$_{KU2}$ is highly immunogenic in NOD/SCID-hu mice and that it preferentially induces responses against the antigens known for being associated with the protection against pathogenic viruses.

2.5. Phenotype and Functional Examinations of Specific T Cells of the Antigen by Flow Cytometry 2.5.1. Monomarking Carried Out on Day Zero (Performed on the Day when the Mouse Spleens were Recovered)

These mono-markings are used in order to examine whether the selected antibodies actually detect those targets on the one hand, and for evaluating the presence and the proportion of human cells in spleens of SCID-hu mice on the other hand.

The non-marked lymphocytes of humanized and non-humanized mice were analyzed in flow cytometry for measuring the fluorescence in the basal state of the cells (negative control).

The detection of CD3+ TLs is carried out with human anti-CD3 Acs coupled with the fluorochrome “Pacific Blue”. These cells form a peak at $10^2$ in the profile of cells isolated in SCID-hu cells vaccinated with the plasmid pCA-LTR-SHIV$_{KU2}$-IN-. This peak is not present in the cells recovered in SCID-non-hu mice.

No significant peak was observed for cells mono-marked with anti-CD4+ Ac (CD4 anti-human PE), whether this is for the control or for our tested sample. This would be due to the anti-CD4 Ac used which would be non-functional.

For detecting CD8+ TLs, a human anti-CD8 monoclonal Ac coupled with the fluorochrome APC/Cy7 was used. It allows detection of a peak located between $10^2$ and $10^3$ in the profile of the cells isolated in SCID-hu mice vaccinated with pCA-LTR-SHIV$_{KU2}$-IN- and not in SCID-non-hu mice.

The proportion of lymphocytes producing GRA molecules was not able to be evaluated because no peak difference was observed on the cells from immunized and non-immunized mice marked with anti-GRA Ac coupled with Alexa Fluor 647.

On the other hand, the cells marked with human anti-IFN-γ Ac coupled with the fluorochrome PE-Cy7 showed a clear peak located at $10^2$ with cells of SCID-hu mice vaccinated with pCA-LTR-SHIV$_{KU2}$-IN- which is absent with cells of non-immunized SCID-non-hu mice.

2.5.2. Phenotyping and Functions of the T Cells in Immunized Animals

In order to examine the phenotype and the functions of the specific T cells of the antigens of the virus, the cells marked with CFSE are incubated for five days with the (Gag, Env and Tat+Rev+Nef) peptides and then re-stimulated for 6 hours with the same peptides. The cells are then marked with the Acs and examined as indicated above.

The results of this analysis show the presence of CD3+ and CD8+ cells which produce IFN-γ and which have GRA molecules especially with the cells from vaccinated NOD/SCID-hu mice. Indeed, at least 6% of the CD8+ TLs produce IFN-γ and 1.7% produce GRA A in immunized NOD/SCID-hu mice, versus only 2.5% and 0.6% respectively in control mice. These results demonstrate the presence of CD3+, CD8+ activated cells which produce GRA and IFN-γ, which corresponds to an effector cellular immune response induced by our vaccine pCA-LTR-SHIV$_{KU2}$-IN-.

2.6. Analysis of the Immune and Humoral Responses in Macaques 2.6.1. Analysis of the Immune Responses of T Cells by the ELISPOT IFN-λ Test A fraction of the mononuclear cells isolated from blood samples taken was used for evaluating the proportion of cells secreting IFN-λ in response to stimulation by the viral Gag, Pol, Env and Tat+Rev+Nef antigens by means of a commercial kit. The results of the first 20 weeks of the analysis are shown in table 3. They clearly show that following a single administration of the vaccinal vector CAL-SHIV-IN-, all the animals developed cellular immune responses characterized by specific cells of the antigens, which secrete IFN-λ. These responses are heterogenous according to the animals which have CMH-1 haplotypes different from each other. The immune responses are characterized by the presence of a first primary response peak at 2-4 weeks post-immunization (PI), and then of more belated responses from 8-10 weeks PI, and this in the absence of a second immunization. It is of great interest to note that the intensity of the second peak is often much greater than that of the first peak especially for the BX80 animal where the number of cells secreting IFN-λ is multiplied by 3.

TABLE 3

Summary of the proportions of T cells secreting gamma interferon cytokine (IFN-λ) in response to the stimulation by the viral antigens (Gag, Pol, Env and Tat + Rev + Nef) expressed by the vaccine in vaccinated monkeys. The figures correspond to the numbers of secreting cells forming one spot per million ($10^6$) of mononuclear cells of peripheral blood (PBMC). The weeks of analysis are indicated at the top of the table.

| | | Post-Immunization week | | | | | | | | | | | |
|---|---|---|---|---|---|---|---|---|---|---|---|---|---|
| | | 1 | 2 | 3 | 4 | 6 | 8 | 10 | 12 | 14 | 16 | 18 | 20 |
| Animal | Ag | Number of spots/million PBMCs in response to the antigens (Ag) | | | | | | | | | | | |
| BX80 | Gag | 208 | 821 | 666 | 472 | 317 | 504 | 538 | 474 | 226 | 574 | 621 | 862 |
| | Pol | 0 | 105 | 17 | 350 | 15 | 32 | 0 | 97 | 27 | 11 | 11 | 168 |
| | Env | 0 | 84 | 1 | 7 | 124 | 625 | 753 | 67 | 36 | 41 | 48 | 132 |
| | TRN | 0 | 64 | 0 | 107 | 137 | 1238 | 1663 | 1084 | 728 | 1215 | 800 | 1752 |
| BX83 | Gag | 0 | 565 | 1033 | 443 | 147 | 0 | 488 | 377 | 69 | 152 | 96 | 298 |
| | Pol | 0 | 33 | 75 | 193 | 0 | 0 | 340 | 145 | 19 | 0 | 0 | 12 |
| | Env | 0 | 87 | 49 | 72 | 0 | 0 | 1035 | 60 | 40 | 25 | 9 | 20 |
| | TRN | 0 | 51 | 204 | 116 | 0 | 0 | 731 | 393 | 195 | 224 | 143 | 432 |
| BX84 | Gag | 0 | 1279 | 703 | 752 | 300 | 380 | 161 | 427 | 155 | 461 | 91 | 1269 |
| | Pol | 1 | 88 | 36 | 24 | 15 | 5 | 8 | 80 | 0 | 19 | 9 | 44 |
| | Env | 1 | 340 | 85 | 105 | 48 | 57 | 21 | 72 | 13 | 96 | 57 | 217 |
| | TRN | 0 | 205 | 73 | 128 | 27 | 416 | 417 | 761 | 59 | 272 | 79 | 228 |
| BX72 | Gag | 16 | 388 | 1989 | 1220 | 813 | 885 | 840 | 1795 | 0 | 85 | 472 | 1344 |
| | Pol | 0 | 205 | 17 | 45 | 8 | 0 | 13 | 0 | 0 | 0 | 7 | 120 |
| | Env | 7 | 79 | 57 | 56 | 12 | 168 | 56 | 5 | 0 | 0 | 12 | 132 |
| | TRN | 5 | 35 | 161 | 192 | 92 | 692 | 445 | 736 | 0 | 25 | 119 | 587 |
| BX78 | Gag | 8 | 668 | 163 | 213 | 45 | 52 | 76 | 555 | 24 | 83 | 80 | 227 |
| | Pol | 0 | 548 | 60 | 20 | 0 | 31 | 0 | 104 | 132 | 1 | 0 | 59 |
| | Env | 0 | 491 | 68 | 97 | 437 | 181 | 0 | 259 | 24 | 15 | 19 | 73 |
| | TRN | 3 | 296 | 279 | 39 | 0 | 84 | 824 | 685 | 17 | 69 | 39 | 275 |

2.6.2. Analysis of the Immune Responses of T Cells by Multiparameter Flow Cytometry in Vaccinated Monkeys The results of the analysis by multiparameter flow cytometry will confirm those obtained by ELISPOT by revealing that all the animals developed a response consisting of T cells which proliferate and which are specific of all the antigens expressed by the vaccinal vector (Table 4). These responses are heterogenous among the animals and also reveal a first primary response phase which extends up to about 8 weeks PI, followed by a contraction phase (2-4 weeks) and then by a re-emergence phase. This longitudinal tracking of the immune response by multiparameter flow cytometry is continued until the virulent test with the test virus SIVmac251 which is conducted in week 52.

TABLE 4

Summary of the values of the CD4+ and CD8+ proliferating T cells in response to the antigenic stimulations at the moment of the primary expansion phases, of the contraction and finally re-emergence or secondary expansion phases in vaccinated monkeys. The weeks corresponding to each of the phases are indicated. The numbers correspond to the percentages of specific T cells of each of the antigens which proliferate in response to the stimulation as compared with the total number of T cells.

| Animals | Ag | Proportion of T cells which proliferate in response to the antigens (Ag) | | | | |
|---|---|---|---|---|---|---|
| | | Type | Week (−1) | Week (3-6) | Week (8-20) | Week (22-26) |
| BX80 | Gag | CD8+ | 0.5 | 3.6 | 0.4 | 1.5 |
| | | CD4+ | 0.1 | 0.1 | 0.1 | 0.4 |
| | Pol | CD8+ | ND | 0.6 | 0.2 | 0.7 |
| | | CD4+ | ND | 0.7 | 0.1 | 0.6 |
| | Env | CD8+ | 0.3 | 0.5 | 0.1 | 1.4 |
| | | CD4+ | 0.5 | 1.3 | 0.2 | 0.5 |

TABLE 4-continued

Summary of the values of the CD4+ and CD8+ proliferating T cells in response to the antigenic stimulations at the moment of the primary expansion phases, of the contraction and finally re-emergence or secondary expansion phases in vaccinated monkeys. The weeks corresponding to each of the phases are indicated. The numbers correspond to the percentages of specific T cells of each of the antigens which proliferate in response to the stimulation as compared with the total number of T cells.

| Animals | Ag | Proportion of T cells which proliferate in response to the antigens (Ag) | | | | |
|---|---|---|---|---|---|---|
| | TRN | CD8+ | 0 | 4.8 | 0.8 | 1.6 |
| | | CD4+ | 0.3 | 1.2 | 0.2 | 0.5 |
| | | Type | Week (−1) | Week (2) | Week (8-20) | Week (22-26) |
| BX83 | Gag | CD8+ | 0.2 | 1.7 | 0.5 | 1.6 |
| | | CD4+ | 0.1 | 0.6 | 0.4 | 0.9 |
| | Pol | CD8+ | ND | ND | 0.3 | 0.7 |
| | | CD4+ | ND | 0.3 | 0.2 | 0.5 |
| | Env | CD8+ | 0.1 | ND | 0.5 | 1.2 |
| | | CD4+ | 0.3 | ND | 0.3 | 0.7 |
| | TRN | CD8+ | 0.4 | 1.5 | 0.6 | 2.3 |
| | | CD4+ | 0.2 | 0.8 | 0.3 | 0.5 |
| | | Type | Week (−1) | Week (3-6) | Week (8-22) | Week (24-26) |
| BX84 | Gag | CD8+ | 0.1 | 1.1 | 0.3 | 2.6 |
| | | CD4+ | 0.1 | 0.3 | 0.1 | 0.8 |
| | Pol | CD8+ | ND | 0.3 | 0.2 | 0.7 |
| | | CD4+ | ND | 0.3 | 0.2 | 0.5 |
| | Env | CD8+ | 0.1 | 1.1 | 0.3 | 0.9 |
| | | CD4+ | 0.2 | 0.8 | 0.3 | 0.7 |
| | TRN | CD8+ | 0 | 1.3 | 0.7 | 1.1 |
| | | CD4+ | 0.2 | 0.8 | 0.3 | 0.5 |
| | | Type | Week (−1) | Week (3-6) | Week (8-20) | Week (22-26) |
| BX72 | Gag | CD8+ | 0 | 4.2 | 0.7 | 3.0 |
| | | CD4+ | 0 | 0.6 | 0.2 | 0.4 |
| | Pol | CD8+ | ND | 0.7 | 0.2 | 0.7 |
| | | CD4+ | ND | 1.3 | 0.1 | 0.1 |
| | Env | CD8+ | 0.2 | 1.0 | 0.5 | 0.6 |
| | | CD4+ | 0.3 | 1.4 | 0.5 | 2.3 |
| | TRN | CD8+ | 0.1 | 0.9 | 0.3 | 1.5 |
| | | CD4+ | 0.1 | 1.7 | 0.4 | 0.9 |
| | | Type | Week (−1) | Week (3-6) | Week (8-18) | Week (20-32) |
| BX78 | Gag | CD8+ | 0 | 3.4 | 1.1 | 3.7 |
| | | CD4+ | 0.1 | 1.3 | 0.6 | 2.9 |
| | Pol | CD8+ | ND | 1.1 | 0.3 | 1.1 |
| | | CD4+ | ND | 0.6 | 0.2 | 1.3 |
| | Env | CD8+ | 0.2 | 1.4 | 0.4 | 1.2 |
| | | CD4+ | 0.3 | 0.6 | 0.6 | 2.5 |
| | TRN | CD8+ | 0.3 | 1.9 | 0.8 | 2.1 |
| | | CD4+ | 0.3 | 1.2 | 0.5 | 2.1 |

2.6.3. Analysis of the Humoral Response in Macaques

Detection of the anti-antigen antibodies of SHIV was carried out with a commercial ELISA kit which allows detection of the anti-Env antibodies of the HIV-1. The longitudinal examination of the serums harvested at each blood sampling point showed the presence of anti-Env antibodies from week 20 PI in the BX80 animal and from week 8 for the BX73 animal. The presence of antibodies in positive sera was confirmed by Western blot against proteins of the SHIV showing a strong signal against the Gag-p27 protein as well as a signal against the gp160/gp120 glycoproteins.

2.6.4. Conclusion

These results clearly demonstrate that a single injection of vaccinal DNA (CAL-SHIV-IN-) gives the possibility of inducing T cell and humoral (antibody) immune responses. The T cell responses are directed against all the viral antigens expressed by the vaccinal vector. They are persistent and follow a conventional expansion, contraction and storage-in-memory scheme. The presence of memory T cells of the central type and of memory effector cells was confirmed by the phenotyping.

Figure 17:
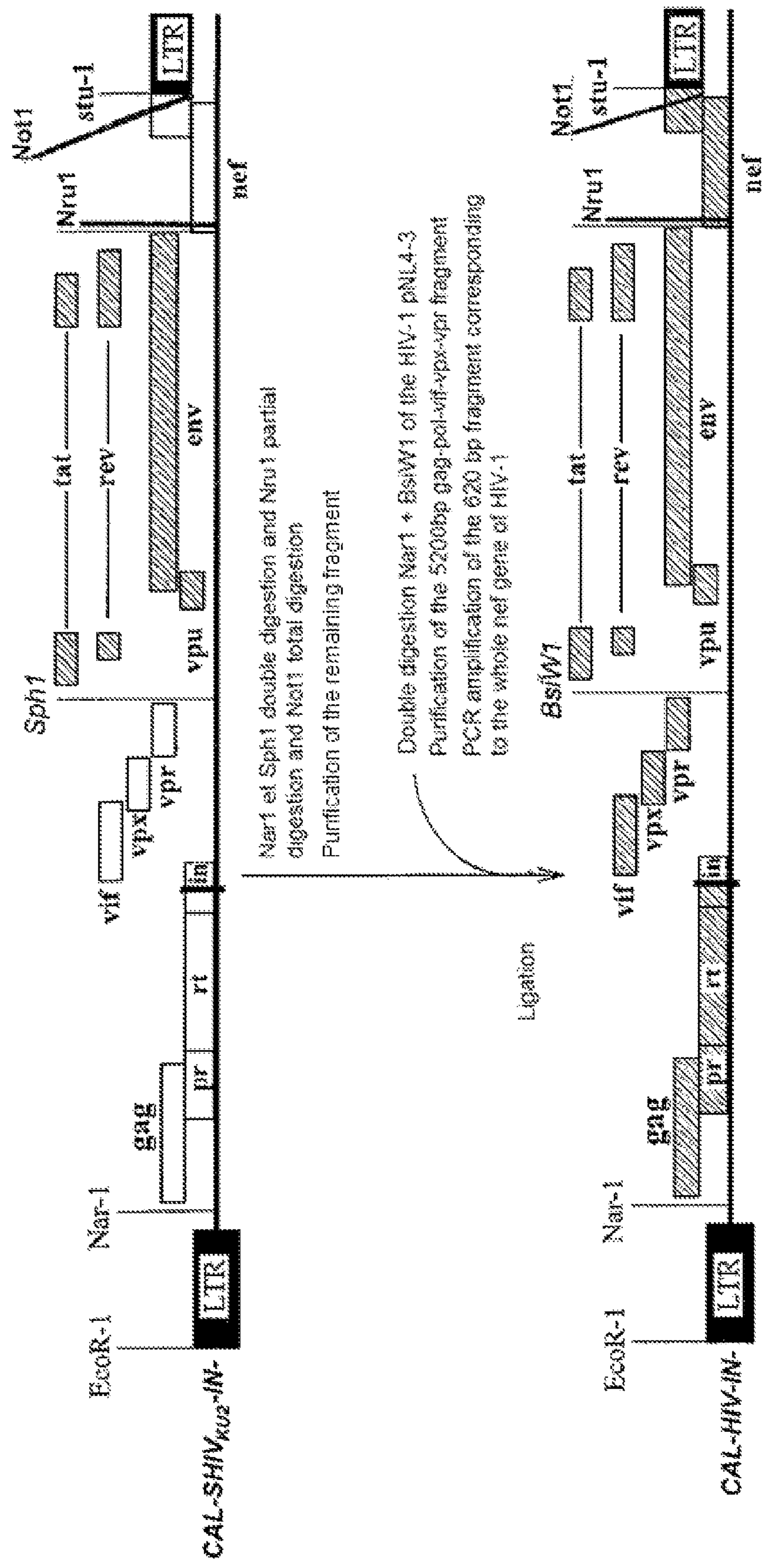
FIG. 17: Illustration of the preparation of the vector CAL-HIV-IN-.
Figure 18:
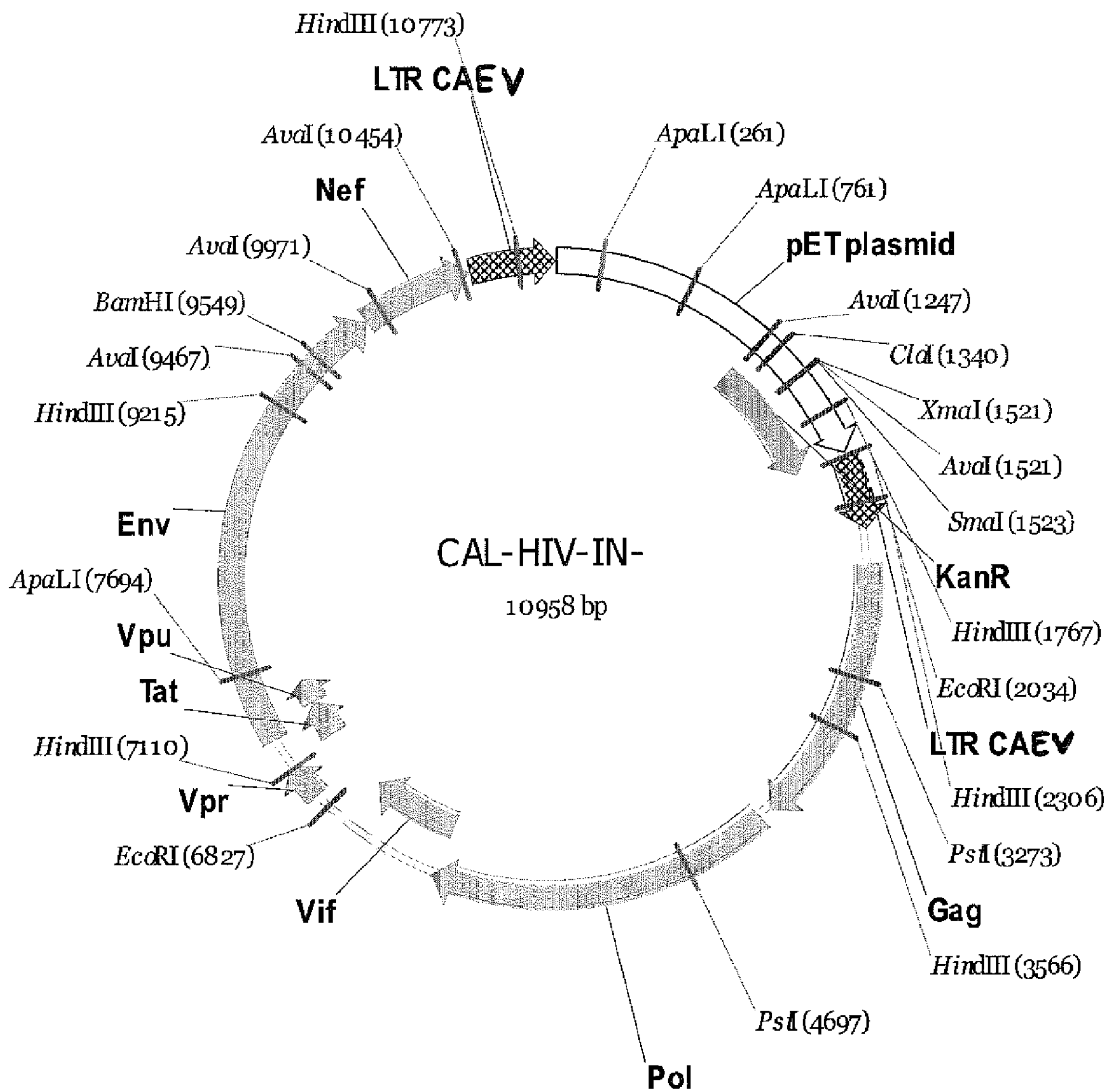
FIG. 18: Schematic illustration of the vector CAL-HIV-IN-.

2.7. Construction and Functional Analysis of a Novel Vector Expressing the Whole of the Antigens of the HIV-1: The Vector CAL-HIV-IN- From the genome of the vector CAL-SHIV$_{KU2}$-IN-, the gag, pol, vif, vpx and vpr genes of the SIV were deleted following double digestion with the Nar1 and Sph1 enzymes, and the nef gene of the SIV was deleted following the partial digestion with the Nru1 enzyme and the total digestion with the Not 1 enzyme. The remaining fragment was then purified. This fragment, bearing the tat, rev and env genes of the HIV framed with the RTLs of the CAEV and transported by the plasmid pET, was used for introducing the 5 kb fragment bearing the gag, pol, vif, vpx and vpr genes of the HIV-1 and the 620 bp fragment bearing the nef gene of the HIV-1, and generating the vector CAL-HIV-IN- (FIG. 17). The CAL-HIV-IN- vector, deleted from the sequences coding for the integrase, consists in the sequence SEQ ID NO: 18.

2.7.1. Evaluation of the Functionality: Effect of Plasmid DNA on the Cells

The DNA of this vector was introduced into the GHOST-CXCR4 and HEK-293 T cells by transfection using the ExGen and the procedure recommended by the manufacturer. The transfected GHOST-CXR4 cells had then become fluorescent confirming expression of the viral proteins of the HIV-1 by the vaccinal vector and more particularly the Tat protein which transactivates the expression of the GFP (Green Fluorescent Protein) gene under the control of the RTL of the HIV.

The supernatant of the HEK-293T cells transfected with the vaccinal vector CAL-HIV-IN- was used for inoculating the M8166, indicating CD4+ T cells which developed cytopathic effects, characteristics of HIV infection. These results provide the proof that the proteins expressed by the vaccinal vector assembled into viral particles allowing infection of the M8166 indicator cells. These cells with the cytopathic effects did not produce any viruses capable of again infecting the M8166 indicator cells and inducing cytopathic effects. This result indicates that CAL-HIV-IN- is associated with a single replication cycle in the absence of integration.

In order to evaluate the viral proteins produced after transfection, the supernatants of the transfected HEK-293T cells with the vaccinel vector, were harvested 24 h, 48 h and 72 h post-transfection and then examinated for the presence of Gag p24 antigens with ELISA. The measurements of the amounts of this protein are indicated in Table 5. They show increasing accumulation of this protein ranging from 100 ng/ml at 24 h up to 135 ng/ml at 72 h post-transfection.

TABLE 5

Evaluation of the Gag p24 protein of the HIV-1 secreted in the supernatant of HEK 293T cells transfected with the vaccinal vector CAL-HIV-IN-. Quantification of the protein p24 accumulated in the supernatant of the HEK 293T cells after 24, 48 and 72 hours post-transfection with the DNA of the vector CAL-HIV-IN-.

| | 24 h | 48 h | 72 h |
|---|---|---|---|
| Gag p24 concentration | 100 ng/ml | 110 ng/ml | 135 ng/ml |

2.7.2. Immunization of BALB/C Mice and Characterization of the Induced Immune Responses Three groups of BALB/c mice (6 per group) of 6 weeks old were used: two groups were used for immunization and the third group is a control group. The two groups of immunized mice were injected with 100 μg/mouse DNA of the vector CAL-HIV-IN- via the intramuscular route. The animals of a group were sacrificed after two weeks and the other ones at three weeks post-immunization (PI). The control mice were sacrificed at two weeks PI. The spleens of each of the mice were taken, the splenocytes were isolated and then used either for the ELISPOT test or for the analysis in multiparameter flow cytometry as described above. The results of the analysis by ELISPOT are indicated in Table 6. They show the presence of specific cells of all the antigens which secrete IFN-λ. The majority of these cells are specific of Gag and Tat+Rev+Nef antigens. The responses at 2 and 3 weeks post-immunization are substantially similar.

TABLE 6

Summary of the results of the analysis by ELISPOT on the splenocytes of BABL/c mice immunized with the vaccinal vector CAL-HIV-IN- at 2 and 3 weeks post-immunization. The isolated splenocytes of the mouse spleens immunized with 100 μg per mouse via an intramuscular route were examined with the ELISPOT IFN-λ test for evaluating the number of T cells secreting the cytokine in response to the stimulations with the pools of peptides (Gag, Env and Tat + Rev + Nef, TRN). The averages of the number of spots for each antigen and for the 6 examined mice after 2 and 3 weeks post-immunization are indicated.

| | Medium without any peptide | Gag | Tat + Rev + Nef | Env |
|---|---|---|---|---|
| 2 weeks | 10 | 45 | 50 | 17 |
| 3 weeks | 5 | 35 | 55 | 15 |

The results of the analysis by flow cytometry (Table 7) demonstrate specific CD4+ and CD8+ T cell immune responses of all the antigens expressed by the vaccinal vector CAL-HIV-IN-.

TABLE 7

Summary of the results of the analysis by multiparameter flow cytometry. The figures correspond to the percentages of specific T cells of each of the antigens which proliferate in response to the antigenic stimulation, based on the total number of T cells.

| | Medium without any peptide | Gag | Tat + Rev + Nef | Env |
|---|---|---|---|---|
| CD3 + CD4+ | 0.16 | 0.26 | 0.40 | 0.18 |
| CD3 + CD8+ | 0.20 | 0.27 | 0.50 | 0.25 |

The invention claimed is:

1. A nucleic acid comprising a chimeric retroviral genome, in which said chimeric retroviral genome comprises:

Long terminal repeat sequences (LTR) positioned 5' and 3' of a first retrovirus, said first retrovirus being the Caprine Arthritis Encephalitis Virus (CAEV), and at least one viral gene of a second retrovirus, said second retrovirus not being the first retrovirus, wherein the chimeric retroviral genome comprises the gag, pol, vif, vpx, vpr, nef, tat, rev, vpu and env genes of said second retrovirus, and wherein said pol gene is mutated to delete nucleic acid sequences encoding an integrase protein to an extent sufficient to abolish any integrating activity of said integrase protein.

2. The nucleic acid according to claim 1, wherein said second retrovirus is a lentivirus.

3. The nucleic acid according to claim 2, wherein said lentivirus is selected from the human immunodeficiency virus of type I (HIV-1), the HIV-2, the simian immunodeficiency virus (SIV), the feline immunodeficiency virus (FIV), or the equine infectious anaemia virus (EIAV).

4. A recombinant vector comprising the nucleic acid according to claim 1.

5. An immunogenic or vaccinal composition comprising the nucleic acid according to claim 1.

6. A nucleic acid comprising a chimeric retroviral genome, in which said chimeric retroviral genome comprises:

Long terminal repeat sequences (LTR) positioned 5' and 3' of a first retrovirus, said first retrovirus being the Caprine Arthritis Encephalitis Virus (CAEV), and at least one viral gene of a second retrovirus, said second retrovirus not being the first retrovirus;

wherein the chimeric retroviral genome further comprises at least one viral gene of a third retrovirus, said third retrovirus being different from said first and second retroviruses; and wherein the chimeric retroviral genome comprises the gag, pol, vif, vpx, vpr, nef, tat, rev, vpu, and env genes each of said genes being of either but not both of said second or third retrovirus, and wherein if said at least one viral gene of said second retrovirus or said at least one viral gene of said third retrovirus is a pol gene then said pol gene is mutated to delete nucleic acid sequences encoding an integrase protein to an extent sufficient to abolish any integrating activity of said integrase protein.

7. The nucleic acid according to claim 6, wherein said at least one gene of said second retrovirus, or said at least one gene of said third retrovirus, is selected from the gag, pol, vif, vpx, vpr, nef, tat, rev, vpu and env genes.

8. The nucleic acid according to claim 6, wherein the chimeric retroviral genome comprises the gag, pol, vif, vpx, vpr, nef genes of said second retrovirus and the tat, rev, vpu and env genes of said third retrovirus.

9. The nucleic acid according to claim 6, wherein said second and third retroviruses are each a lentivirus.

10. The nucleic acid according to claim 9, wherein said lentivirus is selected from the group consisting of human immunodeficiency virus type I (HIV-1), human immunodeficiency virus type II (HIV-2), simian immunodeficiency virus (SIV), feline immunodeficiency virus (FIV), or equine infectious anaemia virus (EIAV).

11. The nucleic acid according to claim 6, wherein said retroviral chimeric genome comprises the gag, pol, vif, vpx, and vpr genes of SIV and the nef, tat, rev, vpu and env genes of HIV-1.

12. The nucleic acid according to claim 6, wherein said retroviral chimeric genome comprises at least one of the gag, pol, vif, vpx, vpr, nef, tat, rev, vpu and env genes of HIV-1 and comprises at least one of the gag, pol, vif, vpx, vpr, nef, tat, rev, vpu and env genes of HIV-2.

13. The nucleic acid according to claim 6, wherein said second retrovirus is a lentivirus.

14. The nucleic acid according to claim 6, wherein said chimeric retroviral genome comprises one of the nucleic acid sequences according to SEQ ID NO: 1, SEQ ID NO: 2 and SEQ ID NO: 6, and wherein said pol gene, when it is present, is mutated to delete nucleic acid sequences encoding an integrase protein to an extent sufficient to abolish any integrating activity of said integrase protein.

15. A recombinant vector comprising the nucleic acid according to claim 6.

16. An immunogenic or vaccinal composition comprising the nucleic acid according to claim 6.

17. A nucleic acid comprising a chimeric retroviral genome, wherein said chimeric retroviral genome comprises one of the nucleic acid sequences according to SEQ ID NO: 1, SEQ ID NO: 2 and SEQ ID NO: 6.

* * * * *

SEQUENCE LISTING

```
<160> NUMBER OF SEQ ID NOS: 18

<210> SEQ ID NO 1
<211> LENGTH: 10340
<212> TYPE: DNA
<213> ORGANISM: Artificial Sequence
<220> FEATURE:
<223> OTHER INFORMATION: Genome retroviral SHIV

<400> SEQUENCE: 1

gaattcactg tgagacatgg gctaaagagg actaataaca agctaggcca aattcctgta      60

aatcacttgg ggggttataa gaaaagcaag ttcactatga caaagcaaaa tgtaaaggcc     120

aaattcctgt aaatcacttg gggggttata agaaaagcaa gttcactatg acaaagcaaa     180

atgtaaccgc aagtgctgac agatgtaaca gctgacatat cagctgatgc ttgctcatgc     240

tgacactgta gctctgagct gtatataagg agaagcttgc tgcttgcact tcagagttct     300

aggagagtcc ctcctagtct ctcctctccg aggaggtacc gagacctcaa aataaaggag     360

tgattgcctt actgccgagt ggagagtgat tactgagcgg ccggtgtatc gggagtcgtc     420

ccttaatctg tgcaatacca gagcggctct cgcagctggc gcccgaacag ggacttgaag     480

gagagtgaga gactcctgag tacggctgag tgaaggcagt aagggcggca ggaaccaacc     540

acgacggagt gctcctataa aggcgcgggt cggtaccaga cggcgtgagg agcgggagag     600

gaagaggcct ccggttgcag gtgagtgcaa cacaaaaaag aaatagctgt cttttatcca     660

ggaaggggta ataagataga gtgggagatg ggcgtgagaa actccgtctt gtcagggaag     720
```

```
aaagcagatg aattagaaaa aattaggcta cgacccaacg gaaagaaaaa gtacatgttg    780
aagcatgtag tatgggcagc aaatgaatta gatagatttg gattagcaga aagcctgttg    840
gagaacaaag aaggatgtca aaaaatactt tcggtcttag ctccattagt gccaacaggc    900
tcagaaaatt taaaaagcct ttataatact gtctgcgtca tctggtgcat tcacgcagaa    960
gagaaagtga aacacactga ggaagcaaaa cagatagtgc agagacacct agtggtggaa   1020
ataggaacaa cagaaactat gccaaaaaca agtagaccaa cagcaccatc tagcggcaga   1080
ggaggaaatt acccagtaca acaaataggt ggtaactatg tccacctgcc attaagcccg   1140
agaacattaa atgcctgggt aaaattgata gaggaaaaga aatttggagc agaagtagtg   1200
ccaggatttc aggcactgtc agaaggttgc accccctatg acattaatca gatgttaaat   1260
tgtgtgggag accatcaagc ggctatgcag attatcagag atattataaa cgaggaggct   1320
gcagattggg acttgcagca cccacaacca gctccacaac aaggacaact tagggagccg   1380
tcaggatcag atattgcagg aacaactagt tcagtagatg aacaaatcca gtggatgtac   1440
agacaacaga accccatacc agtaggcaac atttacagga gatggatcca actggggttg   1500
caaaaatgtg tcagaatgta taacccaaca aacattctag atgtaaaaca agggccaaaa   1560
gagccatttc agagctatgt agacaggttc tacaaaagtt taagagcaga acagacagat   1620
gcagcagtaa agaattggat gactcaaaca ctgctgattc aaaatgctaa cccagattgc   1680
aagctagtgc tgaaggggct gggtgtgaat cccaccctag aagaaatgct gacggcttgt   1740
caaggagtag gggggccggg acagaaggct agattaatgg cagaagccct gaaagaggcc   1800
ctcgcaccag tgcctatccc ttttgcagca gcccaacaga ggggaccaag aaagccaatt   1860
aagtgttgga attgtgggaa agagggacac tctgcaaggc aatgcagagc cccaagaaga   1920
cagggatgct ggaaatgtgg aaaaatggac catgttatgg ccaaatgccc agacagacag   1980
gcgggttttt taggccttgg tccatgggga aagaagcccc gcaatttccc catggctcaa   2040
gtgcatcagg ggctgatgcc aactgctccc ccagaggacc cagctgtgga tctgctaaag   2100
aactacatgc agttgggcaa gcagcagaga gaaaagcaga gagaaagcag agagaagcct   2160
tacaaggagg tgacagagga tttgctgcac ctcaattctc tctttggagg agaccagtag   2220
tcactgctca tattgaagga cagcctgtag aagtattact ggatacaggg gctgatgatt   2280
ctattgtaac aggaatagag ttaggtccac attataccccc aaaaatagta ggaggaatag   2340
gaggttttat taatactaaa gaatacaaaa atgtagaaat agaagtttta ggcaaaagga   2400
ttaaagggac aatcatgaca ggggacaccc cgattaacat ttttggtaga aatttgctaa   2460
cagctctggg gatgtctcta aattttccca tagctaaagt agagcctgta aaagtcgcct   2520
taaagccagg aaagaatgga ccaaaattga agcagtggcc attatcaaaa gaaaagatag   2580
ttgcattaag agaaatctgg gaaaagatgg aaaaggatgg tcagttggag gaagctcccc   2640
cgaccaatcc atacaacacc cccacatttg ctataaagaa aaaggataag aacaaatgga   2700
gaatgctgat agattttagg gaactaaata gggtcactca ggactttacg gaagtccaat   2760
taggaatacc acaccctgca ggattagcaa aaaggaaaag aattacagta ctggatatag   2820
gtgatgcata tttctccata cctctagatg aagaatttag gcagtacact gcctttactt   2880
taccatcagt aaataatgca gagccaggaa aacgatacat ttataaggtt ctgcctcagg   2940
gatggaaggg gtcaccagcc atcttccaat acactatgag acatgtgcta gaacccttca   3000
ggaaggcaaa tccagatgtg accttagtcc agtatatgga tgacatctta atagctagtg   3060
acaggacaga cctggaacat gacagggtag ttttacagtc aaaggaactc ttgaatagca   3120
```

-continued

```
tagggttttc taccccagaa gagaaattcc aaaaagatcc cccatttcaa tggatggggt   3180
acgaattgtg gccaacaaaa tggaagttgc aaaagataga gttgccacaa agagagacct   3240
ggacagtgaa tgatatacag aagttagtag gagtattaaa ttgggcagct caaatttatc   3300
caggtataaa aaccaaacat ctctgtaggt taattagagg aaaaatgact ctaacagagg   3360
aagttcagtg gactgagatg gcagaagcag aatatgagga aaataaaata attctcagtc   3420
aggaacaaga aggatgttat taccaagaag gcaagccatt agaagccacg gtaataaaga   3480
gtcaggacaa tcagtggtct tataaaattc accaagaaga caaaatactg aaagtaggaa   3540
aatttgcaaa gataaagaat acacatacca atggagtgag actattagca catgtaatac   3600
agaaaatagg aaaggaagca atagtgatct ggggacaggt cccaaaattc cacttaccag   3660
ttgagaagga tgtatgggaa cagtggtgga cagactattg gcaggtaacc tggataccgg   3720
aatgggattt tatctcaaca ccaccgctag taagattagt cttcaatcta gtgaaggacc   3780
ctatagaggg agaagaaacc tattatacag atggatcgtg taataaacag tcaaaagaag   3840
ggaaagcagg atatatcaca gataggggca aagacaaagt aaaagtgtta gaacagacta   3900
ctaatcaaca agcagaattg gaagcatttc tcatggcatt gacagactca gggccaaagg   3960
caaatattat agtagattca caatatgtta tgggaataat aacaggatgc cctacagaat   4020
cagagagcag gctagttaat caaataatag aagaaatgat taaaaagtca gaaatttatg   4080
tagcatgggt accagcacac aaaggtatag gaggaaacca agaaatagac cacctagtta   4140
gtcaagggat tagacaagtt ctcttcttgg aaaagataga gccagcacaa gaagaacatg   4200
ataaatacca tagtaatgta aaagaattgg tattcaaatt tggattaccc agaatagtgg   4260
ccagacagat agtagacacc tgtgataaat gccatcagaa aggagaggct atacatgggc   4320
aggtaaattc agatctaggg acttggcaaa tggattgtac ccatctagag ggaaaaataa   4380
tcatagttgc agtacatgta gctagtggat tcatagaagc agaggtaatt ccacaagaga   4440
caggaagaca gacagcacta tttctgttaa aattggcagg cagatggcct attacacatc   4500
tacacacaga taatggtgct aactttgctt cgcaagaagt aaagatggtt gcatggtggg   4560
cagggataga gcacaccttt ggggtaccat acaatccaca gagtcaggga gtagtggaag   4620
caatgaatca ccacctgaaa aatcaaatag atagaatcag ggaacaagca aattcagtag   4680
aaaccatagt attaatggca gttcattgca tgaattttaa aagaagggga ggaatagggg   4740
atatgactcc agcagaaaga ttaattaaca tgatcactac agaacaagag atacaatttc   4800
aacaatcaaa aaactcaaaa tttaaaaatt ttcgggtcta ttacagagaa ggcagagatc   4860
aactgtggaa gggacccggt gagctattgt ggaaagggga aggagcagtc atcttaaagg   4920
tagggacaga cattaaggta gtacccagaa gaaaggctaa aattatcaaa gattatggag   4980
gaggaaaaga ggtggatagc agttcccaca tggaggatac cggagaggtt agagaggtgg   5040
catagcctca taaaatatct gaaatataaa actaaagatc tacaaaaggt ttgctatgtg   5100
ccccatttta aggtcggatg ggcatggtgg acctgcagca gagtaatctt cccactacag   5160
gaaggaagcc atttagaagt acaagggtat tggcatttga caccagaaaa agggtggctc   5220
agtacttatg cagtgaggat aacctggtac tcaaagaact tttggacaga tgtaacacca   5280
aactatgcag acattttact gcatagcact tatttccctt gctttacagc gggagaagtg   5340
agaagggcca tcaggggaga acaactgctg tcttgctgca ggttcccgag agctcataag   5400
caccaggtac caagcctaca gtacttagca ctgaaagtag taagcgatgt cagatcccag   5460
ggagagaatc ccacctggaa acagtggaga agagacaata ggagaggcct tcgaatggct   5520
```

```
aaacagaaca gtagaggaga taaacagaga ggcggtaaac cacctaccaa gggagctaat   5580
tttccaggtt tggcaaaggt cttgggaata ctggcatgat gaacaaggga tgtcaccaag   5640
ctatgtaaaa tacagatact tgtgtttaat acaaaaggct ttatttatgc attgcaagaa   5700
aggctgtaga tgtctagggg aaggacatgg ggcaggggga tggagaccag gacctcctcc   5760
tcctccccct ccaggactag cataaatgga agaaagacct ccagaaaatg aaggaccaca   5820
aagggaacca tgggatgaat gggtagtgga ggttttggaa gaactgaaag aagaagcttt   5880
aaaacatttt gatcctcgct tgctaactgc ccttggtaat catatctata atcgtcacgg   5940
agacactcta gagggagcag gagaactcat tagaatcctc caacgagcgc tcttcatgca   6000
tttcagaggc ggatgcatcc actccagaat cggccaacct gggggaggaa atcctctctc   6060
agctataccg ccctctagaa gcatgctgta gagcaagaaa tggagccagt agatcctaga   6120
ctagagccct ggaagcatcc aggaagtcag cctaaaactg cttgtaccaa ttgctattgt   6180
aaaaagtgtt gctttcattg ccaagtttgt ttcataacaa aagccttagg catctcctat   6240
ggcaggaaga agcggagaca gcgacgaaga gctcatcaga acagtcagac tcatcaagct   6300
tctctatcaa agcagtaagt agtacatgta acgcaaccta taccaatagt agcaatagta   6360
gcattagtag tagcaataat aatagcaata gttgtgtggt ccatagtaat catagaatat   6420
aggaaaatat taagacaaag aaaaatagac aggttaattg atagactaat agaaagagca   6480
gaagacagtg gcaatgagag tgaaggagaa atatcagcac ttgtggagat gggggtggag   6540
atggggcacc atgctccttg ggatgttgat gatctgtagt gctacagaaa aattgtgggt   6600
cacagtctat tatggggtac ctgtgtggaa ggaagcaacc accactctat tttgtgcatc   6660
agatgctaaa gcatatgata cagaggcaca taatgtttgg gccacacatg cctgtgtacc   6720
cacagacccc aacccacaag aagtagtatt ggtaaatgtg acagaaaatt ttaacatgtg   6780
gaaaaatgac atggtagaac agatgcatga ggatataatc agtttatggg atcaaagcct   6840
aaagccatgt gtaaaattaa ccccactctg tgttagttta aattgcactg atttgaagaa   6900
tgatactaat accaatagta gtagcgggag aatgataatg gagaaaggag agataaaaaa   6960
ctgctctttc aatatcagca caagcataag aggtaaggtg cagaaagaat atgcattttt   7020
ttataaactt gatataatac caatagataa tgatactacc agctatacgt tgacaagttg   7080
taacacctca gtcatttcac aggcctgtcc aaaggtatcc tttgagccaa ttcccataca   7140
ttattgtgcc ccggctggtt ttgcgattct aaaatgtaat aataagacgt tcaatggaac   7200
aggaccatgt acaaatgtca gcacagtaca atgtacacat ggaattaggc cagtagtatc   7260
aactcaactg ctgttaaatg gcagtctagc agaagaagag gtagtaatta gatctgtcaa   7320
tttcatggac aatgctaaaa ccataatagt acagctgaac acatctgtag aaattaattg   7380
tacaagaccc agcaacaata caataaaaag aatccgtatc cagagaggac cagggagagc   7440
atttgttaca atgggaaaaa taggaaatat gagacaagca cattgtaaca ttagtagagc   7500
aaaatggaat aacactttaa aacagatagc tagcaaatta agagaacaat ttggaaataa   7560
taaaacaata atctttaagc aatcctcagg aggggaccca gaaattgtaa cgcacagttt   7620
taattgtgga ggggaatttt tctactgtaa ttcaacacaa ctgtttaata gtacttggtt   7680
taatagtact tggagtactg aagggtcaaa taacactgaa ggaagtggca caatcaccct   7740
cccatgcaga ataaaacaaa ttataaacat gtggcagaaa gtaggaaaag caatgtatgc   7800
ccctcccatc agtggacaaa ttagatgttc atcaaatatt acagggctgc tattaacaag   7860
```

```
agatggtggt aagggcaaca atgagtccga gatcttcaga cctggaggag gagatatgag   7920
ggacaattgg agaagtgaat tatataaata taaagtagta aaaattgaac cattaggagt   7980
agcacccacc aaggcaaaga gaagagtggt gcagagagaa aaaagagcag tgggaatagg   8040
agctttgttc cttgggttct tgggagcagc aggaagcact atgggcgcag cgtcaatgac   8100
gctgacggta caggccagac aattattgtc tggtatagtg cagcagcaga acaatttgct   8160
gagggctatt gaggcgcaac agcatctgtt gcaactcaca gtctggggca tcaagcagct   8220
ccaggcaaga atcctggctg tggaaagata cctaaaggat caacagctcc tggggatttg   8280
gggttgctct ggaaaactca tttgcaccac tgctgtgcct tggaatgcta gttggagtaa   8340
taaatctctg gaacagattt ggaatcacat gacctggatg gagtgggaca gagaaattaa   8400
caattacaca agcttaatac actccttaat tgaagaatcg caaaaccagc aagaaaagaa   8460
tgaacaagaa ttattggaat tagataaatg ggcaagtttg tggaattggt ttgacataac   8520
aaattggctg tggtatataa aattattcat aatgatagta ggaggcttgg taggtttaag   8580
aatagttttt gctgtacttt ctatagtgaa tagagttagg cagggatatt caccattatc   8640
gtttcagacc cacctcccaa ccccgagggg acccgacagg cccgaaggaa tagaagaaga   8700
aggtggagag agagacagag acagatccat tcgattagtg aacggatcct tggcacttat   8760
ctgggacgat ctacggagcc tgtgcctctt cagctaccac cgcttgagag acttactctt   8820
gattgtaacg aggactgtgg aacttctggg acgcaggggg tgggaagccc tcaaatattg   8880
gtggaatctc ctacagtatt ggagtcagga actaaagaat agtgctgtta gcttgctcaa   8940
tgccatagcc atagcagtag ctgagggaac agatagggtt atagaagtag tccaaggagc   9000
ttgtagagct attcgctaca tacctagaag aataagacag ggcttggaaa ggattttgct   9060
ataagattcg agatgggtgg agctatttcc atgaggcggt ccaggcagtc tagagatctg   9120
cgacagagac tcttgcgggc gcgtggggag acttatggga gactcttaga agaggtggaa   9180
gatggatact cgcgatcccc aggaggatta gacaagggct tgagctcact ctcttgtgag   9240
ggacagaaat acaatcaggg acagtatatg aatactccat ggagagaccc agctgaagag   9300
agagaaaaat tagcatacag aaaacaaaat atggatgata tagatgagga agatgataac   9360
ttggtagggg tatcagtgag gccaagagtt cccctaagaa caatgagtta caaattggca   9420
atagacatgt ctcattttat aaaagaaaag gggggaactgg aagggatctt ttacagtgca   9480
agaagacata gaatcttaga catgtactta gaaaaggaaa aaggcatcat accagattgg   9540
caggattaca cctcaggacc aggaattaga tacccaaaga catttggctg gctatggaaa   9600
ttagtccctg taaatgtatc agatgaggca caggaggatg aagagcatta tttaatgcat   9660
ccagctcaaa cttcccagtg ggatgaccct tggagagagg ttctagcatg gaagtttgat   9720
ccaactctgg cctacactta tgaggcatat gttagatacc cagaagagtt tggaagcaag   9780
tcaggcctgt cagaggaaga ggttaaaaga aggctaaccg caagaggcct tcttaacatg   9840
gctgacaaga aggaaactcg ctgagcggcc gcactgtgag acatgggcta aagaggacta   9900
ataacaagct aggccaaatt cctgtaaatc acttgggggg ttataagaaa agcaagttca   9960
ctatgacaaa gcaaaatgta aaggccaaat tcctgtaaat cacttggggg gttataagaa  10020
aagcaagttc actatgacaa agcaaaatgt aaccgcaagt gctgacagat gtaacagctg  10080
acatatcagc tgatgcttgc tcatgctgac actgtagctc tgagctgtat ataaggagaa  10140
gcttgctgct tgcacttcag agttctagga gagtccctcc tagtctctcc tctccgagga  10200
ggtaccgaga cctcaaaata aaggagtgat tgccttactg ccgagtggag agtgattact  10260
```

```
gagcggccgg tgtatcggga gtcgtccctt aatctgtgca ataccagagc ggctctcgca  10320

gctgtcgacc tcgagggggg                                              10340


<210> SEQ ID NO 2
<211> LENGTH: 9696
<212> TYPE: DNA
<213> ORGANISM: Artificial Sequence
<220> FEATURE:
<223> OTHER INFORMATION: Genome retroviral

<400> SEQUENCE: 2

aattcactgt gagacatggg ctaaagagga ctaataacaa gctaggccaa attcctgtaa     60

atcacttggg gggttataag aaaagcaagt tcactatgac aaagcaaaat gtaaaggcca    120

aattcctgta aatcacttgg ggggttataa gaaaagcaag ttcactatga caaagcaaaa    180

tgtaaccgca agtgctgaca gatgtaacag ctgacatatc agctgatgct tgctcatgct    240

gacactgtag ctctgagctg tatataagga gaagcttgct gcttgcactt cagagttcta    300

ggagagtccc tcctagtctc tcctctccga ggaggtaccg agacctcaaa ataaaggagt    360

gattgcctta ctgccgagtg gagagtgatt actgagcggc cggtgtatcg ggagtcgtcc    420

cttaatctgt gcaataccag agcggctctc gcagctggcg cccgaacagg gacttgaaag    480

cgaaagtaaa gccagaggag atctctcgac gcaggactcg gcttgctgaa gcgcgcacgg    540

caagaggcga ggggcggcga ctggtgagta cgccaaaaat tttgactagc ggaggctaga    600

aggagagaga tgggtgcgag agcgtcggta ttaagcgggg gagaattaga taaatgggaa    660

aaaattcggt taaggccagg gggaaagaaa caatataaac taaaacatat agtatgggca    720

agcagggagc tagaacgatt cgcagttaat cctggccttt tagagacatc agaaggctgt    780

agacaaatac tgggacagct acaaccatcc cttcagacag gatcagaaga acttagatca    840

ttatataata caatagcagt cctctattgt gtgcatcaaa ggatagatgt aaaagacacc    900

aaggaagcct tagataagat agaggaagag caaaacaaaa gtaagaaaaa ggcacagcaa    960

gcagcagctg acacaggaaa caacagccag gtcagccaaa attaccctat agtgcagaac   1020

ctccaggggc aaatggtaca tcaggccata tcacctagaa ctttaaatgc atgggtaaaa   1080

gtagtagaag agaaggcttt cagcccagaa gtaataccca tgttttcagc attatcagaa   1140

ggagccaccc cacaagattt aaataccatg ctaaacacag tgggggggaca tcaagcagcc   1200

atgcaaatgt taaaagagac catcaatgag gaagctgcag aatgggatag attgcatcca   1260

gtgcatgcag ggcctattgc accaggccag atgagagaac caaggggaag tgacatagca   1320

ggaactacta gtacccttca ggaacaaata ggatggatga cacataatcc acctatccca   1380

gtaggagaaa tctataaaag atggataatc ctgggattaa ataaaatagt aagaatgtat   1440

agccctacca gcattctgga cataagacaa ggaccaaagg aaccctttag agactatgta   1500

gaccgattct ataaaactct aagagccgag caagcttcac aagaggtaaa aaattggatg   1560

acagaaacct tgttggtcca aaatgcgaac ccagattgta agactatttt aaaagcattg   1620

ggaccaggag cgacactaga agaaatgatg acagcatgtc agggagtggg gggacccggc   1680

cataaagcaa gagttttggc tgaagcaatg agccaagtaa caaatccagc taccataatg   1740

atacagaaag gcaattttag gaaccaaaga aagactgtta agtgtttcaa ttgtggcaaa   1800

gaagggcaca tagccaaaaa ttgcagggcc cctaggaaaa agggctgttg gaaatgtgga   1860

aaggaaggac accaaatgaa agattgtact gagagacagg ctaatttttt agggaagatc   1920
```

```
tggccttccc acaagggaag gccagggaat tttcttcaga gcagaccaga gccaacagcc   1980
ccaccagaag agagcttcag gtttggggaa gagacaacaa ctccctctca gaagcaggag   2040
ccgatagaca aggaactgta tcctttagct tccctcagat cactctttgg cagcgacccc   2100
tcgtcacaat aaagataggg gggcaattaa aggaagctct attagataca ggagcagatg   2160
atacagtatt agaagaaatg aatttgccag gaagatggaa accaaaaatg atagggggaa   2220
ttggaggttt tatcaaagta ggacagtatg atcagatact catagaaatc tgcggacata   2280
aagctatagg tacagtatta gtaggaccta cacctgtcaa cataattgga agaaatctgt   2340
tgactcagat tggctgcact ttaaattttc ccattagtcc tattgagact gtaccagtaa   2400
aattaaagcc aggaatggat ggcccaaaag ttaaacaatg gccattgaca gaagaaaaaa   2460
taaaagcatt agtagaaatt tgtacagaaa tggaaaagga aggaaaaatt tcaaaaattg   2520
ggcctgaaaa tccatacaat actccagtat ttgccataaa gaaaaaagac agtactaaat   2580
ggagaaaatt agtagatttc agagaactta ataagagaac tcaagatttc tgggaagttc   2640
aattaggaat accacatcct gcagggttaa aacagaaaaa atcagtaaca gtactggatg   2700
tgggcgatgc atatttttca gttcccttag ataaagactt caggaagtat actgcattta   2760
ccatacctag tataaacaat gagacaccag ggattagata tcagtacaat gtgcttccac   2820
agggatggaa aggatcacca gcaatattcc agtgtagcat gacaaaaatc ttagagcctt   2880
ttagaaaaca aaatccagac atagtcatct atcaatacat ggatgatttg tatgtaggat   2940
ctgacttaga aatagggcag catagaacaa aaatagagga actgagacaa catctgttga   3000
ggtggggatt taccacacca gacaaaaaac atcagaaaga acctccattc ctttggatgg   3060
gttatgaact ccatcctgat aaatggacag tacagcctat agtgctgcca gaaaaggaca   3120
gctggactgt caatgacata cagaaattag tgggaaaatt gaattgggca agtcagattt   3180
atgcagggat taaagtaagg caattatgta aacttcttag gggaaccaaa gcactaacag   3240
aagtagtacc actaacagaa gaagcagagc tagaactggc agaaaacagg gagattctaa   3300
aagaaccggt acatggagtg tattatgacc catcaaaaga cttaatagca gaaatacaga   3360
agcaggggca aggccaatgg acatatcaaa tttatcaaga gccatttaaa aatctgaaaa   3420
caggaaaata tgcaagaatg aagggtgccc acactaatga tgtgaaacaa ttaacagagg   3480
cagtacaaaa aatagccaca gaaagcatag taatatgggg aaagactcct aaatttaaat   3540
tacccataca aaaggaaaca tgggaagcat ggtggacaga gtattggcaa gccacctgga   3600
ttcctgagtg ggagtttgtc aataccccto ccttagtgaa gttatggtac cagttagaga   3660
aagaacccat aataggagca gaaactttct atgtagatgg ggcagccaat agggaaacta   3720
aattaggaaa agcaggatat gtaactgaca gaggaagaca aaaagttgtc cccctaacgg   3780
acacaacaaa tcagaagact gagttacaag caattcatct agctttgcag gattcgggat   3840
tagaagtaaa catagtgaca gactcacaat atgcattggg aatcattcaa gcacaaccag   3900
ataagagtga atcagagtta gtcagtcaaa taatagagca gttaataaaa aaggaaaaag   3960
tctacctggc atgggtacca gcacacaaag gaattggagg aaatgaacaa gtagatgggt   4020
tggtcagtgc tggaatcagg aaagtactat ttttagatgg aatagataag gcccaagaag   4080
aacatgagaa atatcacagt aattggagag caatggctag tgattttaac ctaccacctg   4140
tagtagcaaa agaaatagta gccagctgtg ataaatgtca gctaaaaggg gaagccatgc   4200
atggacaagt agactgtagc ccaggaatat ggcagctaga ttgtacacat ttagaaggaa   4260
aagttatctt ggtagcagtt catgtagcca gtggatatat agaagcagaa gtaattccag   4320
```

```
cagagacagg gcaagaaaca gcatacttcc tcttaaaatt agcaggaaga tggccagtaa   4380
aaacagtaca tacagacaat ggcagcaatt tcaccagtac tacagttaag gccgcctgtt   4440
ggtgggcggg gatcaagcag gaatttggca ttccctacaa tccccaaagt caaggagtaa   4500
tagaatctat gaataaagaa ttaaagaaaa ttataggaca ggtaagagat caggctgaac   4560
atcttaagac agcagtacaa atggcagtat tcatccacaa ttttaaaaga aaaggggga   4620
ttggggggta cagtgcaggg gaaagaatag tagacataat agcaacagac atacaaacta   4680
aagaattaca aaaacaaatt acaaaaattc aaaattttcg ggtttattac agggacagca   4740
gagatccagt ttggaaagga ccagcaaagc tcctctggaa aggtgaaggg gcagtagtaa   4800
tacaagataa tagtgacata aaagtagtgc caagaagaaa agcaaagatc atcagggatt   4860
atggaaaaca gatggcaggt gatgattgtg tggcaagtag acaggatgag gattaacaca   4920
tggaaaagat tagtaaaaca ccatatgtat atttcaagga aagctaagga ctggttttat   4980
agacatcact atgaaagtac taatccaaaa ataagttcag aagtacacat cccactaggg   5040
gatgctaaat tagtaataac aacatattgg ggtctgcata caggagaaag agactggcat   5100
ttgggtcagg gagtctccat agaatggagg aaaaagagat atagcacaca agtagaccct   5160
gacctagcag accaactaat tcatctgcac tattttgatt gtttttcaga atctgctata   5220
agaaatacca tattaggacg tatagttagt cctaggtgtg aatatcaagc aggacataac   5280
aaggtaggat ctctacagta cttggcacta gcagcattaa taaaaccaaa acagataaag   5340
ccacctttgc ctagtgttag gaaactgaca gaggacagat ggaacaagcc ccagaagacc   5400
aagggccaca gagggagcca tacaatgaat ggacactaga gcttttagag gaacttaaga   5460
gtgaagctgt tagacatttt cctaggatat ggctccataa cttaggacaa catatctatg   5520
aaacttacgg ggatacttgg gcaggagtgg aagccataat aagaattctg caacaactgc   5580
tgtttatcca tttcagaatt gggtgtcgac atagcagaat aggcgttact cgacagagga   5640
gagcaagaaa tggagccagt agatcctaga ctagagccct ggaagcatcc aggaagtcag   5700
cctaaaactg cttgtaccaa ttgctattgt aaaaagtgtt gctttcattg ccaagtttgt   5760
ttcatgacaa aagccttagg catctcctat ggcaggaaga agcggagaca gcgacgaaga   5820
gctcatcaga acagtcagac tcatcaagct tctctatcaa agcagtaagt agtacatgta   5880
atgcaaccta taatagtagc aatagtagca ttagtagtag caataataat agcaatagtt   5940
gtgtggtcca tagtaatcat agaatatagg aaaatattaa gacaaagaaa aatagacagg   6000
ttaattgata gactaataga aagagcagaa gacagtggca atgagagtga aggagaagta   6060
tcagcacttg tggagatggg ggtggaaatg gggcaccatg ctccttggga tattgatgat   6120
ctgtagtgct acagaaaaat tgtgggtcac agtctattat ggggtacctg tgtggaagga   6180
agcaaccacc actctatttt gtgcatcaga tgctaaagca tatgatacag aggtacataa   6240
tgtttgggcc acacatgcct gtgtacccac agaccccaac ccacaagaag tagtattggt   6300
aaatgtgaca gaaaatttta acatgtggaa aaatgacatg gtagaacaga tgcatgagga   6360
tataatcagt ttatgggatc aaagcctaaa gccatgtgta aaattaaccc cactctgtgt   6420
tagtttaaag tgcactgatt tgaagaatga tactaatacc aatagtagta gcgggagaat   6480
gataatggag aaaggagaga taaaaaactg ctctttcaat atcagcacaa gcataagaga   6540
taaggtgcag aaagaatatg cattctttta taaacttgat atagtaccaa tagataatac   6600
cagctatagg ttgataagtt gtaacacctc agtcattaca caggcctgtc caaaggtatc   6660
```

```
ctttgagcca attcccatac attattgtgc cccggctggt tttgcgattc taaaatgtaa   6720
taataagacg ttcaatggaa caggaccatg tacaaatgtc agcacagtac aatgtacaca   6780
tggaatcagg ccagtagtat caactcaact gctgttaaat ggcagtctag cagaagaaga   6840
tgtagtaatt agatctgcca atttcacaga caatgctaaa accataatag tacagctgaa   6900
cacatctgta gaaattaatt gtacaagacc caacaacaat acaagaaaaa gtatccgtat   6960
ccagagggga ccagggagag catttgttac aataggaaaa ataggaaata tgagacaagc   7020
acattgtaac attagtagag caaaatggaa tgccacttta aaacagatag ctagcaaatt   7080
aagagaacaa tttggaaata ataaaacaat aatctttaag caatcctcag gaggggaccc   7140
agaaattgta acgcacagtt ttaattgtgg aggggaattt ttctactgta attcaacaca   7200
actgtttaat agtacttggt ttaatagtac ttggagtact gaagggtcaa ataacactga   7260
aggaagtgac acaatcacac tcccatgcag aataaaacaa tttataaaca tgtggcagga   7320
agtaggaaaa gcaatgtatg cccctcccat cagtggacaa attagatgtt catcaaatat   7380
tactgggctg ctattaacaa gagatggtgg taataacaac aatgggtccg agatcttcag   7440
acctggagga ggcgatatga gggacaattg gagaagtgaa ttatataaat ataaagtagt   7500
aaaaattgaa ccattaggag tagcacccac caaggcaaag agaagagtgg tgcagagaga   7560
aaaaagagca gtgggaatag gagctttgtt ccttgggttc ttgggagcag caggaagcac   7620
tatgggctgc acgtcaatga cgctgacggt acaggccaga caattattgt ctgatatagt   7680
gcagcagcag aacaatttgc tgagggctat tgaggcgcaa cagcatctgt tgcaactcac   7740
agtctggggc atcaaacagc tccaggcaag aatcctggct gtggaaagat acctaaagga   7800
tcaacagctc ctggggattt ggggttgctc tggaaaactc atttgcacca ctgctgtgcc   7860
ttggaatgct agttggagta ataaatctct ggaacagatt tggaataaca tgacctggat   7920
ggagtgggac agagaaatta acaattacac aagcttaata cactccttaa ttgaagaatc   7980
gcaaaaccag caagaaaaga atgaacaaga attattggaa ttagataaat gggcaagttt   8040
gtggaattgg tttaacataa caaattggct gtggtatata aaattattca taatgatagt   8100
aggaggcttg gtaggtttaa gaatagtttt tgctgtactt tctatagtga atagagttag   8160
gcagggatat tcaccattat cgtttcagac ccacctccca atcccgaggg gacccgacag   8220
gcccgaagga atagaagaag aaggtggaga gagagacaga gacagatcca ttcgattagt   8280
gaacggatcc ttagcactta tctgggacga tctgcggagc ctgtgcctct tcagctacca   8340
ccgcttgaga gacttactct tgattgtaac gaggattgtg gaacttctgg gacgcagggg   8400
gtgggaagcc ctcaaatatt ggtggaatct cctacagtat tggagtcagg aactaaagaa   8460
tagtgctgtt aacttgctca atgccacagc catagcagta gctgagggga cagatagggt   8520
tatagaagta ttacaagcag cttatagagc tattcgccac atacctagaa gaataagaca   8580
gggcttggaa aggattttgc tataagatgg gtggcaagtg gtcaaaaagt agtgtgattg   8640
gatggcctgc tgtaagggaa agaatgagac gagctgagcc agcagcagat ggggtgggag   8700
cagtatctcg agacctagaa aaacatggag caatcacaag tagcaataca gcagctaaca   8760
atgctgcttg tgcctggcta gaagcacaag aggaggaaga ggtgggtttt ccagtcacac   8820
ctcaggtacc tttaagacca atgacttaca aggcagctgt agatcttagc cactttttaa   8880
aagaaaaggg gggactggaa gggctaattc actcccaaag aagacaagat atccttgatc   8940
tgtggatcta ccacacacaa ggctacttcc ctgattggca gaactacaca ccagggccag   9000
gggtcagata tccactgacc tttggatggt gctacaagct agtaccagtt gagccagata   9060
```

```
aggtagaaga ggccaataaa ggagagaaca ccagcttgtt acaccctgtg agcctgcatg   9120

gaatggatga ccctgagaga gaagtgttag agtggaggtt tgacagccgc ctagcatttc   9180

atcacgtggc ccgagagctg catccggagt acttcaagaa ctgctgacat cgagcttgaa   9240

ttcactgtga gacatgggct aaagaggact aataacaagc taggccaaat tcctgtaaat   9300

cacttggggg gttataagaa aagcaagttc actatgacaa agcaaaatgt aaaggccaaa   9360

ttcctgtaaa tcacttgggg ggttataaga aaagcaagtt cactatgaca aagcaaaatg   9420

taaccgcaag tgctgacaga tgtaacagct gacatatcag ctgatgcttg ctcatgctga   9480

cactgtagct ctgagctgta tataaggaga agcttgctgc ttgcacttca gagttctagg   9540

agagtccctc ctagtctctc ctctccgagg aggtaccgag acctcaaaat aaaggagtga   9600

ttgccttact gccgagtgga gagtgattac tgagcggccg gtgtatcggg agtcgtccct   9660

taatctgtgc aataccagag cggctctcgc agctgc                             9696
```

<210> SEQ ID NO 3
<211> LENGTH: 458
<212> TYPE: DNA
<213> ORGANISM: Artificial Sequence
<220> FEATURE:
<223> OTHER INFORMATION: LTR CAEV

<400> SEQUENCE: 3

```
aattcactgt gagacatggg ctaaagagga ctaataacaa gctaggccaa attcctgtaa     60

atcacttggg gggttataag aaaagcaagt tcactatgac aaagcaaaat gtaaaggcca    120

aattcctgta aatcacttgg ggggttataa gaaaagcaag ttcactatga caaagcaaaa    180

tgtaaccgca agtgctgaca gatgtaacag ctgacatatc agctgatgct tgctcatgct    240

gacactgtag ctctgagctg tatataagga gaagcttgct gcttgcactt cagagttcta    300

ggagagtccc tcctagtctc tcctctccga ggaggtaccg agacctcaaa ataaaggagt    360

gattgcctta ctgccgagtg gagagtgatt actgagcggc cggtgtatcg ggagtcgtcc    420

cttaatctgt gcaataccag agcggctctc gcagctgc                            458
```

<210> SEQ ID NO 4
<211> LENGTH: 9972
<212> TYPE: DNA
<213> ORGANISM: Artificial Sequence
<220> FEATURE:
<223> OTHER INFORMATION: Genome retroviral

<400> SEQUENCE: 4

```
aattcactgt gagacatggg ctaaagagga ctaataacaa gctaggccaa attcctgtaa     60

atcacttggg gggttataag aaaagcaagt tcactatgac aaagcaaaat gtaaaggcca    120

aattcctgta aatcacttgg ggggttataa gaaaagcaag ttcactatga caaagcaaaa    180

tgtaaccgca agtgctgaca gatgtaacag ctgacatatc agctgatgct tgctcatgct    240

gacactgtag ctctgagctg tatataagga gaagcttgct gcttgcactt cagagttcta    300

ggagagtccc tcctagtctc tcctctccga ggaggtaccg agacctcaaa ataaaggagt    360

gattgcctta ctgccgagtg gagagtgatt actgagcggc cggtgtatcg ggagtcgtcc    420

cttaatctgt gcaataccag agcggctctc gcagctgggc gcctgaacag ggacttgaag    480

gagagtgaga gactcctgag tacggctgag tgaaggcagt aagggcggca ggaaccaacc    540

acgacggagt gctcctataa aggcgcgggt cggtaccaga cggcgtgagg agcgggagag    600
```

```
gaagaggcct ccggttgcag gtaagtgcaa cacaaaaaag aaatagctgt cttttatcca    660
ggaaggggta ataagataga gtgggagatg ggcgtgagaa actccgtctt gtcagggaag    720
aaagcagatg aattagaaaa aattaggcta cgacccaacg gaaagaaaaa gtacatgttg    780
aagcatgtag tatgggcagc aaatgaatta gatagatttg gattagcaga aagcctgttg    840
gagaacaaag aaggatgtca aaaaatactt tcggtcttag ctccattagt gccaacaggc    900
tcagaaaatt taaaaagcct ttataatact gtctgcgtca tctggtgcat tcacgcagaa    960
gagaaagtga aacacactga ggaagcaaaa cagatagtgc agagacacct agtggtggaa   1020
acaggaacaa cagaaactat gccaaaaaca agtagaccaa cagcaccatc tagcggcaga   1080
ggaggaaatt acccagtaca acaaataggt ggtaactatg tccacctgcc attaagcccg   1140
agaacattaa atgcctgggt aaaattgata gaggaaaaga aatttggagc agaagtagtg   1200
ccaggatttc aggcactgtc agaaggttgc acccccctatg acattaatca gatgttaaat   1260
tgtgtgggag accatcaagc ggctatgcag attatcagag atattataaa cgaggaggct   1320
gcagattggg acttgcagca cccacaacca gctccacaac aaggacaact tagggagccg   1380
tcaggatcag atattgcagg aacaactagt tcagtagatg aacaaatcca gtggatgtac   1440
agacaacaga accccatacc agtaggcaac atttacagga gatggatcca actggggttg   1500
caaaaatgtg tcagaatgta taacccaaca aacattctag atgtaaaaca agggccaaaa   1560
gagccatttc agagctatgt agacaggttc tacaaaagtt taagagcaga acagacagat   1620
gcagcagtaa agaattggat gactcaaaca ctgctgattc aaaatgctaa cccagattgc   1680
aagctagtgc tgaaggggct gggtgtgaat cccaccctag aagaaatgct gacggcttgt   1740
caaggagtag gggggccggg acagaaggct agattaatgg cagaagccct gaaagaggcc   1800
ctcgcaccag tgccaatccc ttttgcagca gcccaacaga ggggaccaag aaagccaatt   1860
aagtgttgga attgtgggaa agagggacac tctgcaaggc aatgcagagc cccaagaaga   1920
cagggatgct ggaaatgtgg aaaaatggac catgttatgg ccaaatgccc agacagacag   1980
gcgggttttt taggccttgg tccatgggga aagaagcccc gcaatttccc catggctcaa   2040
gtgcatcagg ggctgatgcc aactgctccc ccagaggacc cagctgtgga tctgctaaag   2100
aactacatgc agttgggcaa gcagcagaga gaaaagcaga gagaaagcag agagaagcct   2160
tacaaggagg tgacagagga tttgctgcac ctcaattctc tctttggagg agaccagtag   2220
tcactgctca tattgaagga cagcctgtag aagtattact ggatacaggg gctgatgatt   2280
ctattgtaac aggaatagag ttaggtccac attatacccc aaaaatagta ggaggaatag   2340
gaggttttat taatactaaa gaatacaaaa atgtagaaat agaagtttta ggcaaaagga   2400
ttaaagggac aatcatgaca ggggacaccc cgattaacat ttttggtaga aatttgctaa   2460
cagctctggg gatgtctcta aattttccca tagctaaagt agagcctgta aaagtcgcct   2520
taaagccagg aaaggatgga ccaaaattga agcagtggcc attatcaaaa gaaaagatag   2580
ttgcattaag agaaatctgt gaaaagatgg aaaaggatgg tcagttggag gaagctcccc   2640
cgaccaatcc atacaacacc cccacatttg ctataaagaa aaaggataag aacaaatgga   2700
gaatgctgat agattttagg gaactaaata gggtcactca ggactttacg gaagtccaat   2760
taggaatacc acaccctgca ggactagcaa aaaggaaaag aattacagta ctggatatag   2820
gtgatgcata tttctccata cctctagatg aagaatttag gcagtacact gcctttactt   2880
taccatcagt aaataatgca gagccaggaa aacgatacat ttataaggtt ctgcctcagg   2940
gatggaaggg gtcaccagcc atcttccaat acactatgag acatgtgcta gaacccttca   3000
```

```
ggaaggcaaa tccagatgtg accttagtcc agtatatgga tgacatctta atagctagtg   3060
acaggacaga cctggaacat gacagggtag ttttacagtc aaaggaactc ttgaatagca   3120
tagggttttc taccccagaa gagaaattcc aaaaagatcc cccatttcaa tggatggggt   3180
acgaattgtg gccaacaaaa tggaagttgc aaaagataga gttgccacaa agagagacct   3240
ggacagtgaa tgatatacag aagttagtag gagtattaaa ttgggcagct caaatttatc   3300
caggtataaa aaccaaacat ctctgtaggt taattagagg aaaaatgact ctaacagagg   3360
aagttcagtg gactgagatg gcagaagcag aatatgagga aaataaaata attctcagtc   3420
aggaacaaga aggatgttat taccaagaag gcaagccatt agaagccacg gtaataaaga   3480
gtcaggacaa tcagtggtct tataaaattc accaagaaga caaaatactg aaagtaggaa   3540
aatttgcaaa gataaagaat acacatacca atggagtgag actattagca catgtaatac   3600
agaaaatagg aaaggaagca atagtgatct ggggacaggt cccaaaattc cacttaccag   3660
ttgagaagga tgtatgggaa cagtggtgga cagactattg gcaggtaacc tggataccgg   3720
aatgggattt tatctcaaca ccaccgctag taagattagt cttcaatcta gtgaaggacc   3780
ctatagaggg agaagaaacc tattatacag atggatcatg taataaacag tcaaaagaag   3840
ggaaagcagg atatatcaca gataggggca aagacaaagt aaaagtgtta gaacagacta   3900
ctaatcaaca agcagaattg gaagcatttc tcatggcatt gacagactca gggccaaagg   3960
caaatattat agtagattca caatatgtta tgggaataat aacaggatgc cctacagaat   4020
cagagagcag gctagttaat caaataatag aagaaatgat taaaaagtca gaaatttatg   4080
tagcatgggt accagcacac aaaggtatag gaggaaacca agaaatagac cacctagtta   4140
gtcaagggat tagacaagtt ctcttcttgg aaaagataga gccagcacaa gaagaacatg   4200
ataaatacca tagtaatgta aaagaattgg tattcaaatt tggattaccc agaatagtgg   4260
ccagacagat agtagacacc tgtgataaat gtcatcagaa aggagaggct atacatgggc   4320
aggcaaattc agatctaggg acttggcaaa tggattgtac ccatctagag ggaaaaataa   4380
tcatagttgc agtacatgta gctagtggat tcatagaagc agaggtaatt ccacaagaga   4440
caggaagaca gacagcacta tttctgttaa aattggcagg cagatggcct attacacatc   4500
tacacacaga taatggtgct aactttgctt cgcaagaagt aaagatggtt gcatggtggg   4560
cagggataga gcacaccttt ggggtaccat acaatccaca gagtcaggga gtagtggaag   4620
caatgaatca ccacctgaaa aatcaaatag atagaatcag ggaacaagca aattcagtag   4680
aaaccatagt attaatggca gttcattgca tgaattttaa aagaagggga ggaatagggg   4740
atatgactcc agcagaaaga ttaattaaca tgatcactac agaacaagag atacaatttc   4800
aacaatcaaa aaactcaaaa tttaaaaatt ttcgggtcta ttacagagaa ggcagagatc   4860
aactgtggaa gggacccggt gagctattgt ggaaagggga aggagcagtc atcttaaagg   4920
tagggacaga cattaaggta gtacccagaa gaaaggctaa aattatcaaa gattatggag   4980
gaggaaaaga ggtggatagc agttcccaca tggaggatac cggagaggct agagaggtgg   5040
catagcctca taaaatatct gaaatataaa actaaagatc tacaaaaggt ttgctatgtg   5100
ccccatttta aggtcggatg ggcatggtgg acctgcagca gagtaatctt cccactacag   5160
gaaggaagcc atttagaagt acaagggtat tggcatttga caccagaaaa agggtggctc   5220
agtacttatg cagtgaggat aacctggtac tcaaagaact tttggacaga tgtaacacca   5280
aactatgcag acattttact gcatagcact tatttccctt gctttacagc gggagaagtg   5340
```

```
agaagggcca tcaggggaga acaactgctg tcttgctgca ggttcccgag agctcataag   5400
taccaggtac caagcctaca gtacttagca ctgaaagtag taagcgatgt cagatcccag   5460
ggagagaatc ccacctggaa acagtggaga agagacaata ggagaggcct tcgaatggct   5520
aaacagaaca gtagaggaga taaacagaga ggcggtaaac cacctaccaa gggagctaat   5580
tttccaggtt tggcaaaggt cttgggaata ctggcatgat gaacaaggga tgtcaccaag   5640
ctatgtaaaa tacagatact tgtgtttaat acaaaaggct ttatttatgc attgcaagaa   5700
aggctgtaga tgtctagggg aaggacatgg ggcagggggga tggagaccag gacctcctcc   5760
tcctccccct ccaggactag cataaatgga agaaagacct ccagaaaatg aaggaccaca   5820
aagggaacca tgggatgaat gggtagtgga ggttctggaa gaactgaaag aagaagcttt   5880
aaaacatttt gatcctcgct tgctaactgc acttggtaat catatctata atagacatgg   5940
agacaccctt gagggagcag gagaactcat tagaatcctc caacgagcgc tcttcatgca   6000
tttcagaggc ggatgcatcc actccagaat cggccaacct gggggaggaa atcctctctc   6060
agctataccg ccctctagaa gcatgctata acacatgcta ttgtaaaaag tgttgctacc   6120
attgccagtt ttgttttctt aaaaaaggct tggggatatg ttatgagcaa tcacgaaaga   6180
gaagaagaac tccgaaaaag gctaaggcta atacatcttc tgcatcaaac aagtaagtat   6240
gggatgtctt gggaatcagc tgcttatcgc catcttgctt ttaagtgtct atgggatcta   6300
ttgtactcta tatgtcacag tcttttatgg tgtaccagct tggaggaatg cgacaattcc   6360
cctcttttgt gcaaccaaga atagggatac ttggggaaca actcagtgcc taccagataa   6420
tggtgattat tcagaagtgg cccttaatgt tacagaaagc tttgatgcct ggaataatac   6480
agtcacagaa caggcaatag aggatgtatg gcaactcttt gagacctcaa taaagccttg   6540
tgtaaaatta tccccattat gcattactat gagatgcaat aaaagtgaga cagatagatg   6600
gggattgaca aaatcaataa caacaacagc atcaacaaca tcaacgacag catcagcaaa   6660
agtagacatg gtcaatgaga ctagttcttg tatagcccag gataattgca caggcttgga   6720
acaagagcaa atgataagct gtaaattcaa catgacaggg ttaaaaagag acaagaaaaa   6780
agagtacaat gaaacttggt actctgcaga tttggtatgt gaacaaggga ataacactgg   6840
taatgaaagt agatgttaca tgaaccactg taacacttct gttatccaag agtcttgtga   6900
caaacattat tgggatgcta ttagatttag gtattgtgca cctccaggtt atgctttgct   6960
tagatgtaat gacacaaatt attcaggctt tatgcctaaa tgttctaagg tggtggtctc   7020
ttcatgcaca aggatgatgg agacacagac ttctacttgg tttggcttta atggaactag   7080
agcagaaaat agaacttata tttactggca tggtagggat aataggacta taattagttt   7140
aaataagtat tataatctaa caatgaaatg tagaagacca ggaaataaga cagttttacc   7200
agtcaccatt atgtctggat tggttttcca ctcacaacca atcaatgata ggccaaagca   7260
ggcatggtgt tggtttggag gaaaatggaa ggatgcaata aaagaggtga agcagaccat   7320
tgtcaaacat cccaggtata ctggaactaa caatactgat aaaatcaatt tgacggctcc   7380
tggaggagga gatccggaag ttaccttcat gtggacaaat tgcagaggag agttcctcta   7440
ctgtaaaatg aattggtttc taaattgggt agaagatagg aatacagcta accagaagcc   7500
aaaggaacag cataaaagga attacgtgcc atgtcatatt agacaaataa tcaacacttg   7560
gcataaagta ggcaaaaatg tttatttgcc tccaagagag ggagacctca cgtgtaactc   7620
cacagtgacc agtctcatag caaacataga ttggattgat ggaaaccaaa ctaatatcac   7680
catgagtgca gaggtggcag aactgtatcg attggaattg ggagattata aattagtaga   7740
```

```
gatcactcca attggcttgg cccccacaga tgtgaagagg tacactactg gtggcacctc   7800
aagaaataaa agaggggtct ttgtgctagg gttcttgggt tttctcgcaa cggcaggttc   7860
tgcaatgggc gcggcgtcgt tgacgctgac cgctcagtcc cgaactttat tggctgggat   7920
agtgcagcaa cagcaacagc tgttggacgt ggtcaagaga caacaagaat tgttgcgact   7980
gaccgtctgg ggaacaaaga acctccagac tagggtcact gccatcgaga agtacttaaa   8040
ggaccaggcg cagctgaatg cttggggatg tgcgtttaga caagtctgcc acactactgt   8100
accatggcca aatgcaagtc taacaccaaa gtggaacaat gagacttggc aagagtggga   8160
gcgaaaggtt gacttcttgg aagaaaatat aacagccctc ctagaggagg cacaaattca   8220
acaagagaag aacatgtatg aattacaaaa gttgaatagc tgggatgtgt ttggcaattg   8280
gtttgacctt gcttcttgga taaagtatat acaatatgga gtttatatag ttgtaggagt   8340
aatactgtta agaatagtga tctatatagt acaaatgcta gctaagttaa ggcaggggta   8400
taggccagtg ttctcttccc caccctctta tttccagcag acccatatcc aacaggaccc   8460
ggcactgcca accagagaag gcaaagaaag agacggtgga gaaggcggtg gcaacagctc   8520
ctggccttgg cagatagaat atattcattt cctgatccgc caactgatac gcctcttgac   8580
ttggctattc agcaactgca gaaccttgct atcgagagta taccagatcc tccaaccaat   8640
actccagagg ctctctgcga ccctacagag gattcgagaa gtcctcagga ctgaactgac   8700
ctacctacaa tatgggtgga gctatttcca tgaggcggtc caggccgtct ggagatctgc   8760
gacagagact cttgcgggcg cgtggggaga cttatgggag actcttagga gaggtggaag   8820
atggatactc gcaatcccca ggaggattag acaagggctt gagctcactc tcttgtgagg   8880
gacagaaata caatcaggga cagtatatga atactccatg gagaaaccca gctgaagaga   8940
gagaaaaatt agcatacaga aaacaaaata tggatgatat agatgagtaa gatgatgact   9000
tggtaggggt atcagtgagg ccaaaagttc ccctaagaac aatgagttac aaattggcaa   9060
tagacatgtc tcattttata aaagaaaagg ggggactgga agggatttat tacagtgcaa   9120
gaagacatag aatcttagac atatacttag aaaaggaaga aggcatcata ccagattggc   9180
aggattacac ctcaggacca ggaattagat acccaaagac atttggctgg ctatggaaat   9240
tagtccctgt aaatgtatca gatgaggcac aggaggatga ggagcattat ttaatgcatc   9300
cagctcaaac ttcccagtgg gatgaccctt ggggagaggt tctagcatgg aagtttgatc   9360
caactctggc ctacacttat gaggcatatg ttagataccc agaagagttt ggaagcaagt   9420
caggcctgtc agaggaagag gttagaagaa ggctaaccgc aagaggcctt cttaacatgg   9480
ctgacaagaa ggaaactcgc tgaaacagca gggacaattc actgtgagac atgggctaaa   9540
gaggactaat aacaagctag gccaaattcc tgtaaatcac ttgggggtt ataagaaaag    9600
caagttcact atgacaaagc aaaatgtaaa ggccaaattc ctgtaaatca cttgggggt    9660
tataagaaaa gcaagttcac tatgacaaag caaaatgtaa ccgcaagtgc tgacagatgt   9720
aacagctgac atatcagctg atgcttgctc atgctgacac tgtagctctg agctgtatat   9780
aaggagaagc ttgctgcttg cacttcagag ttctaggaga gtccctccta gtctctcctc   9840
tccgaggagg taccgagacc tcaaaataaa ggagtgattg ccttactgcc gagtggagag   9900
tgattactga gcggccggtg tatcgggagt cgtcccttaa tctgtgcaat accagagcgg   9960
ctctcgcagc tg                                                      9972
```

<210> SEQ ID NO 5

<211> LENGTH: 10001
<212> TYPE: DNA
<213> ORGANISM: Artificial Sequence
<220> FEATURE:
<223> OTHER INFORMATION: Genome retroviral

<400> SEQUENCE: 5

```
aattcactgt gagacatggg ctaaagagga ctaataacaa gctaggccaa attcctgtaa     60
atcacttggg gggttataag aaaagcaagt tcactatgac aaagcaaaat gtaaaggcca    120
aattcctgta aatcacttgg ggggttataa gaaaagcaag ttcactatga caaagcaaaa    180
tgtaaccgca agtgctgaca gatgtaacag ctgacatatc agctgatgct tgctcatgct    240
gacactgtag ctctgagctg tatataagga gaagcttgct gcttgcactt cagagttcta    300
ggagagtccc tcctagtctc tcctctccga ggaggtaccg agacctcaaa ataaaggagt    360
gattgcctta ctgccgagtg gagagtgatt actgagcggc cggtgtatcg ggagtcgtcc    420
cttaatctgt gcaataccag agcggctctc gcagctgggc gcccgaacag ggacttgaag    480
aagactgaga agccttggaa cacggctgag tgaaggcagt aagggcggca ggaacaaacc    540
acgacggagt gctcctagaa aagcgcaggc cgaggtacca agggcggcgt gtggagcggg    600
agtgaaagag gcctccgggt gaaggtaagt gcctacacca aatacagtag ccagaagggc    660
ttgttatcct acctttagac gggtagaaga ttgtgggaga tgggcgcgag aaactccgtc    720
ttgagaggga aaaaagcaga cgaattagaa aagattaggt tacggcccgg cggaaagaaa    780
aaatataggc taaaacatat tgtgtgggca gcgaatgaat tggacagatt cggattggca    840
gagagcctgt tggagtcaaa agagggttgc caaaaaattc ttacagtttt agatccatta    900
gtaccgacag ggtcagaaaa tttaaaaagc ctttttaata ctgtctgcgt catttggtgt    960
atacacgcag aagagaaagc gaaagatact gaagaagcaa aacaaaaggt acagagacat   1020
ctagtggcag aaacaaaaac tacagaaaaa atgccaagta caagtagacc aacagcacca   1080
cctagcggga acggaggaaa cttccccgta caacaagtgg ccggcaacta tacccatgtg   1140
ccactaagtc cccgaaccct aaatgcttgg gtaaaactag tagaggaaaa gaagttcggg   1200
gcagaagtag tgccaggatt tcaggcactc tcagaaggct gcacgcccta tgatattaat   1260
caaatgctta attgtgtggg cgaccatcaa gcagctatgc aaataatcag ggaaattatt   1320
aatgaagaag cagcagattg ggacgcacaa cacccaatac caggcccctt accagcgggg   1380
cagctcaggg agccaagggg atctgacata gcagggacaa caagcacagt agaagagcag   1440
atccagtgga tgtttaggcc acaaaatcct gtaccagtag gaagcatcta tagaagatgg   1500
atccagatag ggctacagaa gtgcgtcagg atgtacaacc caaccaacat cctagacata   1560
aaacagggac caaaggagcc attccagagt tatgtagata gattctacaa gagcttgagg   1620
gcagaacaaa cagatccagc agtaaaaaat tggatgaccc aaacactgct agtgcagaat   1680
gccaacccag actgtaagtt agtactaaaa ggactaggga taaatcctac cttagaagaa   1740
atgctaaccg cctgtcaggg ggtaggtgga ccaggccaga aagccagatt aatggcagaa   1800
gccttaaagg aggccatggc accagccccc atcccatttg cagcagccca acagagaagg   1860
acaattaagt gctggaattg cggaaaggaa gggcactcgg caagacaatg ccgagcacct   1920
agaagacaag gctgctggaa atgtggcaag gcaggacaca tcatggcaaa atgcccagaa   1980
agacaggcgg gtttttttagg gttgggccca tggggaaaga agccccgcaa tttccctgtg   2040
gcccaaatcc cgcaggggct gacaccaaca gcacccccga tagacccagt agaggaccta   2100
ctagagaagt acatgcagca agggaaaagg cagagagagc agagagagag gccatacaaa   2160
```

```
gaagtgacag aggacttcct gcagctcgag aaacaagaga caccatgcag agagacgaca   2220
gaggacttgc tgcacctcaa ttctctcttt ggaaaagacc agtagtcaca gcacatgttg   2280
agggccagcc agtagaagtt ttgctagaca caggggctga cgactcaata gtagcaggcg   2340
tagagttagg gagcaattat agtccaaaga tagtaggggg aatagggga ttcataaata    2400
ccaaagaata taaaaatgta gaaataagag tattaaataa aagagtaaga gccaccataa   2460
tgacaggtga taccccaatc aacatttttg gcagaaacat tctgacagcc ttaggcatgt   2520
cattaaatct accagtcgcc aagatagaac caataaaaat aatgctgaag ccaggaaagg   2580
atggaccaaa actgagacaa tggcccttaa caaaagaaaa aatagaggca ctaaaagaga   2640
tctgtgagaa aatggaaaga gagggccagc tagaggaggc acctccaact aatccttata   2700
atacccccac atttgcaatc aagaaaaagg acaaaaacaa atggagaatg ctaatagatt   2760
ttagagaact aaacaaggta actcaagact tcacagaaat ccagttagga attccacacc   2820
cagcaggact agccaagaag aaacgaatta ctgtcctaga tgtaggggat gcttactttt   2880
ccataccact acatgaggat tttagacagt atactgcatt tactctacca tcaataaaca   2940
atgctgaacc aggaaaaaga tacatatata aagtctcacc acagggatgg aagggatcac   3000
cagcaatttt tcagtacaca atgaggcagg tcttagaacc attcagaaaa gcaaacccgg   3060
atatcattct cattcagtac atggatgata tcttgatagc cagcgacagg acagatttag   3120
aacatgacag agtggttctg cagctaaagg aacttctaaa tggcctggga ttttccaccc   3180
cagatgagaa gttccaaaaa gaccctccat accaatggat gggctatgaa ctgtggccaa   3240
ctaaatggaa gctgcaaaga atacaattgc cccaaaagga agtatggaca gtcaatgaca   3300
tccaaaaact ggtgggtgtc ctaaattggg cagcacaaat ctacccaggg ataaagacca   3360
gaaacttatg taggttaatc agaggaaaaa tgacactcac agaagaggta cagtggacag   3420
aattagcaga agcggaacta gaagaaaaca aaatcatctt aagccaggaa caagaaggat   3480
gctattacca agaggaaaag gagctagaag caacagtcca aaaagatcaa gacaatcagt   3540
ggacatataa gatacaccag ggaggaaaaa ttctaaaagt aggaaaatat gcaaaggtaa   3600
aaaataccca caccaacgga gtcagactcc tagcacaagt agttcaaaaa ataggaaaag   3660
aagcactagt catttgggga cgaataccaa aatttcacct accagtagaa agagatacct   3720
gggaacagtg gtgggataac tactggcaag tgacatggat cccagactgg gacttcatat   3780
ctaccccgcc actggtcaga ttagtattta acctggtgaa agatcccata ctaggcgcag   3840
aaaccttcta cacagatgga tcctgcaata agcaatcaag agaaggaaaa gcaggataca   3900
taacagatag aggaagagac aaggtgaggc tattagagca aaccaccaat cagcaagcag   3960
aattagaagc ctttgcgatg gcagtaacag actcaggtcc aaaggccaac attatagtag   4020
actcacaata tgtaatggga atagtagcag gccaaccaac agagtcagag agtaaaatag   4080
taaatcaaat catagaagaa atgataaaaa aggaagcaat ctatgttgca tgggtcccag   4140
cccataaagg cataggagga aatcaggagg tagatcactt agtaagtcag ggcatcagac   4200
aagtattatt cctagagaaa atagaacccg ctcaggagga acatgaaaaa tatcatagca   4260
atgtaaaaga actatcccat aaatttggac tgcccaaatt agtggcaaga caaatagtaa   4320
acacatgcac ccaatgtcag cagaaagggg aggctataca tgggcaagta aatgcagaat   4380
taggcacttg gcaaatggac tgcacacact tagaaggaaa aatcattata gtagcagtac   4440
atgttgcaag tggatttata gaagcagaag tcatcccaca ggaatcagga aggcaaacgg   4500
```

```
cactcttcct actaaaactg gccagtaggt ggccaataac acatttgcac acagacaatg   4560
gtgccaactt cacttcacag gaagtaaaga tggtggcatg gtggataggt atagaacaat   4620
ccttcggagt accttacaat ccacaaagcc aaggagtagt ggaagcaatg aatcaccacc   4680
taaaaaatca gataagcaga attagagagc aggcaaacac agtagaaaca atagtactaa   4740
tggcagttca ttgcatgaat tttaaaagga ggggaggaat aggggatatg accccagcag   4800
aaagactaat caatatggtc actgcagaac aggaaataca attcctccaa gcaaaaaatt   4860
caaaattaca aaattttcgg gtctatttca gagaaggcag agatcagctg tggaaaggac   4920
ctggggaact actgtggaag gggacggag cagtcatagt caaggtaggg gctgacataa   4980
aaataatacc aagaaggaaa gctaagatca tcaaagacta tggaggaagg caagagatgg   5040
atagcggttc caacttggag ggtgccaggg aggatggaga ggtggcatag ccttatcaag   5100
tatctaaaat acagaacagg agatctagag aaggtgtgct atgttcccca ccataaggtg   5160
ggatgggcgt ggtggacttg cagcagggta atattcccat taaaaggaga aagtcatctg   5220
gagatacagg catactggaa cctaacacca gaaaaaggat ggctctcctc ctattcagta   5280
agactaactt ggtatacaga aaaattctgg acagatgtta ccccagactg tgcggactcc   5340
ctaatacata gcacttattt ctcttgcttt acggcaggcg aagtaagaag agccatcaga   5400
ggggaaaagc tattatcctg ctgcaactac ccccaagccc ataagtacca ggtaccgtca   5460
ctccagtttc tggccttagt ggtagtgcaa caaaatggca ggccccagag agacaatacc   5520
accaggaaac agtggcgaag aaactatcgg agaggccttc gagtggctag acaggacggt   5580
agaagccata aacagagagg cagtgaacca cctgccccga gagcttattt tccaggtgtg   5640
gcaaaggtcc tggagatact ggcatgatga acaaggaatg tcaataagtt acacaaagta   5700
tagatatttg tgcctaatgc agaaagctat gttcatacat tctaagagag ggtgcacttg   5760
cctgggggga ggacatgggc cgggaggatg gagatcagga cctccccctc ctccccctcc   5820
aggtctagtc taatgactga agcaccaaca gagtctcccc cggaggatag gaccccaccg   5880
agggagccag ggatgagtg ggtaatagaa accctgagag agataaaata agaagcttta   5940
aagcactttg accctcgctt gctaattact cttggcaact atatctatgc tagacatgga   6000
gacacccttg aaggcgccag agggctcatt aggatcctac aacgagccct cctcttgcac   6060
ttcagagcag gatgcggccg ctcaaggatt ggtcagccca ggggacgaaa tcctttatca   6120
gctataccaa cccctagagg catgcgataa caaatgttac tgtaaaaagt gctgctacca   6180
ttgccagatg tgttttttaa acaaggggct cgggatatgg tatgaacgaa agggcagaag   6240
aagaagaact ccgaagaaaa ctaaggctca ttcgtcttct gcatcagaca agtgagtaag   6300
atgtgtggta ggaatcaact atttgttgcc agcttgctag ctagtgcttg cttaatatat   6360
tgcgtccaat atgtgactgt tttctatggc gtgcccgtgt ggagaaatgc atccattccc   6420
ctcttttgtg caactaaaaa tagagatact tggggaacca tacagtgctt gccagacaat   6480
gatgactatc aggaaatagc tttaaatgtg acagaggcct tcgacgcatg gaataataca   6540
gtaacagaac aagcagtaga agatgtctgg agtctatttg agacatcaat aaaaccatgc   6600
gtcaaactaa caccccttatg tgtagcaatg cgttgtaaca gcacaactgc aaaaaacaca   6660
acctccacac caacaaccac cacaacagca aacacaacaa taggagagaa ttcttcatgc   6720
atacgcacag acaactgcac agggttggga gaagaagaga tggtcgactg tcagttcaat   6780
atgacaggat tagagaggga taagaaaaaa ctatataatg aaacatggta ctcaaaagat   6840
gtagtctgtg aatcaaatga caccaagaaa gagaaaacat gttacatgaa ccactgcaac   6900
```

```
acatcagtca tcacagagtc atgtgacaag cactattggg atactatgag gtttagatat   6960
tgtgcaccac cgggttttgc cctgctaaga tgcaatgata ccaattattc aggctttgag   7020
cccaattgtt ctaaggtagt agctgctaca tgtacaagga tgatggaaac gcaaacctcc   7080
acttggtttg gctttaatgg cactagggca gaaaatagaa catatatcta ttggcatggt   7140
agggataata gaactatcat tagcttaaac aagttttata atctcaccgt acattgtaag   7200
aggccaggaa acaagacagt tgtaccaata acactcatgt cagggttagt gtttcactcc   7260
cagccaatca atagaagacc caggcaagca tggtgctggt tcaaaggcga gtggaaggaa   7320
gccatgaagg aggtgaagct aacccttgca aaacatccca ggtataaagg aaccaacgac   7380
acagaaaaaa ttcgttttat agcgccagga gaacgctcag acccagaagt ggcatacatg   7440
tggactaact gcagaggaga atttctctac tgcaatatga cttggttcct caattgggta   7500
gaaaacagaa cgaatcagac acagcacaat tatgtgccat gccatataaa gcaaataatt   7560
aatacctggc acaaggtagg gaaaaatgta tatttgcctc ctagggaagg acagttaacc   7620
tgcaactcta cagtgaccag cataattgct aacattgacg gaggagagaa ccagacaaat   7680
attaccttta gtgcagaggt ggcagaacta taccgattag aattggggga ttataaattg   7740
atagaagtaa caccaattgg ctttgcacct acaccagtaa aagatactcc ctctgctcca   7800
gtgaggaata aaagaggtgt attcgtgcta gggttcttag gttttctcac gacagcagga   7860
gctgcaatgg gcgcggcgtc cttgacgctg tcggctcagt ctcggacttt attggccggg   7920
atagtgcagc aacagcaaca gctgttggac gtggtcaaga gacaacaaga aatgttgcga   7980
ctgaccgtct ggggaacaaa aaatctccag gcaagagtca ctgctatcga gaaatactta   8040
aaggaccagg cgcaactaaa ttcatgggga tgtgcgttta gacaagtctg ccacactact   8100
gtaccatggg taaatgacac cttaacgcct gattggaaca acatgacatg gcaggaatgg   8160
gagcaacgaa tccgcaacct agaggcaaat atcagtgaaa gtttagaaca ggcacaaatc   8220
cagcaagaaa agaacatgta tgaactacaa aaattaaata gctgggatgt ttttggcaac   8280
tggtttgatt taacctcctg gatcaaatat attcagtatg gagtttatat agtagtagga   8340
ataatagttt taagaatagt aatatatgta gtacaaatgt taagtagact tagaaagggc   8400
tataggcctg ttttctcttc cccccccgct tacttccaac agatccatat ccacaaggac   8460
cgggaacagc cagccagaga agaaacagaa gaagacgttg gaaacagcgt tggagacaat   8520
tggtggccct ggccgataag atatatacat ttcctgatcc gccagctgat tcgcctcttg   8580
aacagactat acaacatctg cagggactta ctatccagga gcttccagac cctccaacta   8640
atctcccaga gtcttcggag agcattgaca gcagtcagag actggctgag atttaacaca   8700
gcctacctgc aatatggggg cgagtggatc caagaagcgt tccgagcctt cgcgagggct   8760
acgggagaga ctcttacaaa cgcctggaga ggcttctggg ggacactggg acaaattggg   8820
aggggaatac ttgcagtccc aagaaggatc aggcaggggg cagaaatcgc cctcctgtga   8880
gggacggcgg tatcaacagg gagattttat gaatacccca tggagagccc cagcagaagg   8940
ggagaaaggc tcgtacaagc aacaaaatat ggatgatgta gattcagatg atgatgacct   9000
agtaggggtc cctgtcacac caagagtacc attaagagaa atgacatata ggttggcaag   9060
agatatgtca catttgataa aagaaaaggg gggactggaa gggctgtatt acagtgatag   9120
gagacgtaga gtcctagaca tatacttaga aaaggaagag ggaataattg gagactggca   9180
gaactatact catggaccag gagtaaggta tccaaagttc tttgggtggt tatggaagct   9240
```

```
agtaccagta gatgtcccac aagagggaga tgacagtgag actcactgct tagtgcatcc   9300
agcacaaaca agcaggtttg atgacccgca tggagaaaca ttagtttgga ggtttgaccc   9360
cacgctagct tttagctacg aggcctttat tcgataccca gaggagtttg ggtacaagtc   9420
aggcctgcca gaggatgaat ggaaggcaag actgaaagca agagggatac cgtttagcta   9480
aaaacaggaa cagctatact tggtcagggc aggaagtaac taacagaaaa cagctgagac   9540
tgcaaattca ctgtgagaca tgggctaaag aggactaata acaagctagg ccaaattcct   9600
gtaaatcact tgggggggtta taagaaaagc aagttcacta tgacaaagca aaatgtaaag   9660
gccaaattcc tgtaaatcac ttgggggggtt ataagaaaag caagttcact atgacaaagc   9720
aaaatgtaac cgcaagtgct gacagatgta acagctgaca tatcagctga tgcttgctca   9780
tgctgacact gtagctctga gctgtatata aggagaagct tgctgcttgc acttcagagt   9840
tctaggagag tccctcctag tctctcctct ccgaggaggt accgagacct caaaataaag   9900
gagtgattgc cttactgccg agtggagagt gattactgag cggccggtgt atcgggagtc   9960
gtcccttaat ctgtgcaata ccagagcggc tctcgcagct g                     10001
```

```
<210> SEQ ID NO 6
<211> LENGTH: 9675
<212> TYPE: DNA
<213> ORGANISM: Artificial Sequence
<220> FEATURE:
<223> OTHER INFORMATION: Genome retroviral

<400> SEQUENCE: 6

aattcactgt gagacatggg ctaaagagga ctaataacaa gctaggccaa attcctgtaa     60
atcacttggg gggttataag aaaagcaagt tcactatgac aaagcaaaat gtaaaggcca    120
aattcctgta aatcacttgg ggggttataa gaaaagcaag ttcactatga caaagcaaaa    180
tgtaaccgca agtgctgaca gatgtaacag ctgacatatc agctgatgct tgctcatgct    240
gacactgtag ctctgagctg tatataagga gaagcttgct gcttgcactt cagagttcta    300
ggagagtccc tcctagtctc tcctctccga ggaggtaccg agacctcaaa ataaaggagt    360
gattgcctta ctgccgagtg gagagtgatt actgagcggc cggtgtatcg ggagtcgtcc    420
cttaatctgt gcaataccag agcggctctc gcagctgggc gcccgaacag ggacttgatt    480
gagagtgatt gaggaagtga agctagagca atagaaagct gttaagcaga actcctgctg    540
acctaaatag ggaagcagta gcagacgctg ctaacagtga gtatctctag tgaagcggac    600
tcgagctcat aatcaagtca ttgtttaaag gcccagataa attacatctg gtgactcttc    660
gcggaccttc aagccaggag attcgccgag ggacagtcaa caaggtagga gagattctac    720
agcaacatgg ggaatggaca ggggcgagat tggaaaatgg ccattaagag atgtagtaat    780
gttgctgtag gagtaggggg gaagagtaaa aaatttggag aagggaattt cagatgggcc    840
attagaatgg ctaatgtatc tacaggacga gaacctggtg atataccaga gactttagat    900
caactaaggt tggttatttg cgatttacaa gaaagaagag aaaaatttgg atctagcaaa    960
gaaattgata tggcaattgt gacattaaaa gtctttgcgg tagcaggact tttaaatatg   1020
acggtgtcta ctgctgctgc agctgaaaat atgtattctc aaatgggatt agacactagg   1080
ccatctatga aagaagcagg tggaaaagag gaaggccctc cacaggcata tcctattcaa   1140
acagtaaatg gagtaccaca atatgtagca cttgacccaa aaatggtgtc catttttatg   1200
gaaaaggcaa gagaaggact aggaggtgag gaagttcaac tatggtttac tgccttctct   1260
gcaaatttaa cacctactga catggccaca ttaataatgg ccgcaccagg gtgcgctgca   1320
```

```
gataaagaaa tattggatga aagcttaaag caactgacag cagaatatga tcgcacacat   1380
ccccctgatg ctcccagacc attaccctat tttactgcag cagaaattat gggtatagga   1440
ttaactcaag aacaacaagc agaagcaaga tttgcaccag ctaggatgca gtgtagagca   1500
tggtatctcg aggcattagg aaaattggct gccataaaag ctaagtctcc tcgagctgtg   1560
cagttaagac aaggagctaa ggaagattat tcatccttta tagacagatt gtttgcccaa   1620
atagatcaag aacaaaatac agctgaagtt aagttatatt taaaacagtc attgagcata   1680
gctaatgcta atgcagactg taaaaaggca atgagccacc ttaagccaga aagtacccta   1740
gaagaaaagt tgagagcttg tcaagaaata ggctcaccag gatataaaat gcaactcttg   1800
gcagaagctc ttacaaaagt tcaagtagtg caatcaaaag gatcaggacc agtgtgtttt   1860
aattgtaaaa aaccaggaca tctagcaaga caatgtagag aagtgaaaaa atgtaataaa   1920
tgtggaaaac ctggtcatgt agctgccaaa tgttggcaag gaaatagaaa gaattcggga   1980
aactggaagg cggggcgagc tgcagcccca gtgaatcaaa tgcagcaagc agtaatgcca   2040
tctgcacctc caatggagga gaaactattg gatttataaa ttataataaa gtaggtacta   2100
ctacaacatt agaaaagagg ccagaaatac tcatatttgt aaatggatat cctataaaat   2160
ttttattaga cacaggagca gatataacaa ttttaaatag gagagatttt caagtaaaaa   2220
attctataga aaatggaagg caaaatatga ttggagtagg aggaggaaag agaggaacaa   2280
attatattaa tgtacattta gagattagag atgaaaatta taagacacaa tgtatatttg   2340
gtaatgtttg tgtcttagaa gataactcat taatacaacc attattaggg agagataata   2400
tgattaaatt caatattagg ttagtaatgg ctcaaatttc tgataagatt ccagtagtaa   2460
aagtaaaaat gaaggatcct aataaaggac ctcaaataaa acaatggcca ttaacaaatg   2520
aaaaaattga agccttaaca gaaatagtag aaagactaga aagagaaggg aaagtaaaaa   2580
gagcagatcc aaataatcca tggaatacac cagtatttgc tataaaaaag aaaagtggaa   2640
aatggagaat gctcatagat tttagagaat taaacaaact aactgagaaa ggagcagagg   2700
tccagttggg actacctcat cctgctggtt tacaaataaa aaaacaagta acagtattag   2760
atatagggga tgcatatttc accattcctc ttgatccaga ttatgctcct tatacagcat   2820
ttactttacc tagaaaaaat aatgcgggac caggaaggag atttgtgtgg tgtagtctac   2880
cacaaggctg gattttaagt ccattgatat atcaaagtac attagataat ataatacaac   2940
cttttattag acaaaatcct caattagata tttaccaata tatggatgac atttatatag   3000
gatcaaattt aagtaaaaag gagcataaag aaaaggtaga agaattaaga aaattactat   3060
tatggtgggg atttgaaact ccagaagata aattacagga agaacccccca tatacatgga   3120
tgggttatga attacatcca ttaacatgga caatacaaca gaaacagtta gacattccag   3180
aacagcccac tctaaatgag ttgcaaaaat tagcaggaaa aattaattgg gctagccaag   3240
ctattccaga cttgagtata aaagcattaa ctaacatgat gagaggaaat caaaacctaa   3300
attcaacaag acaatggact aaagaagctc gactggaagt acaaaaggca aaaaaggcta   3360
tagaagaaca agtacaacta ggatactatg accccagtaa ggagttatat gctaaattaa   3420
gtttggtggg accacatcaa ataagttatc aagtatatca gaaggatcca gaaaagatac   3480
tatggtatgg aaaaatgagt agacaaaaga aaaaggcaga aaatacatgt gatatagcct   3540
taagagcatg ctataagata agagaagagt ctattataag aataggaaaa gaaccaagat   3600
atgaaatacc tacttctaga gaagcctggg aatcaaattt aattaattca ccatatctta   3660
```

```
aggccccacc tcctgaggta gaatatatcc atgctgcttt gaatataaag agagcgttaa   3720
gtatgataaa agatgctcca ataccaggag cagaaacatg gtatatagat ggaggtagaa   3780
agctaggaaa agcagcaaaa gcagcctatt ggacagatac aggaaagtgg caagtgatgg   3840
aattagaagg cagtaatcag aaggcagaaa tacaagcatt attattggca ttaaaagcag   3900
gatcagagga gatgaatatt ataacagatt cacaatatgt tataaatatt attcttcaac   3960
aaccagatat gatggaggga atctggcaag aagttttaga agaattggag aagaaaacag   4020
caatatttat agattgggtc ccaggacata aaggtattcc aggaaatgag gaagtagata   4080
agctttgtca aacaatgatg ataatagaag ggatgggat attagataaa aggtcagaag   4140
atgcaggata tgatttatta gctgcaaaag aaatacattt attgccagga gaggtaaaag   4200
taataccaac aggggtaaag ctaatgttgc ctaaaggata ttggggatta ataataggaa   4260
aaagctcgat agggagtaaa ggattggatg tattaggagg ggtaatagac gaaggatatc   4320
gaggtgaaat tggagtaata atgattaatg tatcaagaaa atcaatcacc ttaatggaac   4380
gacaaaagat agcacaatta ataatattgc cttgtaaaca tgaagtatta gaacaaggaa   4440
aagtagtaat ggattcagag agaggagaca atggttatgg gtcaacagga gtattctcct   4500
cttgggttga cagaattgag gaagcagaaa taaatcatga aaaatttcac tcagatccac   4560
agtacttaag gactgaattt aatttaccta aaatggtagc agaagagata agacgaaaat   4620
gcccagtatg cagaatcaga ggagaacaag tgggaggaca attgaaaata gggcctggta   4680
tctggcaaat ggattgcaca cactttgatg gcaaaataat tcttgtgggt atacatgtgg   4740
aatcaggata tatatgggca caaataattt ctcaagaaac tgctgactgt acagttaaag   4800
ctgtcttaca attgttgagt gctcataatg ttactgaatt acaaacagat aatggaccaa   4860
attttaaaaa tcaaaagatg gaaggagtac tcaattacat gggtgtgaaa cataagtttg   4920
gtatcccagg gaacccacag tcacaagcat tagttgaaaa tgtaaatcat acattaaaag   4980
tttggattcg gaaatttttg cctgaaacaa cctccttgga taatgcctta tctctcgctg   5040
tacatagtct caattttaaa agaagaggta ggataggagg gatggcccct tatgaattat   5100
tagcacaaca agaatcctta agaatacaag attatttttc tgcaatacca caaaaattgc   5160
aagcacagtg gatttattat aaagatcaaa aagataagaa atggaaagga ccaatgagag   5220
tagaatactg gggacaggga tcagtattat taaaggatga agagaaggga tattttctta   5280
tacctaggag acacataagg agagttccag aaccctgcgc tcttcctgaa ggggatgagt   5340
gaagaagatt ggcaggtaag tagaagactc tttgcagtgc tccaaggagg agtaaatagc   5400
gctatgctat acatatctag gctacctccg gatgaaagag aaaagtataa aaaagacttc   5460
aagaaaagac tttttgacac agaaacagga tttataaaga gactacggaa agctgaagga   5520
ataaaatgga gctttcatac tagagattat tacataggat atgtcagaga aatggtggca   5580
ggatccacta catcattaag tctaaggatg tatatatata taagtaaccc actatggcat   5640
tctcagtatc gtccaggttt gaaaaatttc aataaggaat ggccttttgt aaatatgtgg   5700
ataaaaacag gatttatgtg ggatgatatt gaaaaacaaa atatttgtat aggaggagaa   5760
gtttcaccag gatggggacc agggatggta ggtatagcaa taaaagcttt tagttgtggc   5820
gaaagaaaga ttgaggctac tcctgtaatg attataagag gagaaataga tccaaaaaaa   5880
tggtgcggag attgttggaa tttaatgtgt cttagaaact cacctccaaa gactttacaa   5940
agactcgcta tgttggcgtg tggcgtgccg gctaagaagt ggcgaggatg ctgtaatcaa   6000
cgctttgttt ctccttacag aacgcctgct gatttagagg tcattcaatc caagcccagc   6060
```

```
tggaacctgt tatggtcggg agaattatga atggaagaca taatagtatt attcaatagg   6120
gtcactgaga aactagaaaa agaattagct atcagaatat ttgtattagc acatcaatta   6180
gaaagggaca aagctattag attactacaa ggattatttt ggagatatag atttaagaaa   6240
ccccgagtag attattgttt atgttggtgg tgttgcaaat tctattattg gcagttgcaa   6300
tctacattat caataactac tgcttagaaa tatttagatt aatatttcat ttgcaacaat   6360
aagaatggca gaaggatttg cagccaatag acaatggata ggactagaag aagctgaaga   6420
gttattagat tttgatatag caacacaaat gagtgaagaa ggaccactaa atccaggagt   6480
aaacccattt agggtacctg gaataacaga aaaagaaaag caaaactact gtaacatatt   6540
acaacctaag ttacaagatc taaggaacga aattcaagag gtaaaactgg aagaaggaaa   6600
tgcaggtaag tttagaagag caagattttt aaggtattct gatgaaagtg tattgtccct   6660
ggttcatgcg ttcataggat attgtatata tttaggtaat cgaaataagt taggatcttt   6720
aagacatgac attgatatag aagcacccca agaagagtgt tataataata gagagaaggg   6780
tacaactgac aatataaaat atggtagacg atgttgccta ggaacggtga ctttgtacct   6840
gattttattt ataggaataa taatatattc acagacaacc aacgctcagg tagtatggag   6900
acttccacca ttagtagtcc cagtagaaga atcagaaata attttttggg attgttgggc   6960
accagaagaa cccgcctgtc aggactttct tggggcaatg atacatctaa aagctaagac   7020
aaatataagt atacgagagg gacctacctt ggggaattgg gctagagaaa tatgggcaac   7080
attattcaaa aaggctacta gacaatgtag aagaggcaga atatggaaaa gatggaatga   7140
gactataaca ggaccatcag gatgtgctaa taacacatgt tataatgttt cagtaatagt   7200
acctgattat cagtgttatt tagatagagt agatacttgg ttacaaggga aaataaatat   7260
atcattatgt ctaacaggag gaaaaatgtt gtacaataaa gttacaaaac aattaagcta   7320
ttgtacagac ccattacaaa tcccactgat caattataca tttggaccta atcaaacatg   7380
tatgtggaat acttcacaaa ttcaggaccc tgaaatacca aaatgtggat ggtggaatca   7440
aatggcctat tataacagtt gtaaatggga agaggcaaaa gtaaagtttc attgtcaaag   7500
aacacagagt cagcctggat catggtttag agcaatctcg tcatggaaac aaagaaatag   7560
atgggagtgg agaccagatt ttgaaagtaa aaaggtgaaa atatctctac agtgcaatag   7620
cacaaaaaac ctaacctttg caatgagaag ttcaggagat tatggagaag taacgggagc   7680
ttggatagag tttggatgtc atagaaataa atcaaaactt catgctgaag caaggtttag   7740
aattagatgt agatggaatg tagggagtaa tacctcgctc attgatacat gtggaaacac   7800
tcaaaaagtt tcaggtgcga atcctgtaga ttgtaccatg tattcaaata aaatgtacaa   7860
ttgttcttta caaaacgggt ttactatgaa ggtagatgac cttattatgc atttcaatat   7920
gaaaaaggct gtagaaatgt ataatattgc tggaaattgg tcttgtacat ctgacttgcc   7980
atcgtcatgg gggtatatga attgtaattg tacaaatagt agtagtagtt atagtggtac   8040
taaaatggca tgtcctagca atcgaggcat cttaaggaat tggtataacc cagtggcagg   8100
attacgacaa tccttagaac agtatcaagt tgtaaaacaa ccagattact tagtggtccc   8160
agaggaagtc atggaatata aacctagaag gaaaagggca gctattcatg ttatgttggc   8220
tcttgcagca gtattatcta ttgccggtgc agggacgggg gctactgcta tagggatggt   8280
aacacaatac caccaagttc tggcaaccca tcaagaagct gtagaaaagg tgactgaagc   8340
cttaaagata aacaacttaa gattagttac attagagcat caagtactag taataggatt   8400
```

aaaagtagaa gctatggaaa aatttttgta tacagctttc gctatgcaag aattaggatg 8460
taatcaaaat caatttttct gcaaaatccc tcctgagttg tggacaaggt ataatatgac 8520
tataaatcaa acaatatgga atcatggaaa tataactttg gggaatggt ataaccaaac 8580 aaaagattta caacaaaagt tttatgaaat aataatggac atagaacaaa ataatgtaca 8640
agggaagaaa gggatacaac aattacaaaa gtgggaagat tgggtaggat ggataggaaa 8700
tattccacaa tatttaaagg gactattggg aggtatcttg ggaataggat taggagtgtt 8760
attattgatt ttatgtttac ctacattggt tgattgtata agaaattgta tccacaagat 8820
actaggatac acagtaattg caatgcctga agtagaagga gaagaaatac aaccacaaat 8880
ggaattgagg agaaatggta ggcaatgtgg catgtctgaa aaagaggagg aatgatgaag 8940
tatctcagac ttattttata agggagatac tgtgctgagt tcttcccttt gaggaaggta 9000
tgtcatatga atccatttcg aatcaaatca aactaataaa gtatgtattg taaggtaaaa 9060
ggaaaagaca aagaagaaga agaaagaaga aagccttcaa gaggatgatg acagagttag 9120
aagatcgctt caggaagcta tttggcacga cttctacaac gggagacagc acagtagatt 9180
ctgaagatga acctcctaaa aaagaaaaaa gggtggacaa ttcactgtga gacatgggct 9240
aaagaggact aataacaagc taggccaaat tcctgtaaat cacttggggg gttataagaa 9300
aagcaagttc actatgacaa agcaaaatgt aaaggccaaa ttcctgtaaa tcacttgggg 9360
ggttataaga aaagcaagtt cactatgaca aagcaaaatg taaccgcaag tgctgacaga 9420
tgtaacagct gacatatcag ctgatgcttg ctcatgctga cactgtagct ctgagctgta 9480
tataaggaga agcttgctgc ttgcacttca gagttctagg agagtccctc ctagtctctc 9540
ctctccgagg aggtaccgag acctcaaaat aaaggagtga ttgccttact gccgagtgga 9600
gagtgattac tgagcggccg gtgtatcggg agtcgtccct taatctgtgc aataccagag 9660
cggctctcgc agctg 9675

<210> SEQ ID NO 7
<211> LENGTH: 10449
<212> TYPE: DNA
<213> ORGANISM: Artificial Sequence
<220> FEATURE:
<223> OTHER INFORMATION: Genome retroviral

<400> SEQUENCE: 7
gaattcactg tgagacatgg gctaaagagg actaataaca agctaggcca aattcctgta 60
aatcacttgg ggggttataa gaaaagcaag ttcactatga caaagcaaaa tgtaaaggcc 120
aaattcctgt aaatcacttg gggggttata agaaaagcaa gttcactatg acaaagcaaa 180
atgtaaccgc aagtgctgac agatgtaaca gctgacatat cagctgatgc ttgctcatgc 240
tgacactgta gctctgagct gtatataagg agaagcttgc tgcttgcact tcagagttct 300
aggagagtcc ctcctagtct ctcctctccg aggaggtacc gagacctcaa aataaaggag 360
tgattgcctt actgccgagt ggagagtgat tactgagcgg ccggtgtatc gggagtcgtc 420
ccttaatctg tgcaatacca gagcggctct cgcagctggc gcccgaacag ggacttgaag 480
gagagtgaga gactcctgag tacggctgag tgaaggcagt aagggcggca ggaaccaacc 540
acgacggagt gctcctataa aggcgcgggt cggtaccaga cggcgtgagg agcgggagag 600
gaagaggcct ccggttgcag gtgagtgcaa cacaaaaaag aaatagctgt cttttatcca 660
ggaaggggta ataagataga gtgggagatg ggcgtgagaa actccgtctt gtcagggaag 720
aaagcagatg aattagaaaa aattaggcta cgacccaacg gaaagaaaaa gtacatgttg 780

```
aagcatgtag tatgggcagc aaatgaatta gatagatttg gattagcaga aagcctgttg    840
gagaacaaag aaggatgtca aaaaatactt tcggtcttag ctccattagt gccaacaggc    900
tcagaaaatt taaaaagcct ttataatact gtctgcgtca tctggtgcat tcacgcagaa    960
gagaaagtga aacacactga ggaagcaaaa cagatagtgc agagacacct agtggtggaa   1020
ataggaacaa cagaaactat gccaaaaaca agtagaccaa cagcaccatc tagcggcaga   1080
ggaggaaatt acccagtaca acaaataggt ggtaactatg tccacctgcc attaagcccg   1140
agaacattaa atgcctgggt aaaattgata gaggaaaaga aatttggagc agaagtagtg   1200
ccaggatttc aggcactgtc agaaggttgc accccctatg acattaatca gatgttaaat   1260
tgtgtgggag accatcaagc ggctatgcag attatcagag atattataaa cgaggaggct   1320
gcagattggg acttgcagca cccacaacca gctccacaac aaggacaact tagggagccg   1380
tcaggatcag atattgcagg aacaactagt tcagtagatg aacaaatcca gtggatgtac   1440
agacaacaga accccatacc agtaggcaac atttacagga gatggatcca actggggttg   1500
caaaaatgtg tcagaatgta taacccaaca aacattctag atgtaaaaca agggccaaaa   1560
gagccatttc agagctatgt agacaggttc tacaaaagtt taagagcaga acagacagat   1620
gcagcagtaa agaattggat gactcaaaca ctgctgattc aaaatgctaa cccagattgc   1680
aagctagtgc tgaaggggct gggtgtgaat cccaccctag aagaaatgct gacggcttgt   1740
caaggagtag gggggccggg acagaaggct agattaatgg cagaagccct gaaagaggcc   1800
ctcgcaccag tgcctatccc ttttgcagca gcccaacaga ggggaccaag aaagccaatt   1860
aagtgttgga attgtgggaa agagggacac tctgcaaggc aatgcagagc cccaagaaga   1920
cagggatgct ggaaatgtgg aaaaatggac catgttatgg ccaaatgccc agacagacag   1980
gcgggttttt taggccttgg tccatgggga aagaagcccc gcaatttccc catggctcaa   2040
gtgcatcagg ggctgatgcc aactgctccc ccagaggacc cagctgtgga tctgctaaag   2100
aactacatgc agttgggcaa gcagcagaga gaaaagcaga gagaaagcag agagaagcct   2160
tacaaggagg tgacagagga tttgctgcac ctcaattctc tctttggagg agaccagtag   2220
tcactgctca tattgaagga cagcctgtag aagtattact ggatacaggg gctgatgatt   2280
ctattgtaac aggaatagag ttaggtccac attataccccc aaaaatagta ggaggaatag   2340
gaggttttat taatactaaa gaatacaaaa atgtagaaat agaagtttta ggcaaaagga   2400
ttaaagggac aatcatgaca ggggacaccc cgattaacat ttttggtaga aatttgctaa   2460
cagctctggg gatgtctcta aattttccca tagctaaagt agagcctgta aaagtcgcct   2520
taaagccagg aaaggatgga ccaaaattga agcagtggcc attatcaaaa gaaaagatag   2580
ttgcattaag agaaatctgt gaaaagatgg aaaaggatgg tcagttggag gaagctcccc   2640
cgaccaatcc atacaacacc cccacatttg ctataaagaa aaaggataag aacaaatgga   2700
gaatgctgat agattttagg gaactaaata gggtcactca ggactttacg gaagtccaat   2760
taggaatacc acaccctgca ggactagcaa aaaggaaaag aattacagta ctggatatag   2820
gtgatgcata tttctccata cctctagatg aagaatttag gcagtacact gcctttactt   2880
taccatcagt aaataatgca gagccaggaa aacgatacat ttataaggtt ctgcctcagg   2940
gatggaaggg gtcaccagcc atcttccaat acactatgag acatgtgcta gaacccttca   3000
ggaaggcaaa tccagatgtg accttagtcc agtatatgga tgacatctta atagctagtg   3060
acaggacaga cctggaacat gacagggtag ttttacagtc aaaggaactc ttgaatagca   3120
```

```
tagggttttc taccccagaa gagaaattcc aaaaagatcc cccatttcaa tggatggggt   3180
acgaattgtg gccaacaaaa tggaagttgc aaaagataga gttgccacaa agagagacct   3240
ggacagtgaa tgatatacag aagttagtag gagtattaaa ttgggcagct caaatttatc   3300
caggtataaa aaccaaacat ctctgtaggt taattagagg aaaaatgact ctaacagagg   3360
aagttcagtg gactgagatg gcagaagcag aatatgagga aaataaaata attctcagtc   3420
aggaacaaga aggatgttat taccaagaag gcaagccatt agaagccacg gtaataaaga   3480
gtcaggacaa tcagtggtct tataaaattc accaagaaga caaaatactg aaagtaggaa   3540
aatttgcaaa gataaagaat acacatacca atggagtgag actattagca catgtaatac   3600
agaaaatagg aaaggaagca atagtgatct ggggacaggt cccaaaattc cacttaccag   3660
ttgagaagga tgtatgggaa cagtggtgga cagactattg gcaggtaacc tggataccgg   3720
aatgggattt tatctcaaca ccaccgctag taagattagt cttcaatcta gtgaaggacc   3780
ctatagaggg agaagaaacc tattatacag atggatcatg taataaacag tcaaaagaag   3840
ggaaagcagg atatatcaca gataggggca aagacaaagt aaaagtgtta gaacagacta   3900
ctaatcaaca agcagaattg gaagcatttc tcatggcatt gacagactca gggccaaagg   3960
caaatattat agtagattca caatatgtta tgggaataat aacaggatgc cctacagaat   4020
cagagagcag gctagttaat caaataatag aagaaatgat taaaaagtca gaaatttatg   4080
tagcatgggt accagcacac aaaggtatag gaggaaacca agaaatagac cacctagtta   4140
gtcaagggat tagacaagtt ctcttcttgg aaaagataga gccagcacaa gaagaacatg   4200
ataaatacca tagtaatgta aaagaattgg tattcaaatt tggattaccc agaatagtgg   4260
ccagacagat agtagacacc tgtgataaat gtcatcagaa aggagaggct atacatgggc   4320
aggcaaattc agatctaggg acttggcaaa tggattgtac ccatctagag ggaaaaataa   4380
tcatagttgc agtacatgta gctagtggat tcatagaagc agaggtaatt ccacaagaga   4440
caggaagaca gacagcacta tttctgttaa aattggcagg cagatggcct attacacatc   4500
tacacacaga taatggtgct aactttgctt cgcaagaagt aaagatggtt gcatggtggg   4560
cagggataga gcacaccttt ggggtaccat acaatccaca gagtcaggga gtagtggaag   4620
caatgaatca ccacctgaaa aatcaaatag atagaatcag ggaacaagca aattcagtag   4680
aaaccatagt attaatggca gttcattgca tgaattttaa aagaagggga ggaatagggg   4740
atatgactcc agcagaaaga ttaattaaca tgatcactac agaacaagag atacaatttc   4800
aacaatcaaa aaactcaaaa tttaaaaatt ttcgggtcta ttacagagaa ggcagagatc   4860
aactgtggaa gggacccggt gagctattgt ggaaagggga ggagcagtca tcttaaaggt   4920
agggacagac attaaggtag tacccagaag aaaggctaaa attatcaaag attatggagg   4980
aggaaaagag gtggatagca gttcccacat ggaggatacc ggagaggcta gagaggtggc   5040
atagtagcct cataaaatat ctgaaatata aaactaaaga tctacaaaag gtttgctatg   5100
tgccccattt taaggtcgga tgggcatggt ggacctgcag cagagtaatc ttcccactac   5160
aggaaggaag ccatttagaa gtacaagggt attggcattt gacaccagaa aaagggtggc   5220
tcagtactta tgcagtgagg ataacctggt actcaaagaa cttttggaca gatgtaacac   5280
caaactatgc agacatttta ctgcatagca cttatttccc ttgctttaca gcgggagaag   5340
tgagaagggc catcagggga gaacaactgc tgtcttgctg caggttcccg agagctcata   5400
agcaccaggt accaagccta cagtacttag cactgaaagt agtaagcgat gtcagatccc   5460
agggagagaa tcccacctgg aaacagtgga gaagagacaa taggagaggc cttcgaatgg   5520
```

```
ctaaacagaa cagtagagga gataaacaga gaggcggtaa accacctacc aagggagcta   5580
attttccagg tttggcaaag gtcttgggaa tactggcatg atgaacaagg gatgtcacca   5640
agctatgtaa aatacagata cttgtgttta atacaaaagg ctttatttat gcattgcaag   5700
aaaggctgta gatgtctagg ggaaggacat ggggcagggg gatggagacc aggacctcct   5760
cctcctcccc ctccaggact agcataaatg gaagaaagac ctccagaaaa tgaaggacca   5820
caaagggaac catgggatga atgggtagtg gaggttttgg aagaactgaa agaagaagct   5880
ttaaaacatt ttgatcctcg cttgctaact gcccttggta atcatatcta taatcgtcac   5940
ggagacactc tagagggagc aggagaactc attagaatcc tccaacgagc gctcttcatg   6000
catttcagag gcggatgcat ccactccaga atcggccaac ctgggggagg aaatcctctc   6060
tcagctatac cgccctctag aagcatgctg tagagcaaga aatggagcca gtagatccta   6120
gactagagcc ctggaagcat ccaggaagtc agcctaaaac tgcttgtacc aattgctatt   6180
gtaaaaagtg ttgctttcat tgccaagttt gtttcataac aaaagcctta ggcatctcct   6240
atggcaggaa gaagcggaga cagcgacgaa gagctcatca gaacagtcag actcatcaag   6300
cttctctatc aaagcagtaa gtagtacatg taacgcaacc tataccaata gtagcaatag   6360
tagcattagt agtagcaata ataatagcaa tagttgtgtg gtccatagta atcatagaat   6420
ataggaaaat attaagacaa agaaaaatag acaggttaat tgatagacta atagaaagag   6480
cagaagacag tggcaatgag agtgaaggag aaatatcagc acttgtggag atgggggtgg   6540
agatggggca ccatgctcct tgggatgttg atgatctgta gtgctacaga aaaattgtgg   6600
gtcacagtct attatggggt acctgtgtgg aaggaagcaa ccaccactct attttgtgca   6660
tcagatgcta aagcatatga tacagaggca cataatgttt gggccacaca tgcctgtgta   6720
cccacagacc ccaacccaca agaagtagta ttggtaaatg tgacagaaaa ttttaacatg   6780
tggaaaaatg acatggtaga acagatgcat gaggatataa tcagtttatg ggatcaaagc   6840
ctaaagccat gtgtaaaatt aaccccactc tgtgttagtt taaattgcac tgatttgaag   6900
aatgatacta ataccaatag tagtagcggg agaatgataa tggagaaagg agagataaaa   6960
aactgctctt tcaatatcag cacaagcata agaggtaagg tgcagaaaga atatgcattt   7020
ttttataaac ttgatataat accaatagat aatgatacta ccagctatac gttgacaagt   7080
tgtaacacct cagtcatttc acaggcctgt ccaaaggtat cctttgagcc aattcccata   7140
cattattgtg ccccggctgg ttttgcgatt ctaaaatgta ataataagac gttcaatgga   7200
acaggaccat gtacaaatgt cagcacagta caatgtacac atggaattag gccagtagta   7260
tcaactcaac tgctgttaaa tggcagtcta gcagaagaag aggtagtaat tagatctgtc   7320
aatttcatgg acaatgctaa aaccataata gtacagctga acacatctgt agaaattaat   7380
tgtacaagac ccagcaacaa tacaataaaa agaatccgta tccagagagg accagggaga   7440
gcatttgtta caatgggaaa aataggaaat atgagacaag cacattgtaa cattagtaga   7500
gcaaaatgga ataacacttt aaaacagata gctagcaaat taagagaaca atttggaaat   7560
aataaaacaa taatctttaa gcaatcctca ggaggggacc cagaaattgt aacgcacagt   7620
tttaattgtg gaggggaatt tttctactgt aattcaacac aactgtttaa tagtacttgg   7680
tttaatagta cttggagtac tgaagggtca aataacactg aaggaagtgg cacaatcacc   7740
ctcccatgca gaataaaaca aattataaac atgtggcaga aagtaggaaa agcaatgtat   7800
gcccctccca tcagtggaca aattagatgt tcatcaaata ttacagggct gctattaaca   7860
```

```
agagatggtg gtaagggcaa caatgagtcc gagatcttca gacctggagg aggagatatg   7920
agggacaatt ggagaagtga attatataaa tataaagtag taaaaattga accattagga   7980
gtagcaccca ccaaggcaaa gagaagagtg gtgcagagag aaaaaagagc agtgggaata   8040
ggagctttgt tccttgggtt cttgggagca gcaggaagca ctatgggcgc agcgtcaatg   8100
acgctgacgg tacaggccag acaattattg tctggtatag tgcagcagca gaacaatttg   8160
ctgagggcta ttgaggcgca acagcatctg ttgcaactca cagtctgggg catcaagcag   8220
ctccaggcaa gaatcctggc tgtggaaaga tacctaaagg atcaacagct cctggggatt   8280
tggggttgct ctggaaaact catttgcacc actgctgtgc cttggaatgc tagttggagt   8340
aataaatctc tggaacagat ttggaatcac atgacctgga tggagtggga cagagaaatt   8400
aacaattaca caagcttaat acactcctta attgaagaat cgcaaaacca gcaagaaaag   8460
aatgaacaag aattattgga attagataaa tgggcaagtt tgtggaattg gtttgacata   8520
acaaattggc tgtggtatat aaaattattc ataatgatag taggaggctt ggtaggttta   8580
agaatagttt ttgctgtact ttctatagtg aatagagtta ggcagggata ttcaccatta   8640
tcgtttcaga cccacctccc aaccccgagg ggacccgaca ggcccgaagg aatagaagaa   8700
gaaggtggag agagagacag agacagatcc attcgattag tgaacggatc cttggcactt   8760
atctgggacg atctacggag cctgtgcctc ttcagctacc accgcttgag agacttactc   8820
ttgattgtaa cgaggactgt ggaacttctg ggacgcaggg ggtgggaagc cctcaaatat   8880
tggtggaatc tcctacagta ttggagtcag gaactaaaga atagtgctgt tagcttgctc   8940
aatgccatag ccatagcagt agctgaggga acagataggg ttatagaagt agtccaagga   9000
gcttgtagag ctattcgcta catacctaga agaataagac agggcttgga aaggattttg   9060
ctataagatt cgagatgggt ggagctattt ccatgaggcg gtccaggcag tctagagatc   9120
tgcgacagag actcttgcgg gcgcgtgggg agacttatgg gagactctta gaagaggtgg   9180
aagatggata ctcgcgatcc ccaggaggat tagacaaggg cttgagctca ctctcttgtg   9240
agggacagaa atacaatcag ggacagtata tgaatactcc atggagagac ccagctgaag   9300
agagagaaaa attagcatac agaaaacaaa atatggatga tatagatgag gaagatgata   9360
acttggtagg ggtatcagtg aggccaagag ttcccctaag aacaatgagt tacaaattgg   9420
caatagacat gtctcatttt ataaaagaaa agggggaact ggaagggatc ttttacagtg   9480
caagaagaca tagaatctta gacatgtact tagaaaagga aaaaggcatc ataccagatt   9540
ggcaggatta cacctcagga ccaggaatta gatacccaaa gacatttggc tggctatgga   9600
aattagtccc tgtaaatgta tcagatgagg cacaggagga tgaagagcat tatttaatgc   9660
atccagctca aacttcccag tggatgacc  cttggagaga ggttctagca tggaagtttg   9720
atccaactct ggcctacact tatgaggcat atgttagata cccagaagag tttggaagca   9780
agtcaggcct gtcagaggaa gaggttaaaa gaaggctaac cgcaagaggc cttcttaaca   9840
tggctgacaa gaaggaaact cgctgagcgg ccgcactgtg agacatgggc taaagaggac   9900
taataacaag ctaggccaaa ttcctgtaaa tcacttgggg ggttataaga aaagcaagtt   9960
cactatgaca aagcaaaatg taaaggccaa attcctgtaa atcacttggg gggttataag  10020
aaaagcaagt tcactatgac aaagcaaaat gtaaccgcaa gtgctgacag atgtaacagc  10080
tgacatatca gctgatgctt gctcatgctg acactgtagc tctgagctgt atataaggag  10140
aagcttgctg cttgcacttc agagttctag gagagtccct cctagtctct cctctccgag  10200
gaggtaccga gacctcaaaa taaaggagtg attgccttac tgccgagtgg agagtgatta  10260
```

```
ctgagcggcc ggtgtatcgg gagtcgtccc ttaatctgtg caataccaga gcggctctcg  10320

cagctgtcga cctcgagggg gggcccggta ccttaattaa ttaaggtacc aggtaagtgt  10380

acccaattcg ccctatagtg agtcgtatta caattcactc gatcgccctt cccaacagtt  10440

gcgcagcct                                                          10449
```

```
<210> SEQ ID NO 8
<211> LENGTH: 1764
<212> TYPE: DNA
<213> ORGANISM: Artificial Sequence
<220> FEATURE:
<223> OTHER INFORMATION: Integrase SIV

<400> SEQUENCE: 8

ttcttggaaa agatagagcc agcacaagaa gaacatgata aataccatag taatgtaaaa     60

gaattggtat tcaagaacct tttctatctc ggtcgtgttc ttcttgtact atttatggta    120

tcattacatt ttcttaacca taagaaattt ggattaccca gaatagtggc cagacagata    180

gtagacacct gtgataaatg tcatcagaaa ggagaggcta tacatgggca ggcaaattca    240

gatctttaaa cctaatgggt cttatcaccg gtctgtctat catctgtgga cactatttac    300

agtagtcttt cctctccgat atgtacccgt ccgtttaagt ctagtaggga cttggcaaat    360

ggattgtacc catctagagg gaaaaataat catagttgca gtacatgtag ctagtggatt    420

catagaagca gaggtaattc cacaatccct gaaccgttta cctaacatgg gtagatctcc    480

ctttttatta gtatcaacgt catgtacatc gatcacctaa gtatcttcgt ctccattaag    540

gtgtagagac aggaagacag acagcactat ttctgttaaa attggcaggc agatggccta    600

ttacacatct acacacagat aatggtgcta actttgcttc gcaatctctg tccttctgtc    660

tgtcgtgata aagacaattt taaccgtccg tctaccggat aatgtgtaga tgtgtgtcta    720

ttaccacgat tgaaacgaag cgttgaagta aagatggttg catggtgggc agggatagag    780

cacacctttg ggtaccatac caatccacag agtcagggag tagtggaagc aatgaatcac    840

caccccttcat ttctaccaac gtaccacccg tccctatctc gtgtggaaac cccatggtat    900

gttaggtgtc tcagtccctc atcaccttcg ttacttagtg gtggtgaaaa atcaaataga    960

tagaatcagg gaacaagcaa attcagtaga aaccatagta ttaatggcag ttcattgcat   1020

gaattttaaa agaaggggag gaatactttt tagtttatct atcttagtcc cttgttcgtt   1080

taagtcatct ttggtatcat aattaccgtc aagtaacgta cttaaaattt tcttcccctc   1140

cttaagggga tatgactcca gcagaaagat taattaacat gatcactaca gaacaagaga   1200

tacaatttca acaatcaaaa aactcaaaat ttaaaaattt tcggtcccct atactgaggt   1260

cgtctttcta attaattgta ctagtgatgt cttgttctct atgttaaagt tgttagtttt   1320

ttgagtttta aatttttaaa agccgtctat tacagagaag gcagagatca actgtggaag   1380

ggacccggtg agctattgtg gaaaggggaa ggagcagtca tcttaaaggt agggacagac   1440

attacagata atgtctcttc cgtctctagt tgacaccttc cctgggccac tcgataacac   1500

ctttcccctt cctcgtcagt agaatttcca tccctgtctg taataggtag tacccagaag   1560

aaaggctaaa attatcaaag attatggagg aggaaaagag gtggatagca gttcccacat   1620

ggaggatacc ggagaggcta gagatccatc atgggtcttc tttccgattt taatagtttc   1680

taatacctcc tccttttctc cacctatcgt caagggtgta cctcctatgg cctctccgat   1740

ctctggtggc atagccaccg tatc                                          1764
```

<210> SEQ ID NO 9
<211> LENGTH: 867
<212> TYPE: DNA
<213> ORGANISM: Artificial Sequence
<220> FEATURE:
<223> OTHER INFORMATION: Integrase HIV-1

<400> SEQUENCE: 9

```
tttttagatg gaatagataa ggcccaagaa gaacatgaga aatatcacag taattggaga      60
gcaatggcta gtgattttaa cctaccacct gtagtagcaa aagaaatagt agccagctgt     120
gataaatgtc agctaaaagg ggaagccatg catggacaag tagactgtag cccaggaata     180
tggcagctag attgtacaca tttagaagga aaagttatct tggtagcagt tcatgtagcc     240
agtggatata tagaagcaga agtaattcca gcagagacag ggcaagaaac agcatacttc     300
ctcttaaaat tagcaggaag atggccagta aaaacagtac atacagacaa tggcagcaat     360
ttcaccagta ctacagttaa ggccgcctgt tggtgggcgg ggatcaagca ggaatttggc     420
attccctaca atccccaaag tcaaggagta atagaatcta tgaataaaga attaaagaaa     480
attataggac aggtaagaga tcaggctgaa catcttaaga cagcagtaca aatggcagta     540
ttcatccaca attttaaaag aaaagggggg attggggggt acagtgcagg ggaaagaata     600
gtagacataa tagcaacaga catacaaact aaagaattac aaaaacaaat tacaaaaatt     660
caaaatttc gggtttatta cagggacagc agagatccag tttggaaagg accagcaaag      720
ctcctctgga aaggtgaagg ggcagtagta atacaagata atagtgacat aaaagtagtg     780
ccaagaagaa aagcaaagat catcagggat tatggaaaac agatggcagg tgatgattgt     840
gtggcaagta gacaggatga ggattaa                                         867
```

<210> SEQ ID NO 10
<211> LENGTH: 1764
<212> TYPE: DNA
<213> ORGANISM: Artificial Sequence
<220> FEATURE:
<223> OTHER INFORMATION: Integrase HIV-2

<400> SEQUENCE: 10

```
ttcctagaga aaatagaacc cgctcaggag gaacatgaaa aataaaggat ctcttttatc      60
ttgggcgagt cctccttgta ctttttattc atagcaatgt aaaagaacta tcccataaat     120
ttggactgcc caaattagtg gcaagacaaa tagtaaacac atgcacccaa tgtcagcaga     180
aaggggagag tatcgttaca ttttcttgat agggtattta aacctgacgg gtttaatcac     240
cgttctgttt atcatttgtg tacgtgggtt acagtcgtct ttcccctcgc tatacatggg     300
caagtaaatg cagaattagg cacttggcaa atggactgca cacacttaga aggaaaaatc     360
attatagtag cagtacatgt tgcaagtgcg atatgtaccc gttcatttac gtcttaatcc     420
gtgaaccgtt tacctgacgt gtgtgaatct tcctttttag taatatcatc gtcatgtaca     480
acgttcacga tttatagaag cagaagtcat cccacaggaa tcaggaaggc aaacggcact     540
cttcctacta aaactggcca gtaggtggcc aataacacat ttgcacacct aaatatcttc     600
gtcttcagta gggtgtcctt agtccttccg tttgccgtga gaaggatgat tttgaccggt     660
catccaccgg ttattgtgta aacgtgtgag acaatggtgc caacttcact tcacaggaag     720
taaagatggt ggcatggtgg ataggtatag aacaatcctt cggagtacct tacaatccac     780
aaagccaatc tgttaccacg gttgaagtga agtgtccttc atttctacca ccgtaccacc     840
tatccatatc ttgttaggaa gcctcatgga atgttaggtg tttcggttgg agtagtggaa     900
```

```
gcaatgaatc accacctaaa aaatcagata agcagaatta gagagcaggc aaacacagta    960
gaaacaatag tactaatggc agttcattcc tcatcacctt cgttacttag tggtggattt   1020
tttagtctat tcgtcttaat ctctcgtccg tttgtgtcat ctttgttatc atgattaccg   1080
tcaagtaagc atgaatttta aaaggagggg aggaataggg gatatgaccc cagcagaaag   1140
actaatcaat atggtcactg cagaacagga aatacaattc ctccaagccg tacttaaaat   1200
tttcctcccc tccttatccc ctatactggg gtcgtctttc tgattagtta taccagtgac   1260
gtcttgtcct ttatgttaag gaggttcgaa aaaattcaaa attacaaaat tttcgggtct   1320
atttcagaga aggcagagat cagctgtgga aaggacctgg ggaactactg tggaaggggg   1380
acggagcatt ttttaagttt taatgtttta aaagcccaga taaagtctct tccgtctcta   1440
gtcgacacct ttcctggacc ccttgatgac accttccccc tgcctcgtgt catagtcaag   1500
gtaggggctg acataaaaat aataccaaga aggaaagcta agatcatcaa agactatgga   1560
ggaaggcaag agatggatag cggttccaca gtatcagttc catccccgac tgtattttta   1620
ttatggttct tcctttcgat tctagtagtt tctgatacct ccttccgttc tctacctatc   1680
gccaaggtac ttggagggtg ccagggagga tggagaggtg gcatagtgaa cctcccacgg   1740
tccctcctac ctctccaccg tatc                                          1764
```

<210> SEQ ID NO 11
<211> LENGTH: 790
<212> TYPE: DNA
<213> ORGANISM: Artificial Sequence
<220> FEATURE:
<223> OTHER INFORMATION: Integrase FIV

<400> SEQUENCE: 11

```
agatccacag tacttaagga ctgaatttaa tttacctaaa atggtagcag aagagataag     60
acgaaaatgc ccagtatgca gaatcagagg agaacaagtg ggaggacaat tgaaaatagg    120
gcctggtatc tggcaaatgg attgcacaca ctttgatggc aaaataattc ttgtgggtat    180
acatgtggaa tcaggatata tatgggcaca aataatttct caagaaactg ctgactgtac    240
agttaaagct gtcttacaat tgttgagtgc tcataatgtt actgaattac aaacagataa    300
tggaccaaat tttaaaaatc aaaagatgga aggagtactc aattacatgg gtgtgaaaca    360
taagtttggt atcccaggga acccacagtc acaagcatta gttgaaaatg taaatcatac    420
attaaaagtt tggattcgga aatttttgcc tgaaacaacc tccttggata atgccttatc    480
tctcgctgta catagtctca attttaaaag aagaggtagg ataggaggga tggcccctta    540
tgaattatta gcacaacaag aatccttaag aatacaagat tatttttctg caataccaca    600
aaaattgcaa gcacagtgga tttattataa agatcaaaaa gataagaaat ggaaaggacc    660
aatgagagta gaatactggg gacagggatc agtattatta aaggatgaag agaagggata    720
ttttcttata cctaggagac acataaggag agttccagaa ccctgcgctc ttcctgaagg    780
ggatgagtga                                                           790
```

<210> SEQ ID NO 12
<211> LENGTH: 8926
<212> TYPE: DNA
<213> ORGANISM: Artificial Sequence
<220> FEATURE:
<223> OTHER INFORMATION: Genome retroviral

<400> SEQUENCE: 12

```
aattcactgt gagacatggg ctaaagagga ctaataacaa gctaggccaa attcctgtaa     60
atcacttggg gggttataag aaaagcaagt tcactatgac aaagcaaaat gtaaaggcca    120
aattcctgta aatcacttgg ggggttataa gaaaagcaag ttcactatga caaagcaaaa    180
tgtaaccgca agtgctgaca gatgtaacag ctgacatatc agctgatgct tgctcatgct    240
gacactgtag ctctgagctg tatataagga gaagcttgct gcttgcactt cagagttcta    300
ggagagtccc tcctagtctc tcctctccga ggaggtaccg agacctcaaa ataaaggagt    360
gattgcctta ctgccgagtg gagagtgatt actgagcggc cggtgtatcg ggagtcgtcc    420
cttaatctgt gcaataccag agcggctctc gcagctggcg cccgaacagg gacttgaaag    480
cgaaagtaaa gccagaggag atctctcgac gcaggactcg gcttgctgaa gcgcgcacgg    540
caagaggcga ggggcggcga ctggtgagta cgccaaaaat tttgactagc ggaggctaga    600
aggagagaga tgggtgcgag agcgtcggta ttaagcgggg gagaattaga taaatgggaa    660
aaaattcggt taaggccagg gggaaagaaa caatataaac taaaacatat agtatgggca    720
agcagggagc tagaacgatt cgcagttaat cctggccttt tagagacatc agaaggctgt    780
agacaaatac tgggacagct acaaccatcc cttcagacag gatcagaaga acttagatca    840
ttatataata caatagcagt cctctattgt gtgcatcaaa ggatagatgt aaaagacacc    900
aaggaagcct tagataagat agaggaagag caaaacaaaa gtaagaaaaa ggcacagcaa    960
gcagcagctg acacaggaaa caacagccag gtcagccaaa attaccctat agtgcagaac   1020
ctccaggggc aaatggtaca tcaggccata tcacctagaa ctttaaatgc atgggtaaaa   1080
gtagtagaag agaaggcttt cagcccagaa gtaataccca tgttttcagc attatcagaa   1140
ggagccaccc cacaagattt aaataccatg ctaaacacag tggggggaca tcaagcagcc   1200
atgcaaatgt taaaagagac catcaatgag gaagctgcag aatgggatag attgcatcca   1260
gtgcatgcag ggcctattgc accaggccag atgagagaac caaggggaag tgacatagca   1320
ggaactacta gtacccttca ggaacaaata ggatggatga cacataatcc acctatccca   1380
gtaggagaaa tctataaaag atggataatc ctgggattaa ataaaatagt aagaatgtat   1440
agccctacca gcattctgga cataagacaa ggaccaaagg aaccctttag agactatgta   1500
gaccgattct ataaaactct aagagccgag caagcttcac aagaggtaaa aaattggatg   1560
acagaaacct tgttggtcca aaatgcgaac ccagattgta agactatttt aaaagcattg   1620
ggaccaggag cgacactaga agaaatgatg acagcatgtc agggagtggg gggacccggc   1680
cataaagcaa gagttttggc tgaagcaatg agccaagtaa caaatccagc taccataatg   1740
atacagaaag gcaattttag gaaccaaaga aagactgtta agtgtttcaa ttgtggcaaa   1800
gaagggcaca tagccaaaaa ttgcagggcc cctaggaaaa agggctgttg gaaatgtgga   1860
aaggaaggac accaaatgaa agattgtact gagagacagg ctaatttttt agggaagatc   1920
tggccttccc acaagggaag gccagggaat tttcttcaga gcagaccaga gccaacagcc   1980
ccaccagaag agagcttcag gtttggggaa gagacaacaa ctccctctca gaagcaggag   2040
ccgatagaca aggaactgta tcctttagct tccctcagat cactctttgg cagcgacccc   2100
tcgtcacaat aaagataggg gggcaattaa aggaagctct attagataca ggagcagatg   2160
atacagtatt agaagaaatg aatttgccag gaagatggaa accaaaaatg atagggggaa   2220
ttggaggttt tatcaaagta ggacagtatg atcagatact catagaaatc tgcggacata   2280
aagctatagg tacagtatta gtaggaccta cacctgtcaa cataattgga agaaatctgt   2340
tgactcagat tggctgcact ttaaattttc ccattagtcc tattgagact gtaccagtaa   2400
```

```
aattaaagcc aggaatggat ggcccaaaag ttaaacaatg gccattgaca gaagaaaaaa   2460
taaaagcatt agtagaaatt tgtacagaaa tggaaaagga aggaaaaatt tcaaaaattg   2520
ggcctgaaaa tccatacaat actccagtat ttgccataaa gaaaaaagac agtactaaat   2580
ggagaaaatt agtagatttc agagaactta ataagagaac tcaagatttc tgggaagttc   2640
aattaggaat accacatcct gcagggttaa aacagaaaaa atcagtaaca gtactggatg   2700
tgggcgatgc atatttttca gttcccttag ataaagactt caggaagtat actgcattta   2760
ccatacctag tataaacaat gagacaccag ggattagata tcagtacaat gtgcttccac   2820
agggatggaa aggatcacca gcaatattcc agtgtagcat gacaaaaatc ttagagcctt   2880
ttagaaaaca aaatccagac atagtcatct atcaatacat ggatgatttg tatgtaggat   2940
ctgacttaga aatagggcag catagaacaa aaatagagga actgagacaa catctgttga   3000
ggtggggatt taccacacca gacaaaaaac atcagaaaga acctccattc ctttggatgg   3060
gttatgaact ccatcctgat aaatggacag tacagcctat agtgctgcca gaaaaggaca   3120
gctggactgt caatgacata cagaaattag tgggaaaatt gaattgggca agtcagattt   3180
atgcagggat taaagtaagg caattatgta aacttcttag gggaaccaaa gcactaacag   3240
aagtagtacc actaacagaa gaagcagagc tagaactggc agaaaacagg gagattctaa   3300
aagaaccggt acatggagtg tattatgacc catcaaaaga cttaatagca gaaatacaga   3360
agcaggggca aggccaatgg acatatcaaa tttatcaaga gccatttaaa aatctgaaaa   3420
caggaaaata tgcaagaatg aagggtgccc acactaatga tgtgaaacaa ttaacagagg   3480
cagtacaaaa aatagccaca gaaagcatag taatatgggg aaagactcct aaatttaaat   3540
tacccataca aaaggaaaca tgggaagcat ggtggacaga gtattggcaa gccacctgga   3600
ttcctgagtg ggagtttgtc aatacccctc ccttagtgaa gttatggtac cagttagaga   3660
aagaacccat aataggagca gaaactttct atgtagatgg ggcagccaat agggaaacta   3720
aattaggaaa agcaggatat gtaactgaca gaggaagaca aaaagttgtc cccctaacgg   3780
acacaacaaa tcagaagact gagttacaag caattcatct agctttgcag gattcgggat   3840
tagaagtaaa catagtgaca gactcacaat atgcattggg aatcattcaa gcacaaccag   3900
ataagagtga atcagagtta gtcagtcaaa taatagagca gttaataaaa aaggaaaaag   3960
tctacctggc atgggtacca gcacacaaag gaattggagg aaatgaacaa gtagatgggt   4020
tggtcagtgc tggaatcagg aaagtactat ttttagatgg aatagataag gcccaagaag   4080
atcagggatt atggaaaaca gatggcaggt gatgattgtg tggcaagtag acaggatgag   4140
gattaacaca tggaaaagat tagtaaaaca ccatatgtat atttcaagga aagctaagga   4200
ctggttttat agacatcact atgaaagtac taatccaaaa ataagttcag aagtacacat   4260
cccactaggg gatgctaaat tagtaataac aacatattgg ggtctgcata caggagaaag   4320
agactggcat ttgggtcagg gagtctccat agaatggagg aaaaagagat atagcacaca   4380
agtagaccct gacctagcag accaactaat tcatctgcac tattttgatt gtttttcaga   4440
atctgctata agaaatacca tattaggacg tatagttagt cctaggtgtg aatatcaagc   4500
aggacataac aaggtaggat ctctacagta cttggcacta gcagcattaa taaaaccaaa   4560
acagataaag ccacctttgc ctagtgttag gaaactgaca gaggacagat ggaacaagcc   4620
ccagaagacc aagggccaca gagggagcca tacaatgaat ggacactaga gcttttagag   4680
gaacttaaga gtgaagctgt tagacatttt cctaggatat ggctccataa cttaggacaa   4740
```

```
catatctatg aaacttacgg ggatacttgg gcaggagtgg aagccataat aagaattctg   4800
caacaactgc tgtttatcca tttcagaatt gggtgtcgac atagcagaat aggcgttact   4860
cgacagagga gagcaagaaa tggagccagt agatcctaga ctagagccct ggaagcatcc   4920
aggaagtcag cctaaaactg cttgtaccaa ttgctattgt aaaaagtgtt gctttcattg   4980
ccaagtttgt ttcatgacaa aagccttagg catctcctat ggcaggaaga agcggagaca   5040
gcgacgaaga gctcatcaga acagtcagac tcatcaagct tctctatcaa agcagtaagt   5100
agtacatgta atgcaaccta taatagtagc aatagtagca ttagtagtag caataataat   5160
agcaatagtt gtgtggtcca tagtaatcat agaatatagg aaaatattaa gacaaagaaa   5220
aatagacagg ttaattgata gactaataga aagagcagaa gacagtggca atgagagtga   5280
aggagaagta tcagcacttg tggagatggg ggtggaaatg gggcaccatg ctccttggga   5340
tattgatgat ctgtagtgct acagaaaaat tgtgggtcac agtctattat ggggtacctg   5400
tgtggaagga agcaaccacc actctatttt gtgcatcaga tgctaaagca tatgatacag   5460
aggtacataa tgtttgggcc acacatgcct gtgtacccac agaccccaac ccacaagaag   5520
tagtattggt aaatgtgaca gaaaatttta acatgtggaa aaatgacatg gtagaacaga   5580
tgcatgagga tataatcagt ttatgggatc aaagcctaaa gccatgtgta aaattaaccc   5640
cactctgtgt tagtttaaag tgcactgatt tgaagaatga tactaatacc aatagtagta   5700
gcgggagaat gataatggag aaaggagaga taaaaaactg ctctttcaat atcagcacaa   5760
gcataagaga taaggtgcag aaagaatatg cattctttta taaacttgat atagtaccaa   5820
tagataatac cagctatagg ttgataagtt gtaacacctc agtcattaca caggcctgtc   5880
caaaggtatc ctttgagcca attcccatac attattgtgc cccggctggt tttgcgattc   5940
taaaatgtaa taataagacg ttcaatggaa caggaccatg tacaaatgtc agcacagtac   6000
aatgtacaca tggaatcagg ccagtagtat caactcaact gctgttaaat ggcagtctag   6060
cagaagaaga tgtagtaatt agatctgcca atttcacaga caatgctaaa accataatag   6120
tacagctgaa cacatctgta gaaattaatt gtacaagacc caacaacaat acaagaaaaa   6180
gtatccgtat ccagagggga ccagggagag catttgttac aataggaaaa ataggaaata   6240
tgagacaagc acattgtaac attagtagag caaaatggaa tgccacttta aaacagatag   6300
ctagcaaatt aagagaacaa tttggaaata ataaaacaat aatctttaag caatcctcag   6360
gaggggaccc agaaattgta acgcacagtt ttaattgtgg aggggaattt ttctactgta   6420
attcaacaca actgtttaat agtacttggt ttaatagtac ttggagtact gaagggtcaa   6480
ataacactga aggaagtgac acaatcacac tcccatgcag aataaaacaa tttataaaca   6540
tgtggcagga agtaggaaaa gcaatgtatg cccctcccat cagtggacaa attagatgtt   6600
catcaaatat tactgggctg ctattaacaa gagatggtgg taataacaac aatgggtccg   6660
agatcttcag acctggagga ggcgatatga gggacaattg gagaagtgaa ttatataaat   6720
ataaagtagt aaaaattgaa ccattaggag tagcacccac caaggcaaag agaagagtgg   6780
tgcagagaga aaaaagagca gtgggaatag gagctttgtt ccttgggttc ttgggagcag   6840
caggaagcac tatgggctgc acgtcaatga cgctgacggt acaggccaga caattattgt   6900
ctgatatagt gcagcagcag aacaatttgc tgagggctat tgaggcgcaa cagcatctgt   6960
tgcaactcac agtctggggc atcaaacagc tccaggcaag aatcctggct gtggaaagat   7020
acctaaagga tcaacagctc ctggggattt ggggttgctc tggaaaactc atttgcacca   7080
ctgctgtgcc ttggaatgct agttggagta ataaatctct ggaacagatt tggaataaca   7140
```

```
tgacctggat ggagtgggac agagaaatta acaattacac aagcttaata cactccttaa   7200

ttgaagaatc gcaaaaccag caagaaaaga atgaacaaga attattggaa ttagataaat   7260

gggcaagttt gtggaattgg tttaacataa caaattggct gtggtatata aaattattca   7320

taatgatagt aggaggcttg gtaggtttaa gaatagtttt tgctgtactt tctatagtga   7380

atagagttag gcagggatat tcaccattat cgtttcagac ccacctccca atcccgaggg   7440

gacccgacag gcccgaagga atagaagaag aaggtggaga gagagacaga gacagatcca   7500

ttcgattagt gaacggatcc ttagcactta tctgggacga tctgcggagc ctgtgcctct   7560

tcagctacca ccgcttgaga gacttactct tgattgtaac gaggattgtg gaacttctgg   7620

gacgcagggg gtgggaagcc ctcaaatatt ggtggaatct cctacagtat tggagtcagg   7680

aactaaagaa tagtgctgtt aacttgctca atgccacagc catagcagta gctgagggga   7740

cagatagggt tatagaagta ttacaagcag cttatagagc tattcgccac atacctagaa   7800

gaataagaca gggcttggaa aggattttgc tataagatgg gtggcaagtg gtcaaaaagt   7860

agtgtgattg gatggcctgc tgtaagggaa agaatgagac gagctgagcc agcagcagat   7920

ggggtgggag cagtatctcg agacctagaa aaacatggag caatcacaag tagcaataca   7980

gcagctaaca atgctgcttg tgcctggcta gaagcacaag aggaggaaga ggtgggtttt   8040

ccagtcacac ctcaggtacc tttaagacca atgacttaca aggcagctgt agatcttagc   8100

cactttttaa aagaaaaggg gggactggaa gggctaattc actcccaaag aagacaagat   8160

atccttgatc tgtggatcta ccacacacaa ggctacttcc ctgattggca gaactacaca   8220

ccagggccag gggtcagata tccactgacc tttggatggt gctacaagct agtaccagtt   8280

gagccagata aggtagaaga ggccaataaa ggagagaaca ccagcttgtt acaccctgtg   8340

agcctgcatg gaatggatga ccctgagaga gaagtgttag agtggaggtt tgacagccgc   8400

ctagcatttc atcacgtggc ccgagagctg catccggagt acttcaagaa ctgctgacat   8460

cgagcttgaa ttcactgtga gacatgggct aaagaggact aataacaagc taggccaaat   8520

tcctgtaaat cacttggggg gttataagaa aagcaagttc actatgacaa agcaaaatgt   8580

aaaggccaaa ttcctgtaaa tcacttgggg ggttataaga aaagcaagtt cactatgaca   8640

aagcaaaatg taaccgcaag tgctgacaga tgtaacagct gacatatcag ctgatgcttg   8700

ctcatgctga cactgtagct ctgagctgta tataaggaga agcttgctgc ttgcacttca   8760

gagttctagg agagtccctc ctagtctctc ctctccgagg aggtaccgag acctcaaaat   8820

aaaggagtga ttgccttact gccgagtgga gagtgattac tgagcggccg gtgtatcggg   8880

agtcgtccct taatctgtgc aataccagag cggctctcgc agctgc                  8926
```

```
<210> SEQ ID NO 13
<211> LENGTH: 9224
<212> TYPE: DNA
<213> ORGANISM: Artificial Sequence
<220> FEATURE:
<223> OTHER INFORMATION: Genome retroviral

<400> SEQUENCE: 13

aattcactgt gagacatggg ctaaagagga ctaataacaa gctaggccaa attcctgtaa     60

atcacttggg gggttataag aaaagcaagt tcactatgac aaagcaaaat gtaaaggcca    120

aattcctgta aatcacttgg ggggttataa gaaaagcaag ttcactatga caaagcaaaa    180

tgtaaccgca agtgctgaca gatgtaacag ctgacatatc agctgatgct tgctcatgct    240
```

```
gacactgtag ctctgagctg tatataagga gaagcttgct gcttgcactt cagagttcta    300
ggagagtccc tcctagtctc tcctctccga ggaggtaccg agacctcaaa ataaaggagt    360
gattgcctta ctgccgagtg gagagtgatt actgagcggc cggtgtatcg ggagtcgtcc    420
cttaatctgt gcaataccag agcggctctc gcagctgggc gcccgaacag ggacttgaag    480
aagactgaga agccttggaa cacggctgag tgaaggcagt aagggcggca ggaacaaacc    540
acgacggagt gctcctagaa aagcgcaggc cgaggtacca agggcggcgt gtggagcggg    600
agtgaaagag gcctccgggt gaaggtaagt gcctacacca aatacagtag ccagaagggc    660
ttgttatcct acctttagac gggtagaaga ttgtgggaga tgggcgcgag aaactccgtc    720
ttgagaggga aaaaagcaga cgaattagaa aagattaggt tacggcccgg cggaaagaaa    780
aaatataggc taaaacatat tgtgtgggca gcgaatgaat tggacagatt cggattggca    840
gagagcctgt tggagtcaaa agagggttgc caaaaaattc ttacagtttt agatccatta    900
gtaccgacag ggtcagaaaa tttaaaaagc ctttttaata ctgtctgcgt catttggtgt    960
atacacgcag aagagaaagc gaaagatact gaagaagcaa aacaaaaggt acagagacat   1020
ctagtggcag aaacaaaaac tacagaaaaa atgccaagta caagtagacc aacagcacca   1080
cctagcggga acggaggaaa cttccccgta caacaagtgg ccggcaacta tacccatgtg   1140
ccactaagtc cccgaaccct aaatgcttgg gtaaaactag tagaggaaaa gaagttcggg   1200
gcagaagtag tgccaggatt tcaggcactc tcagaaggct gcacgcccta tgatattaat   1260
caaatgctta attgtgtggg cgaccatcaa gcagctatgc aaataatcag ggaaattatt   1320
aatgaagaag cagcagattg ggacgcacaa cacccaatac caggcccctt accagcgggg   1380
cagctcaggg agccaagggg atctgacata gcagggacaa caagcacagt agaagagcag   1440
atccagtgga tgtttaggcc acaaaatcct gtaccagtag gaagcatcta tagaagatgg   1500
atccagatag ggctacagaa gtgcgtcagg atgtacaacc caaccaacat cctagacata   1560
aaacagggac caaaggagcc attccagagt tatgtagata gattctacaa gagcttgagg   1620
gcagaacaaa cagatccagc agtaaaaaat tggatgaccc aaacactgct agtgcagaat   1680
gccaacccag actgtaagtt agtactaaaa ggactaggga taaatcctac cttagaagaa   1740
atgctaaccg cctgtcaggg ggtaggtgga ccaggccaga aagccagatt aatggcagaa   1800
gccttaaagg aggccatggc accagccccc atcccatttg cagcagccca acagagaagg   1860
acaattaagt gctggaattg cggaaaggaa gggcactcgg caagacaatg ccgagcacct   1920
agaagacaag gctgctggaa atgtggcaag gcaggacaca tcatggcaaa atgcccagaa   1980
agacaggcgg gtttttaggg gttgggccca tggggaaaga agccccgcaa tttccctgtg   2040
gcccaaatcc cgcaggggct gacaccaaca gcacccccga tagacccagt agaggaccta   2100
ctagagaagt acatgcagca agggaaaagg cagagagagc agagagagag gccatacaaa   2160
gaagtgacag aggacttcct gcagctcgag aaacaagaga caccatgcag agagacgaca   2220
gaggacttgc tgcacctcaa ttctctcttt ggaaaagacc agtagtcaca gcacatgttg   2280
agggccagcc agtagaagtt ttgctagaca caggggctga cgactcaata gtagcaggcg   2340
tagagttagg gagcaattat agtccaaaga tagtaggggg aatagggggga ttcataaata   2400
ccaaagaata taaaaatgta gaaataagag tattaaataa aagagtaaga gccaccataa   2460
tgacaggtga taccccaatc aacatttttg gcagaaacat tctgacagcc ttaggcatgt   2520
cattaaatct accagtcgcc aagatagaac caataaaaat aatgctgaag ccaggaaagg   2580
atggaccaaa actgagacaa tggcccttaa caaaagaaaa aatagaggca ctaaaagaga   2640
```

```
tctgtgagaa aatggaaaga gagggccagc tagaggaggc acctccaact aatccttata   2700
atacccccac atttgcaatc aagaaaaagg acaaaaacaa atggagaatg ctaatagatt   2760
ttagagaact aaacaaggta actcaagact tcacagaaat ccagttagga attccacacc   2820
cagcaggact agccaagaag aaacgaatta ctgtcctaga tgtaggggat gcttactttt   2880
ccataccact acatgaggat tttagacagt atactgcatt tactctacca tcaataaaca   2940
atgctgaacc aggaaaaaga tacatatata aagtctcacc acagggatgg aagggatcac   3000
cagcaatttt tcagtacaca atgaggcagg tcttagaacc attcagaaaa gcaaacccgg   3060
atatcattct cattcagtac atggatgata tcttgatagc cagcgacagg acagatttag   3120
aacatgacag agtggttctg cagctaaagg aacttctaaa tggcctggga ttttccaccc   3180
cagatgagaa gttccaaaaa gaccctccat accaatggat gggctatgaa ctgtggccaa   3240
ctaaatggaa gctgcaaaga atacaattgc cccaaaagga agtatggaca gtcaatgaca   3300
tccaaaaact ggtgggtgtc ctaaattggg cagcacaaat ctacccaggg ataaagacca   3360
gaaacttatg taggttaatc agaggaaaaa tgacactcac agaagaggta cagtggacag   3420
aattagcaga agcggaacta gaagaaaaca aaatcatctt aagccaggaa caagaaggat   3480
gctattacca agaggaaaag gagctagaag caacagtcca aaaagatcaa gacaatcagt   3540
ggacatataa gatacaccag ggaggaaaaa ttctaaaagt aggaaaatat gcaaaggtaa   3600
aaaataccca caccaacgga gtcagactcc tagcacaagt agttcaaaaa ataggaaaag   3660
aagcactagt catttgggga cgaataccaa aatttcacct accagtagaa agagatacct   3720
gggaacagtg gtgggataac tactggcaag tgacatggat cccagactgg gacttcatat   3780
ctaccccgcc actggtcaga ttagtattta acctggtgaa agatcccata ctaggcgcag   3840
aaaccttcta cacagatgga tcctgcaata agcaatcaag agaaggaaaa gcaggataca   3900
taacagatag aggaagagac aaggtgaggc tattagagca aaccaccaat cagcaagcag   3960
aattagaagc ctttgcgatg gcagtaacag actcaggtcc aaaggccaac attatagtag   4020
actcacaata tgtaatggga atagtagcag gccaaccaac agagtcagag agtaaaatag   4080
taaatcaaat catagaagaa atgataaaaa aggaagcaat ctatgttgca tgggtcccag   4140
cccataaagg cataggagga aatcaggagg tagatcactt agtaagtcag ggcatcagac   4200
aagtattatt cctagagaaa atagaaccct aaatcaaaga ctatggagga aggcaagaga   4260
tggatagcgg ttccaacttg gagggtgcca gggaggatgg agaggtggca tagccttatc   4320
aagtatctaa aatacagaac aggagatcta gagaaggtgt gctatgttcc ccaccataag   4380
gtgggatggg cgtggtggac ttgcagcagg gtaatattcc cattaaaagg agaaagtcat   4440
ctggagatac aggcatactg gaacctaaca ccagaaaaag gatggctctc ctcctattca   4500
gtaagactaa cttggtatac agaaaaattc tggacagatg ttaccccaga ctgtgcggac   4560
tccctaatac atagcactta tttctcttgc tttacggcag gcgaagtaag aagagccatc   4620
agaggggaaa agctattatc ctgctgcaac tacccccaag cccataagta ccaggtaccg   4680
tcactccagt ttctggcctt agtggtagtg caacaaaatg gcaggcccca gagagacaat   4740
accaccagga aacagtggcg aagaaactat cggagaggcc ttcgagtggc tagacaggac   4800
ggtagaagcc ataaacagag aggcagtgaa ccacctgccc cgagagctta ttttccaggt   4860
gtggcaaagg tcctggagat actggcatga tgaacaagga atgtcaataa gttacacaaa   4920
gtatagatat ttgtgcctaa tgcagaaagc tatgttcata cattctaaga gagggtgcac   4980
```

-continued

```
ttgcctgggg ggaggacatg ggccgggagg atggagatca ggacctcccc ctcctccccc   5040
tccaggtcta gtctaatgac tgaagcacca acagagtctc cccggagga taggacccca   5100
ccgagggagc caggggatga gtgggtaata gaaaccctga gagagataaa ataagaagct   5160
ttaaagcact ttgaccctcg cttgctaatt actcttggca actatatcta tgctagacat   5220
ggagacaccc ttgaaggcgc cagagggctc attaggatcc tacaacgagc cctcctcttg   5280
cacttcagag caggatgcgg ccgctcaagg attggtcagc ccaggggacg aaatcccttta  5340
tcagctatac caacccctag aggcatgcga taacaaatgt tactgtaaaa agtgctgcta   5400
ccattgccag atgtgttttt taaacaaggg gctcgggata tggtatgaac gaaagggcag   5460
aagaagaaga actccgaaga aaactaaggc tcattcgtct tctgcatcag acaagtgagt   5520
aagatgtgtg gtaggaatca actatttgtt gccagcttgc tagctagtgc ttgcttaata   5580
tattgcgtcc aatatgtgac tgttttctat ggcgtgcccg tgtggagaaa tgcatccatt   5640
cccctctttt gtgcaactaa aaatagagat acttggggaa ccatacagtg cttgccagac   5700
aatgatgact atcaggaaat agctttaaat gtgacagagg ccttcgacgc atggaataat   5760
acagtaacag aacaagcagt agaagatgtc tggagtctat ttgagacatc aataaaacca   5820
tgcgtcaaac taacaccctt atgtgtagca atgcgttgta acagcacaac tgcaaaaaac   5880
acaacctcca caccaacaac caccacaaca gcaaacacaa caataggaga gaattcttca   5940
tgcatacgca cagacaactg cacagggttg ggagaagaag agatggtcga ctgtcagttc   6000
aatatgacag gattagagag ggataagaaa aaactatata atgaaacatg gtactcaaaa   6060
gatgtagtct gtgaatcaaa tgacaccaag aaagagaaaa catgttacat gaaccactgc   6120
aacacatcag tcatcacaga gtcatgtgac aagcactatt gggatactat gaggtttaga   6180
tattgtgcac caccgggttt tgccctgcta agatgcaatg ataccaatta ttcaggcttt   6240
gagcccaatt gttctaaggt agtagctgct acatgtacaa ggatgatgga aacgcaaacc   6300
tccacttggt ttggctttaa tggcactagg gcagaaaata gaacatatat ctattggcat   6360
ggtagggata atagaactat cattagctta aacaagtttt ataatctcac cgtacattgt   6420
aagaggccag gaaacaagac agttgtacca ataacactca tgtcagggtt agtgtttcac   6480
tcccagccaa tcaatagaag acccaggcaa gcatggtgct ggttcaaagg cgagtggaag   6540
gaagccatga aggaggtgaa gctaaccctt gcaaaacatc ccaggtataa aggaaccaac   6600
gacacagaaa aaattcgttt tatagcgcca ggagaacgct cagacccaga agtggcatac   6660
atgtggacta actgcagagg agaatttctc tactgcaata tgacttggtt cctcaattgg   6720
gtagaaaaca gaacgaatca gacacagcac aattatgtgc catgccatat aaagcaaata   6780
attaatacct ggcacaaggt agggaaaaat gtatatttgc ctcctaggga aggacagtta   6840
acctgcaact ctacagtgac cagcataatt gctaacattg acggaggaga gaaccagaca   6900
aatattacct ttagtgcaga ggtggcagaa ctataccgat tagaattggg ggattataaa   6960
ttgatagaag taacaccaat tggctttgca cctacaccag taaaaagata ctcctctgct   7020
ccagtgagga ataaaagagg tgtattcgtg ctagggttct taggttttct cacgacagca   7080
ggagctgcaa tgggcgcggc gtccttgacg ctgtcggctc agtctcggac tttattggcc   7140
gggatagtgc agcaacagca acagctgttg gacgtggtca agagacaaca agaaatgttg   7200
cgactgaccg tctggggaac aaaaaatctc caggcaagag tcactgctat cgagaaatac   7260
ttaaaggacc aggcgcaact aaattcatgg ggatgtgcgt ttagacaagt ctgccacact   7320
actgtaccat gggtaaatga caccttaacg cctgattgga acaacatgac atggcaggaa   7380
```

```
tgggagcaac gaatccgcaa cctagaggca aatatcagtg aaagtttaga acaggcacaa   7440
atccagcaag aaaagaacat gtatgaacta caaaaattaa atagctggga tgtttttggc   7500
aactggtttg atttaacctc ctggatcaaa tatattcagt atggagttta tatagtagta   7560
ggaataatag ttttaagaat agtaatatat gtagtacaaa tgttaagtag acttagaaag   7620
ggctataggc ctgttttctc ttcccccccc gcttacttcc aacagatcca tatccacaag   7680
gaccgggaac agccagccag agaagaaaca gaagaagacg ttggaaacag cgttggagac   7740
aattggtggc cctggccgat aagatatata catttcctga tccgccagct gattcgcctc   7800
ttgaacagac tatacaacat ctgcagggac ttactatcca ggagcttcca gaccctccaa   7860
ctaatctccc agagtcttcg gagagcattg acagcagtca gagactggct gagatttaac   7920
acagcctacc tgcaatatgg gggcgagtgg atccaagaag cgttccgagc cttcgcgagg   7980
gctacgggag agactcttac aaacgcctgg agaggcttct gggggacact gggacaaatt   8040
gggaggggaa tacttgcagt cccaagaagg atcaggcagg gggcagaaat cgccctcctg   8100
tgagggacgg cggtatcaac agggagattt tatgaatacc ccatggagag ccccagcaga   8160
aggggagaaa ggctcgtaca agcaacaaaa tatggatgat gtagattcag atgatgatga   8220
cctagtaggg gtccctgtca caccaagagt accattaaga gaaatgacat ataggttggc   8280
aagagatatg tcacatttga taaaagaaaa ggggggactg gaagggctgt attacagtga   8340
taggagacgt agagtcctag acatatactt agaaaaggaa gagggaataa ttggagactg   8400
gcagaactat actcatggac caggagtaag gtatccaaag ttctttgggt ggttatggaa   8460
gctagtacca gtagatgtcc cacaagaggg agatgacagt gagactcact gcttagtgca   8520
tccagcacaa acaagcaggt ttgatgaccc gcatggagaa acattagttt ggaggtttga   8580
ccccacgcta gcttttagct acgaggcctt tattcgatac ccagaggagt ttgggtacaa   8640
gtcaggcctg ccagaggatg aatggaaggc aagactgaaa gcaagaggga taccgtttag   8700
ctaaaaacag gaacagctat acttggtcag ggcaggaagt aactaacaga aaacagctga   8760
gactgcaaat tcactgtgag acatgggcta aagaggacta ataacaagct aggccaaatt   8820
cctgtaaatc acttgggggg ttataagaaa agcaagttca ctatgacaaa gcaaaatgta   8880
aaggccaaat tcctgtaaat cacttggggg gttataagaa aagcaagttc actatgacaa   8940
agcaaaatgt aaccgcaagt gctgacagat gtaacagctg acatatcagc tgatgcttgc   9000
tcatgctgac actgtagctc tgagctgtat ataaggagaa gcttgctgct tgcacttcag   9060
agttctagga gagtccctcc tagtctctcc tctccgagga ggtaccgaga cctcaaaata   9120
aaggagtgat tgccttactg ccgagtggag agtgattact gagcggccgg tgtatcggga   9180
gtcgtccctt aatctgtgca ataccagagc ggctctcgca gctg                    9224
```

```
<210> SEQ ID NO 14
<211> LENGTH: 8975
<212> TYPE: DNA
<213> ORGANISM: Artificial Sequence
<220> FEATURE:
<223> OTHER INFORMATION: Genome retroviral

<400> SEQUENCE: 14
```

```
aattcactgt gagacatggg ctaaagagga ctaataacaa gctaggccaa attcctgtaa     60
atcacttggg gggttataag aaaagcaagt tcactatgac aaagcaaaat gtaaaggcca    120
aattcctgta aatcacttgg ggggttataa gaaaagcaag ttcactatga caaagcaaaa    180
```

```
tgtaaccgca agtgctgaca gatgtaacag ctgacatatc agctgatgct tgctcatgct    240
gacactgtag ctctgagctg tatataagga gaagcttgct gcttgcactt cagagttcta    300
ggagagtccc tcctagtctc tcctctccga ggaggtaccg agacctcaaa ataaaggagt    360
gattgcctta ctgccgagtg gagagtgatt actgagcggc cggtgtatcg ggagtcgtcc    420
cttaatctgt gcaataccag agcggctctc gcagctgggc gcccgaacag ggacttgatt    480
gagagtgatt gaggaagtga agctagagca atagaaagct gttaagcaga actcctgctg    540
acctaaatag ggaagcagta gcagacgctg ctaacagtga gtatctctag tgaagcggac    600
tcgagctcat aatcaagtca ttgtttaaag gcccagataa attacatctg gtgactcttc    660
gcggaccttc aagccaggag attcgccgag ggacagtcaa caaggtagga gagattctac    720
agcaacatgg ggaatggaca ggggcgagat tggaaaatgg ccattaagag atgtagtaat    780
gttgctgtag gagtaggggg gaagagtaaa aaatttggag aagggaattt cagatgggcc    840
attagaatgg ctaatgtatc tacaggacga gaacctggtg atataccaga gactttagat    900
caactaaggt tggttatttg cgatttacaa gaaagaagag aaaaatttgg atctagcaaa    960
gaaattgata tggcaattgt gacattaaaa gtctttgcgg tagcaggact tttaaatatg   1020
acggtgtcta ctgctgctgc agctgaaaat atgtattctc aaatgggatt agacactagg   1080
ccatctatga aagaagcagg tggaaaagag gaaggccctc cacaggcata tcctattcaa   1140
acagtaaatg gagtaccaca atatgtagca cttgacccaa aaatggtgtc catttttatg   1200
gaaaaggcaa gagaaggact aggaggtgag gaagttcaac tatggtttac tgccttctct   1260
gcaaatttaa cacctactga catggccaca ttaataatgg ccgcaccagg gtgcgctgca   1320
gataaagaaa tattggatga aagcttaaag caactgacag cagaatatga tcgcacacat   1380
ccccctgatg ctcccagacc attaccctat tttactgcag cagaaattat gggtatagga   1440
ttaactcaag aacaacaagc agaagcaaga tttgcaccag ctaggatgca gtgtagagca   1500
tggtatctcg aggcattagg aaaattggct gccataaaag ctaagtctcc tcgagctgtg   1560
cagttaagac aaggagctaa ggaagattat tcatccttta tagacagatt gtttgcccaa   1620
atagatcaag aacaaaatac agctgaagtt aagttatatt taaaacagtc attgagcata   1680
gctaatgcta atgcagactg taaaaaggca atgagccacc ttaagccaga aagtacccta   1740
gaagaaaagt tgagagcttg tcaagaaata ggctcaccag gatataaaat gcaactcttg   1800
gcagaagctc ttacaaaagt tcaagtagtg caatcaaaag gatcaggacc agtgtgtttt   1860
aattgtaaaa aaccaggaca tctagcaaga caatgtagag aagtgaaaaa atgtaataaa   1920
tgtggaaaac ctggtcatgt agctgccaaa tgttggcaag gaaatagaaa gaattcggga   1980
aactggaagg cggggcgagc tgcagcccca gtgaatcaaa tgcagcaagc agtaatgcca   2040
tctgcacctc caatggagga gaaactattg gatttataaa ttataataaa gtaggtacta   2100
ctacaacatt agaaaagagg ccagaaatac tcatatttgt aaatggatat cctataaaat   2160
ttttattaga cacaggagca gatataacaa ttttaaatag gagagatttt caagtaaaaa   2220
attctataga aaatggaagg caaaatatga ttggagtagg aggaggaaag agaggaacaa   2280
attatattaa tgtacattta gagattagag atgaaaatta taagacacaa tgtatatttg   2340
gtaatgtttg tgtcttagaa gataactcat taatacaacc attattaggg agagataata   2400
tgattaaatt caatattagg ttagtaatgg ctcaaatttc tgataagatt ccagtagtaa   2460
aagtaaaaat gaaggatcct aataaaggac ctcaaataaa acaatggcca ttaacaaatg   2520
aaaaaattga agccttaaca gaaatagtag aaagactaga aagagaaggg aaagtaaaaa   2580
```

```
gagcagatcc aaataatcca tggaatacac cagtatttgc tataaaaaag aaaagtggaa   2640
aatggagaat gctcatagat tttagagaat taaacaaact aactgagaaa ggagcagagg   2700
tccagttggg actacctcat cctgctggtt tacaaataaa aaaacaagta acagtattag   2760
atatagggga tgcatatttc accattcctc ttgatccaga ttatgctcct tatacagcat   2820
ttactttacc tagaaaaaat aatgcgggac caggaaggag atttgtgtgg tgtagtctac   2880
cacaaggctg gattttaagt ccattgatat atcaaagtac attagataat ataatacaac   2940
cttttattag acaaaatcct caattagata tttaccaata tatggatgac atttatatag   3000
gatcaaattt aagtaaaaag gagcataaag aaaaggtaga agaattaaga aaattactat   3060
tatggtgggg atttgaaact ccagaagata aattacagga agaacccccca tatacatgga   3120
tgggttatga attacatcca ttaacatgga caatacaaca gaaacagtta gacattccag   3180
aacagcccac tctaaatgag ttgcaaaaat tagcaggaaa aattaattgg gctagccaag   3240
ctattccaga cttgagtata aaagcattaa ctaacatgat gagaggaaat caaaacctaa   3300
attcaacaag acaatggact aaagaagctc gactggaagt acaaaaggca aaaaaggcta   3360
tagaagaaca agtacaacta ggatactatg accccagtaa ggagttatat gctaaattaa   3420
gtttggtggg accacatcaa ataagttatc aagtatatca gaaggatcca gaaaagatac   3480
tatggtatgg aaaaatgagt agacaaaaga aaaaggcaga aaatacatgt gatatagcct   3540
taagagcatg ctataagata agagaagagt ctattataag aataggaaaa gaaccaagat   3600
atgaaatacc tacttctaga gaagcctggg aatcaaattt aattaattca ccatatctta   3660
aggccccacc tcctgaggta gaatatatcc atgctgcttt gaatataaag agagcgttaa   3720
gtatgataaa agatgctcca ataccaggag cagaaacatg gtatatagat ggaggtagaa   3780
agctaggaaa agcagcaaaa gcagcctatt ggacagatac aggaaagtgg caagtgatgg   3840
aattagaagg cagtaatcag aaggcagaaa tacaagcatt attattggca ttaaaagcag   3900
gatcagagga gatgaatatt ataacagatt cacaatatgt tataaatatt attcttcaac   3960
aaccagatat gatggaggga atctggcaag aagttttaga agaattggag aagaaaacag   4020
caatatttat agattgggtc ccaggacata aaggtattcc aggaaatgag gaagtagata   4080
agctttgtca aacaatgatg ataaatagaag gggatgggat attagataaa aggtcagaag   4140
atgcaggata tgatttatta gctgcaaaag aaatacattt attgccagga gaggtaaaag   4200
taataccaac aggggtaaag ctaatgttgc ctaaaggata ttggggatta ataataggaa   4260
aaagctcgat agggagtaaa ggattggatg tattaggagg ggtaatagac gaaggatatc   4320
gaggtgaaat tggagtaata atgattaatg tatcaagaaa atcaatcacc ttaatggaac   4380
gacaaaagat agcacaatta ataatattgc cttgtaaaca tgaagtatta gaacaaggaa   4440
aagtagtaat ggattcagag agaggagaca atggttatgg gtcaacagga gtattctcct   4500
cttgggttga cagaattgag gaagcagaaa taaatcatga aaaatttcac tcagatccac   4560
agagaaggga tattttctta tacctaggag acacataagg agagttccag aaccctgcgc   4620
tcttcctgaa ggggatgagt gaagaagatt ggcaggtaag tagaagactc tttgcagtgc   4680
tccaaggagg agtaaatagc gctatgctat acatatctag gctacctccg gatgaaagag   4740
aaaagtataa aaaagacttc aagaaaagac tttttgacac agaaacagga tttataaaga   4800
gactacggaa agctgaagga ataaaatgga gctttcatac tagagattat tacataggat   4860
atgtcagaga aatggtggca ggatccacta catcattaag tctaaggatg tatatatata   4920
```

```
taagtaaccc actatggcat tctcagtatc gtccaggttt gaaaaatttc aataaggaat   4980
ggccttttgt aaatatgtgg ataaaaacag gatttatgtg ggatgatatt gaaaaacaaa   5040
atatttgtat aggaggagaa gtttcaccag gatggggacc agggatggta ggtatagcaa   5100
taaaagcttt tagttgtggc gaaagaaaga ttgaggctac tcctgtaatg attataagag   5160
gagaaataga tccaaaaaaa tggtgcggag attgttggaa tttaatgtgt cttagaaact   5220
cacctccaaa gactttacaa agactcgcta tgttggcgtg tggcgtgccg gctaagaagt   5280
ggcgaggatg ctgtaatcaa cgctttgttt ctccttacag aacgcctgct gatttagagg   5340
tcattcaatc caagcccagc tggaacctgt tatggtcggg agaattatga atggaagaca   5400
taatagtatt attcaatagg gtcactgaga aactagaaaa agaattagct atcagaatat   5460
ttgtattagc acatcaatta gaaagggaca aagctattag attactacaa ggattatttt   5520
ggagatatag atttaagaaa ccccgagtag attattgttt atgttggtgg tgttgcaaat   5580
tctattattg gcagttgcaa tctacattat caataactac tgcttagaaa tatttagatt   5640
aatatttcat ttgcaacaat aagaatggca gaaggatttg cagccaatag acaatggata   5700
ggactagaag aagctgaaga gttattagat tttgatatag caacacaaat gagtgaagaa   5760
ggaccactaa atccaggagt aaacccattt agggtacctg gaataacaga aaaagaaaag   5820
caaaactact gtaacatatt acaacctaag ttacaagatc taaggaacga aattcaagag   5880
gtaaaactgg aagaaggaaa tgcaggtaag tttagaagag caagattttt aaggtattct   5940
gatgaaagtg tattgtccct ggttcatgcg ttcataggat attgtatata tttaggtaat   6000
cgaaataagt taggatcttt aagacatgac attgatatag aagcacccca agaagagtgt   6060
tataataata gagagaaggg tacaactgac aatataaaat atggtagacg atgttgccta   6120
ggaacggtga ctttgtacct gattttattt ataggaataa taatatattc acagacaacc   6180
aacgctcagg tagtatggag acttccacca ttagtagtcc cagtagaaga atcagaaata   6240
attttttggg attgttgggc accagaagaa cccgcctgtc aggactttct tggggcaatg   6300
atacatctaa aagctaagac aaatataagt atacgagagg gacctacctt ggggaattgg   6360
gctagagaaa tatgggcaac attattcaaa aaggctacta gacaatgtag aagaggcaga   6420
atatggaaaa gatggaatga gactataaca ggaccatcag gatgtgctaa taacacatgt   6480
tataatgttt cagtaatagt acctgattat cagtgttatt tagatagagt agatacttgg   6540
ttacaaggga aaataaatat atcattatgt ctaacaggag gaaaaatgtt gtacaataaa   6600
gttacaaaac aattaagcta ttgtacagac ccattacaaa tcccactgat caattataca   6660
tttggaccta atcaaacatg tatgtggaat acttcacaaa ttcaggaccc tgaaatacca   6720
aaatgtggat ggtggaatca aatggcctat tataacagtt gtaaatggga agaggcaaaa   6780
gtaaagtttc attgtcaaag aacacagagt cagcctggat catggtttag agcaatctcg   6840
tcatggaaac aaagaaatag atgggagtgg agaccagatt ttgaaagtaa aaaggtgaaa   6900
atatctctac agtgcaatag cacaaaaaac ctaacctttg caatgagaag ttcaggagat   6960
tatggagaag taacgggagc ttggatagag tttggatgtc atagaaataa atcaaaactt   7020
catgctgaag caaggtttag aattagatgt agatggaatg tagggagtaa tacctcgctc   7080
attgatacat gtggaaacac tcaaaaagtt tcaggtgcga atcctgtaga ttgtaccatg   7140
tattcaaata aaatgtacaa ttgttcttta caaaacgggt ttactatgaa ggtagatgac   7200
cttattatgc atttcaatat gaaaaaggct gtagaaatgt ataatattgc tggaaattgg   7260
tcttgtacat ctgacttgcc atcgtcatgg gggtatatga attgtaattg tacaaatagt   7320
```

```
agtagtagtt atagtggtac taaaatggca tgtcctagca atcgaggcat cttaaggaat   7380

tggtataacc cagtggcagg attacgacaa tccttagaac agtatcaagt tgtaaaacaa   7440

ccagattact tagtggtccc agaggaagtc atggaatata aacctagaag gaaaagggca   7500

gctattcatg ttatgttggc tcttgcagca gtattatcta ttgccggtgc agggacgggg   7560

gctactgcta tagggatggt aacacaatac caccaagttc tggcaaccca tcaagaagct   7620

gtagaaaagg tgactgaagc cttaaagata aacaacttaa gattagttac attagagcat   7680

caagtactag taataggatt aaaagtagaa gctatggaaa aatttttgta tacagctttc   7740

gctatgcaag aattaggatg taatcaaaat caatttttct gcaaaatccc tcctgagttg   7800

tggacaaggt ataatatgac tataaatcaa acaatatgga atcatggaaa tataactttg   7860

ggggaatggt ataaccaaac aaaagattta caacaaaagt tttatgaaat aataatggac   7920

atagaacaaa ataatgtaca agggaagaaa gggatacaac aattacaaaa gtgggaagat   7980

tgggtaggat ggataggaaa tattccacaa tatttaaagg gactattggg aggtatcttg   8040

ggaataggat taggagtgtt attattgatt ttatgtttac ctacattggt tgattgtata   8100

agaaattgta tccacaagat actaggatac acagtaattg caatgcctga agtagaagga   8160

gaagaaatac aaccacaaat ggaattgagg agaaatggta ggcaatgtgg catgtctgaa   8220

aaagaggagg aatgatgaag tatctcagac ttattttata agggagatac tgtgctgagt   8280

tcttcccttt gaggaaggta tgtcatatga atccatttcg aatcaaatca aactaataaa   8340

gtatgtattg taaggtaaaa ggaaaagaca aagaagaaga agaaagaaga aagccttcaa   8400

gaggatgatg acagagttag aagatcgctt caggaagcta tttggcacga cttctacaac   8460

gggagacagc acagtagatt ctgaagatga acctcctaaa aaagaaaaaa gggtggacaa   8520

ttcactgtga gacatgggct aaagaggact aataacaagc taggccaaat tcctgtaaat   8580

cacttggggg gttataagaa aagcaagttc actatgacaa agcaaaatgt aaaggccaaa   8640

ttcctgtaaa tcacttgggg ggttataaga aaagcaagtt cactatgaca aagcaaaatg   8700

taaccgcaag tgctgacaga tgtaacagct gacatatcag ctgatgcttg ctcatgctga   8760

cactgtagct ctgagctgta tataaggaga agcttgctgc ttgcacttca gagttctagg   8820

agagtccctc ctagtctctc ctctccgagg aggtaccgag acctcaaaat aaaggagtga   8880

ttgccttact gccgagtgga gagtgattac tgagcggccg gtgtatcggg agtcgtccct   8940

taatctgtgc aataccagag cggctctcgc agctg                              8975
```

<210> SEQ ID NO 15
<211> LENGTH: 9702
<212> TYPE: DNA
<213> ORGANISM: Artificial Sequence
<220> FEATURE:
<223> OTHER INFORMATION: Genome retroviral

<400> SEQUENCE: 15

```
aattcactgt gagacatggg ctaaagagga ctaataacaa gctaggccaa attcctgtaa     60

atcacttggg gggttataag aaaagcaagt tcactatgac aaagcaaaat gtaaaggcca    120

aattcctgta aatcacttgg ggggttataa gaaaagcaag ttcactatga caaagcaaaa    180

tgtaaccgca agtgctgaca gatgtaacag ctgacatatc agctgatgct tgctcatgct    240

gacactgtag ctctgagctg tatataagga gaagcttgct gcttgcactt cagagttcta    300

ggagagtccc tcctagtctc tcctctccga ggaggtaccg agacctcaaa ataaaggagt    360
```

```
gattgcctta ctgccgagtg gagagtgatt actgagcggc cggtgtatcg ggagtcgtcc    420
cttaatctgt gcaataccag agcggctctc gcagctgggc gcctgaacag ggacttgaag    480
gagagtgaga gactcctgag tacggctgag tgaaggcagt aagggcggca ggaaccaacc    540
acgacggagt gctcctataa aggcgcgggt cggtaccaga cggcgtgagg agcgggagag    600
gaagaggcct ccggttgcag gtaagtgcaa cacaaaaaag aaatagctgt cttttatcca    660
ggaaggggta ataagataga gtgggagatg ggcgtgagaa actccgtctt gtcagggaag    720
aaagcagatg aattagaaaa aattaggcta cgacccaacg gaaagaaaaa gtacatgttg    780
aagcatgtag tatgggcagc aaatgaatta gatagatttg gattagcaga aagcctgttg    840
gagaacaaag aaggatgtca aaaaatactt tcggtcttag ctccattagt gccaacaggc    900
tcagaaaatt taaaaagcct ttataatact gtctgcgtca tctggtgcat tcacgcagaa    960
gagaaagtga aacacactga ggaagcaaaa cagatagtgc agagacacct agtggtggaa   1020
acaggaacaa cagaaactat gccaaaaaca agtagaccaa cagcaccatc tagcggcaga   1080
ggaggaaatt acccagtaca acaaataggt ggtaactatg tccacctgcc attaagcccg   1140
agaacattaa atgcctgggt aaaattgata gaggaaaaga aatttggagc agaagtagtg   1200
ccaggatttc aggcactgtc agaaggttgc accccctatg acattaatca gatgttaaat   1260
tgtgtgggag accatcaagc ggctatgcag attatcagag atattataaa cgaggaggct   1320
gcagattggg acttgcagca cccacaacca gctccacaac aaggacaact tagggagccg   1380
tcaggatcag atattgcagg aacaactagt tcagtagatg aacaaatcca gtggatgtac   1440
agacaacaga accccatacc agtaggcaac atttacagga gatggatcca actggggttg   1500
caaaaatgtg tcagaatgta taacccaaca aacattctag atgtaaaaca agggccaaaa   1560
gagccatttc agagctatgt agacaggttc tacaaaagtt taagagcaga acagacagat   1620
gcagcagtaa agaattggat gactcaaaca ctgctgattc aaaatgctaa cccagattgc   1680
aagctagtgc tgaaggggct gggtgtgaat cccaccctag aagaaatgct gacggcttgt   1740
caaggagtag gggggccggg acagaaggct agattaatgg cagaagccct gaaagaggcc   1800
ctcgcaccag tgccaatccc ttttgcagca gcccaacaga ggggaccaag aaagccaatt   1860
aagtgttgga attgtgggaa agagggacac tctgcaaggc aatgcagagc cccaagaaga   1920
cagggatgct ggaaatgtgg aaaaatggac catgttatgg ccaaatgccc agacagacag   1980
gcgggttttt taggccttgg tccatgggga aagaagcccc gcaatttccc catggctcaa   2040
gtgcatcagg ggctgatgcc aactgctccc ccagaggacc cagctgtgga tctgctaaag   2100
aactacatgc agttgggcaa gcagcagaga gaaaagcaga gagaaagcag agagaagcct   2160
tacaaggagg tgacagagga tttgctgcac ctcaattctc tctttggagg agaccagtag   2220
tcactgctca tattgaagga cagcctgtag aagtattact ggatacaggg gctgatgatt   2280
ctattgtaac aggaatagag ttaggtccac attatacccc aaaaatagta ggaggaatag   2340
gaggttttat taatactaaa gaatacaaaa atgtagaaat agaagtttta ggcaaaagga   2400
ttaaagggac aatcatgaca ggggacaccc cgattaacat ttttggtaga aatttgctaa   2460
cagctctggg gatgtctcta aattttccca tagctaaagt agagcctgta aaagtcgcct   2520
taaagccagg aaaggatgga ccaaaattga agcagtggcc attatcaaaa gaaaagatag   2580
ttgcattaag agaaatctgt gaaaagatgg aaaaggatgg tcagttggag gaagctcccc   2640
cgaccaatcc atacaacacc cccacatttg ctataaagaa aaaggataag aacaaatgga   2700
gaatgctgat agattttagg gaactaaata gggtcactca ggactttacg gaagtccaat   2760
```

```
taggaatacc acaccctgca ggactagcaa aaaggaaaag aattacagta ctggatatag   2820
gtgatgcata tttctccata cctctagatg aagaatttag gcagtacact gcctttactt   2880
taccatcagt aaataatgca gagccaggaa aacgatacat ttataaggtt ctgcctcagg   2940
gatggaaggg gtcaccagcc atcttccaat acactatgag acatgtgcta gaacccttca   3000
ggaaggcaaa tccagatgtg accttagtcc agtatatgga tgacatctta atagctagtg   3060
acaggacaga cctggaacat gacagggtag ttttacagtc aaaggaactc ttgaatagca   3120
tagggttttc taccccagaa gagaaattcc aaaaagatcc cccatttcaa tggatggggt   3180
acgaattgtg gccaacaaaa tggaagttgc aaaagataga gttgccacaa agagagacct   3240
ggacagtgaa tgatatacag aagttagtag gagtattaaa ttgggcagct caaatttatc   3300
caggtataaa aaccaaacat ctctgtaggt taattagagg aaaaatgact ctaacagagg   3360
aagttcagtg gactgagatg gcagaagcag aatatgagga aaataaaata attctcagtc   3420
aggaacaaga aggatgttat taccaagaag gcaagccatt agaagccacg gtaataaaga   3480
gtcaggacaa tcagtggtct tataaaattc accaagaaga caaaatactg aaagtaggaa   3540
aatttgcaaa gataaagaat acacatacca atggagtgag actattagca catgtaatac   3600
agaaaatagg aaaggaagca atagtgatct ggggacaggt cccaaaattc cacttaccag   3660
ttgagaagga tgtatgggaa cagtggtgga cagactattg gcaggtaacc tggataccgg   3720
aatgggattt tatctcaaca ccaccgctag taagattagt cttcaatcta gtgaaggacc   3780
ctatagaggg agaagaaacc tattatacag atggatcatg taataaacag tcaaaagaag   3840
ggaaagcagg atatatcaca gataggggca aagacaaagt aaaagtgtta gaacagacta   3900
ctaatcaaca agcagaattg gaagcatttc tcatggcatt gacagactca gggccaaagg   3960
caaatattat agtagattca caatatgtta tgggaataat aacaggatgc cctacagaat   4020
cagagagcag gctagttaat caaataatag aagaaatgat taaaaagtca gaaatttatg   4080
tagcatgggt accagcacac aaaggtatag gaggaaacca agaaatagac cacctagtta   4140
gtcaagggat tagacaagtt ctcttcttgg aaaagataga gacagcacta tttctgttaa   4200
aattggcagg cagatggcct attacacatc tacacacaga taatggtgct aactttgctt   4260
cgcaagaagt aaagatggtt gcatggtggg cagggataga gcacaccttt ggggtaccat   4320
acaatccaca gagtcaggga gtagtggaag caatgaatca ccacctgaaa aatcaaatag   4380
atagaatcag ggaacaagca aattcagtag aaaccatagt attaatggca gttcattgca   4440
tgaattttaa aagaagggga ggaatagggg atatgactcc agcagaaaga ttaattaaca   4500
tgatcactac agaacaagag atacaatttc aacaatcaaa aaactcaaaa tttaaaaatt   4560
ttcgggtcta ttacagagaa ggcagagatc aactgtggaa gggacccggt gagctattgt   4620
ggaaagggga aggagcagtc atcttaaagg tagggacaga cattaaggta gtacccagaa   4680
gaaaggctaa aattatcaaa gattatggag gaggaaaaga ggtggatagc agttcccaca   4740
tggaggatac cggagaggct agagaggtgg catagcctca taaaatatct gaaatataaa   4800
actaaagatc tacaaaaggt ttgctatgtg ccccatttta aggtcggatg ggcatggtgg   4860
acctgcagca gagtaatctt cccactacag gaaggaagcc atttagaagt acaagggtat   4920
tggcatttga caccagaaaa agggtggctc agtacttatg cagtgaggat aacctggtac   4980
tcaaagaact tttggacaga tgtaacacca aactatgcag acattttact gcatagcact   5040
tatttccctt gctttacagc gggagaagtg agaagggcca tcaggggaga acaactgctg   5100
```

```
tcttgctgca ggttcccgag agctcataag taccaggtac caagcctaca gtacttagca   5160
ctgaaagtag taagcgatgt cagatcccag ggagagaatc ccacctggaa acagtggaga   5220
agagacaata ggagaggcct tcgaatggct aaacagaaca gtagaggaga taaacagaga   5280
ggcggtaaac cacctaccaa gggagctaat tttccaggtt tggcaaaggt cttgggaata   5340
ctggcatgat gaacaaggga tgtcaccaag ctatgtaaaa tacagatact tgtgtttaat   5400
acaaaaggct ttatttatgc attgcaagaa aggctgtaga tgtctagggg aaggacatgg   5460
ggcaggggga tggagaccag gacctcctcc tcctcccct ccaggactag cataaatgga    5520
agaaagacct ccagaaaatg aaggaccaca aagggaacca tgggatgaat gggtagtgga   5580
ggttctggaa gaactgaaag aagaagcttt aaaacatttt gatcctcgct tgctaactgc   5640
acttggtaat catatctata atagacatgg agacaccctt gagggagcag gagaactcat   5700
tagaatcctc caacgagcgc tcttcatgca tttcagaggc ggatgcatcc actccagaat   5760
cggccaacct gggggaggaa atcctctctc agctataccg ccctctagaa gcatgctata   5820
acacatgcta ttgtaaaaag tgttgctacc attgccagtt ttgttttctt aaaaaaggct   5880
tggggatatg ttatgagcaa tcacgaaaga gaagaagaac tccgaaaaag gctaaggcta   5940
atacatcttc tgcatcaaac aagtaagtat gggatgtctt gggaatcagc tgcttatcgc   6000
catcttgctt ttaagtgtct atgggatcta ttgtactcta tatgtcacag tcttttatgg   6060
tgtaccagct tggaggaatg cgacaattcc cctcttttgt gcaaccaaga atagggatac   6120
ttggggaaca actcagtgcc taccagataa tggtgattat tcagaagtgg cccttaatgt   6180
tacagaaagc tttgatgcct ggaataatac agtcacagaa caggcaatag aggatgtatg   6240
gcaactcttt gagacctcaa taaagccttg tgtaaaatta tccccattat gcattactat   6300
gagatgcaat aaaagtgaga cagatagatg ggattgaca aaatcaataa caacaacagc    6360
atcaacaaca tcaacgacag catcagcaaa agtagacatg gtcaatgaga ctagttcttg   6420
tatagcccag gataattgca caggcttgga acaagagcaa atgataagct gtaaattcaa   6480
catgacaggg ttaaaaagag acaagaaaaa agagtacaat gaaacttggt actctgcaga   6540
tttggtatgt gaacaaggga ataacactgg taatgaaagt agatgttaca tgaaccactg   6600
taacacttct gttatccaag agtcttgtga caaacattat tgggatgcta ttagatttag   6660
gtattgtgca cctccaggtt atgctttgct tagatgtaat gacacaaatt attcaggctt   6720
tatgcctaaa tgttctaagg tggtggtctc ttcatgcaca aggatgatgg agacacagac   6780
ttctacttgg tttggcttta atggaactag agcagaaaat agaacttata tttactggca   6840
tggtagggat aataggacta taattagttt aaataagtat tataatctaa caatgaaatg   6900
tagaagacca ggaaataaga cagttttacc agtcaccatt atgtctggat tggttttcca   6960
ctcacaacca atcaatgata ggccaaagca ggcatggtgt tggtttggag gaaaatggaa   7020
ggatgcaata aaagaggtga agcagaccat tgtcaaacat cccaggtata ctggaactaa   7080
caatactgat aaaatcaatt tgacggctcc tggaggagga gatccggaag ttaccttcat   7140
gtggacaaat tgcagaggag agttcctcta ctgtaaaatg aattggtttc taaattgggt   7200
agaagatagg aatacagcta accagaagcc aaaggaacag cataaaagga attacgtgcc   7260
atgtcatatt agacaaataa tcaacacttg gcataaagta ggcaaaaatg tttatttgcc   7320
tccaagagag ggagacctca cgtgtaactc cacagtgacc agtctcatag caaacataga   7380
ttggattgat ggaaaccaaa ctaatatcac catgagtgca gaggtggcag aactgtatcg   7440
attggaattg ggagattata aattagtaga gatcactcca attggcttgg cccccacaga   7500
```

```
tgtgaagagg tacactactg gtggcacctc aagaaataaa agaggggtct ttgtgctagg   7560

gttcttgggt tttctcgcaa cggcaggttc tgcaatgggc gcggcgtcgt tgacgctgac   7620

cgctcagtcc cgaactttat tggctgggat agtgcagcaa cagcaacagc tgttggacgt   7680

ggtcaagaga caacaagaat tgttgcgact gaccgtctgg ggaacaaaga acctccagac   7740

tagggtcact gccatcgaga agtacttaaa ggaccaggcg cagctgaatg cttggggatg   7800

tgcgtttaga caagtctgcc acactactgt accatggcca aatgcaagtc taacaccaaa   7860

gtggaacaat gagacttggc aagagtggga gcgaaaggtt gacttcttgg aagaaaatat   7920

aacagccctc ctagaggagg cacaaattca acaagagaag aacatgtatg aattacaaaa   7980

gttgaatagc tgggatgtgt ttggcaattg gtttgacctt gcttcttgga taaagtatat   8040

acaatatgga gtttatatag ttgtaggagt aatactgtta agaatagtga tctatatagt   8100

acaaatgcta gctaagttaa ggcaggggta taggccagtg ttctcttccc caccctctta   8160

tttccagcag acccatatcc aacaggaccc ggcactgcca accagagaag gcaaagaaag   8220

agacggtgga gaaggcggtg gcaacagctc ctggccttgg cagatagaat atattcattt   8280

cctgatccgc caactgatac gcctcttgac ttggctattc agcaactgca gaaccttgct   8340

atcgagagta taccagatcc tccaaccaat actccagagg ctctctgcga ccctacagag   8400

gattcgagaa gtcctcagga ctgaactgac ctacctacaa tatgggtgga gctatttcca   8460

tgaggcggtc caggccgtct ggagatctgc gacagagact cttgcgggcg cgtggggaga   8520

cttatgggag actcttagga gaggtggaag atggatactc gcaatcccca ggaggattag   8580

acaagggctt gagctcactc tcttgtgagg gacagaaata caatcaggga cagtatatga   8640

atactccatg gagaaaccca gctgaagaga gagaaaaatt agcatacaga aaacaaaata   8700

tggatgatat agatgagtaa gatgatgact tggtaggggt atcagtgagg ccaaaagttc   8760

ccctaagaac aatgagttac aaattggcaa tagacatgtc tcattttata aaagaaaagg   8820

ggggactgga agggatttat tacagtgcaa gaagacatag aatcttagac atatacttag   8880

aaaaggaaga aggcatcata ccagattggc aggattacac ctcaggacca ggaattagat   8940

acccaaagac atttggctgg ctatggaaat tagtccctgt aaatgtatca gatgaggcac   9000

aggaggatga ggagcattat ttaatgcatc cagctcaaac ttcccagtgg gatgaccctt   9060

ggggagaggt tctagcatgg aagtttgatc caactctggc ctacacttat gaggcatatg   9120

ttagataccc agaagagttt ggaagcaagt caggcctgtc agaggaagag gttagaagaa   9180

ggctaaccgc aagaggcctt cttaacatgg ctgacaagaa ggaaactcgc tgaaacagca   9240

gggacaattc actgtgagac atgggctaaa gaggactaat aacaagctag gccaaattcc   9300

tgtaaatcac ttggggggtt ataagaaaag caagttcact atgacaaagc aaaatgtaaa   9360

ggccaaattc ctgtaaatca cttggggggt tataagaaaa gcaagttcac tatgacaaag   9420

caaaatgtaa ccgcaagtgc tgacagatgt aacagctgac atatcagctg atgcttgctc   9480

atgctgacac tgtagctctg agctgtatat aaggagaagc ttgctgcttg cacttcagag   9540

ttctaggaga gtccctccta gtctctcctc tccgaggagg taccgagacc tcaaaataaa   9600

ggagtgattg ccttactgcc gagtggagag tgattactga gcggccggtg tatcgggagt   9660

cgtcccttaa tctgtgcaat accagagcgg ctctcgcagc tg                      9702
```

<210> SEQ ID NO 16
<211> LENGTH: 12856
<212> TYPE: DNA

```
<213> ORGANISM: Artificial Sequence
<220> FEATURE:
<223> OTHER INFORMATION: Vecteur pCA-LTR-SHIV-KU2

<400> SEQUENCE: 16

gaattcactg tgagacatgg gctaaagagg actaataaca agctaggcca aattcctgta     60

aatcacttgg ggggttataa gaaaagcaag ttcactatga caaagcaaaa tgtaaaggcc    120

aaattcctgt aaatcacttg gggggttata agaaaagcaa gttcactatg acaaagcaaa    180

atgtaaccgc aagtgctgac agatgtaaca gctgacatat cagctgatgc ttgctcatgc    240

tgacactgta gctctgagct gtatataagg agaagcttgc tgcttgcact tcagagttct    300

aggagagtcc ctcctagtct ctcctctccg aggaggtacc gagacctcaa aataaaggag    360

tgattgcctt actgccgagt ggagagtgat tactgagcgg ccggtgtatc gggagtcgtc    420

ccttaatctg tgcaatacca gagcggctct cgcagctggc gcccgaacag ggacttgaag    480

gagagtgaga gactcctgag tacggctgag tgaaggcagt aagggcggca ggaaccaacc    540

acgacggagt gctcctataa aggcgcgggt cggtaccaga cggcgtgagg agcgggagag    600

gaagaggcct ccggttgcag gtgagtgcaa cacaaaaaag aaatagctgt cttttatcca    660

ggaaggggta ataagataga gtgggagatg ggcgtgagaa actccgtctt gtcagggaag    720

aaagcagatg aattagaaaa aattaggcta cgacccaacg gaaagaaaaa gtacatgttg    780

aagcatgtag tatgggcagc aaatgaatta gatagatttg gattagcaga aagcctgttg    840

gagaacaaag aaggatgtca aaaaatactt tcggtcttag ctccattagt gccaacaggc    900

tcagaaaatt taaaaagcct ttataatact gtctgcgtca tctggtgcat tcacgcagaa    960

gagaaagtga aacacactga ggaagcaaaa cagatagtgc agagacacct agtggtggaa   1020

ataggaacaa cagaaactat gccaaaaaca agtagaccaa cagcaccatc tagcggcaga   1080

ggaggaaatt acccagtaca acaaatcggt ggtaactatg tccacctgcc attaagcccg   1140

agaacattaa atgcctgggt aaaattgata gaggaaaaga aatttggagc agaagtagtg   1200

ccaggatttc aggcactgtc agaaggttgc acccccctatg acattaatca gatgttaaat   1260

tgtgtgggag accatcaagc ggctatgcag attatcagag atattataaa cgaggaggct   1320

gcagattggg acttgcagca cccacaacca gctccacaac aaggacaact tagggagccg   1380

tcaggatcag atattgcagg aacaactagt tcagtagatg aacaaatcca gtggatgtac   1440

agacaacaga accccatacc agtaggcaac atttacagga gatggatcca actggggttg   1500

caaaaatgtg tcagaatgta taacccaaca aacattctag atgtaaaaca agggccaaaa   1560

gagccatttc agagctatgt agacaggttc tacaaaagtt taagagcaga acagacagat   1620

gcagcagtaa agaattggat gactcaaaca ctgctgattc aaaatgctaa cccagattgc   1680

aagctagtgc tgaaggggct gggtgtgaat cccaccctag aagaaatgct gacggcttgt   1740

caaggagtag gggggccggg acagaaggct agattaatgg cagaagccct gaaagaggcc   1800

ctcgcaccag tgcctatccc ttttgcagca gcccaacaga ggggaccaag aaagccaatt   1860

aagtgttgga attgtgggaa agagggacac tctgcaaggc aatgcagagc cccaagaaga   1920

cagggatgct ggaaatgtgg aaaaatggac catgttatgg ccaaatgccc agacagacag   1980

gcgggttttt taggccttgg tccatgggga aagaagcccc gcaatttccc catggctcaa   2040

gtgcatcagg ggctgatgcc aactgctccc ccagaggacc cagctgtgga tctgctaaag   2100

aactacatgc agttgggcaa gcagcagaga gaaaagcaga gagaaagcag agagaagcct   2160

tacaaggagg tgacagagga tttgctgcac ctcaattctc tctttggagg agaccagtag   2220
```

```
tcactgctca tattgaagga cagcctgtag aagtattact ggatacaggg gctgatgatt   2280
ctattgtaac aggaatagag ttaggtccac attatacccc aaaaatagta ggaggaatag   2340
gaggttttat taatactaaa gaatacaaaa atgtagaaat agaagtttta ggcaaaagga   2400
ttaaagggac aatcatgaca ggggacaccc cgattaacat ttttggtaga aatttgctaa   2460
cagctctggg gatgtctcta aattttccca tagctaaagt agagcctgta aaagtcgcct   2520
taaagccagg aaaggatgga ccaaaattga agcagtggcc attatcaaaa gaaaagatag   2580
ttgcattaag agaaatctgt gaaaagatgg aaaaggatgg tcagttggag gaagctcccc   2640
cgaccaatcc atacaacacc cccacatttg ctataaagaa aaaggataag aacaaatgga   2700
gaatgctgat agattttagg gaactaaata gggtcactca ggactttacg gaagtccaat   2760
taggaatacc acaccctgca ggactagcaa aaaggaaaag aattacagta ctggatatag   2820
gtgatgcata tttctccata cctctagatg aagaatttag gcagtacact gcctttactt   2880
taccatcagt aaataatgca gagccaggaa aacgatacat ttataaggtt ctgcctcagg   2940
gatggaaggg gtcaccagcc atcttccaat acactatgag acatgtgcta gaacccttca   3000
ggaaggcaaa tccagatgtg accttagtcc agtatatgga tgacatctta atagctagtg   3060
acaggacaga cctggaacat gacagggtag ttttacagtc aaaggaactc ttgaatagca   3120
tagggttttc taccccagaa gagaaattcc aaaaagatcc cccatttcaa tggatggggt   3180
acgaattgtg gccaacaaaa tggaagttgc aaaagataga gttgccacaa agagagacct   3240
ggacagtgaa tgatatacag aagttagtag gagtattaaa ttgggcagct caaatttatc   3300
caggtataaa aaccaaacat ctctgtaggt taattagagg aaaaatgact ctaacagagg   3360
aagttcagtg gactgagatg gcagaagcag aatatgagga aaataaaata attctcagtc   3420
aggaacaaga aggatgttat taccaagaag gcaagccatt agaagccacg gtaataaaga   3480
gtcaggacaa tcagtggtct tataaaattc accaagaaga caaaatactg aaagtaggaa   3540
aatttgcaaa gataaagaat acacatacca atggagtgag actattagca catgtaatac   3600
agaaaatagg aaaggaagca atagtgatct ggggacaggt cccaaaattc cacttaccag   3660
ttgagaagga tgtatgggaa cagtggtgga cagactattg gcaggtaacc tggataccgg   3720
aatgggattt tatctcaaca ccaccgctag taagattagt cttcaatcta gtgaaggacc   3780
ctatagaggg agaagaaacc tattatacag atggatcatg taataaacag tcaaaagaag   3840
ggaaagcagg atatatcaca gataggggca aagacaaagt aaaagtgtta gaacagacta   3900
ctaatcaaca agcagaattg gaagcatttc tcatggcatt gacagactca gggccaaagg   3960
caaatattat agtagattca caatatgtta tgggaataat aacaggatgc cctacagaat   4020
cagagagcag gctagttaat caaataatag aagaaatgat taaaaagtca gaaatttatg   4080
tagcatgggt accagcacac aaaggtatag gaggaaacca agaaatagac cacctagtta   4140
gtcaagggat tagacaagtt ctcttcttgg aaaagataga gccagcacaa gaagaacatg   4200
ataaatacca tagtaatgta aaagaattgg tattcaaatt tggattaccc agaatagtgg   4260
ccagacagat agtagacacc tgtgataaat gtcatcagaa aggagaggct atacatgggc   4320
aggcaaattc agatctaggg acttggcaaa tggattgtac ccatctagag ggaaaaataa   4380
tcatagttgc agtacatgta gctagtggat tcatagaagc agaggtaatt ccacaagaga   4440
caggaagaca gacagcacta tttctgttaa aattggcagg cagatggcct attacacatc   4500
tacacacaga taatggtgct aactttgctt cgcaagaagt aaagatggtt gcatggtggg   4560
```

```
cagggataga gcacaccttt ggggtaccat acaatccaca gagtcaggga gtagtggaag   4620
caatgaatca ccacctgaaa aatcaaatag atagaatcag ggaacaagca aattcagtag   4680
aaaccatagt attaatggca gttcattgca tgaattttaa aagaagggga ggaatagggg   4740
atatgactcc agcagaaaga ttaattaaca tgatcactac agaacaagag atacaatttc   4800
aacaatcaaa aaactcaaaa tttaaaaatt ttcgggtcta ttacagagaa ggcagagatc   4860
aactgtggaa gggacccggt gagctattgt ggaaaggggga ggagcagtca tcttaaaggt   4920
agggacagac attaaggtag tacccagaag aaaggctaaa attatcaaag attatggagg   4980
aggaaaagag gtggatagca gttcccacat ggaggatacc ggagaggcta gagaggtggc   5040
atagtagcct cataaaatat ctgaaatata aaactaaaga tctacaaaag gtttgctatg   5100
tgccccattt taaggtcgga tggcatggt ggacctgcag cagagtaatc ttcccactac   5160
aggaaggaag ccatttagaa gtacaagggt attggcattt gacaccagaa aaagggtggc   5220
tcagtactta tgcagtgagg ataacctggt actcaaagaa cttttggaca gatgtaacac   5280
caaactatgc agacatttta ctgcatagca cttatttccc ttgctttaca gcgggagaag   5340
tgagaagggc catcagggga gaacaactgc tgtcttgctg caggttcccg agagctcata   5400
agcaccaggt accaagccta cagtacttag cactgaaagt agtaagcgat gtcagatccc   5460
agggagagaa tcccacctgg aaacagtgga gaagagacaa taggagaggc cttcgaatgg   5520
ctaaacagaa cagtagagga gataaacaga gaggcggtaa accacctacc aagggagcta   5580
attttccagg tttggcaaag gtcttgggaa tactggcatg atgaacaagg gatgtcacca   5640
agctatgtaa aatacagata cttgtgttta atacaaaagg ctttatttat gcattgcaag   5700
aaaggctgta gatgtctagg ggaaggacat ggggcagggg gatggagacc aggacctcct   5760
cctcctcccc ctccaggact agcataaatg gaagaaagac ctccagaaaa tgaaggacca   5820
caaagggaac catgggatga atgggtagtg gaggttttgg aagaactgaa agaagaagct   5880
ttaaaacatt ttgatcctcg cttgctaact gcccttggta atcatatcta taatcgtcac   5940
ggagacactc tagagggagc aggagaactc attagaatcc tccaacgagc gctcttcatg   6000
catttcagag gcggatgcat ccactccaga atcggccaac ctgggggagg aaatcctctc   6060
tcagctatac cgccctctag aagcatgctg tagagcaaga aatggagcca gtagatccta   6120
gactagagcc ctggaagcat ccaggaagtc agcctaaaac tgcttgtacc aattgctatt   6180
gtaaaaagtg ttgctttcat tgccaagttt gtttcataac aaaagcctta ggcatctcct   6240
atggcaggaa gaagcggaga cagcgacgaa gagctcatca gaacagtcag actcatcaag   6300
cttctctatc aaagcagtaa gtagtacatg taacgcaacc tataccaata gtagcaatag   6360
tagcattagt agtagcaata ataatagcaa tagttgtgtg gtccatagta atcatagaat   6420
ataggaaaat attaagacaa agaaaaatag acaggttaat tgatagacta atagaaagag   6480
cagaagacag tggcaatgag agtgaaggag aaatatcagc acttgtggag atgggggtgg   6540
agatggggca ccatgctcct tgggatgttg atgatctgta gtgctacaga aaaattgtgg   6600
gtcacagtct attatggggt acctgtgtgg aaggaagcaa ccaccactct attttgtgca   6660
tcagatgcta aagcatatga tacagaggca cataatgttt gggccacaca tgcctgtgta   6720
cccacagacc ccaacccaca agaagtagta ttggtaaatg tgacagaaaa ttttaacatg   6780
tggaaaaatg acatggtaga acagatgcat gaggatataa tcagtttatg ggatcaaagc   6840
ctaaagccat gtgtaaaatt aaccccactc tgtgttagtt taaattgcac tgatttgaag   6900
aatgatacta ataccaatag tagtagcggg agaatgataa tggagaaagg agagataaaa   6960
```

```
aactgctctt tcaatatcag cacaagcata agaggtaagg tgcagaaaga atatgcattt   7020
ttttataaac ttgatataat accaatagat aatgatacta ccagctatac gttgacaagt   7080
tgtaacacct cagtcatttc acaggcctgt ccaaaggtat cctttgagcc aattcccata   7140
cattattgtg ccccggctgg ttttgcgatt ctaaaatgta ataataagac gttcaatgga   7200
acaggaccat gtacaaatgt cagcacagta caatgtacac atggaattag gccagtagta   7260
tcaactcaac tgctgttaaa tggcagtcta gcagaagaag aggtagtaat tagatctgtc   7320
aatttcatgg acaatgctaa aaccataata gtacagctga acacatctgt agaaattaat   7380
tgtacaagac ccagcaacaa tacaataaaa agaatccgta tccagagagg accagggaga   7440
gcatttgtta caatgggaaa aataggaaat atgagacaag cacattgtaa cattagtaga   7500
gcaaaatgga ataacacttt aaaacagata gctagcaaat taagagaaca atttggaaat   7560
aataaaacaa taatctttaa gcaatcctca ggaggggacc cagaaattgt aacgcacagt   7620
tttaattgtg gaggggaatt tttctactgt aattcaacac aactgtttaa tagtacttgg   7680
tttaatagta cttggagtac tgaagggtca aataacactg aaggaagtgg cacaatcacc   7740
ctcccatgca gaataaaaca aattataaac atgtggcaga aagtaggaaa agcaatgtat   7800
gcccctccca tcagtggaca aattagatgt tcatcaaata ttacagggct gctattaaca   7860
agagatggtg gtaagggcaa caatgagtcc gagatcttca gacctggagg aggagatatg   7920
agggacaatt ggagaagtga attatataaa tataaagtag taaaaattga accattagga   7980
gtagcaccca ccaaggcaaa gagaagagtg gtgcagagag aaaaaagagc agtgggaata   8040
ggagctttgt tccttgggtt cttgggagca gcaggaagca ctatgggcgc agcgtcaatg   8100
acgctgacgg tacaggccag acaattattg tctggtatag tgcagcagca gaacaatttg   8160
ctgagggcta ttgaggcgca acagcatctg ttgcaactca cagtctgggg catcaagcag   8220
ctccaggcaa gaatcctggc tgtggaaaga tacctaaagg atcaacagct cctggggatt   8280
tggggttgct ctggaaaact catttgcacc actgctgtgc cttggaatgc tagttggagt   8340
aataaatctc tggaacagat ttggaatcac atgacctgga tggagtggga cagagaaatt   8400
aacaattaca caagcttaat acactcctta attgaagaat cgcaaaacca gcaagaaaag   8460
aatgaacaag aattattgga attagataaa tgggcaagtt tgtggaattg gtttgacata   8520
acaaattggc tgtggtatat aaaattattc ataatgatag taggaggctt ggtaggttta   8580
agaatagttt ttgctgtact ttctatagtg aatagagtta ggcagggata ttcaccatta   8640
tcgtttcaga cccacctccc aaccccgagg ggacccgaca ggcccgaagg aatagaagaa   8700
gaaggtggag agagagacag agacagatcc attcgattag tgaacggatc cttggcactt   8760
atctgggacg atctacggag cctgtgcctc ttcagctacc accgcttgag agacttactc   8820
ttgattgtaa cgaggactgt ggaacttctg ggacgcaggg ggtgggaagc cctcaaatat   8880
tggtggaatc tcctacagta ttggagtcag gaactaaaga atagtgctgt tagcttgctc   8940
aatgccatag ccatagcagt agctgaggga acagataggg ttatagaagt agtccaagga   9000
gcttgtagag ctattcgcta catacctaga agaataagac agggcttgga aaggattttg   9060
ctataagatt cgagatgggt ggagctattt ccatgaggcg gtccaggcag tctagagatc   9120
tgcgacagag actcttgcgg gcgcgtgggg agacttatgg gagactctta gaagaggtgg   9180
aagatggata ctcgcgatcc ccaggaggat tagacaaggg cttgagctca ctctcttgtg   9240
agggacagaa atacaatcag ggacagtata tgaatactcc atggagagac ccagctgaag   9300
```

```
agagagaaaa attagcatac agaaaacaaa atatggatga tatagatgag gaagatgata   9360
acttggtagg ggtatcagtg aggccaagag ttcccctaag aacaatgagt tacaaattgg   9420
caatagacat gtctcatttt ataaaagaaa agggggaact ggaagggatc ttttacagtg   9480
caagaagaca tagaatctta gacatgtact tagaaaagga aaaaggcatc ataccagatt   9540
ggcaggatta cacctcagga ccaggaatta gatacccaaa gacatttggc tggctatgga   9600
aattagtccc tgtaaatgta tcagatgagg cacaggagga tgaagagcat tatttaatgc   9660
atccagctca aacttcccag tgggatgacc cttggagaga ggttctagca tggaagtttg   9720
atccaactct ggcctacact tatgaggcat atgttagata cccagaagag tttggaagca   9780
agtcaggcct gtcagaggaa gaggttaaaa gaaggctaac cgcaagaggc cttcttaaca   9840
tggctgacaa gaaggaaact cgctgagcgg ccgcactgtg agacatgggc taaagaggac   9900
taataacaag ctaggccaaa ttcctgtaaa tcacttgggg ggttataaga aaagcaagtt   9960
cactatgaca aagcaaaatg taaaggccaa attcctgtaa atcacttggg gggttataag  10020
aaaagcaagt tcactatgac aaagcaaaat gtaaccgcaa gtgctgacag atgtaacagc  10080
tgacatatca gctgatgctt gctcatgctg acactgtagc tctgagctgt atataaggag  10140
aagcttgctg cttgcacttc agagttctag gagagtccct cctagtctct cctctccgag  10200
gaggtaccga gacctcaaaa taaaggagtg attgccttac tgccgagtgg agagtgatta  10260
ctgagcggcc ggtgtatcgg gagtcgtccc ttaatctgtg caataccaga gcggctctcg  10320
cagctgtcga cctcgagggg gggcccggta ccttaattaa ttaaggtacc aggtaagtgt  10380
acccaattcg ccctatagtg agtcgtatta caattcactc gatcgccctt cccaacagtt  10440
gcgcagcctg aatggcgaat ggagatccaa tttttaagtg tataatgtgt taaactactg  10500
attctaattg tttgtgtatt ttagattcac agtcccaagg ctcatttcag gcccctcagt  10560
cctcacagtc tgttcatgat cataatcagc cataccacat ttgtagaggt tttacttgct  10620
ttaaaaaacc tcccacacct ccccctgaac ctgaaacata aaatgaatgc aattgttgtt  10680
gttaacttgt ttattgcagc ttataatggt tacaaataaa gcaatagcat cacaaatttc  10740
acaaataaag catttttttc actgcattct agttgtggtt tgtccaaact catcaatgta  10800
tcttaacgcg taaattgtaa gcgttaatgc ttcacgacca cgctgatgag ctttaccgca  10860
gctgcctcgc gcgtttcggt gatgacggtg aaaacctctg acacatgcag ctcccggaga  10920
cggtcacagc ttgtctgtaa gcggatgccg ggagcagaca agcccgtcag ggcgcgtcag  10980
cgggtgttgg cgggtgtcgg ggcgcagcca tgacccagtc acgtagcgat agcggagtgt  11040
atactggctt aactatgcgg catcagagca gattgtactg agagtgcacc atatatgcgg  11100
tgtgaaatac cgcacagatg cgtaaggaga aaataccgca tcaggcgctc ttccgcttcc  11160
tcgctcactg actcgctgcg ctcggtcgtt cggctgcggc gagcggtatc agctcactca  11220
aaggcggtaa tacggttatc cacagaatca ggggataacg caggaaagaa catgtgagca  11280
aaaggccagc aaaaggccag gaaccgtaaa aaggccgcgt tgctggcgtt tttccatagg  11340
ctccgccccc ctgacgagca tcacaaaaat cgacgctcaa gtcagaggtg gcgaaacccg  11400
acaggactat aaagatacca ggcgtttccc cctggaagct ccctcgtgcg ctctcctgtt  11460
ccgaccctgc cgcttaccgg atacctgtcc gcctttctcc cttcgggaag cgtggcgctt  11520
tctcatagct cacgctgtag gtatctcagt tcggtgtagg tcgttcgctc caagctgggc  11580
tgtgtgcacg aaccccccgt tcagcccgac cgctgcgcct tatccggtaa ctatcgtctt  11640
gagtccaacc cggtaagaca cgacttatcg ccactggcag cagccactgg taacaggatt  11700
```

```
agcagagcga ggtatgtagg cggtgctaca gagttcttga agtggtggcc taactacggc  11760

tacactagaa ggacagtatt tggtatctgc gctctgctga agccagttac cttcggaaaa  11820

agagttggta gctcttgatc cggcaaacaa accaccgctg gtagcggtgg tttttttgtt  11880

tgcaagcagc agattacgcg cagaaaaaaa ggatctcaag aagatccttt gatcttttct  11940

acggggtctg acgctcagtg gaacgaaaac tcacgttaag ggattttggt catgaacaat  12000

aaaactgtct gcttacataa acagtaatac aaggggtgtt atgagccata ttcaacggga  12060

aacgtcttgc tcgaggccgc gattaaattc caacatggat gctgatttat atgggtataa  12120

atgggctcgc gataatgtcg ggcaatcagg tgcgacaatc tatcgattgt atgggaagcc  12180

cgatgcgcca gagttgtttc tgaaacatgg caaaggtagc gttgccaatg atgttacaga  12240

tgagatggtc agactaaact ggctgacgga atttatgcct cttccgacca tcaagcattt  12300

tatccgtact cctgatgatg catggttact caccactgcg atccccggga aaacagcatt  12360

ccaggtatta gaagaatatc ctgattcagg tgaaaatatt gttgatgcgc tggcagtgtt  12420

cctgcgccgg ttgcattcga ttcctgtttg taattgtcct tttaacagcg atcgcgtatt  12480

tcgtctcgct caggcgcaat cacgaatgaa taacggtttg gttgatgcga gtgattttga  12540

tgacgagcgt aatggctggc ctgttgaaca agtctggaaa gaaatgcata agcttttgcc  12600

attctcaccg gattcagtcg tcactcatgg tgatttctca cttgataacc ttatttttga  12660

cgaggggaaa ttaataggtt gtattgatgt tggacgagtc ggaatcgcag accgatacca  12720

ggatcttgcc atcctatgga actgcctcgg tgagttttct ccttcattac agaaacggct  12780

ttttcaaaaa tatggtattg ataatcctga tatgaataaa ttgcagtttc atttgatgct  12840

cgatgagttt ttctaa                                                  12856
```

<210> SEQ ID NO 17
<211> LENGTH: 12854
<212> TYPE: DNA
<213> ORGANISM: Artificial Sequence
<220> FEATURE:
<223> OTHER INFORMATION: Vecteur pCA-LTR-SHIV-KU2-IN-

<400> SEQUENCE: 17

```
gaattcactg tgagacatgg gctaaagagg actaataaca agctaggcca aattcctgta     60

aatcacttgg ggggttataa gaaaagcaag ttcactatga caaagcaaaa tgtaaaggcc    120

aaattcctgt aaatcacttg gggggttata agaaaagcaa gttcactatg acaaagcaaa    180

atgtaaccgc aagtgctgac agatgtaaca gctgacatat cagctgatgc ttgctcatgc    240

tgacactgta gctctgagct gtatataagg agaagcttgc tgcttgcact tcagagttct    300

aggagagtcc ctcctagtct ctcctctccg aggaggtacc gagacctcaa aataaaggag    360

tgattgcctt actgccgagt ggagagtgat tactgagcgg ccggtgtatc gggagtcgtc    420

ccttaatctg tgcaatacca gagcggctct cgcagctggc gcccgaacag ggacttgaag    480

gagagtgaga gactcctgag tacggctgag tgaaggcagt aagggcggca ggaaccaacc    540

acgacggagt gctcctataa aggcgcgggt cggtaccaga cggcgtgagg agcgggagag    600

gaagaggcct ccggttgcag gtgagtgcaa cacaaaaaag aaatagctgt cttttatcca    660

ggaaggggta ataagataga gtgggagatg ggcgtgagaa actccgtctt gtcagggaag    720

aaagcagatg aattagaaaa aattaggcta cgacccaacg gaaagaaaaa gtacatgttg    780

aagcatgtag tatgggcagc aaatgaatta gatagatttg gattagcaga aagcctgttg    840
```

```
gagaacaaag aaggatgtca aaaaatactt tcggtcttag ctccattagt gccaacaggc    900

tcagaaaatt taaaaagcct ttataatact gtctgcgtca tctggtgcat tcacgcagaa    960

gagaaagtga aacacactga ggaagcaaaa cagatagtgc agagacacct agtggtggaa   1020

ataggaacaa cagaaactat gccaaaaaca agtagaccaa cagcaccatc tagcggcaga   1080

ggaggaaatt acccagtaca acaaataggt ggtaactatg tccacctgcc attaagcccg   1140

agaacattaa atgcctgggt aaaattgata gaggaaaaga aatttggagc agaagtagtg   1200

ccaggatttc aggcactgtc agaaggttgc accccctatg acattaatca gatgttaaat   1260

tgtgtgggag accatcaagc ggctatgcag attatcagag atattataaa cgaggaggct   1320

gcagattggg acttgcagca cccacaacca gctccacaac aaggacaact tagggagccg   1380

tcaggatcag atattgcagg aacaactagt tcagtagatg aacaaatcca gtggatgtac   1440

agacaacaga accccatacc agtaggcaac atttacagga gatggatcca actggggttg   1500

caaaaatgtg tcagaatgta taacccaaca aacattctag atgtaaaaca agggccaaaa   1560

gagccatttc agagctatgt agacaggttc tacaaaagtt taagagcaga acagacagat   1620

gcagcagtaa agaattggat gactcaaaca ctgctgattc aaaatgctaa cccagattgc   1680

aagctagtgc tgaaggggct gggtgtgaat cccaccctag aagaaatgct gacggcttgt   1740

caaggagtag gggggccggg acagaaggct agattaatgg cagaagccct gaaagaggcc   1800

ctcgcaccag tgcctatccc ttttgcagca gcccaacaga ggggaccaag aaagccaatt   1860

aagtgttgga attgtgggaa agagggacac tctgcaaggc aatgcagagc cccaagaaga   1920

cagggatgct ggaaatgtgg aaaaatggac catgttatgg ccaaatgccc agacagacag   1980

gcgggttttt taggccttgg tccatgggga aagaagcccc gcaatttccc catggctcaa   2040

gtgcatcagg ggctgatgcc aactgctccc ccagaggacc cagctgtgga tctgctaaag   2100

aactacatgc agttgggcaa gcagcagaga gaaaagcaga gagaaagcag agagaagcct   2160

tacaaggagg tgacagagga tttgctgcac ctcaattctc tctttggagg agaccagtag   2220

tcactgctca tattgaagga cagcctgtag aagtattact ggatacaggg gctgatgatt   2280

ctattgtaac aggaatagag ttaggtccac attatacccc aaaaatagta ggaggaatag   2340

gaggttttat taatactaaa gaatacaaaa atgtagaaat agaagtttta ggcaaaagga   2400

ttaaagggac aatcatgaca ggggacaccc cgattaacat tttggtagaa aatttgctaa   2460

cagctctggg gatgtctcta aattttccca tagctaaagt agagcctgta aaagtcgcct   2520

taaagccagg aaagaatgga ccaaaattga agcagtggcc attatcaaaa gaaaagatag   2580

ttgcattaag agaaatctgg gaaaagatgg aaaaggatgg tcagttggag gaagctcccc   2640

cgaccaatcc atacaacacc cccacatttg ctataaagaa aaaggataag aacaaatgga   2700

gaatgctgat agattttagg gaactaaata gggtcactca ggactttacg gaagtccaat   2760

taggaatacc acaccctgca ggattagcaa aaaggaaaag aattacagta ctggatatag   2820

gtgatgcata tttctccata cctctagatg aagaatttag gcagtacact gcctttactt   2880

taccatcagt aaataatgca gagccaggaa aacgatacat ttataaggtt ctgcctcagg   2940

gatggaaggg gtcaccagcc atcttccaat acactatgag acatgtgcta gaacccttca   3000

ggaaggcaaa tccagatgtg accttagtcc agtatatgga tgacatctta atagctagtg   3060

acaggacaga cctggaacat gacagggtag ttttacagtc aaaggaactc ttgaatagca   3120

tagggttttc taccccagaa gagaaattcc aaaaagatcc cccatttcaa tggatggggt   3180

acgaattgtg gccaacaaaa tggaagttgc aaaagataga gttgccacaa agagagacct   3240
```

```
ggacagtgaa tgatatacag aagttagtag gagtattaaa ttgggcagct caaatttatc   3300

caggtataaa aaccaaacat ctctgtaggt taattagagg aaaaatgact ctaacagagg   3360

aagttcagtg gactgagatg gcagaagcag aatatgagga aaataaaata attctcagtc   3420

aggaacaaga aggatgttat taccaagaag gcaagccatt agaagccacg gtaataaaga   3480

gtcaggacaa tcagtggtct tataaaattc accaagaaga caaaatactg aaagtaggaa   3540

aatttgcaaa gataaagaat acacatacca atggagtgag actattagca catgtaatac   3600

agaaaatagg aaaggaagca atagtgatct ggggacaggt cccaaaattc cacttaccag   3660

ttgagaagga tgtatgggaa cagtggtgga cagactattg gcaggtaacc tggataccgg   3720

aatgggattt tatctcaaca ccaccgctag taagattagt cttcaatcta gtgaaggacc   3780

ctatagaggg agaagaaacc tattatacag atggatcgtg taataaacag tcaaaagaag   3840

ggaaagcagg atatatcaca gataggggca aagacaaagt aaaagtgtta gaacagacta   3900

ctaatcaaca agcagaattg gaagcatttc tcatggcatt gacagactca gggccaaagg   3960

caaatattat agtagattca caatatgtta tgggaataat aacaggatgc cctacagaat   4020

cagagagcag gctagttaat caaataatag aagaaatgat taaaaagtca gaaatttatg   4080

tagcatgggt accagcacac aaaggtatag gaggaaacca agaaatagac cacctagtta   4140

gtcaagggat tagacaagtt ctcttcttgg aaaagataga gccagcacaa gaagaacatg   4200

ataaatacca tagtaatgta aaagaattgg tattcaaatt tggattaccc agaatagtgg   4260

ccagacagat agtagacacc tgtgataaat gccatcagaa aggagaggct atacatgggc   4320

aggtaaattc agatctaggg acttggcaaa tggattgtac ccatctagag ggaaaaataa   4380

tcatagttgc agtacatgta gctagtggat tcatagaagc agaggtaatt ccacaagaga   4440

caggaagaca gacagcacta tttctgttaa aattggcagg cagatggcct attacacatc   4500

tacacacaga taatggtgct aactttgctt cgcaagaagt aaagatggtt gcatggtggg   4560

cagggataga gcacaccttt ggggtaccat acaatccaca gagtcaggga gtagtggaag   4620

caatgaatca ccacctgaaa aatcaaatag atagaatcag ggaacaagca aattcagtag   4680

aaaccatagt attaatggca gttcattgca tgaattttaa aagaagggga ggaatagggg   4740

atatgactcc agcagaaaga ttaattaaca tgatcactac agaacaagag atacaatttc   4800

aacaatcaaa aaactcaaaa tttaaaaatt ttcgggtcta ttacagagaa ggcagagatc   4860

aactgtggaa gggacccggt gagctattgt ggaaagggga aggagcagtc atcttaaagg   4920

tagggacaga cattaaggta gtacccagaa gaaaggctaa aattatcaaa gattatggag   4980

gaggaaaaga ggtggatagc agttcccaca tggaggatac cggagaggtt agagaggtgg   5040

catagcctca taaaatatct gaaatataaa actaaagatc tacaaaaggt ttgctatgtg   5100

ccccatttta aggtcggatg ggcatggtgg acctgcagca gagtaatctt cccactacag   5160

gaaggaagcc atttagaagt acaagggtat tggcatttga caccagaaaa agggtggctc   5220

agtacttatg cagtgaggat aacctggtac tcaaagaact tttggacaga tgtaacacca   5280

aactatgcag acattttact gcatagcact tatttccctt gctttacagc gggagaagtg   5340

agaagggcca tcaggggaga acaactgctg tcttgctgca ggttcccgag agctcataag   5400

caccaggtac caagcctaca gtacttagca ctgaaagtag taagcgatgt cagatcccag   5460

ggagagaatc ccacctggaa acagtggaga agagacaata ggagaggcct tcgaatggct   5520

aaacagaaca gtagaggaga taaacagaga ggcggtaaac cacctaccaa gggagctaat   5580
```

```
tttccaggtt tggcaaaggt cttgggaata ctggcatgat gaacaaggga tgtcaccaag   5640
ctatgtaaaa tacagatact tgtgtttaat acaaaaggct ttatttatgc attgcaagaa   5700
aggctgtaga tgtctagggg aaggacatgg ggcagggggga tggagaccag gacctcctcc   5760
tcctcccccct ccaggactag cataaatgga agaaagacct ccagaaaatg aaggaccaca   5820
aagggaacca tgggatgaat gggtagtgga ggttttggaa gaactgaaag aagaagcttt   5880
aaaacatttt gatcctcgct tgctaactgc ccttggtaat catatctata atcgtcacgg   5940
agacactcta gagggagcag gagaactcat tagaatcctc caacgagcgc tcttcatgca   6000
tttcagaggc ggatgcatcc actccagaat cggccaacct gggggaggaa atcctctctc   6060
agctataccg ccctctagaa gcatgctgta gagcaagaaa tggagccagt agatcctaga   6120
ctagagccct ggaagcatcc aggaagtcag cctaaaactg cttgtaccaa ttgctattgt   6180
aaaaagtgtt gctttcattg ccaagtttgt ttcataacaa aagccttagg catctcctat   6240
ggcaggaaga agcggagaca gcgacgaaga gctcatcaga acagtcagac tcatcaagct   6300
tctctatcaa agcagtaagt agtacatgta acgcaaccta taccaatagt agcaatagta   6360
gcattagtag tagcaataat aatagcaata gttgtgtggt ccatagtaat catagaatat   6420
aggaaaatat taagacaaag aaaaatagac aggttaattg atagactaat agaaagagca   6480
gaagacagtg gcaatgagag tgaaggagaa atatcagcac ttgtggagat gggggtggag   6540
atggggcacc atgctccttg ggatgttgat gatctgtagt gctacagaaa aattgtgggt   6600
cacagtctat tatggggtac ctgtgtggaa ggaagcaacc accactctat tttgtgcatc   6660
agatgctaaa gcatatgata cagaggcaca taatgtttgg gccacacatg cctgtgtacc   6720
cacagacccc aacccacaag aagtagtatt ggtaaatgtg acagaaaatt ttaacatgtg   6780
gaaaaatgac atggtagaac agatgcatga ggatataatc agtttatggg atcaaagcct   6840
aaagccatgt gtaaaattaa ccccactctg tgttagttta aattgcactg atttgaagaa   6900
tgatactaat accaatagta gtagcgggag aatgataatg gagaaaggag agataaaaaa   6960
ctgctctttc aatatcagca caagcataag aggtaaggtg cagaaagaat atgcattttt   7020
ttataaactt gatataatac caatagataa tgatactacc agctatacgt tgacaagttg   7080
taacacctca gtcatttcac aggcctgtcc aaaggtatcc tttgagccaa ttcccataca   7140
ttattgtgcc ccggctggtt ttgcgattct aaaatgtaat aataagacgt tcaatggaac   7200
aggaccatgt acaaatgtca gcacagtaca atgtacacat ggaattaggc cagtagtatc   7260
aactcaactg ctgttaaatg gcagtctagc agaagaagag gtagtaatta gatctgtcaa   7320
tttcatggac aatgctaaaa ccataatagt acagctgaac acatctgtag aaattaattg   7380
tacaagaccc agcaacaata caataaaaag aatccgtatc cagagaggac cagggagagc   7440
atttgttaca atgggaaaaa taggaaatat gagacaagca cattgtaaca ttagtagagc   7500
aaaatggaat aacactttaa aacagatagc tagcaaatta agagaacaat ttggaaataa   7560
taaaacaata atctttaagc aatcctcagg aggggaccca gaaattgtaa cgcacagttt   7620
taattgtgga ggggaatttt tctactgtaa ttcaacacaa ctgtttaata gtacttggtt   7680
taatagtact tggagtactg aagggtcaaa taacactgaa ggaagtggca caatcaccct   7740
cccatgcaga ataaaacaaa ttataaacat gtggcagaaa gtaggaaaag caatgtatgc   7800
ccctcccatc agtggacaaa ttagatgttc atcaaatatt acagggctgc tattaacaag   7860
agatggtggt aagggcaaca atgagtccga gatcttcaga cctggaggag gagatatgag   7920
ggacaattgg agaagtgaat tatataaata taaagtagta aaaattgaac cattaggagt   7980
```

```
agcacccacc aaggcaaaga gaagagtggt gcagagagaa aaaagagcag tgggaatagg   8040
agctttgttc cttgggttct tgggagcagc aggaagcact atgggcgcag cgtcaatgac   8100
gctgacggta caggccagac aattattgtc tggtatagtg cagcagcaga acaatttgct   8160
gagggctatt gaggcgcaac agcatctgtt gcaactcaca gtctggggca tcaagcagct   8220
ccaggcaaga atcctggctg tggaaagata cctaaaggat caacagctcc tggggatttg   8280
gggttgctct ggaaaactca tttgcaccac tgctgtgcct tggaatgcta gttggagtaa   8340
taaatctctg gaacagattt ggaatcacat gacctggatg gagtgggaca gagaaattaa   8400
caattacaca agcttaatac actccttaat tgaagaatcg caaaaccagc aagaaaagaa   8460
tgaacaagaa ttattggaat tagataaatg ggcaagtttg tggaattggt ttgacataac   8520
aaattggctg tggtatataa aattattcat aatgatagta ggaggcttgg taggtttaag   8580
aatagttttt gctgtacttt ctatagtgaa tagagttagg cagggatatt caccattatc   8640
gtttcagacc cacctcccaa ccccgagggg acccgacagg cccgaaggaa tagaagaaga   8700
aggtggagag agagacagag acagatccat tcgattagtg aacggatcct tggcacttat   8760
ctgggacgat ctacggagcc tgtgcctctt cagctaccac cgcttgagag acttactctt   8820
gattgtaacg aggactgtgg aacttctggg acgcaggggg tgggaagccc tcaaatattg   8880
gtggaatctc ctacagtatt ggagtcagga actaaagaat agtgctgtta gcttgctcaa   8940
tgccatagcc atagcagtag ctgagggaac agatagggtt atagaagtag tccaaggagc   9000
ttgtagagct attcgctaca tacctagaag aataagacag ggcttggaaa ggattttgct   9060
ataagattcg agatgggtgg agctatttcc atgaggcggt ccaggcagtc tagagatctg   9120
cgacagagac tcttgcgggc gcgtggggag acttatggga gactcttaga agaggtggaa   9180
gatggatact cgcgatcccc aggaggatta gacaagggct tgagctcact ctcttgtgag   9240
ggacagaaat acaatcaggg acagtatatg aatactccat ggagagaccc agctgaagag   9300
agagaaaaat tagcatacag aaaacaaaat atggatgata tagatgagga agatgataac   9360
ttggtagggg tatcagtgag gccaagagtt cccctaagaa caatgagtta caaattggca   9420
atagacatgt ctcattttat aaaagaaaag ggggaactgg aagggatctt ttacagtgca   9480
agaagacata gaatcttaga catgtactta gaaaaggaaa aaggcatcat accagattgg   9540
caggattaca cctcaggacc aggaattaga tacccaaaga catttggctg gctatggaaa   9600
ttagtccctg taaatgtatc agatgaggca caggaggatg aagagcatta tttaatgcat   9660
ccagctcaaa cttcccagtg ggatgaccct tggagagagg ttctagcatg gaagtttgat   9720
ccaactctgg cctacactta tgaggcatat gttagatacc cagaagagtt tggaagcaag   9780
tcaggcctgt cagaggaaga ggttaaaaga aggctaaccg caagaggcct tcttaacatg   9840
gctgacaaga aggaaactcg ctgagcggcc gcactgtgag acatgggcta aagaggacta   9900
ataacaagct aggccaaatt cctgtaaatc acttgggggg ttataagaaa agcaagttca   9960
ctatgacaaa gcaaaatgta aaggccaaat tcctgtaaat cacttggggg gttataagaa  10020
aagcaagttc actatgacaa agcaaaatgt aaccgcaagt gctgacagat gtaacagctg  10080
acatatcagc tgatgcttgc tcatgctgac actgtagctc tgagctgtat ataaggagaa  10140
gcttgctgct tgcacttcag agttctagga gagtccctcc tagtctctcc tctccgagga  10200
ggtaccgaga cctcaaaata aaggagtgat tgccttactg ccgagtggag agtgattact  10260
gagcggccgg tgtatcggga gtcgtccctt aatctgtgca ataccagagc ggctctcgca  10320
```

```
gctgtcgacc tcgagggggg gcccggtacc ttaattaatt aaggtaccag gtaagtgtac  10380
ccaattcgcc ctatagtgag tcgtattaca attcactcga tcgcccttcc caacagttgc  10440
gcagcctgaa tggcgaatgg agatccaatt tttaagtgta taatgtgtta aactactgat  10500
tctaattgtt tgtgtatttt agattcacag tcccaaggct catttcaggc ccctcagtcc  10560
tcacagtctg ttcatgatca taatcagcca taccacattt gtagaggttt tacttgcttt  10620
aaaaaacctc ccacacctcc ccctgaacct gaaacataaa atgaatgcaa ttgttgttgt  10680
taacttgttt attgcagctt ataatggtta caaataaagc aatagcatca caaatttcac  10740
aaataaagca tttttttcac tgcattctag ttgtggtttg tccaaactca tcaatgtatc  10800
ttaacgcgta aattgtaagc gttaatgctt cacgaccacg ctgatgagct ttaccgcagc  10860
tgcctcgcgc gtttcggtga tgacggtgaa aacctctgac acatgcagct cccggagacg  10920
gtcacagctt gtctgtaagc ggatgccggg agcagacaag cccgtcaggg cgcgtcagcg  10980
ggtgttggcg ggtgtcgggg cgcagccatg acccagtcac gtagcgatag cggagtgtat  11040
actggcttaa ctatgcggca tcagagcaga ttgtactgag agtgcaccat atatgcggtg  11100
tgaaataccg cacagatgcg taaggagaaa ataccgcatc aggcgctctt ccgcttcctc  11160
gctcactgac tcgctgcgct cggtcgttcg gctgcggcga gcggtatcag ctcactcaaa  11220
ggcggtaata cggttatcca cagaatcagg ggataacgca ggaaagaaca tgtgagcaaa  11280
aggccagcaa aaggccagga accgtaaaaa ggccgcgttg ctggcgtttt tccataggct  11340
ccgcccccct gacgagcatc acaaaaatcg acgctcaagt cagaggtggc gaaacccgac  11400
aggactataa agataccagg cgtttccccc tggaagctcc ctcgtgcgct ctcctgttcc  11460
gaccctgccg cttaccggat acctgtccgc ctttctccct tcgggaagcg tggcgctttc  11520
tcatagctca cgctgtaggt atctcagttc ggtgtaggtc gttcgctcca agctgggctg  11580
tgtgcacgaa ccccccgttc agcccgaccg ctgcgcctta tccggtaact atcgtcttga  11640
gtccaacccg gtaagacacg acttatcgcc actggcagca gccactggta acaggattag  11700
cagagcgagg tatgtaggcg gtgctacaga gttcttgaag tggtggccta actacggcta  11760
cactagaagg acagtatttg gtatctgcgc tctgctgaag ccagttacct tcggaaaaag  11820
agttggtagc tcttgatccg gcaaacaaac caccgctggt agcggtggtt tttttgtttg  11880
caagcagcag attacgcgca gaaaaaaagg atctcaagaa gatcctttga tcttttctac  11940
ggggtctgac gctcagtgga acgaaaactc acgttaaggg attttggtca tgaacaataa  12000
aactgtctgc ttacataaac agtaatacaa ggggtgttat gagccatatt caacgggaaa  12060
cgtcttgctc gaggccgcga ttaaattcca acatggatgc tgatttatat gggtataaat  12120
gggctcgcga taatgtcggg caatcaggtg cgacaatcta tcgattgtat gggaagcccg  12180
atgcgccaga gttgtttctg aaacatggca aaggtagcgt tgccaatgat gttacagatg  12240
agatggtcag actaaactgg ctgacggaat ttatgcctct tccgaccatc aagcatttta  12300
tccgtactcc tgatgatgca tggttactca ccactgcgat ccccgggaaa acagcattcc  12360
aggtattaga agaatatcct gattcaggtg aaaatattgt tgatgcgctg gcagtgttcc  12420
tgcgccggtt gcattcgatt cctgtttgta attgtccttt taacagcgat cgcgtatttc  12480
gtctcgctca ggcgcaatca cgaatgaata acggtttggt tgatgcgagt gattttgatg  12540
acgagcgtaa tggctggcct gttgaacaag tctggaaaga aatgcataag cttttgccat  12600
tctcaccgga ttcagtcgtc actcatggtg atttctcact tgataacctt atttttgacg  12660
aggggaaatt aataggttgt attgatgttg gacgagtcgg aatcgcagac cgataccagg  12720
```

```
atcttgccat cctatggaac tgcctcggtg agttttctcc ttcattacag aaacggcttt  12780

ttcaaaaata tggtattgat aatcctgata tgaataaatt gcagtttcat ttgatgctcg  12840

atgagttttt ctaa                                                    12854
```

<210> SEQ ID NO 18
<211> LENGTH: 10958
<212> TYPE: DNA
<213> ORGANISM: Artificial Sequence
<220> FEATURE:
<223> OTHER INFORMATION: Vecteur CAL-HIV-IN-

<400> SEQUENCE: 18

```
ctggcgccca cgaccacgct gatgagcttt accgcagctg cctcgcgcgt ttcggtgatg     60

acggtgaaaa cctctgacac atgcagctcc cggagacggt cacagcttgt ctgtaagcgg    120

atgccgggag cagacaagcc cgtcagggcg cgtcagcggg tgttggcggg tgtcggggcg    180

cagccatgac ccagtcacgt agcgatagcg gagtgtatac tggcttaact atgcggcatc    240

agagcagatt gtactgagag tgcaccatat atgcggtgtg aaataccgca cagatgcgta    300

aggagaaaat accgcatcag gcgctcttcc gcttcctcgc tcactgactc gctgcgctcg    360

gtcgttcggc tgcggcgagc ggtatcagct cactcaaagg cggtaatacg gttatccaca    420

gaatcagggg ataacgcagg aaagaacatg tgagcaaaag gccagcaaaa ggccaggaac    480

cgtaaaaagg ccgcgttgct ggcgtttttc cataggctcc gcccccctga cgagcatcac    540

aaaaatcgac gctcaagtca gaggtggcga aacccgacag gactataaag ataccaggcg    600

tttccccctg gaagctccct cgtgcgctct cctgttccga ccctgccgct taccggatac    660

ctgtccgcct ttctcccttc gggaagcgtg gcgctttctc atagctcacg ctgtaggtat    720

ctcagttcgg tgtaggtcgt tcgctccaag ctgggctgtg tgcacgaacc ccccgttcag    780

cccgaccgct gcgccttatc cggtaactat cgtcttgagt ccaacccggt aagacacgac    840

ttatcgccac tggcagcagc cactggtaac aggattagca gagcgaggta tgtaggcggt    900

gctacagagt tcttgaagtg gtggcctaac tacggctaca ctagaaggac agtatttggt    960

atctgcgctc tgctgaagcc agttaccttc ggaaaaagag ttggtagctc ttgatccggc   1020

aaacaaacca ccgctggtag cggtggtttt tttgtttgca agcagcagat tacgcgcaga   1080

aaaaaaggat ctcaagaaga tcctttgatc ttttctacgg ggtctgacgc tcagtggaac   1140

gaaaactcac gttaagggat tttggtcatg aacaataaaa ctgtctgctt acataaacag   1200

taatacaagg ggtgttatga gccatattca acgggaaacg tcttgctcga ggccgcgatt   1260

aaattccaac atggatgctg atttatatgg gtataaatgg gctcgcgata atgtcgggca   1320

atcaggtgcg acaatctatc gattgtatgg gaagcccgat gcgccagagt tgtttctgaa   1380

acatggcaaa ggtagcgttg ccaatgatgt tacagatgag atggtcagac taaactggct   1440

gacggaattt atgcctcttc cgaccatcaa gcattttatc cgtactcctg atgatgcatg   1500

gttactcacc actgcgatcc ccgggaaaac agcattccag gtattagaag aatatcctga   1560

ttcaggtgaa aatattgttg atgcgctggc agtgttcctg cgccggttgc attcgattcc   1620

tgtttgtaat tgtcctttta acagcgatcg cgtatttcgt ctcgctcagg cgcaatcacg   1680

aatgaataac ggtttggttg atgcgagtga ttttgatgac gagcgtaatg gctggcctgt   1740

tgaacaagtc tggaaagaaa tgcataagct tttgccattc tcaccggatt cagtcgtcac   1800

tcatggtgat ttctcacttg ataaccttat ttttgacgag gggaaattaa taggttgtat   1860
```

```
tgatgttgga cgagtcggaa tcgcagaccg ataccaggat cttgccatcc tatggaactg   1920
cctcggtgag ttttctcctt cattacagaa acggcttttt caaaaatatg gtattgataa   1980
tcctgatatg aataaattgc agtttcattt gatgctcgat gagtttttct aagaattcac   2040
tgtgagacat gggctaaaga ggactaataa caagctaggc caaattcctg taaatcactt   2100
ggggggttat aagaaaagca agttcactat gacaaagcaa aatgtaaagg ccaaattcct   2160
gtaaatcact tggggggtta taagaaaagc aagttcacta tgacaaagca aaatgtaacc   2220
gcaagtgctg acagatgtaa cagctgacat atcagctgat gcttgctcat gctgacactg   2280
tagctctgag ctgtatataa ggagaagctt gctgcttgca cttcagagtt ctaggagagt   2340
ccctcctagt ctctcctctc cgaggaggta ccgagacctc aaaataaagg agtgattgcc   2400
ttactgccga gtggagagtg attactgagc ggccggtgta tcgggagtcg tcccttaatc   2460
tgtgcaatac cagagcggct ctcgcagctg gcgcccgaac agggacttga aagcgaaagt   2520
aaagccagag gagatctctc gacgcaggac tcggcttgct gaagcgcgca cggcaagagg   2580
cgaggggcgg cgactggtga gtacgccaaa aattttgact agcggaggct agaaggagag   2640
agatgggtgc gagagcgtcg gtattaagcg ggggagaatt agataaatgg gaaaaaattc   2700
ggttaaggcc agggggaaag aaacaatata aactaaaaca tatagtatgg gcaagcaggg   2760
agctagaacg attcgcagtt aatcctggcc ttttagagac atcagaaggc tgtagacaaa   2820
tactgggaca gctacaacca tcccttcaga caggatcaga agaacttaga tcattatata   2880
atacaatagc agtcctctat tgtgtgcatc aaaggataga tgtaaaagac accaaggaag   2940
ccttagataa gatagaggaa gagcaaaaca aaagtaagaa aaaggcacag caagcagcag   3000
ctgacacagg aaacaacagc caggtcagcc aaaattaccc tatagtgcag aacctccagg   3060
ggcaaatggt acatcaggcc atatcaccta gaactttaaa tgcatgggta aaagtagtag   3120
aagagaaggc tttcagccca gaagtaatac ccatgttttc agcattatca gaaggagcca   3180
ccccacaaga tttaaatacc atgctaaaca cagtgggggg acatcaagca gccatgcaaa   3240
tgttaaaaga gaccatcaat gaggaagctg cagaatggga tagattgcat ccagtgcatg   3300
cagggcctat tgcaccaggc cagatgagag aaccaagggg aagtgacata gcaggaacta   3360
ctagtaccct tcaggaacaa ataggatgga tgacacataa tccacctatc ccagtaggag   3420
aaatctataa aagatggata atcctgggat taaataaaat agtaagaatg tatagcccta   3480
ccagcattct ggacataaga caaggaccaa aggaaccctt tagagactat gtagaccgat   3540
tctataaaac tctaagagcc gagcaagctt cacaagaggt aaaaaattgg atgacagaaa   3600
ccttgttggt ccaaaatgcg aacccagatt gtaagactat tttaaaagca ttgggaccag   3660
gagcgacact agaagaaatg atgacagcat gtcagggagt ggggggaccc ggccataaag   3720
caagagtttt ggctgaagca atgagccaag taacaaatcc agctaccata atgatacaga   3780
aaggcaattt taggaaccaa agaaagactg ttaagtgttt caattgtggc aaagaagggc   3840
acatagccaa aaattgcagg gcccctagga aaaagggctg ttggaaatgt ggaaaggaag   3900
gacaccaaat gaaagattgt actgagagac aggctaattt tttagggaag atctggcctt   3960
cccacaaggg aaggccaggg aattttcttc agagcagacc agagccaaca gccccaccag   4020
aagagagctt caggtttggg gaagagacaa caactccctc tcagaagcag gagccgatag   4080
acaaggaact gtatccttta gcttccctca gatcactctt tggcagcgac ccctcgtcac   4140
aataaagata ggggggcaat taaaggaagc tctattagat acaggagcag atgatacagt   4200
attagaagaa atgaatttgc caggaagatg gaaaccaaaa atgatagggg gaattggagg   4260
```

```
ttttatcaaa gtaggacagt atgatcagat actcatagaa atctgcggac ataaagctat   4320
aggtacagta ttagtaggac ctacacctgt caacataatt ggaagaaatc tgttgactca   4380
gattggctgc actttaaatt ttcccattag tcctattgag actgtaccag taaaattaaa   4440
gccaggaatg gatggcccaa aagttaaaca atggccattg acagaagaaa aaataaaagc   4500
attagtagaa atttgtacag aaatggaaaa ggaaggaaaa atttcaaaaa ttgggcctga   4560
aaatccatac aatactccag tatttgccat aaagaaaaaa gacagtacta aatggagaaa   4620
attagtagat ttcagagaac ttaataagag aactcaagat ttctgggaag ttcaattagg   4680
aataccacat cctgcagggt taaaacagaa aaaatcagta acagtactgg atgtgggcga   4740
tgcatatttt tcagttccct tagataaaga cttcaggaag tatactgcat ttaccatacc   4800
tagtataaac aatgagacac cagggattag atatcagtac aatgtgcttc cacagggatg   4860
gaaaggatca ccagcaatat tccagtgtag catgacaaaa atcttagagc cttttagaaa   4920
acaaaatcca gacatagtca tctatcaata catggatgat ttgtatgtag gatctgactt   4980
agaaataggg cagcatagaa caaaaataga ggaactgaga caacatctgt tgaggtgggg   5040
atttaccaca ccagacaaaa aacatcagaa agaacctcca ttcctttgga tgggttatga   5100
actccatcct gataaatgga cagtacagcc tatagtgctg ccagaaaagg acagctggac   5160
tgtcaatgac atacagaaat tagtgggaaa attgaattgg gcaagtcaga tttatgcagg   5220
gattaaagta aggcaattat gtaaacttct taggggaacc aaagcactaa cagaagtagt   5280
accactaaca gaagaagcag agctagaact ggcagaaaac agggagattc taaaagaacc   5340
ggtacatgga gtgtattatg acccatcaaa agacttaata gcagaaatac agaagcaggg   5400
gcaaggccaa tggacatatc aaatttatca agagccattt aaaaatctga aaacaggaaa   5460
atatgcaaga atgaagggtg cccacactaa tgatgtgaaa caattaacag aggcagtaca   5520
aaaaatagcc acagaaagca tagtaatatg gggaaagact cctaaattta aattacccat   5580
acaaaaggaa acatgggaag catggtggac agagtattgg caagccacct ggattcctga   5640
gtgggagttt gtcaataccc ctcccttagt gaagttatgg taccagttag agaaagaacc   5700
cataatagga gcagaaactt tctatgtaga tggggcagcc aatagggaaa ctaaattagg   5760
aaaagcagga tatgtaactg acagaggaag acaaaaagtt gtccccctaa cggacacaac   5820
aaatcagaag actgagttac aagcaattca tctagctttg caggattcgg gattagaagt   5880
aaacatagtg acagactcac aatatgcatt gggaatcatt caagcacaac cagataagag   5940
tgaatcagag ttagtcagtc aaataataga gcagttaata aaaaaggaaa aagtctacct   6000
ggcatgggta ccagcacaca aaggaattgg aggaaatgaa caagtagatg ggttggtcag   6060
tgctggaatc aggaaagtac tatttttaga tggaatagat aaggcccaag aagatcaggg   6120
attatggaaa acagatggca ggtgatgatt gtgtggcaag tagacaggat gaggattaac   6180
acatggaaaa gattagtaaa acaccatatg tatatttcaa ggaaagctaa ggactggttt   6240
tatagacatc actatgaaag tactaatcca aaaataagtt cagaagtaca catcccacta   6300
ggggatgcta aattagtaat aacaacatat tggggtctgc atacaggaga aagagactgg   6360
catttgggtc agggagtctc catagaatgg aggaaaaaga gatatagcac acaagtagac   6420
cctgacctag cagaccaact aattcatctg cactattttg attgtttttc agaatctgct   6480
ataagaaata ccatattagg acgtatagtt agtcctaggt gtgaatatca agcaggacat   6540
aacaaggtag gatctctaca gtacttggca ctagcagcat taataaaacc aaaacagata   6600
aagccacctt tgcctagtgt taggaaactg acagaggaca gatggaacaa gccccagaag   6660
```

```
accaagggcc acagagggag ccatacaatg aatggacact agagctttta gaggaactta   6720
agagtgaagc tgttagacat tttcctagga tatggctcca taacttagga caacatatct   6780
atgaaactta cggggatact tgggcaggag tggaagccat aataagaatt ctgcaacaac   6840
tgctgtttat ccatttcaga attgggtgtc gacatagcag aataggcgtt actcgacaga   6900
ggagagcaag aaatggagcc agtagatcct agactagagc cctggaagca tccaggaagt   6960
cagcctaaaa ctgcttgtac caattgctat tgtaaaaagt gttgctttca ttgccaagtt   7020
tgtttcatga caaaagcctt aggcatctcc tatggcagga agaagcggag acagcgacga   7080
agagctcatc agaacagtca gactcatcaa gcttctctat caaagcagta agtagtacat   7140
gtaatgcaac ctataatagt agcaatagta gcattagtag tagcaataat aatagcaata   7200
gttgtgtggt ccatagtaat catagaatat aggaaaatat taagacaaag aaaaatagac   7260
aggttaattg atagactaat agaaagagca gaagacagtg gcaatgagag tgaaggagaa   7320
gtatcagcac ttgtggagat gggggtggaa atggggcacc atgctccttg ggatattgat   7380
gatctgtagt gctacagaaa aattgtgggt cacagtctat tatggggtac ctgtgtggaa   7440
ggaagcaacc accactctat tttgtgcatc agatgctaaa gcatatgata cagaggtaca   7500
taatgtttgg gccacacatg cctgtgtacc cacagacccc aacccacaag aagtagtatt   7560
ggtaaatgtg acagaaaatt ttaacatgtg gaaaaatgac atggtagaac agatgcatga   7620
ggatataatc agtttatggg atcaaagcct aaagccatgt gtaaaattaa ccccactctg   7680
tgttagttta aagtgcactg atttgaagaa tgatactaat accaatagta gtagcgggag   7740
aatgataatg gagaaaggag agataaaaaa ctgctctttc aatatcagca caagcataag   7800
agataaggtg cagaaagaat atgcattctt ttataaactt gatatagtac caatagataa   7860
taccagctat aggttgataa gttgtaacac ctcagtcatt acacaggcct gtccaaaggt   7920
atcctttgag ccaattccca tacattattg tgccccggct ggttttgcga ttctaaaatg   7980
taataataag acgttcaatg gaacaggacc atgtacaaat gtcagcacag tacaatgtac   8040
acatggaatc aggccagtag tatcaactca actgctgtta aatggcagtc tagcagaaga   8100
agatgtagta attagatctg ccaatttcac agacaatgct aaaaccataa tagtacagct   8160
gaacacatct gtagaaatta attgtacaag acccaacaac aatacaagaa aaagtatccg   8220
tatccagagg ggaccaggga gagcatttgt tacaatagga aaaataggaa atatgagaca   8280
agcacattgt aacattagta gagcaaaatg gaatgccact ttaaaacaga tagctagcaa   8340
attaagagaa caatttggaa ataataaaac aataatcttt aagcaatcct caggaggga   8400
cccagaaatt gtaacgcaca gttttaattg tggaggggaa tttttctact gtaattcaac   8460
acaactgttt aatagtactt ggtttaatag tacttggagt actgaagggt caaataacac   8520
tgaaggaagt gacacaatca cactcccatg cagaataaaa caatttataa acatgtggca   8580
ggaagtagga aaagcaatgt atgcccctcc catcagtgga caaattagat gttcatcaaa   8640
tattactggg ctgctattaa caagagatgg tggtaataac aacaatgggt ccgagatctt   8700
cagacctgga ggaggcgata tgagggacaa ttggagaagt gaattatata aatataaagt   8760
agtaaaaatt gaaccattag gagtagcacc caccaaggca aagagaagag tggtgcagag   8820
agaaaaaaga gcagtgggaa taggagcttt gttccttggg ttcttgggag cagcaggaag   8880
cactatgggc tgcacgtcaa tgacgctgac ggtacaggcc agacaattat tgtctgatat   8940
agtgcagcag cagaacaatt tgctgagggc tattgaggcg caacagcatc tgttgcaact   9000
cacagtctgg ggcatcaaac agctccaggc aagaatcctg gctgtggaaa gatacctaaa   9060
```

-continued

```
ggatcaacag ctcctgggga tttggggttg ctctggaaaa ctcatttgca ccactgctgt   9120
gccttggaat gctagttgga gtaataaatc tctggaacag atttggaata acatgacctg   9180
gatggagtgg gacagagaaa ttaacaatta cacaagctta atacactcct taattgaaga   9240
atcgcaaaac cagcaagaaa agaatgaaca agaattattg gaattagata aatgggcaag   9300
tttgtggaat tggtttaaca taacaaattg gctgtggtat ataaaattat tcataatgat   9360
agtaggaggc ttggtaggtt taagaatagt tttgctgta ctttctatag tgaatagagt   9420
taggcaggga tattcaccat tatcgtttca gacccacctc ccaatcccga ggggacccga   9480
caggcccgaa ggaatagaag aagaaggtgg agagagagac agagacagat ccattcgatt   9540
agtgaacgga tccttagcac ttatctggga cgatctgcgg agcctgtgcc tcttcagcta   9600
ccaccgcttg agagacttac tcttgattgt aacgaggatt gtggaacttc tgggacgcag   9660
ggggtgggaa gccctcaaat attggtggaa tctcctacag tattggagtc aggaactaaa   9720
gaatagtgct gttaacttgc tcaatgccac agccatagca gtagctgagg ggacagatag   9780
ggttatagaa gtattacaag cagcttatag agctattcgc cacataccta gaagaataag   9840
acagggcttg gaaaggattt tgctataaga tgggtggcaa gtggtcaaaa agtagtgtga   9900
ttggatggcc tgctgtaagg gaaagaatga gacgagctga gccagcagca gatggggtgg   9960
gagcagtatc tcgagaccta gaaaaacatg gagcaatcac aagtagcaat acagcagcta  10020
acaatgctgc ttgtgcctgg ctagaagcac aagaggagga agaggtgggt tttccagtca  10080
cacctcaggt acctttaaga ccaatgactt acaaggcagc tgtagatctt agccactttt  10140
taaaagaaaa ggggggactg gaagggctaa ttcactccca aagaagacaa gatatccttg  10200
atctgtggat ctaccacaca caaggctact tccctgattg gcagaactac acaccagggc  10260
caggggtcag atatccactg acctttggat ggtgctacaa gctagtacca gttgagccag  10320
ataaggtaga agaggccaat aaaggagaga acaccagctt gttacaccct gtgagcctgc  10380
atggaatgga tgaccctgag agagaagtgt tagagtggag gtttgacagc cgcctagcat  10440
ttcatcacgt ggcccgagag ctgcatccgg agtacttcaa gaactgctga catcgagctt  10500
aattcactgt gagacatggg ctaaagagga ctaataacaa gctaggccaa attcctgtaa  10560
atcacttggg gggttataag aaaagcaagt tcactatgac aaagcaaaat gtaaaggcca  10620
aattcctgta aatcacttgg ggggttataa gaaaagcaag ttcactatga caaagcaaaa  10680
tgtaaccgca agtgctgaca gatgtaacag ctgacatatc agctgatgct tgctcatgct  10740
gacactgtag ctctgagctg tatataagga gaagcttgct gcttgcactt cagagttcta  10800
ggagagtccc tcctagtctc tcctctccga ggaggtaccg agacctcaaa ataaaggagt  10860
gattgcctta ctgccgagtg gagagtgatt actgagcggc cggtgtatcg ggagtcgtcc  10920
cttaatctgt gcaataccag agcggctctc gcagctgc                          10958
```